United States Patent
DeNinno et al.

[11] Patent Number: 5,591,884
[45] Date of Patent: Jan. 7, 1997

[54] DOPAMINE AGONISTS

[75] Inventors: Michael P. DeNinno, Gales Ferry, Conn.; Richard J. Perner, Gurnee, Ill.

[73] Assignee: Abbott Laboratories, Abbott Park, Ill.

[21] Appl. No.: 461,330

[22] Filed: Jun. 5, 1995

Related U.S. Application Data

[60] Division of Ser. No. 442,236, May 30, 1995, which is a continuation-in-part of Ser. No. 998,161, Dec. 29, 1992, abandoned, which is a continuation-in-part of PCT/US90/02864 May 22, 1990, which is a continuation-in-part of Ser. No. 359,448, May 31, 1989, Pat. No. 4,963,568.

[51] Int. Cl.$^6$ .......................... C07F 5/04; C07C 49/105; C07C 43/205
[52] U.S. Cl. ............... 558/286; 558/287; 558/288; 558/298; 560/55; 560/61; 562/2; 564/152; 564/155; 564/156; 564/161; 564/169; 564/182; 568/308; 568/442; 568/607; 568/608; 568/609; 568/611; 568/630; 568/631
[58] Field of Search ........................ 558/286, 287, 558/288, 298; 560/55, 61; 562/2; 564/152, 155, 156, 161, 169, 182; 568/607, 608, 609, 611, 630, 631, 644, 648, 308, 442

[56] References Cited

U.S. PATENT DOCUMENTS 4,994,486 2/1991 Schoenleber et al. .............. 514/456

Primary Examiner—Joseph McKane
Attorney, Agent, or Firm—Monte R. Browder; Mona Anand; Thomas D. Brainard

[57] ABSTRACT

Novel compounds having the formula

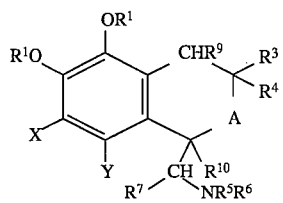

and the pharmaceutically acceptable salts, esters and amides thereof, wherein A is —O—, —S— or —$CR^2R^8$—;

$R^1$, $R^2$, $R^3$, $R^4$, $R^5$, $R^6$, $R^7$, $R^8$, $R^9$, $R^{10}$, X and Y are specifically defined; and up to one combination of (a) $R^2$ and $R^5$, (b) $R^5$ and $R^6$, (c) $R^5$ and $R^7$, (d) $R^6$ and $R^7$, and (e) $R^7$ and Y, taken together with the atoms to which they are attached, may form a ring, the compounds being useful for treating dopamine-related neurological, psychological and cardiovascular disorders as well as in the treatment of cognitive impairment, attention deficit disorder, and substance abuse and other addictive behavior disorders.

Also disclosed are intermediates and processes useful in the preparation of the above compounds.

1 Claim, No Drawings

DOPAMINE AGONISTS

This application is a divisional of U.S. Ser. No. 08/442,236, filed May 30, 1995, still pending, which is a continuation-in-part of U.S. application Ser. No. 07/998,161, filed on Dec. 29, 1992, now abandoned, which is a continuation-in-part of International Application No. PCT/US90/02864, filed May 22, 1990, now abandoned, which is a continuation-in-part of U.S. application Ser. No. 07/359,448, filed May 31, 1989, and issued on Oct. 16, 1990 as U.S. Pat. No. 4,963,568.

TECHNICAL FIELD

This invention relates to novel compounds which are selective dopamine agonists useful for treating dopamine-related neurological, psychological, cardiovascular, cognitive and behavioral disorders.

BACKGROUND OF THE INVENTION

Dopamine is an important neurotransmitter in the central nervous system (CNS), and also has several important roles in the peripheral nervous system such as in the control of the supply of blood to the kidneys and in autonomic ganglion transmission.

It is now widely accepted that dopamine receptors in the CNS can be divided into two general categories, designated D-1 and D-2 receptors. The division was originally based on biochemical and pharmacological differences between the two receptor types, but further evidence supporting this division has recently come from study of the molecular biology of dopamine receptors in the CNS. The dopamine D-1 receptor is linked to the enzyme adenylate cyclase through a stimulatory G protein, such that stimulation of this receptor by dopamine or a dopamine D-1 receptor agonist causes an increase in the production of 3',5'-cyclic adenosine monophosphate (cAMP).

The D-2 receptor, on the other hand, also regulates important functional activity within the CNS, although the biochemical events which follow stimulation of this receptor by dopamine or a D-2 receptor agonist are not as well understood. Autoreceptors on dopaminergic neurons which have the pharmacological properties of D-2 receptors are thought to control both the firing rate of these cells as well as the release of dopamine from the nerve terminals. It is also known that stimulation of the D-2 receptors in the intermediate lobe of the pituitary gland causes a decrease in cAMP production and that stimulation of the D-2 receptors on the mammotrophs of the anterior pituitary gland suppresses prolactin secretion. Dopaminergic neurons are also affected by and interact with other neurotransmitter systems in the CNS, as for example D-2 receptors on the cholinergic interneurons in the striatum (one of the components of the basal ganglia) regulating the release of acetylcholine from these cells.

Dopamine involvement has been proposed for several diverse neurological and psychological disorders. One disorder involving dopamine is Parkinson's Disease. Dopamine occurs at high concentration within the nerve terminals in the basal ganglia of the mammalian brain. In the early 1960's, the loss of striatal dopamine was established as a chemical marker of Parkinson's Disease. This deficiency is still thought to be primary to the etiology of the disease state.

L-DOPA (3,4-dihydroxyphenylalanine), which is used in conjunction with a peripheral aromatic amino acid decarboxylase inhibitor and often supplemented with anticholinergic agents, has been shown to be useful in the treatment of Parkinson's Disease. The response to L-DOPA is thought to be a result of the conversion of L-DOPA to dopamine within the striatum, and is linked to stimulation of both the D-1 and D-2 receptors.

The success of L-DOPA therapy has led to the testing of other compounds capable of mimicking the post-synaptic receptor actions of dopamine. Such direct-acting agents might offer the therapeutic advantages of greater potency, increased duration of action, or fewer side effects over L-DOPA. For example, bromocryptine, the direct-acting dopamine agonist most widely used in the treatment of Parkinson's Disease, lowers the amount of L-DOPA required to achieve the maximal therapeutic response and allows for a delay in the onset of L-DOPA therapy. However, the response to bromocryptine alone is not as great as that observed with L-DOPA.

Another disorder in which dopamine has been implicated is schizophrenia. Psychoses are serious psychiatric illnesses characterized by abnormal behavior which may include delusions, hallucinations, violence, mania and serious long-lasting depression. Of these, schizophrenia is the most common, involving disturbance of thought processes, hallucinations and loss of touch with reality. The theory of schizophrenia as a disease of the CNS was first formalized by Kraepelin and Bleuler in the early 1900's. It was not until chlorpromazine was discovered by Delay and Daniker in the early 1950's, however, that drug management of this disease was possible.

The pioneering work of Carlsson and others led to the now widely-held dopamine theory of schizophrenia. According to this theory, schizophrenia is caused by an excess of dopamine in the brain. Several lines of evidence support this hypothesis. For example, chronic abuse of stimulants such as amphetamines, known to enhance dopaminergic activity in the brain, can lead to a paranoid psychosis that is almost indistinguishable from classic paranoid schizophrenia. The mechanism of action proposed for drugs with anti-schizophrenic activity is the blockade by these compounds of the dopamine receptors and, consequently, the prevention of excess receptor stimulation. In the mid 1970's, it was observed that virtually all of the currently used antipsychotic agents could displace radiolabeled haloperidol (a dopamine antagonist) from striatal dopamine receptors with a good correlation between average effective clinical dose and drug binding affinity.

Unfortunately, the currently-available antipsychotic agents frequently produce undesirable side-effects, the most common of which are the so-called extrapyramidal effects that include bizarre involuntary movements and Parkinson-like effects. Sedation and hypotension are also common side-effects. Because of these often severe side-effects and the high incidence of patients unresponsive to currently-available drugs, more potent and more selective agents are needed.

It is also recognized that depressive conditions and related affective disorders result from a reduction in the central nervous system of certain biogenic amine neurotransmitters such as dopamine (D), noradrenaline (NA) and serotonin (5-HT). Affective disorders are characterized by changes in mood as the primary clinical manifestation. Disturbances of mood are the most common psychiatric disorders in adults, with 18–23% of women and 8–11% of men experiencing at least one major depressive episode. Currently-available antidepressant drugs work primarily by raising the levels of the biogenic amine neurotransmitters either by inhibition of the neuronal uptake of the neurotransmitters or by inhibition of the metabolic enzymes responsible for convening the biogenic amines to inactive metabolites. Unfortunately, there are major drawbacks to the use of currently-available agents for treating affective disorders. For example, no antidepressant drug to date has proven to be superior to electroconvulsive shock therapy in the treatment of severe, suicidal depression. Other problems with the use of available drugs are delayed onset of activity, poor efficacy, anticholinergic effects at therapeutic doses, cardiotoxicity, convulsions and the danger of taking a fatal overdose. There also exists a large number of untreated individuals and treatment-resistant patients in need of effective therapy. A role for direct-acting dopamine agonists in antidepressant therapy has been suggested based on the effects observed for several dopamine agonists in various animal models used for predicting antidepressant activity such as the "mouse behavioral despair test".

A role for dopamine has been established in several other neurological functions, such as cognitive function and attention mechanisms. Animal studies implicate dopamine in attention-related behaviors involving search and exploratory activity, distractibility, response rate, discriminability and the switching of attention. A therapeutic role in the treatment of cognitive impairment and attention deficit disorders has therefore been proposed and is under active investigation for compounds which mimic the receptor activity of dopamine.

Dopamine has been also used in the treatment of shock, congestive heart failure and renal failure. Stimulation of the peripheral D-1 receptors causes vasodilation, particularly in the renal and mesenteric vascular beds where large numbers of these receptors are found. The utility of dopamine has been limited, however, by its ability to cause vasoconstriction at higher concentrations, presumably due to its secondary effects on adrenergic receptors and by its emetic effects due to peripheral D-2 stimulation. Agents selective for the peripheral D-1 receptors may offer significant advantages over currently used treatments for these and other related disorders.

Published evidence suggests that dopamine also has a central role in the brain's reward system. For example, it has been reported that animals trained to self-administer cocaine will increase their consumption of this drug after treatment with either a D-1 or a D-2 receptor antagonist. It was proposed that the animals would increase the amount of cocaine administered in order to maintain the elevated dopamine levels responsible for the drugs euphorigenic and reinforcing properties. The dopamine D-1 agonist, SKF 38393, has been reported to decrease food intake by rats presumably by direct action of the drug on neural feeding mechanisms. Because of this interrelationship between dopamine and reward, dopaminergic agents could be useful for the treatment of substance abuse and other addictive behavior disorders including cocaine addiction, nicotine addiction and eating disorders.

Dopaminergic agents such as the compounds of the present invention that mimic the actions of dopamine and show selectivity for the different dopamine receptor subtypes are needed in order to obtain the anticipated physiological responses discussed above, separate from other possibly less desirable effects.

Related 5-hydroxy dopaminergic compounds were reported in U.S. Pat. No. 4,994,486, which is also a continuation-in-part of U.S. application Ser. No. 359,448, and compounds having somewhat related structures to the novel compounds of the instant invention have been disclosed in published European Patent Applications Nos. 321968 and 325963 and in French Patent No. 2,407,212. However, the 1-aminomethyl tetrahydronaphthalene derivatives of EP 0321968 are unsubstituted at the 3-position and are substituted on the amino group with an n-propyl group or an n-propyl and an additional phenoxyethyl group; the 1-aminomethyl tetrahydronaphthalene derivatives of EP 0325963 are substituted on the amino group with an aryl-substituted or heterocycle-substituted alkyl group; and in the 1-aminoalkyl-substituted isochroman and thioisochroman compounds of the French Patent, the amino group of the 1-amino alkyl group must be in a 6-membered ring containing one or two nitrogen atoms and is further substituted with a nitrogen substituent, an aryl group or a benzimidazole group.

SUMMARY OF THE INVENTION

In on aspect of the present invention are disclosed dopaminergic compounds of the formula I:

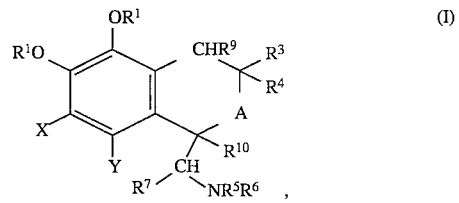

as well as pharmaceutically acceptable salts, esters and amides thereof, wherein:

A is —O—, —S—, or —CR$^2$R$^8$—, where R$^2$ and R$^8$ are as defined below;

R$^1$ is selected from hydrogen and a readily-cleavable group, as defined below; or is a catechol-protecting group, as defined below;

R$^2$ is selected from hydrogen, methyl, ethyl, hydroxymethyl, hydroxyethyl, halomethyl, haloethyl, aminomethyl and aminoethyl, or, taken together with R$^5$ and the atoms to which each is attached (as well as any intervening atoms) forms a 5- or 6-membered ring containing only one heteroatom, the nitrogen shown above in formula I;

R$^3$ is selected from:
  $C_4$–$C_{10}$-alkyl, as defined below,
  substituted $C_1$–$C_5$-alkyl, as defined below,
  $C_2$–$C_{12}$-alkenyl, as defined below,
  substituted $C_2$–$C_5$-alkenyl, as defined below,
  $C_2$–$C_{12}$-alkynyl, as defined below,
  substituted $C_2$–$C_5$-alkynyl, as defined below.
  cyclo-$C_3$–$C_{10}$-alkyl, as defined below,
  substituted cyclo-$C_3$–$C_{10}$-alkyl, as defined below,
  carbocyclic-$C_6$–$C_{10}$-aryl, as defined below,
  substituted carbocyclic-$C_6$–$C_{10}$-aryl, as defined below,
  carbocyclic-$C_6$–$C_{10}$-aryloxy-$C_1$–$C_5$-alkyl, as defined below,
  substituted carbocyclic-$C_6$–$C_{10}$-aryloxy-$C_1$–$C_5$-alkyl, as defined below,
  carbocyclic-$C_6$–$C_{10}$-aryl-$C_1$–$C_5$-alkyl, as defined below,
  substituted carbocyclic-$C_6$–$C_{10}$-aryl-$C_1$–$C_5$-alkyl, as defined below,
  Het, as defined below,
  substituted Het, as defined below,
  Het-$C_1$–$C_5$-alkyl, as defined below, and
  substituted Het-$C_1$–$C_5$-alkyl, as defined below,
  or, taken together with R$^4$ and the atom to which both are attached, forms a spirocyclo-$C_3$–$C_{10}$-alkyl ring, as defined below;

$R^4$ is selected from hydrogen and $C_1$–$C_{10}$-alkyl, or, taken together with $R^3$ and the atom to which both are attached, forms a spirocyclo-$C_3$–$C_{10}$-alkyl ring, or, taken together with $R^9$, forms a bond;

$R^5$ is selected from:
  hydrogen,
  $C_1$–$C_3$-alkyl,
  hydroxy-$C_2$–$C_3$-alkyl,
  amino-$C_2$–$C_3$-alkyl,
  $C_1$–$C_3$-alkoxy-$C_2$–$C_3$-alkyl, as defined below,
  $C_2$–$C_3$-alkenyl,
  $C_2$–$C_3$-alkynyl,
  cyclo-$C_3$–$C_5$-alkyl,
  $C_1$–$C_8$-alkanoyl, as defined below,
  a readily-cleavable group,
  an amino acid, as defined below, and
  a dipeptide, as defined below;
or, taken together with one of $R^6$ and $R^7$ and the atoms to which each is attached (as well as any intervening atoms), forms a pyrrolidine ring; or, when A is —$CR^2R^8$— and $R^8$ is hydrogen, is taken together with $R^2$ and the atoms to which each is attached (as well as any intervening atoms) to form a 5- or 6-membered ring containing only one heteroatom, namely, the nitrogen shown in formula I:

$R^6$ is selected from hydrogen and $C_1$–$C_3$-alkyl; or, taken together with $R^5$ and the atom to each is attached, forms a pyrrolidine ring;

$R^7$ is hydrogen or $C_1$–$C_5$-alkyl; or, taken together with $R^5$ and the atoms to which each is attached (as well as any intervening atoms), forms a pyrrolidine ring; or, taken together with Y and the atoms to which each is attached (as well as any intervening atoms), forms a 5-, 6- or 7-membered carbocyclic ring;

$R^8$ is hydrogen or, taken together with $R^{10}$, forms a bond;

$R^9$ is hydrogen or, taken together with $R^4$, forms a bond;

$R^{10}$ is hydrogen or, taken together with $R^8$, forms a bond;

X is selected from hydrogen, halogen, methyl and ethyl;

Y is selected from hydrogen, halogen, methyl and ethyl; or, taken together with $R^7$ and the atoms to which each is attached (as well as any intervening atoms), forms a 5-, 6- or 7-membered carbocyclic ring.

The compounds of the present invention are limited, however, in that (i) at least one of X and Y must be hydrogen when Y is not combined in a ring; and (ii) only one of the following combinations of groups and the atoms to which they are attached may be taken together to form a ring as described above: (a) $R^2$ and $R^5$, (b) $R^5$ and $R^6$, (c) $R^5$ and $R^7$, (d) $R^6$ and $R^7$, and (e) $R^7$ and Y.

The compounds of formula I have the ability to bind and activate dopamine receptors in the central and peripheral nervous systems, thus mimicing the activity of dopamine, and are therefore expected to be useful in the treatment of dopamine-related neurological, psychological and cardiovascular disorders, as well as in the treatment of substance abuse and other addictive behavior disorders, cognitive impairment and attention deficit disorder.

In a second aspect of the present invention, pharmaceutical compositions are disclosed which comprise a therapeutically-effective amount of the compound of formula I and a pharmaceutically-acceptable carrier or diluent.

DETAILED DESCRIPTION OF THE INVENTION

Representative of the compounds of the invention are those compounds of formula I in which A is —O—; $R^9$ is hydrogen; and $R^1$, $R^3$, $R^4$, $R^5$, $R^6$, $R^7$, $R^{10}$, X and Y are as defined above.

In another particular embodiment of the invention are compounds of formula I in which A is —S—; $R^5$ is hydrogen, $C_1$–$C_3$-alkyl or $C_1$–$C_8$-alkanoyl; $R^6$, $R^7$, and $R^9$ are hydrogen; and $R^1$, $R^3$, $R^4$, $R^{10}$, X and Y are as described above.

In a further particular embodiment of the invention are compounds of formula I in which A is —$CR^2R^8$—: and $R^1$, $R^2$, $R^3$, $R^4$, $R^5$, $R^6$, $R^7$, $R^8$, $R^9$, $R^{10}$, X and Y are as defined above.

In a preferred embodiment of the invention are compounds of formula I in which (a) A is —$CR^2R^8$—; (b) $R^2$ and $R^5$, taken together with the atoms to which each is attached, form a 5- or 6-membered ring; (c) $R^7$ and $R^9$ are each hydrogen; and (d) $R^1$, $R^3$, $R^4$, $R^6$, $R^8$, $R^{10}$, X and Y are as defined above. Such compounds have the formula:

where w is 1 or 2.

In another preferred embodiment of the invention are compounds of formula I in which (a) $R^7$ and Y, taken together with the atoms to which each is attached, form a 5-, 6- or 7-membered ring; and (b) $R^1$, $R^2$, $R^3$, $R^4$, $R^5$, $R^6$, $R^8$, $R^9$, $R^{10}$ and X are as defined above. Such compounds have the formula:

As to each of the above embodiments, preferred compounds include (i) those in which $R^3$ is selected from $C_4$–$C_{10}$-alkyl, substituted $C_1$–$C_5$-alkyl, cyclo-$C_3$–$C_{10}$-alkyl, substituted cyclo-$C_3$–$C_{10}$-alkyl, carbocyclic-$C_6$–$C_{10}$-aryl, substituted carbocyclic-$C_6$–$C_{10}$-aryl, carbocyclic-$C_6$–$C_{10}$-aryl-$C_1$–$C_5$-alkyl, substituted carbocyclic-$C_6$–$C_{10}$-aryl-$C_1$–$C_5$-alkyl, Het, substituted Het, Het-$C_1$–$C_5$-alkyl, and substituted Het-$C_1$–$C_5$-alkyl, or, taken together with $R^4$ and the atom to which $R^3$ and $R^4$ are both attached, forms a spirocyclo-$C_3$–$C_{10}$-alkyl ring, and/or (ii) those in which $R^5$ and $R^6$ are hydrogen, or where one of $R^5$ and $R^6$ is methyl and the other is hydrogen.

The following compounds are representative of the compounds of the invention:

1-Aminomethyl-5,6-bis(trimethylacetoxy)-3-phenyl-3,4-dihydronaphthalene;

[1,3-cis]1-Aminomethyl-3-n-butyl-5,6-dihydroxy-3,4-dihydro-1H-2-benzopyran;

[1,3-cis]1-Aminomethyl-3-cyclopentylmethyl-5,6-dihydroxy-3,4-dihydro-1H-2-benzopyran;

[1,3-cis]1-Aminomethyl-3-cyclooctyl-5,6-dihydroxy-3,4-dihydro-1H-2-benzopyran;

[1,3-cis]3-n-Butyl-5,6-dihydroxy-1-methylaminomethyl-3,4-dihydro-1H-2-benzopyran;

[3-cis]3-(1-Adamantyl)-5,6-dihydroxy-1-methylaminomethyl-3,4-dihydro-1H-2-benzopyran
5,6-Bis(acetoxy)-1-(alanyl-alanyl)aminomethyl-3-phenyl-3,4-dihydronaphthalene;
5,6-Bis(acetoxy)-1-(g-glutamyl)aminomethyl-3-phenyl-3,4-dihydronaphthalene;
5,6-Bis(acetoxy)-1-(alanyl)aminomethyl-3-phenyl-3,4-dihydronaphthalene;
5,6-Bis(acetoxy)-1-(methionyl)aminomethyl-3-phenyl-3,4-dihydronaphthalene;
1-(Alanyl-alanyl)aminomethyl-5,6-bis(benzoyloxy)-3-phenyl-3,4-dihydronaphthalene;
[1R*,2S*,3S*]1-Aminomethyl-5,6-dihydroxy-2-(2-hydroxy-1-ethyl) -3-phenyl-1,2,3,4-tetrahydronaphthalene;
[1,3-cis]1-Aminomethyl-5,6-dihydroxy-3-(3-hydroxyphenyl)-1,2,3,4-tetrahydronaphthalene;
1-Aminomethyl-5,6-dihydroxy-3-phenylnaphthalene;
[1,3-cis]1-Aminomethyl-3-benzyloxymethyl-5,6-dihydroxy-3,4-dihydro-1H-2-benzopyran;
[1,3-cis]1-Aminomethyl-3,4-dihydro-5,6-dihydroxy-3-(diphenyl)methyl-1H-2-benzopyran;
[1,3-cis]1-Aminomethyl-3,4-dihydro-5,6-dihydroxy-3-(3'-methyl-2'-n-pentyl) -1H-2-bezopyran;
[1,3-cis]1-Aminomethyl-3,4-dihydro-5,6-dihydroxy-3-(1'-but-3'-ene)-1H-2-benzopyran;
[1,3-cis]1-Aminomethyl-3,4-dihydro-5,6-dihydroxy-3-(6'-methyl-2'-hept-5'-ene)-1H-2-benzopyran;
[1,3-cis]1-Aminomethyl-3-cyclooctyl-5,6-dihydroxy-3,4-dihydro-1H-2-benzopyran;
[1R*,8S *,9aR *]1-Amino-5,6-dihydroxy-2,3,7,8,9,9a-hexahydro-8-phenylphenalene;
[1S *,8S *,9aR *]1-Amino-5,6-dihydroxy-2,3,7,8,9,9a-hexahydro-8-phenylphenalene;
6,7-Dihydroxy-4-phenyl-2,3,4,5-tetrahydro-1H-benzo[e]isoindole;
[1R,3S]3-(1-Adamantyl)-1-aminomethyl-3,4-dihydro-5,6-dihydroxy-1H-2-benzopyran;
1-Aminomethyl-5,6-bis(benzoyloxy)-3-phenyl-3,4-dihydronaphthalene;
5-Aminomethyl-7-(2-naphthyl)-7,8-dihydronaphthalene-1,2-diol;
5-Aminomethyl-7-(1-naphthyl)-7,8-dihydronaphthalene-1,2-diol;
1-Aminomethyl-5,6-bis(butoxy)-3-phenyl-3,4-dihydronaphthalene;
1-Aminomethyl-5,6-bis(isobutoxy)-3-phenyl-3,4-dihydronaphthalene;
1-Aminomethyl-5,6-bis(methyl succinyloxy)-3-phenyl-3,4-dihydronaphthalene;
1-Acetylaminomethyl-5,6-bis(acetyloxy)-3-phenyl-3,4-dihydronaphthalene;
5-N-Acetylmethylaminomethyl-3-phenyl-7,8-dihydronaphthalene-1,2-diol;
1-Aminomethyl-5,6-bis(propionyloxy)-3-phenyl-3,4-dihydronaphthalene;
1-Aminomethyl-5,6-bis(phenylaminocarbonyloxy)-3-phenyl-3,4-dihydronaphthalene;
1-Aminomethyl-5,6-bis(methoxycarbonyloxy)-3-phenyl-3,4-dihydronaphthalene;
1-Aminomethyl-5,6-bis(isopropyl succinyloxy)-3-phenyl-3,4-dihydronaphthalene;
1-Aminomethyl-5,6-bis(dimethylaminocarbonyloxy)-3-phenyl-3,4-dihydronaphthalene;
1-Aminomethyl-5,6-bis(beta-alanoyloxy)-3-phenyl-3,4-dihydronaphthalene;
1-Aminomethyl-5,6-bis(ethoxycarbonyloxy)-3-phenyl-3,4-dihydronaphthalene;
1-Aminomethyl-5,6-bis(benzylaminocarbonyloxy)-3-phenyl-3,4-dihydronaphthalene;
1-Aminomethyl-5,6-bis(methylaminocarbonyloxy)-3-phenyl-3,4-dihydronaphthalene;
5,6-Bis(acetyloxy)-1-t-butyloxycarbonylaminomethyl-3-phenyl-3,4-dihydronaphthalene;
1-Aminomethyl-5,6-bis(p-methoxybenzoyloxy)-3-phenyl-3,4-dihydronaphthalene;
1-Aminomethyl-5,6-bis(methylaminocarbonyloxy)-3-phenyl-3,4-dihydronaphthalene;
[1,3-cis]1-Aminomethyl-5,6-dihydroxy-3-phenyl-3,4-dihydro-1H-2-benzothiopyran;
[1,3-cis]1-Aminomethyl-5,6-dihydroxy-3-(3-methoxyphenyl)-3,4-dihydro-1H-2-benzopyran;
[1,3-cis]5,6-Dihydroxy-1-methylaminomethyl-3-phenyl-3,4-dihydro-1H-2-benzothiopyran;
[1,3-cis]3-(1-Adamantyl)-5,6-dihydroxy-1-methylaminomethyl-3,4-dihydro-1H-2-benzopyran;
[1,3-trans]3-(1-Adamantyl)-1-aminomethyl-5,6-dihydroxy-3,4-dihydro-1H-2-benzopyran;
[1,3-trans]1-Aminomethyl-5,6-dihydroxy-3-(4-methoxybenzyl)-3,4-dihydro-1H-2-benzopyran;
[1,3-cis]5,6-Dihydroxy-3-(4-methoxybenzyl)-1-methylaminomethyl-3,4-dihydro-1H-2-benzopyran;
[1S,3S]3-(1-Adamantyl)-1-aminomethyl-5,6-dihydroxy-3,4-dihydro-1H-2-benzopyran;
[1R,3R]3-(1-Adamantyl)-1-aminomethyl-5,6-dihydroxy-3,4-dihydro-1H-2-benzopyran;
[1R,2'R,3S]5,6-Dihydroxy-3-phenyl-1-(2'-pyrrolidinyl)-3,4-dihydro-1H-2-benzopyran;
[1,3-cis]1-Aminomethyl-5,6-dihydroxy-3-(2-(1-oxoisoindole)methyl)-3,4-dihydro-1H-2-benzopyran;
[1R,2'S,3S]5,6-Dihydroxy-3-phenyl-1-(2'-pyrrolidinyl)-3,4-dihydro-1H-2-benzopyran;
[1,3-cis]5,6-Dihydroxy-1-methylaminomethyl-3-phenyl-3,4-dihydro-1H-2-benzopyran;
5-Phenyl-1,2,3,4,5,6,-hexahydrobenzo[h]isoquinoline-7,8-diol;
2-Methyl-5-phenyl-1,2,3,4,5,6,-hexahydrobenzo[h]isoquinoline-7,8-diol;
[1S,1R,3S]3,4-Dihydro-5,6-dihydroxy-1-methylaminomethyl-3-phenyl-1H-2-benzopyran;
[1,3-cis]1-Aminomethyl-3-cyclohexylmethyl-3,4-dihydro-5,6-dihydroxy-1H-2-benzopyran;
[1,3-cis]1-Aminomethyl-5,6-dihydroxy-3-isobutyl-3,4-dihydro-1H-2-benzopyran;
[1,3-cis]3-(1-Adamantylmethyl)-1-aminomethyl-5,6-dihydroxy-3,4-dihydro-1H-2-benzopyran;
[1,3-cis]3-(1-Adamantylmethyl)-5,6-dihydroxy-1-methylaminomethyl-3,4-dihydro-1H-2-benzopyran;
[1,3-cis]3-Cyclohexylmethyl-5,6-dihydroxy-1-methylaminomethyl-3,4-dihydro-1H-2-benzopyran;
[1,3-cis]1-Allylaminomethyl-3-n-butyl-5,6-dihydroxy-3,4-dihydro-1H-2-benzopyran;
[1,3-cis]1-Aminomethyl-3-(2-cyclohexylethyl)-5,6-dihydroxy-3,4-dihydro-1H-2-benzopyran;
[1,3-cis]1-Aminomethyl-5,6-dihydroxy-3-(ethylmalonamidomethyl)-3,4-dihydro-1H-2-benzopyran;
1'-Aminomethyl-5',6'-dihydroxyspiro[cycloheptane-1,3'-(3',4'-dihydro-1'H-2'-benzopyran)];
1'-Aminomethyl-5',6'-dihydroxyspiro[cyclooctane-1,3'-(3',4'-dihydro-1'H-2'-benzopyran)];
5',6'-Dihydroxy-1'-methylaminomethylspiro[cycloheptane-1,3'-(3',4'-dihydro-1'H-2'-benzopyran)];
[1,3-cis]3-(1-Adamantyl)-1-aminomethyl-8-bromo-5,6-dihydroxy-3,4-dihydro-1H-2-benzopyran;
5',6'-Dihydroxy-1'-methylaminomethylspiro[cyclooctane-1,3'-(3',4'-dihydro-1'H-2'-benzopyran)];

[1,3-cis]1-Allylaminomethyl-5,6-dihydroxy-3-phenyl-3,4-dihydro-1H-2-benzopyran; 1'-Aminomethyl-5',6'-dihydroxyspiro[tetrahydropyran-4,3'-(3',4'-dihydro-1'H-2'-benzopyran)];

5',6'-Dihydroxy-1'-methylaminomethylspiro[tetrahydropyran-4,3'-(3',4'-dihydro-1'H-2'-benzopyran)];

[1R,3S]3-t-Butyl-5,6-dihydroxy-1-methylaminomethyl-3,4-dihydro-1H-2-benzopyran;

[1,3-trans]1-Aminomethyl-5,6-dihydroxy-3-phenyl-3,4-dihydro-1H-2-benzopyran;

[1S,3R]5,6-dihydroxy-3-phenyl-1-(2(R)-pyrrolidinyl)-3,4-dihydro-1H-2-benzopyran;

[1,3-cis]3-(1-Adamantyl)-1-aminomethyl-5,6-dihydroxy-7-fluoro-3,4-dihydro-1H-2-benzopyran;

[1,3-cis]1-Aminomethyl-5,6-dihydroxy-3-(4-ethoxy-2,3,5,6-tetrafluorophenylmethyl)-3,4-dihydro-1H-2-benzopyran;

5'-Aminomethylspiro[cyclohexane-1,7'-(7',8'-dihydronaphthalene)]-1',2'-diol;

[1,3-cis]1-Aminomethyl-5,6-dihydroxy-3-(4-trifluoromethylphenyl)-3,4-dihydro-1H-2-benzopyran;

[1,3-cis]1-Aminomethyl-5,6-dihydroxy-3-(3-trifluoromethylphenyl)-3,4-dihydro-1H-2-benzopyran;

5'-Aminomethylspiro[cyclohexane-1,7'-(5',6',7',8'-tetrahydronaphthalene)]-1',2'-diol;

[1R,3S]1-Aminomethyl-3-t-butyl-5,6-dihydroxy-3,4-dihydro-1H-2-benzopyran;

[1,3-cis]3-Allyl-1-aminomethyl-5,6-dihydroxy-3,4-dihydro-1H-2-benzopyran;

2'-Methylspiro[cyclohexane-1.5'-(1',2',3',4',5',6'-hexahydrobenzo[h]isoquinoline)]-7',8'-diol;

Spiro[cyclohexane-1,5'-(1',2',3',4',5',6'-hexahydro-benzo[h]isoquinoline)]-7',8'-diol;

[1R,3S]3-t-Butyl-5,6-dihydroxy-1-dimethylaminomethyl-3,4-dihydro-1H-2-benzopyran;

[1,3-cis]5,6-Dihydroxy-1-methylaminomethyl-3-n-pentyl-3,4-dihydro-1H-2-benzopyran;

(5R)-5-Phenyl-1,2,3,4,5,6,-hexahydrobenzo[h]isoquinoline-7,8-diol;

Spiro[cyclopentane-1,5'-(1',2',3',4',5',6'-hexahydro-benzo[h]isoquinoline)]-7',8'-diol;

2'-Methylspiro[cyclopentane-1,5'-(1',2',3',4',5',6'-hexahydrobenzo[h]isoquinoline)]-7',8'-diol;

5'-Aminomethylspiro[cyclopentane-1,7'-(5,6,7',8'-tetrahydro-naphthalene)]-1',2'-diol;

[1R,3S]3-(1-Adamantyl)-1-aminomethyl-5,6-dihydroxy-7-fluoro-3,4-dihydro-1H-2-benzopyran;

[1R,3S]3-(1-Adamantyl)-5,6-dihydroxy-7-fluoro-1-methylaminomethyl-3,4-dihydro-1H-2-benzopyran;

[1R,3S]3-t-Butyl-5,6-dihydroxy-1-ethylaminomethyl-3,4-dihydro-1H-2-benzopyran;

[1R,3S]1-Allylaminomethyl-3-t-butyl-5,6-dihydroxy-3,4-dihydro-1H-2-benzopyran;

[1,3-cis]3-t-Butylmethyl-5,6-dihydroxy-1-methylaminomethyl-3,4-dihydro-1H-2-benzopyran;

5'-Aminomethylspiro[cycloheptane-1,7'-(5',6',7',8'-tetrahydronaphthalene)]-1',2'-diol;

5-Aminomethylspiro[cycloheptane-1,7'-(7',8'-dihydronaphthalene)]-1',2'-diol;

Spiro[cycloheptane-1,5'-(1',2',3',4',5',6'-hexahydrobenzo[h]isoquinoline)]-7',8'-diol;

[1R,3S]1-Allylaminomethyl-5,6-dihydroxy-3-phenyl-3,4-dihydro-1H-2-benzopyran;

[1,3-cis]1-Aminomethyl-3-t-butylmethyl-5,6-dihydroxy-3,4-dihydro-1H-2-benzopyran;

[1,3-cis]1-Aminomethyl-5,6-dihydroxy-3-(3R-but-1-enyl))-3,4-dihydro-1H-2-benzopyran;

5-Aminomethyl-7-t-butyl-7,8-dihydronaphthalene-1,2-diol;

[5,7-cis]-5-Aminomethyl-7-t-butyl-5,6,7,8-tetrahydronaphthalene-1,2-diol;

[1R,3S]3-t-Butyl-5,6-dihydroxy-1-n-propylaminomethyl-3,4-dihydro-1H-2-benzopyran;

5-t-Butyl-1,2,3,4,5,6,-hexahydrobenzo[h]isoquinoline-7,8-diol;

5-Cyclohexyl-1,2,3,4,5,6,-hexahydrobenzo[h]isoquinoline-7,8-diol;

5-Cyclopentylmethyl-1,2,3,4,5,6,-hexahydrobenzo[h]isoquinoline-7,8-diol;

[1R,3S]3-(1-Adamantyl)-5,6-dihydroxy-1-dimethylaminomethyl-3,4-dihydro-1H-2-benzopyran;

Spiro[cyclooctane-1,5'-(1',2',3',4',5',6'-hexahydrobenzo[h]isoquinoline)]-7',8'-diol;

[1R,3R]1-Aminomethyl-3-(2,2-dimethylpropyl)-3,4-dihydro-5,6-dihydroxy-1H-2-benzopyran;

[1,3-cis]1-Aminomethyl-3-cyclopentylmethyl-3,4-dihydro-5,6-dihydroxy-1H-2-benzopyran;

[1R,3R]1-Aminomethyl-3-(2-methylpropyl)-3,4-dihydro-5,6-dihydroxy-1H-2-benzopyran;

[1R,3R]1-Methylaminomethyl-3-(2,2-dimethylpropyl)-3,4-dihydro-5,6-dihydroxy-1H-2-benzopyran;

[1,3-cis]1-Methylaminomethyl-3-cyclopentylmethyl-3,4-dihydro-5,6-dihydroxy-1H-2-benzopyran;

[1R,3R]1-Methylaminomethyl-3-(2-methylpropyl)-3,4-dihydro-5,6-dihydroxy-1H-2-benzopyran;

[1,3-cis]1-(N,N-Dimethylamino)methyl-3-(2,2-dimethylpropyl)-3,4-dihydro-5,6-dihydroxy-1H-2-benzopyran;

1'-Aminomethyl-3',4'-dihydro-5',6'-dihydroxyspiro[cyclononane-1,3'-(1'H-2'-benzopyran)];

[1,3-cis]1-Aminomethyl-3-(1-methylcyclohexyl)-3,4-dihydro-5,6-dihydroxy-1H-2-benzopyran;

[1,3-cis]1-Aminomethyl-3-(1-phenylcyclohexyl)-3,4-dihydro-5,6-dihydroxy-1H-2-benzopyran;

3',4'-Dihydro-5',6'-dihydroxy-1'-methylaminomethylspiro[cyclononane-1,3'-(1'H-2'-benzopyran)];

[1,3-cis]1-(N,N-Dimethylamino)methyl-3-(1-phenylcyclohexyl)-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

1R,2S-1-(N,N-Dimethylamino)methyl-3-phenyl-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

[1,3-cis]1-(N,N-Dimethylamino)methyl-3-cyclohexyl-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

1-Aminomethyl-3-adamantyl-5,6-dihydroxy-3,4-dihydronaphthalene;

1'-Aminomethyl-3',4'-dihydro-5',6'-dihydroxyspiro[cyclononane-1,3'-naphthalene];

1-Aminomethyl-3-(2,2-dimethylpropyl)-5,6-dihydroxy-3,4-dihydronaphthalene;

1'-Aminomethyl-3',4'-dihydro-5',6'-dihydroxyspiro[cyclodecane-1,3'-naphthalene];

1-Aminomethyl-3-adamantyl-5,6-dihydroxy-1,2,3,4-tetrahydronaphthalene;

1'-Aminomethyl-1',2',3',4'-tetrahydro-5',6'-dihydroxyspiro[cyclononane-1,3'-naphthalene];

1'-Aminomethyl-1',2',3',4'-tetrahydro-5',6'-dihydroxyspiro[cyclodecane-1,3'-naphthalene];

5-Adamantyl-1,2,3,4,5,6-hexahydrobenzo[h]isoquinoline-7,8-diol;

(5R)-1,2,3,4,5,6-Hexahydro-5-phenylbenzo[h]isoquinoline-7,8-diol;

1',2',3',4',5',6'-Hexahydro-7',8'-dihydroxyspiro[cyclodecane-1,5'-benzo[h]-isoquinoline];

1',2',3',4',5',6'-Hexahydro-7',8'-dihydroxyspiro[cyclononane-1,5'-benzo[h]-isoquinoline];

5-(2,2-Dimethylpropyl)-1,2,3,4,5,6-hexahydrobenzo[h]isoquinoline-7,8-diol;

5-Butyl-1,2,3,4,5,6-hexahydrobenzo[h]isoquinoline-7,8-diol;

5-(2,2-Dimethylpropyl)-1,2,3,4,5,6-hexahydro-2-methylbenzo[h]isoquinoline-7,8-diol;

5-(Cyclopentylmethyl)-1,2,3,4,5,6-hexahydro-2-methylbenzo[h]isoquinoline-7,8-diol;

(5R)-1,2,3,4,5,6-hexahydro-2-methyl-5-phenylbenzo[h]isoquinoline-7,8-diol;

(5S)-1,2,3,4,5,6-hexahydro-2-methyl-5-phenylbenzo[h]isoquinoline-7,8-diol;

1',2',3',4',5',6'-Hexahydro-7',8'-dihydroxy-2'-methylspiro[cyclononane-1,5'-benzo[h]isoquinoline];

1',2',3',4',5',6'-Hexahydro-7',8'-dihydroxy-2'-methylspiro[cycloheptane-1,5'-benzo[h]isoquinoline];

1',2',3',4',5',6'-Hexahydro-7',8'-dihydroxy-2'-methylspiro[cyclooctane-1,5'-benzo[h]isoquinoline];

2-Ethyl-1',2',3',4',5',6'-hexahydro-7',8'-dihydroxy-spiro[cycloheptane-1,5'-benzo[h]isoquinoline]; and 1',2',3',4',5a',6',8a'-Octahydro-7',8'-dihydroxy-2'-methylspiro[cycloheptane-1,5'-benzo[h]isoquinoline];

and pharmaceutically acceptable salts thereof.

The following compounds are representative of the preferred compounds of the invention:

[1,3-cis]1-Aminomethyl-3-n-butyl-5,6-dihydroxy-3,4-dihydro-1H-2-benzopyran;

[1,3-cis]1-Aminomethyl-3-cyclopentylmethyl-5,6-dihydroxy-3,4-dihydro-1H-2-benzopyran;

[1,3-cis]1-Aminomethyl-3-cyclooctyl-5,6-dihydroxy-3,4-dihydro-1H-2-benzopyran;

[1,3-cis]3-n-Butyl-5,6-dihydroxy-1-methylaminomethyl-3,4-dihydro-1H-2-benzopyran;

[1,3-cis]3-(1-Adamantyl)-5,6-dihydroxy-1-methylaminomethyl-3,4-dihydro-1H-2-benzopyran;

[1,3-cis]5,6-Dihydroxy-3-phenyl-1-(2'R*-pyrrolidinyl)-1,2,3,4-tetrahydro-naphthalene;

[1,3-trans]5,6-Dihydroxy-3-phenyl-1-(2'R*-pyrrolidinyl)-1,2,3,4-tetrahydronaphthalene;

[1,3-cis]5,6-Dihydroxy-1-methylaminomethyl-3-phenyl-1,2,3,4-tetrahydronaphthalene;

[1,3-cis]1-Aminomethyl-5,6-dihydroxy-3-(3-hydroxyphenyl)-1,2,3,4-tetrahydro-naphthalene;

1-Aminomethyl-5,6-dihydroxy-3-phenylnaphthalene;

[1,3-cis]1-Aminomethyl-3-benzyloxymethyl-5,6-dihydroxy-3,4-dihydro-1H-2-benzopyran;

[1R*,8S*,9aR*]1-Amino-5,6-dihydroxy-2,3,7,8,9,9a-hexahydro-8-phenylphenalene;

[1S*,8S*,9aR*]1-Amino-5,6-dihydroxy-2,3,7,8,9,9a-hexahydro-8-phenylphenalene;

6,7-Dihydroxy-4-phenyl-2,3,4,5-tetrahydro-1H-benzo[e]isoindole;

[1R,3S]3-(1-Adamantyl)-1-aminomethyl-3,4-dihydro-5,6-dihydroxy-1H-2-benzopyran;

1-Aminomethyl-5,6-bis(benzoyloxy)-3-phenyl-3,4-dihydronaphthalene;

Spiro[cyclopentane-1,5'-(1',2',3',4',5',6',-hexahydrobenzo[h]isoquinoline)]-7',8'-diol;

Spiro[cyclohexane-1,5'-(1',2',3',4',5',6',-hexahydrobenzo[h]isoquinoline)]-7',8'-diol;

Spiro[cycloheptane-1,5'-(1',2',3',4',5',6',-hexahydro-benzo[h]isoquinoline)]-7',8'-diol;

Spiro[cyclooctane-1,5'-(1',2',3',4',5',6',-hexahydro-benzo[h]isoquinoline)]-7',8'-diol;

5-Phenyl-1,2,3,4,5,6,-hexahydrobenzo[h]isoquinoline-7,8-diol;

2-Methyl-5-phenyl-1,2,3,4,5,6,-hexahydrobenzo[h]isoquinoline-7,8-diol;

Spiro[cyclooctane-1,5'-(1',2',3',4',5',6',-hexahydro-benzo[h]isoquinoline)]-7',8'-diol;

5-Cyclohexyl-1,2,3,4,5,6,-hexahydrobenzo[h]isoquinoline-7,8-diol;

5-Cyclopentylmethyl-1,2,3,4,5,6,-hexahydrobenzo[h]isoquinoline-7,8-diol;

[1,3-cis]1-Aminomethyl-5,6-dihydroxy-3-(3-methoxyphenyl)-3,4-dihydro-1H-2-benzopyran;

[1,3-cis]3-(1-Adamantyl)-5,6-dihydroxy-1-methylaminomethyl-3,4-dihydro-1H-2-benzopyran;

[1R,3S]5,6-Dihydroxy-1-methylaminomethyl-3-phenyl-3,4-dihydro-1H-2-benzopyran;

[1,3-cis]1-Aminomethyl-3-cyclohexylmethyl-5,6-dihydroxy-3,4-dihydro-1H-2-benzopyran;

[1,3-cis]1-Aminomethyl-5,6-dihydroxy-3-isobutyl-3,4-dihydro-1H-2-benzopyran;

[1,3-cis]3-(1-Adamantylmethyl)-1-aminomethyl-5,6-dihydroxy-3,4-dihydro-1H-2-benzopyran;

[1,3-cis]3-(1-Adamantylmethyl)-5,6-dihydroxy-1-methylaminomethyl-3,4-dihydro-1H-2-benzopyran;

[1,3-cis]3-Cyclohexylmethyl-5,6-dihydroxy-1-methylaminomethyl-3,4-dihydro-1H-2-benzopyran;

1'-Aminomethyl-5',6'-dihydroxyspiro[cycloheptane-1,3'-(3',4'-dihydro-1'H-2'-benzopyran)];

1'-Aminomethyl-5',6'-dihydroxyspiro[cyclooctane-1,3'-(3',4'-dihydro-1'H-2'-benzopyran)];

5',6'-Dihydroxy-1'-methylaminomethylspiro[cycloheptane-1,3'-(3',4'-dihydro-1'H-2'-benzopyran)];

5',6'-Dihydroxy-1'0-methylaminomethylspiro[cyclooctane-1,3'-(3',4'-dihydro-1'H-2'benzopyran)];

[1,3-cis]1-Allylaminomethyl-5,6-dihydroxy-3-phenyl-3,4-dihydro-1H-2-benzopyran;

[1R,3S]3-t-Butyl-5,6-dihydroxy-1-methylaminomethyl-3,4-dihydro-1H-2-benzopyran;

[1,3-trans]1-Aminomethyl-5,6-dihydroxy-3-phenyl-3,4-dihydro-1H-2-benzopyran;

[1,3-cis]1-Aminomethyl-5,6-dihydroxy-3-(4-ethoxy-2,3,5,6-tetrafluorophenylmethyl)-3,4-dihydro-1H-2-benzopyran;

[1,3-cis]1-Aminomethyl-5,6-dihydroxy-3-(4-trifluoromethylphenyl)-3,4-dihydro-1H-2-benzopyran;

[1,3-cis]1-Aminomethyl-5,6-dihydroxy-3-(3-trifluoromethylphenyl)-3,4-dihydro-1H-2-benzopyran;

[1,3-cis]3-Allyl-1-aminomethyl-5,6-dihydroxy-3,4-dihydro-1H-2-benzopyran;

[1R,3S]3-t-Butyl-5,6-dihydroxy-1-dimethylaminomethyl-3,4-dihydro-1H-2-benzopyran;

[1,3-cis]5,6-Dihydroxy-1-methylaminomethyl-3-n-pentyl-3,4-dihydro-1H-2-benzopyran;

[1R,3S]1-Aminomethyl-3-t-butyl-5,6-dihydroxy-3,4-dihydro-1H-2-benzopyran;

[1R,3S]3-(1-Adamantyl)-1-aminomethyl-5,6-dihydroxy-7-fluoro-1H-2-benzopyran;

[1R,3S]3-(1-Adamantyl)-5,6-dihydroxy-7-fluoro-1-methylaminomethyl-3,4-dihydro-1H-2-benzopyran;

[1,3-cis]3-t-Butyl-5,6-dihydroxy-1-ethylaminomethyl-3,4-dihydro-1H-2-benzopyran;

[1,3-cis]3-t-Butylmethyl-5,6-dihydroxy-1-methylaminomethyl-3,4-dihydro-1H-2-benzopyran;

[1,3-cis]1-Allylaminomethyl-5,6-dihydroxy-3-phenyl-3,4-dihydro-1H-2-benzopyran;

[1,3-cis]1-Aminomethyl-3-t-butylmethyl-5,6-dihydroxy-3,4-dihydro-1H-2-benzopyran;

[1,3-cis]1-aminomethyl-5,6-dihydroxy-3-(3R-but-1-enyl))-3,4-dihydro-1H-2-benzopyran;

[1R,3S]3-(1-Adamantyl)-5,6-dihydroxy-1-dimethylaminomethyl-3,4-dihydro-1H-2-benzopyran;

[1R,3R]1-Aminomethyl-3-(2,2-dimethylpropyl)-3,4-dihydro-5,6-dihydroxy-1H-2-benzopyran;

[1,3-cis]1-Aminomethyl-3-cyclopentylmethyl-3,4-dihydro-5,6-dihydroxy-1H-2-benzopyran;

[1R,3R]1-Aminomethyl-3-(2-methylpropyl)-3,4-dihydro-5,6-dihydroxy-1H-2-benzopyran;

[1R,3R]1-Methylaminomethyl-3-(2,2-dimethylpropyl)-3,4-dihydro-5,6-dihydroxy-1H-2-benzopyran;

[1,3-cis]1-Methylaminomethyl-3-cyclopentylmethyl-3,4-dihydro-5,6-dihydroxy-1H-2-benzopyran;

[1R,3R]1-Methylaminomethyl-3-(2-methylpropyl)-3,4-dihydro-5,6-dihydroxy-1H-2-benzopyran;

[1,3-cis]1-(N,N-dimethylamino)methyl-3-(2,2-dimethylpropyl)-3,4-dihydro-5,6-dihydroxy-1H-2-benzopyran;

1'-Aminomethyl-3',4'-dihydro-5',6'-dihydroxyspiro[cyclononane-1,3'-(1'H-2'-benzopyran)];

[1,3-cis]1-Aminomethyl-3-(1-methylcyclohexyl)-3,4-dihydro-5,6-dihydroxy-1H-2-benzopyran;

[1,3-cis]1-Aminomethyl-3-(1-phenylcyclohexyl)-3,4-dihydro-5,6-dihydroxy-1H-2-benzopyran;

1'-Methylaminomethyl-3',4'-dihydro-5',6'-dihydroxyspiro[cyclononane-1,3'-(1'H-2-benzopyran)];

[1,3-cis]1-(N,N-Dimethylamino)methyl-3-(1-phenylcyclohexyl)-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

1R,2S-1-(N,N-Dimethylamino)methyl-3-phenyl-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

[1,3-cis]1-(N,N-Dimethylamino)methyl-3-cyclohexyl-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

(5R)-1,2,3,4,5,6-hexahydro-5-phenylbenzo[h]isoquinoline-7,8-diol;

5-Butyl-1,2,3,4,5,6-hexahydrobenzo[h]isoquinoline-7,8-diol;

(5R)-1,2,3,4,5,6-hexahydro-2-methyl-5-phenylbenzo[h]isoquinoline-7,8-diol;

(5S)-1,2,3,4,5,6-hexahydro-2-methyl-5-phenylbenzo[h]isoquinoline-7,8-diol;

1',2',3',4',5',6'-Hexahydro-7',8'-dihydroxy-2'-methylspiro[cycloheptane-1,5'-benzo[h]isoquinoline]; and 1',2',3',4',5',6'-Hexahydro-7',8'-dihydroxy-2'-methylspiro[cyclooctane-1,5'-benzo[h]isoquinoline];

and pharmaceutically acceptable salts thereof.

The following compounds are representative of the more preferred compounds of the invention:

[1R,3S]3-(1-Adamantyl)-1-aminomethyl-5,6-dihydroxy-7-fluoro-3,4-dihydro-1H-2-benzopyran;

2-Methyl-5-phenyl-1,2,3,4,5,6,-hexahydrobenzo[h]isoquinoline-7,8-diol;

(5R)-1,2,3,4,5,6-hexahydro-2-methyl-5-phenylbenzo[h]isoquinoline-7,8-diol;

(5S)-1,2,3,4,5,6-hexahydro-2-methyl-5-phenylbenzo[h]isoquinoline-7,8-diol;

1',2',3',4',5',6'-Hexahydro-7',8'-dihydroxy-2'-methylspiro[cycloheptane-1,5'-benzo[h]isoquinoline ];

[1R,3R]1-Aminomethyl-3-(2,2-dimethylpropyl)-3,4-dihydro-5,6-dihydroxy-1H-2-benzopyran;

[1R,3R]1-Aminomethyl-3-(2-methylpropyl)-3,4-dihydro-5,6-dihydroxy-1H-2-benzopyran;

[1R,3R]1-Methylaminomethyl-3-(2,2-dimethylpropyl)-3,4-dihydro-5,6-dihydroxy-1H-2-benzopyran;

[1R,3R]1-Methylaminomethyl-3-(2-methylpropyl)-3,4-dihydro-5,6-dihydroxy-1H-2-benzopyran;

[1,3-cis]1-(N,N-Dimethylamino)methyl-3-(1-methylcyclohexyl)-3,4-dihydro-5,6-dihydroxy-1H-2-benzopyran;

1R,3S-1-(N,N-Dimethylamino)methyl-3-phenyl-3,4-dihydro-5,6-dihydroxy-1H-2-benzopyran; and

[1,3-cis]1-(N,N-Dimethylamino)methyl-3-cyclohexyl-3,4-dihydro-5,6-dihydroxy-1H-2-benzopyran;

and pharmaceutically acceptable salts thereof.

In another aspect of the present invention are disclosed synthetic intermediates which are useful in the preparation of the compounds of formula I. Such intermediate compounds have the formula Ia:

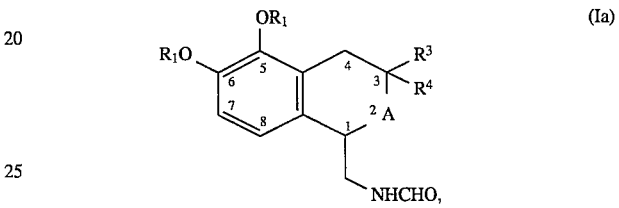

(Ia)

where A is —O— or —S—;

$R^1$ is a catechol-protecting group;

$R^3$ is selected from $C_4$–$C_{10}$-alkyl, substituted $C_1$–$C_5$-alkyl, $C_2$–$C_{12}$-alkenyl, $C_2$–$C_{12}$-alkynyl, cyclo-$C_3$–$C_{10}$-alkyl, carbocyclic-$C_6$–$C_{10}$-aryl, carbocyclic$C_6$–$C_{10}$-aryl-$C_1$–$C_5$-alkyl, and Het; and $R^4$ is selected from hydrogen and $C_1$–$C_{10}$-alkyl;

or, taken together, $R^3$ and $R^4$ and the carbon atom to which both are attached form a spiro-$C_3$–$C_{10}$-cycloalkyl ring.

In a further aspect of the present invention is disclosed a novel process for preparing the compounds of formula Ia, comprising reacting an intermediate having the formula:

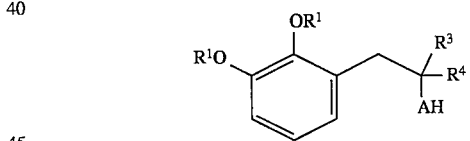

where A, $R^1$, $R^3$, and $R^4$ are as described above in connection with formula Ia, with N-formylaminoacetaldehyde dimethyl acetal in the presence of an acid catalyst selected from boron trifluoride etherate, zinc triflate, trimethylsilyl triflate and methanesulfonic acid.

In yet another aspect of the present invention are disclosed chiral intermediate compounds useful in the preparation of the compounds of formula I. Such chiral compounds have the formula Ib:

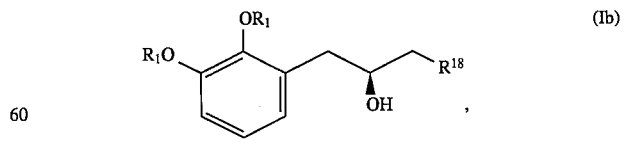

(Ib)

where $R^1$ is a catechol-protecting group and $R^{18}$ is substituted $C_3$–$C_9$-alkyl.

In still another aspect of the present invention is disclosed a novel process for preparing the chiral compounds of formula Ib, comprising the steps of (a) reacting an intermediate having the formula:

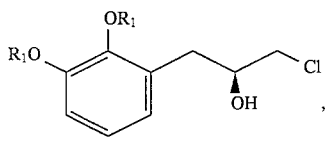

where R¹ is a catechol-protecting group, with a strong base to form a chiral epoxide of the formula:

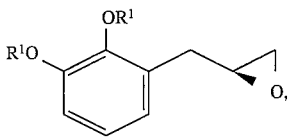

and (b) reacting the epoxide with an organometallic substituted $C_3$–$C_9$-alkyl compound in a non-polar organic solvent to give a compound of formula 1b.

Certain compounds of this invention may possess one or more asymmetric centers and may exist in optically active forms. Additional asymmetric centers may be present in a substituent group, such as an alkyl group. Pure d-isomers and pure l-isomers, racemic mixtures of the isomers, and mixtures thereof are intended to be within the scope of this invention. In particular, the stereochemistry at the 1- and 3-positions, as shown in formula I, may independently be either [R] or [S] unless specifically noted otherwise. Chiral forms of certain compounds of this invention are contemplated and are specifically included within the scope of this invention.

The term "alkanoyl", as used herein, means a carbonyl group linked to an alkyl group, as defined below, of the size indicated.

The term "alkanoylamino" means an alkanoyl group, as defined above, of the size indicated, connected to an amino group.

The term "alkenyl" means straight or branched carbon chain radicals of the size indicated containing at least one carbon-to-carbon double bond. Representative of such radicals are ethenyl, n-propenyl, isopropenyl, n-butenyl, isobutenyl, 2-ethylhexenyl, n-octenyl, 2,4-dimethylpentenyl, and the like.

The term "alkoxy" means an oxygen atom linked by an ether bond to an alkyl group, as defined below, of the size indicated. Examples of alkoxy groups are methoxy, ethoxy, t-butoxy, and the like.

The term "alkyl" means a straight- or branched-chain carbon radical of the size indicated. Representative of alkyl radicals are methyl, ethyl, n-propyl, isopropyl, n-butyl, sec-butyl, isobutyl, t-butyl, 2-ethylhexyl, n-octyl, 2,4-dimethylpentyl, and the like.

The term "alkylamino" means an alkyl group, as defined above, of the size indicated, attached to an amino group. This definition includes the dialkylamino group. Examples include methylamino, ethylamino, dimethylamino, and the like.

The term "alkynyl" is used herein to mean straight or branched carbon chain radicals of the size indicated containing at least one carbon-to-carbon triple bond. Representative of such radicals are ethynyl, n-propynyl, butynyl, 3-ethylhexynyl, n-octynyl, 4-methylpentynyl, and the like.

The terms "amino acid" and "dipeptide", as used herein, refer, respectively, to a single α-amino acid or two alpha-amino acids joined by an amide (peptide) bond. The amino acids may be any of the naturally-occurring amino acids such as, for example, valine, glycine, norvaline, alanine, glutamic acid, glutamine, aspartic acid, leucine, isoleucine, proline, methionine, phenylalanine, or the like, or they may be synthetic amino acids such as cyclohexylalanine, for example. The amino acids may be in the L or D configuration or may be represented by a mixture of the two isomers. If not specified, amino acid substituents are optically active and have the L configuration.

The term "carbocyclic-$C_6$–$C_{10}$-aryl" as used herein refers to aromatic radicals having six to ten carbon atoms in a single or fused ring system. Representative examples include phenyl, 1-naphthyl, 2-naphthyl, and the like.

The term "carbocyclic $C_6$–$C_{10}$-aryloxy" means an oxygen atom linked by an ether bond to a carbocyclic-$C_6$–$C_{10}$-aryl group, as defined above, and exemplified by phenoxy, benzyloxy, and the like.

The term "carbocyclic $C_6$–$C_{10}$-aryloxyalkyl" means a carbocyclic $C_6$–$C_{10}$-aryloxy group, as defined above, attached to an alkyl group, as defined above.

The term "carbocyclic arylalkyl" means an alkyl group, as defined above, of the size indicated substituted with a carbocyclic-$C_6$–$C_{10}$-aryl group, as defined above. Representative examples of carbocyclic-$C_6$–$C_{10}$-arylalkyl groups are benzyl and phenylethyl groups.

The term "catechol-protecting groups" as used herein refers to groups used to derivatize catechol hydroxyl oxygen atoms in order to prevent undesired reactions or degradation during a synthesis. The term "protecting group" is well known in the art and refers to substituents on functional groups of compounds undergoing chemical transformation which prevent undesired reactions and degradations during a synthesis; see, for example, T. H. Greene, *Protective Groups in Organic Synthesis*. John Wiley & Sons, New York (1981). These derivatizing groups may be selected from phenol-protecting groups or they may be selected from those groups which are particularly suitable for the protection of catechols because of the proximity of the two hydroxyl functions on the catechol ring. Commonly used catechol-protecting groups include dimethyl ethers, dibenzyl ethers, cyclohexylidene ketals, methylene acetals, acetonide derivatives, diphenylmethylene ketals, cyclic borate esters, cyclic carbonate esters, cyclic carbamates and the like.

The term "cycloalkyl" as used herein refers to a $C_3$-and-up monocyclic, $C_4$-and-up bicyclic or $C_5$-and-up tricyclic cyclic group, of the size indicated, that are fully saturated or partially unsaturated, such as cyclopropane, cyclobutane, cyclopentane, cyclohexane, cyclohexene, cycloheptane, cycloheptene, cyclooctane, cyclooctene, cycloctadiene, bicycloheptane, bicyclooctane, adamantane, norbornane, norbornene, camphene, pinene, and the like.

The term "cycloalkyl-alkyl" means a cycloalkyl group of the size indicated attached to an alkyl of the size indicated, for example cyclo-$C_3$–$C_8$-alkyl-$C_1$–$C_{10}$-alkyl.

The term "fused" is used herein to mean two cyclic groups having at least two atoms in common to both rings.

The term "haloalkyl" refers to a alkyl group of the size indicated, as defined below, bearing at least one halogen substituent, for example chloroethyl and trifluoromethyl.

The terms "halo" or "halogen" refer to bromo, chloro, fluoro and iodo.

The term "Het" refers to a three- to twelve-atom monocyclic or four- to twelve-atom bicyclic ring containing one-to-three heteroatoms independently selected from N, O and S, with the remaining atoms being carbon. In the 3- or 4-membered rings, there may be only one hetero-atom, selected from N, O, and S. In the 5- or 6-membered tings there may be from 1 to 3 nitrogen atoms, one N and one S, or one N and one O. Examples of Het include furan, tetrahydrofuran, thiophene, pyrrolidine, pyridine, piperidine, isoxazole, indole, quinoline, isoquinoline, tetrahydroisoquinoline, benzofuran and the like.

The term "Het-alkyl" means a Het, as defined above, attached to an alkyl of the size indicated, for example, Het-$C_1$-$C_5$-alkyl.

The term "readily-cleavable group" is used herein to mean substituents which are rapidly cleaved in vivo, for example, by hydrolysis in blood, to yield the parent compounds of formula I. Readily-cleavable groups include those substituents commonly referred to as "prodrug moieties". T. Higuchi and V. Stella provide a thorough discussion of the prodrug concept in *Pro-drugs as Novel Delivery Systems*, Vol 14 of the A.C.S. Symposium Series, American Chemical Society (1975). Examples of readily-cleavable groups include acetyl, trimethylacetyl, butanoyl, methyl succinoyl, t-butyl succinoyl, ethoxycarbonyl, methoxycarbonyl, benzoyl, 3-aminocyclohexylidenyl, and the like.

The term "spirocycloalkyl" means a cycloalkyl ring, as defined above, of the size indicated bonded to another ring in such a way that a single carbon atom is common to both rings.

The term "substituted alkenyl" means an alkenyl group, as defined above, mono-substituted with cyclo-$C_3$-$C_8$-alkyl, carbocyclic $C_6$-$C_{10}$-aryl, amino, hydroxy, $C_1$-$C_4$-alkoxy or with a pyrrolidine, piperidine, pyridine, quinoline, isoquinoline, thiophene or isoxazole heterocycle.

The term "substituted alkoxy" means an oxygen atom linked by an ether bond to a substituted alkyl group, as defined below, of the size indicated.

The term "substituted alkyl", as used herein, refers to an alkyl group, as defined above, of the size indicated, that may be mono- or independently di-substituted with a group selected from selected from halogen, hydroxy, $C_1$-$C_4$-alkoxy, amino, $C_1$-$C_4$-alkyl amino, $C_3$-$C_8$-cycloalkyl and $C_1$-$C_4$-alkanoylamino.

The term "substituted alkylamino" means a substituted alkyl group, as defined above, of the size indicated, attached to an amine group.

The term "substituted alkynyl" means an alkynyl group mono-substituted with cyclo-$C_3$-$C_8$-alkyl, carbocyclic $C_6$-$C_{10}$-aryl, or with a Het as defined below.

The term "substituted carbocyclic-$C_6$-$C_{10}$-aryl" means a carbocyclic-$C_6$-$C_{10}$-aryl group, as defined above, substituted with 1-to-5 non-hydrogen substituents, for example, halogen, hydroxy, $C_1$-$C_4$-alkyl, $C_1$-$C_4$-alkoxy, or one phenyl group or one trifluoromethyl group in conjunction with 0-to-4 of the said non-hydrogen substituents.

The term "substituted carbocyclic-$C_6$-$C_{10}$-arylalkyl" means a substituted carbocyclic-$C_6$-$C_{10}$-aryl, as defined above, attached to an alkyl group, as defined above, of the size indicated.

The term "substituted carbocyclic-$C_6$-$C_{10}$-aryloxy" means an oxygen atom linked by an ether bond to a substituted carbocyclic $C_6$-$C_{10}$-aryl group, as defined above.

The term "substituted carbocyclic $C_6$-$C_{10}$-aryloxyalkyl" means a substituted carbocyclic $C_6$-$C_{10}$-aryloxy group, as defined above, attached to an alkyl group, as defined above.

The term "substituted cycloalkyl" means a cycloalkyl group, as defined above, of the size indicated, that may be mono- or di-substituted with a group selected from halogen, hydroxy, $C_1$-$C_4$-alkoxy, amino, $C_1$-$C_4$-alkyl amino, and $C_1$-$C_4$-alkanoylamino.

The term "substituted Het" refers to a Het, as defined above, that may possess 1 to 3 substituents selected from halogen, hydroxy, $C_1$-$C_4$-alkoxy, amino, $C_1$-$C_4$-alkyl amino, and $C_1$-$C_4$-alkanoylamino.

The term "substituted Het-alkyl" means a Het-alkyl group, as defined above, that may possess 1 to 3 substituents selected from halogen, hydroxy, $C_1$-$C_{10}$-alkoxy, amino, $C_1$-$C_4$-alkyl amino, and $C_1$-$C_4$-alkanoylamino.

The term "administration" of the dopaminergic agent or composition, as used herein, refers to systemic use as when taken orally, parenterally, by inhalation spray, by nasal, rectal or buccal routes, or topically in dosage form unit formulations containing conventional nontoxic pharmaceutically acceptable carriers, adjuvants and vehicles as desired.

The term "parenteral" as used herein includes intravenous, intramuscular, intraperitoneal, intrasternal, subcutaneous and intraarticular injection and infusion techniques.

By "pharmaceutically acceptable" it is meant those salts, amides and esters which are, within the scope of sound medical judgement, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders. Pharmaceutically acceptable salts are well known in the art. For example, S. M Berge, et al. describe pharmaceutically acceptable salts in detail in *J. Pharmaceutical Sciences*, 66:1–19 (1977). The salts can be prepared in situ during the final isolation and purification of the compounds of formula I, or separately by reacting the free base function with a suitable organic acid. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like. Examples of pharmaceutically acceptable, nontoxic amides of the compounds of formula I include amides derived from $C_1$-$C_6$-alkyl carboxylic acids wherein the alkyl groups are straight or branched chain, aromatic carboxylic acids such as derivatives of benzoic acid and heterocyclic carboxylic acids such as furan-2-carboxylic acid or nicotinic acid. Amides of the compounds of formula I may be prepared according to conventional methods. It is understood that amides of the compounds of the present invention include amino acid and polypeptide derivatives of the amines of formula I.

As used herein, the term "pharmaceutically acceptable carriers" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically acceptable antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically effective amount" of the dopaminergic agent is meant a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

The term "affective disorder" as used herein refers to disorders that are characterized by changes in mood as the primary clinical manifestation, for example, depression.

The term "antipsychotic agent" as used herein refers to drugs used extensively in the symptomatic management of all forms of schizophrenia, organic psychosis, the manic phase of manic depressive illness and other acute idiopathic illnesses and occasionally used in depression or in severe anxiety.

The term "attention deficit disorder" refers to a recently classified pediatric neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the cognitive (information processing) functions of perceiving, thinking and remembering.

The term "dopamine-related cardiovascular disorders" as used herein refers to conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which, because the role of dopamine in the cardiovascular system is presently incompletely defined, are still under investigation, for example use in renal failure.

The term "dopamine-related neurological and psychological disorders" as used herein refers to behavioral disorders, such as psychoses and addictive behavior disorders; affective disorders, such as major depression; and movement disorders such as Parkinson's Disease, Huntington's Disease and Gilles de la Tourette's syndrome; which have been linked, pharmacologically and/or clinically, to either insufficient or excessive functional dopaminergic activity in the CNS. Also included are miscellaneous indications for which dopaminergic agents have been found to be clinically useful. Examples of such indications are disorders characterized by vomiting, such as uremia, gastroenteritis, carcinomatosis, radiation sickness, and emesis caused by a variety of drugs; intractable hiccough and alcoholic hallucinosis.

"Normal dopamine levels" are those levels of dopamine that are found in the brains of control subjects and are usually measured as levels of the dopamine metabolites homovanillic acid (3-methoxy-4-hydroxyphenylacetic acid) and 3,4-dihydroxyphenylacetic acid. Abnormal dopamine levels are those levels that are not within the range of dopamine levels found in the brains of control subjects.

The term "substance abuse" is used herein to mean periodic or continued self-administration of psychoactive substances in the absence of medical indications and despite the presence of persistent or recurrent social, occupational, psychological or physical problems that the person knows are caused by or may be exacerbated by continued use of the substance.

The total daily dose of the compounds of this invention administered to a host in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

The compounds of the present invention may be administered alone or in combination or in concurrent therapy with other agents which effect the dopaminergic system such as L-dopa, amantadine, apomorphine or bromocryptine; and with cholinergic agents, for example, benztropine, biperiden, ethopromazine, procyclidine, trihexylphenidyl and the like. The compounds of the present invention may also be co-administered with agents, for example enzyme inhibitors, which block their metabolic transformation outside the CNS.

This invention also provides pharmaceutical compositions in unit dosage forms, comprising a therapeutically effective amount of a compound (or compounds) of this invention in combination with a conventional pharmaceutical carrier.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In general, the compounds of this invention are synthesized by reaction schemes I through XVI as illustrated below. It should be understood that $R^1$–$R^7$ as used herein correspond to the R groups identified by formula I. The oxygens of the catechol groups can be derivatized with "protecting groups" or "leaving groups" which are known in the art and can be prepared by conventional methods. These derivatizing groups can be selected from among phenol derivatives and derivatives which are suitable to catechols because of the proximity of the two hydroxyl functions. Commonly used phenol derivatives are ethers, for example alkyl, alkenyl, and cycloalkyl ethers (such as methyl, isopropyl, t-butyl, cyclopropylmethyl, cyclohexyl, allyl ethers and the like); alkoxyalkyl ethers such as methoxymethyl or methoxyethoxymethyl ether and the like; alkylthioalkyl ethers such as methylthiomethyl ether; tetrahydropyranyl ethers, arylalkyl ethers (such as benzyl, o-nitrobenzyl, 9-anthrylmethyl, 4-picolyl ethers and the like); trialkylsilyl ethers such as trimethylsilyl, triethylsilyl, t-butyldimethylsilyl ethers and the like; alkyl esters such as acetates, propionates, n-butyrates, isobutyrates, trimethylacetates, benzoates and the like; substituted alkyl esters such as 3-(methoxycarbonyl)propionate, 3-aminopropionate, 3-(t-butoxycarbonyl)propionate and the like; carbonates such as methyl ethyl, 2,2,2-trichloroethyl, vinyl, benzyl and the like; carbamates such as methyl, isobutyl, phenyl, benzyl, dimethyl, and the like; and sulfonates such as methanesulfonate, trifluoromethanesulfonate, toluenesulfonate and the like. Commonly used catechol derivatives include cyclic acetals and ketals such as methylene acetal, acetonide derivatives, cyclohexylidene ketal, diphenylmethylene ketal and the like; cyclic esters such as borate esters, cyclic carbonate esters and the like.

The condensation of amino groups (such as those present in the certain of the compounds of this invention) with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z), o-chloro-benzyloxycarbonyl ((2-Cl)Z), p-nitrobenzyloxycarbonyl (Z(NO2)), p-methoxybenzyloxycarbonyl (Z(OMe)), t-butoxycarbonyl (Boc), t-amyloxycarbonyl (Aoc), isoborneal-oxycarbonyl, adamantyloxycarbonyl (Adoc), 2-(4-biphenyl)-2-propyloxy carbonyl (Bpoc), 9-fluorenylmethoxycarbonyl (Fmoc), methylsulfonylethoxy carbonyl (Msc), trifluoroacetyl, phthalyl, formyl, 2-nitrophenylsulfenyl (Nps), diphenylphosphinothioyl (Ppt) and dimethylphosphinothioyl (Mpt).

The examples of protecting groups for carboxyl groups involve, for example, benzyl ester (OBn), cyclohexyl ester, 4-nitrobenzyl ester (OBnNO2), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group ($N^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like, and the thiol group in cysteine may be protected with benzyl, p-methoxybenzyl, triphenylmethyl, acetomidomethyl, ethylcarbamyl, 4-methylbenzyl (4-MeBn, 2,4,6,-trimethylbenzyl (Tmb) and the like, and the hydroxy group in serine may be protected with benzyl (Bn), t-butyl, acetyl, tetrahydropyranyl (THP) and the like.

The compounds of formulae I A and I B are synthesized by the method discussed herein. 2,3-Dihydroxybenzaldehyde (which has the two catechol hydroxy groups protected by, for example, alkyl groups preferably methyl groups) and a substituted acetic acid derivative, such as phenyl acetic acid, are condensed in the presence of a dehydrating agent, such as acetic anhydride, and a proton acceptor such as triethylamine (TEA) to give compound 2. The carboxylic acid (or acid derivative such as the methyl or ethyl ester) of compound 2 is reduced by a reducing agent such as lithium aluminum hydride (LAH) preferably in an ether solvent such as tetrahydrofuran (THF). The leaving group ability of the hydroxyl group of compound 3 is enhanced by derivatizing it with, for example, methanesulfonyl chloride, in the presence of a proton acceptor such as TEA, and it is then convened to the cyano compound 4 by nucleophilic displacement with a salt of cyanic acid such as sodium cyanide in a polar solvent such as dimethyl sulfoxide (DMSO). The cyano group is hydrolyzed to the corresponding carboxylic acid group under basic conditions using, for example, aqueous sodium hydroxide, and the naphthalenone derivative (compound 5) is prepared by intramolecular acylation of the protected catechol ring using a dehydrating agent such as polyphosphoric acid or methanesulfonic acid/tri-fluoroacetic acid. Compound 5 is converted to the corresponding cyanohydrin by treatment with a nucleophilic cyano derivative such as trimethylsilylcyanide and the cyano alcohol is reduced to the amine (compound 6) by treatment with a reducing agent such as LAH, preferably in a ether solvent such as diethyl ether. The 1-hydroxyl group is eliminated from compound 6 by heating it under acidic conditions, e.g. in isopropyl alcohol saturated with hydrochloric acid, to produce the dihydronaphthalene derivative (compound 7). Compound I A is produced when the catechol hydroxyl groups of compound 7 are deprotected with, for example, boron tribromide or boron trichloride in an inert solvent such as dichloroethane or methylene chloride. Compound 7 is also hydrogenated to the corresponding tetrahydronaphthalene derivative in the presence of a catalyst such as palladium or platinum on carbon and then deprotected with e.g. boron tribromide or boron trichloride to produce IB. In the preferred embodiments of compounds I A and I B, $R^3$ is phenyl or cyclohexyl and X is bromo or chloro.

Scheme I B

The compounds of formula I are alternately synthesized by the method discussed herein. 2,3-Dihydroxybenzaldehyde with both the catechol hydroxyl protected as described in Example I and the aldehyde group derivatized as its dithiane is treated with a base such as n-butyl lithium to generate the anion (compound 8), and condensed with an alpha-beta unsaturated acid derivative such as ethyl cinnamate in the presence of dimethyl-2-imidizolidinone to produce compound 9. The dithiane group is removed from compound 9 by treatment with hydrogen in the presence of a catalyst such as Raney nickel and converted to compound 5 as described in Scheme IA. Compound 5 is further converted to IA and IB as described in Scheme IA.

Scheme II

The compounds of formulae II A and II B are prepared by the method illustrated in Scheme II. The naphthalenones of formula 5 are treated sequentially with a suitable base such as lithium bis(trimethylsilyl)amide and a haloacetic acid ester, for example ethyl bromoacetate, to afford the compounds of formula 10. Compounds of formula 10 are converted to compounds of formula 11 by treatment with diethylaluminum cyanide under anhydrous conditions, followed by cyclization in aqueous mineral acid, for example aqueous hydrochloric acid. Compounds of formula 11 are reduced using a suitable reagent such as LAH followed by elimination with an acid such as hydrogen chloride in isopropanol to afford compounds of formula 12. Compounds of formula 12 are treated with a suitable reagent for removal of the catechol protecting groups, for example boron tribromide, to yield the compounds of formula II A.

Alternately, compounds of formula 11 are converted to compounds of formula 13 by treatment with a mineral acid in anhydrous alcohol. The compounds of formula 13 are, in turn, converted to compounds of formula 14 by treatment with magnesium followed by aqueous mineral acid and reduction using a suitable reagent such as LAH. The compounds of formula 14 are then treated with a suitable reagent for the removal of the catechol protecting groups, for example boron tribromide to afford the compounds of formula II B.

Compounds of formulae III A–III E are synthesized by the methods illustrated in Scheme Ill. Naphthalenones of formula 5 are alkylated to afford the compounds of formula 15 by treatment with a suitable base(for example lithium bis(trimethylsilyl)amide and a suitable alkylating agent such as allyl bromide. The compounds of formula 15 are converted to the compounds of formula 16 by sequential treatment with trimethylsilyl cyanide and a suitable reducing agent such as LAH. The compounds of formula 16 are, in turn, cyclized to the compounds of formula 17 by treatment with a suitably reactive carbonic acid derivative such as 1,1'-carbonyldiimidazole.

Compounds of formula III A are prepared by reduction of compounds of formula 17 with a suitable reagent (for example by hydrogenation using a suitable catalyst such as palladium on carbon), followed by treatment with a suitable reagent for removal of the catechol protecting groups such as boron tribromide resulting in simultaneous elimination of carbon dioxide to afford the desired amines.

Compounds of formula III B are prepared by hydrogenation of compounds of formula 17 using a suitable catalyst such as palladium hydroxide on carbon, followed by treatment with a suitable reagent for removal of the catechol protecting groups such as boron tribromide.

Compounds of formulae III C, III D and III E are prepared from compounds of formula 20. Compounds of formula 17 are converted to compounds of formula 20 by hydroboration/oxidation under standard conditions. Compounds of formula 20 are converted to compounds of formula III C by treatment with 3 equivalents of boron tribromide. Compounds of formula 20 are converted to compounds of formula III D by treatment with 4.5 equivalents of boron tribromide. Compounds of formula 20 are converted to compounds of formula III E by reductive opening of the oxazolidinone ring followed by treatment with a suitable reagent for removal of the catechol protecting groups such as boron tribromide.

Scheme IV

The compounds of formula IV A, IV B and IV C are synthesized by the method discussed herein. A catechol (compound 22 wherein $R^1$ is selected from alkyl groups such as methyl or both $R^1$ groups together form a spiro cycloalkyl group such as cyclohexyl) is reacted in the presence of a base, such as n-butyl lithium, with an epoxide such as compound 23 (wherein $R^4$ is hydrogen and $R^3$ is preferably selected from cyclohexyl, phenyl, ethyl, p-methoxyphenoxymethyl, phenoxymethyl, o-phenylphenoxymethyl, p-t-butylphenoxymethyl, p-bromophenoxymethyl, adamantyl, benzyl, phenylethyl, n-octyl, n-hexyl, 1-hex-5-enyl, n-decyl, t-butyl or benzyloxymethyl; or $R^3$ and $R^4$ together form a spirocycloalkyl group,such as cyclohexyl), to produce compound 24.

Compound 24 can be oxidized to the corresponding ketone with an oxidizing agent such as pyridinium chlorochromate (PCC) and the resultant ketone can be stereoselectively reduced with, for example, B-chlorodiisopinocampheylborane (as described in Example 46) to give the optically active isomers of compound 24.

Compound 24 is condensed with a bromoaldehyde such as bromoacetaldehyde dimethyl acetal or 3-bromopropionaldehyde dimethyl acetal to form the substituted benzopyran derivative 26. Compound 26 is converted to compound 27 by treatment with a nucleophilic azide such as lithium azide in a polar solvent such as dimethyl formamide, followed by reduction of the azido compound, for example with LAH. Compound 27 is converted to IV A by generation of the amine salt in acidic solution and deprotection of the catechol hydroxyl groups in acid solution. Compound 27 is converted to compound IV B by treatment with ethyl fore, ate followed by reduction with, for example LAH and generation of the amine salt with deprotection of the catechol hydroxyl groups in acidic solution. Compound 26 is converted to IV C by treatment with an amine such as allyl amine, cyclopropylamine or pyrrolidine, followed by deprotection of the catechol hydroxyl groups and generation of the amine salt in acidic solution. In the case wherein the epoxide 23 is substituted with a benzyloxymethyl group (i.e. $R^3$=benzyloxymethyl), $R^3$ is further elaborated as shown in Scheme V.

Scheme V

The compounds of formula V A, V B, V C, V D and V E are synthesized by the methods illustrated in Scheme V. $R^1$ is defined in Scheme IV. Compound of formula 28 are alkylated with an epoxide of formula 29 (wherein Bn is benzyl, z is an integer from 0 to 6, and $R^{12}$ is a substituent selected from the group $R^3$) to afford compounds of formula 30. Compounds of formula 30 are condensed with N-formylamino-acetaldehyde dimethyl acetal in the presence of a catalyst selected from boron trifluoride etherate, zinc triflate, trimethylsilyl triflate, methanesulfonic acid, p-toluenesulfonic acid and polyphosphoric acid to afford the isochromans of formula 31. The formyl group is removed and replaced with a t-butyloxycarbonyl protecting group and the hydroxy group is deprotected preferably by hydrogenolysis to afford the compounds of formula 32.

Compounds of formula V A are prepared by removal of the amino and catechol protecting group from the compounds of formula 32 in acidic solution. Compounds of formula V B are prepared from the compounds of formula 32 by the following to sequence of reactions: activation of the hydroxymethyl group, for example by reaction with methanesulfonyl chloride; displacement with a nucleophilic azide such as lithium azide to give the azidomethyl compound; followed by reduction of the azido group to give the compounds of formula 33 and deprotection of the amine and the catechol hydroxyls with an acid such as hydrochloric acid in alcohol.

Compounds of formula V C are prepared from the compounds of formula 33 by acylation of the free amino group followed by simultaneous removal of the amine and catechol protecting groups in acidic solution.

Alternately, compounds of formula 31 are converted to compounds of formula 34 by hydrogenolysis followed by activation of the hydroxymethyl group, for example by reaction with methanesulfonyl chloride ant displacement with a nucleophilic azide such as lithium azide. The compounds of formula 34 are, in turn, converted to compounds of formula V D by reduction of the formyl group and the azido group followed by removal of the catechol protecting groups in acidic solution. The compounds of formula 34 are also converted to the compounds of formula V E by reduction of the azido group, formylation of the free amino, simultaneous reduction of both formyl groups to methylamino groups and treatment with a suitable reagent for the removal of the catechol protecting groups.

Alternately, compounds of formula 32 are converted to compounds of formula V F by activation of the 3-hydroxymethyl group, for example by reaction with methanesulfonyl chloride followed by displacement with a nucleophilic amine, $NHR^9R^{10}$, in which $R^9$ and $R^{10}$ are independently selected from H and lower alkyl or $R^9$ and $R^{10}$ together form a ring containing a nitrogen atom such as pyrrolinyl or piperidinyl or morpholino, followed by deprotection of the amino group and the catechol hydroxyls in acidic solution.

Scheme VI

According to reaction Scheme VI A, compound of formula 35, wherein R1 is as defined in Scheme IV, are converted to compounds of formula 36 by treatment with oxalyl chloride followed by treatment with O-methyl N-methyl hydroxylamine. Compounds of formula 36 reacted with furan in the presence of a suitable base such as n-butyl lithium to afford the compounds of formula 37. The furan ring and the ketone are then reduced, for example by hydrogenation using a suitable catalyst such as palladium on carbon to afford the compounds of formula 24. Compounds of formula 24 are valuable intermediates and can be converted to the isochroman and isothiochroman compounds of the present invention by any of the methods shown in Schemes IV, V, VII and VIII.

Chiral compounds may be prepared according to Scheme VI B, wherein compounds of formula 22, wherein R 1 is as defined in Scheme IV, are converted into compounds of formula 38 by treatment with a strong base, such as n-butyl lithium, followed by reaction with chiral epichlorohydrin. The chiral compounds of formula 38 are converted into the chiral epoxides of formula 38A by treatment with a strong base, such as NaOH or KOH in a polar organic solvent, such as a mixture of ether and alcohol. The chiral 38A is then reacted with an organometallic compound, for example, an alkyl magnesium halide, an organocuprate or a lithium acetylide, for example, in a non-polar organic solvent, to prepare the chiral alcohol of formula 38B. The compound 38B is reacted with N-formylaminoacetaldehyde dimethyl acetal in the presence of an acid catalyst as described in Scheme XVIA below, followed by hydrolysis of the formyl group to give chiral compounds of formula 39. Compounds of formula 39 can be either hydrolyzed or reduced followed by conversion to the HCl salt to give certain chiral compounds of formula VIB directly. Alternately, the formyl group can be replaced with an amino protecting group and the intermediate further modified to give other compounds of formula I. for example as illustrated in Scheme V above.

Scheme VIIA

Compounds of formulae 43 or 44, where either X or Y is Br or Cl, are synthesized by the method illustrated in in Scheme VIIA. Compounds of formula IVA are protected at the amino position with a suitable N-protecting group, such as BOC, AOC, or ADOC, for example, by reaction with the appropriate reagent, to give the compounds of formula 42. These compounds are then reacted with a brominating or chlorinating reagent, such as free bromine or chlorine, HOCl, HOBr, N-bromosuccinimide, or N-chlorosuccinimide, for example, and the protecting group is removed by hydrolysis with the appropriate reagent. A mixture of compounds 43 and 44 is obtained, which may be separated by standard procedures in the art.

Scheme VIIB

Compounds of formula 46, where either X or Y is fluoro, methyl or ethyl are synthesized by the procedure outlined in Scheme VIIB. The compounds 45, analogous to the compounds of formula 22 of Scheme IV, are reacted according to the procedures given in Scheme IV, in order to prepare the desired compounds of formula 46, where X or Y is fluoro, methyl, or ethyl. These compounds may be taken further to prepare the compounds where the nitrogen is substituted, as illustrated in Schemes IV or IX.

Scheme VIII

The compounds of formula VIII are synthesized by the methods illustrated in Scheme VIII. Intermediates of formula 24 are convened to the corresponding thio compounds of formula 40 by treatment with triphenylphosphine and diisopropylazodicarboxylate, followed by treatment with thioacetic acid to afford an intermediate thiolacetate which was treated with a suitable reagent such as LAH. The compounds of formula 40 are valuable intermediates and are convened to the compounds of formula VIII and the thio equivalents of compounds IV, V, VI and VII by the methods illustrated in Schemes IV–VII.

Scheme IX

The compounds of formula IX A and IX B are synthesized by the method discussed herein. $R^1$, $R^2$ and $R^3$ are defined in Scheme I. Compound 5 is converted to the cyanohydrin by treatment with a nucleophilic cyano derivative such as dimethylsilyl cyanide in the presence of a catalyst such as aluminum trichloride. The cyanohydrin is dehydrated to the a,b-unsaturated nitrile by treatment with a dehydrating agent such as TFA/p-toluenesulfonic acid and the unsaturated nitrile reduced to the saturated nitrile (compound 46) by treatment with a reducing agent such as sodium borohydride. The nitrite group is hydrolyzed to a carboxylic acid group (compound 47) and the acid convened to the N-methoxy-N-methyl amide 48 by sequential treatment with an activating agent, such as oxalyl chloride, to generate the acid chloride, and N-methoxymethylamine. Compound 48 is convened to a mixture of the diastereomeric pyrrolidinyl derivatives 49 and 50 by treatment with 2,2,5,5-tetramethyl-1-aza-2,5-disilacyclopentane-1-propyl magnesium bromide (by the procedure given in *Tetrahedron Letters* 25:5271–5274 (1984)) followed by reduction with a reducing agent such as sodium borohydride, and the diastereomers are separated chromatographically. The separated isomers 49 and 50 are convened to IX A and IX B, respectively, by treatment with boron trihalide, preferably boron tribromide.

Scheme X

The compounds X A and X B are synthesized by the method discussed herein. $R^1$–$R^3$ are defined in Scheme I. Compound 5 is converted to compound 51 by treatment with dimethyl succinate in the presence of a base such as potassium t-butoxide. Compound 51 is reduced to the corresponding 1,2,3,4-tetrahydronaph-thalene and the tricyclic ring system is formed by treating compound 51, with a dehydrating agent such as polyphosphoric acid. Four isomeric products are obtained. Two of the isomers, compounds 52 and 53, are carried on to X A and X B, respectively. Reduction of the 3-keto group of compounds 52 and 53 with, for example hydrogen in the presence of a catalyst such as palladium on carbon support is followed by hydrolysis of the ester in basic solution to give compounds 54 and 55, respectively. Compounds 54 and 55 are each treated with diphenylphosphoryl azide and benzyl alcohol in the presence of a base such as triethylamine to give the carbobenzyloxy protected amino derivatives, which are deprotected by hydrogenolysis using, for example, palladium on carbon support as a catalyst, and demethylation using, for example, boron tribromide to give X A and X B.

Scheme XI

The compounds of formula XI are synthesized by the method described herein. $R^1$–$R^3$ are defined in Scheme I. Compound 5 is converted to the α-bromoketone by treatment with a brominating agent such as phenyltrimethylammonium tribromide. The bromide undergoes nucleophilic displacement, for example, with the anion of thiophenol to give the α-thiophenylketone compound 56. The ketone is reduced to the alcohol with a reducing agent such as sodium borohydride and the hydroxy group is eliminated with a dehydrating agent such as p-toluenesulfonic acid to give the thio-enoelether. The sulfur atom of the thio-enoelether is oxidized to the sulfoxide with an oxidizing agent such as mCPBA to give compound 57. The amine component is made by a nucleophilic displacement on chloromethyltrimethylsilane by an amine (compound 58), such as benzylamine. The imine is formed by treatment of the amine with an aldehyde such as formaldehyde and then an alcohol, such as methanol, is added to form the alkoxymethyl amine compound 60. Compound 60 is then reacted with the sulfoxide (compound 57) in the presence of an acid, such as TFA to generate the azomethine ylid in situ which traps the activated double bond of the a, b-unsaturated sulfoxide to give a 1,3-dipolar addition adduct which, on heating, spontaneously undergoes elimination to give the cyclization/elimination product, compound 61. The nitrogen can be deprotected by treatment with an acylating agent, such as 1-chloroethylchloroformate followed by acyl group removal with a nucleophile, such as methanol to give compound 62. The catechol is deprotected by treatment with a boron trihalide, preferably boron tribromide to give XI.

Scheme XII

The compounds of formulae XII A, XII B and XII C are synthesized by the methods described herein. $R^1$ and $R^3$ are defined in Scheme I. Compounds of the formula 12 are reduced by catalytic hydrogenation using a suitable catalyst such as palladium hydroxide to afford the compounds of formula 63. The compounds of formula 63 are treated with a suitable reagent for protecting the amino group, for example benzyloxycarbonyl chloride, followed by a suitable reagent for activating the hydroxyl group such as methanesulfonyl chloride to afford the compounds of formula 64. The compounds of formula 64 are, in turn, cyclized by treatment with a suitable base for example sodium hydride in DMF and deprotected with acid, for example by treatment with hydrogen bromide in acetic acid, to afford the compounds of formula XII B.

Alternately, the compounds of formula 12 are convened to the compounds of formula 65 by treatment with a suitable reagent for protecting the amino group, for example benzyloxycarbonyl chloride, followed by a suitable reagent for activating the hydroxyl group such as methanesulfonyl chloride to afford the compounds of formula 65. The compounds of formula 65 are, in turn, cyclized by treatment with a suitable base for example sodium hydride in DMF and deprotected with acid, for example by treatment with hydrogen bromide in acetic acid to afford the compounds of formula XII A.

The compounds of formula 11 are treated with a suitable reducing agent such as LAH to afford the compounds of formula 66. The compounds of formula 66 are treated with an appropriately reactive carbonic acid derivative, for example carbonyl diimidazole to afford the oxazolidinones of formula 67. The compounds of formula 67 are reduced by catalytic hydrogenation using a suitable catalyst such as palladium hydroxide to afford the compounds of formula 68. The compounds of formula 68 are treated with a suitable reagent for protecting the amino group, for example benzyloxycarbonyl chloride, followed by a suitable reagent for activating the hydroxyl group such as methanesulfonyl chloride to afford the compounds of formula 69. The compounds of formula 69 are, in turn, cyclized by treatment with a suitable base for example sodium hydride in DMF and deprotected with acid, for example by treatment with hydrogen bromide in acetic acid, to afford the compounds of formula XII C.

Scheme XIII

The compounds of formulae XIII A and XIII B are synthesized by the methods described herein. $R^1$ and $R^3$ are defined in Scheme I. The compounds of formula 20 are treated with a suitable acid such as hydrogen chloride in a suitable solvent, for example isopropyl alcohol or ethyl alcohol or diethyl ether, in order to open the oxazolidinone ring with the elimination of carbon dioxide. The resultant amino alcohols are treated with a suitable reagent for protecting the amino group, for example benzyloxycarbonyl chloride, followed by a suitable reagent for activating the hydroxyl group such as methanesulfonyl chloride to afford the compounds of formula 70. The compounds of formula 70 are, in turn, cyclized by treatment with a suitable base for example sodium hydride in DMF and deprotected with acid, for example by treatment with hydrogen bromide in acetic acid, to afford the compounds of formula XIII A.

The compounds of formula 21 are treated with a suitable reagent for protecting the amino group, for example benzyloxycarbonyl chloride, followed by a suitable reagent for activating the hydroxyl group such as methanesulfonyl chloride to afford the compounds of formula 71. The compounds of formula 71 are, in turn, cyclized by treatment with a suitable base for example sodium hydride in DMF and deprotected with acid, for example by treatment with hydrogen bromide in acetic acid, to afford the compounds of formula XIII B.

Scheme XIV

The compounds of formulae XIV A and XIV B are synthesized by the methods described herein. Compounds of formula 5 are converted to compounds of formula 72 by treatment with dimethyl malonate in the presence of a base such as potassium t-butoxide. The tricyclic ting system is formed by treating a compound of formula 72, with an acid such as polyphosphoric acid, followed by reduction of the keto group with, for example, triethylsilane in trifluoroacetic acid to afford a compound of formula 73. Hydrolysis of the ester group in basic solution affords compounds of formula 74. Compounds of formula 74 are treated with diphenylphosphoryl azide and benzyl alcohol in the presence of a base such as triethylamine to give the carbobenzyloxy protected amino derivatives, which are deprotected along with the catechol hydroxyl groups using, for example, hydrogen bromide in acetic acid to give XIV A.

Alternately the compounds of formula 72 are reduced by catalytic hydrogenation using a suitable catalyst such as palladium hydroxide to afford the compounds of formula 75. The compounds of formula 75 are, in turn, converted to the compounds of formula XIV B by the same series of chemical transformations described above for the conversion of compounds of formula 72 to compounds of formula XIV A.

Scheme XV

The compounds of formulae XV A and XV B are synthesized by the methods described herein. $R^1$ and $R^3$ are defined in Scheme I. The compounds of formula 5 are converted to compounds of formula 51 by treatment with dimethyl succinate in the presence of a base such as potassium t-butoxide. The compounds of formula 51 are, in turn, treated with a suitable reducing agent for reducing the acid, for example borane, to afford the corresponding hydroxy compounds of formula 78. The compounds of formula 78 are treated with a suitable reagent to activate the hydroxyl group, for example methanesulfonyl chloride, followed by displacement with a nucleophic cyano derivative such as sodium cyanide to afford the compounds of formula 79. The tricyclic ring structure is formed by an intramolecular Houben-Hoesch reaction using hydrogen chloride and zinc dichloride to give the compounds of formula 80. Reduction of the keto group using, for example, triethylsilane in trifluoroacetic acid, followed by hydrolysis of the ester group in basic solution affords compounds of formula 81. Compounds of formula 81 are treated with diphenylphosphoryl azide and benzyl alcohol in the presence of a base such as triethylamine to give the carbobenzyloxy protected amino derivatives, which are deprotected along with the catechol hydroxyls using, for example, hydrogen bromide in acetic acid, to give XV A.

Alternately the compounds of formula 78 are reduced by catalytic hydrogenation using a suitable catalyst such as palladium hydroxide to afford the compounds of formula 82. The compounds of formula 82 are, in turn, convened to the compounds of formula XV B by the same series of chemical transformations described above for the conversion of compounds of formula 78 to compounds of formula XIV A.

Scheme XVIA

The process illustrated in Reaction Scheme XVIA is a novel and practical method for ring closure in the synthesis of the isochroman and thioisochroman compounds of the present invention. Compounds of the formula 24 are condensed with N-formylamino-acetaldehyde dimethyl acetal in the presence of an acid catalyst to afford the compounds of formula XVIA. The reaction is carried out in an inert solvent, for example a chlorinated solvent such as methylene chloride or 1,2-dichloroethane, an ether solvent such as diethyl ether or THF, or a polar aprotic solvent such as acetonitrile. The reaction is carried out in the temperature range of from about 0° C. to about 100° C. The preferred reaction temperature is determined by the choice of solvent, the choice of catalyst and the amount of catalyst present. In general, reactions in chlorinated solvents are carried out at lower temperatures than reactions in more polar solvents and larger amounts of catalyst require lower reaction temperatures. The formylamino reagent (compounds of formula 86) is present in the reaction mixture at from about 1 to about 4 equivalents, preferably from about 1.5 to about 2.0 equivalents. The catalyst is preferably selected from boron trifluoride etherate, trimethylsilyl triflate, zinc triflate, polyphosphoric acid, methanesulfonic acid and p-toluene sulfonic acid. The amount of catalyst present in the reaction mixture depends on the catalyst used, the solvent and reaction temperature. Generally, the catalyst is present in the range of from about 1 mole % to about 3 equivalents. Most preferably the reaction is carried with either 1 mole % trimethylsilyl triflate in refluxing acetonitrile or with 5 mole % boron trifluoride etherate in refluxing acetonitrile. The reactions are monitored by TLC analysis to determine the optimum reaction time for good yields with minimum product degradation and this time varies with choice of solvent, catalyst and reaction temperature.

The compounds of formula XVI A are valuable intermediates in the synthesis of the compounds of formula I in which A is an oxygen or a sulfur atom (isochromans and thioisochromans). Compounds of formula XVI can be either hydrolyzed or reduced to give certain compounds of formula I directly. Alternately, the formyl group can be replaced with an amino protecting group and the intermediate further modified to give other compounds of formula I, for example as illustrated in Scheme V below. Compounds of formula XVI A can be either hydrolyzed or reduced to give certain compounds of formula I directly.

Scheme XVIB

The process illustrated in Scheme XVIB is a practical method for preparing isochroman or thioisochroman compounds substituted with pyrrolidine at the 1-position. The compounds of formula 24 are condensed with the dimethyl acetal of prolinaldehyde in the presence of an acid catalyst to afford the compounds of formula XVI B. Chiral or racemic proline aldehyde may be used. The reaction is carried out in an inert solvent, for example a chlorinated solvent such as methylene chloride or 1,2-dichloroethane, an ether solvent such as diethyl ether or THF, or a polar aprotic solvent such as acetonitrile. The reaction is carried out in the temperature range of from about 0° C. to about 100° C. The preferred reaction temperature is determined by the choice of solvent, the choice of catalyst and the amount of catalyst present. In general, reactions in chlorinated solvents are carried out at lower temperatures than reactions in more polar solvents and larger amounts of catalyst require lower reaction temperatures. The formylamino reagent (compounds of formula 86) is present in the reaction mixture at from about 1 to about 4 equivalents, preferably from about 1.5 to about 2.0 equivalents. The catalyst is preferably selected from boron trifluoride etherate, trimethylsilyl triflate, zinc gate, polyphosphoric acid, methanesulfonic acid and p-toluene sulfonic acid. The amount of catalyst present in the reaction mixture depends on the catalyst used, the solvent and reaction temperature. Generally, the catalyst is present in the range of from about 1 mole % to about 3 equivalents. Most preferably the reaction is carried with either 1 mole % trimethylsilyl triflate in refluxing acetonitrile or with 5 mole % boron trifluoride etherate in refluxing acetonitrile. The reactions are monitored by TLC analysis to determine the optimum reaction time for good yields with minimum product degradation and this time varies with choice of solvent, catalyst and reaction temperature.

The compounds of formula XVI B are valuable intermediates in the synthesis of the compounds of formula I in which A is an oxygen or a sulfur atom (isochromans and thioisochromans).

Scheme XVII

Compounds of formula I, as represented by the compounds of formula XVII A–D, are alternately synthesized by the methods described herein. An ester compound of formula 86, wherein $R^3$ and $R^4$ are as described in Scheme IV, is treated with a strong base, preferably LDA, and reacted with a bromomethyl catechol derivative of compound 87, wherein $R^1$ is as described in Scheme I. The intermediate is reduced with a reducing agent such as LAH to produce the compound 88.

Compound 88 is selectively oxidized to the aldehyde 89, preferably by reaction with sulfur trioxide-pyridine, triethylamine and DMSO. Compound 89 is reacted with LiTMS-dithiane to form the thiane derivative of the aldehyde. This intermediate is made to undergo an internal ring closure by reacting it with $HgCl_2$, 5% aqueous methyl cyanide to produce compound 90.

The tetralone compound 90 is then converted to the aminomethyl compound 91 by reactions described in Scheme I for conversion of compound 5 to compound 7. Compound 91 may then be converted to the free catechol compound XVII A as described in Scheme I, or it may be converted to compound 92, where $R^5$ is not hydrogen, as described in Scheme IV, or by additional alkanoylation followed by reduction to give the amino-disubstituted compounds similar to compounds IVC as described in Scheme IV.

Compound 93 is obtained by catalytic reduction as described in Scheme I.

Compounds XVII B, C, and D are obtained by the appropriate deprotection as described previously.

Scheme XVIII

Compounds XVIII A–D are synthesized by the methods illustrated in Scheme XVIII. $R^1$, $R^3$, $R^4$ and $R^6$ are as described in Scheme XVII. Compounds of formula 90 are converted into compound 95 by the reactions described for converting compound 5 into compound 11 in Scheme II. The lactone 95 is reduced with LAH in THF to produce the amino diol compound 96, which by reaction with $PBr_3$ in methylene chloride undergoes ring closure to form compound 97. Deprotection of compound 97, by methods described earlier, produces compound XVIII A.

Alternately, compound 97 may be alkylated at the ring-nitrogen position, by the amino alkylation procedures referred to above, to produce compound 98, which upon deprotection is converted into compound XVIII B.

Also, alternately compound 97 is converted into compound 100 by catalytic hydrogenation over a catalyst as described earlier, which may then be deprotected to give compound XVIII D.

Compound 99 may be formed by the alkylation of compound 100 or alternately by catalytic reduction of compound 98. Deprotection of compound 99 produces compound XVIII C.

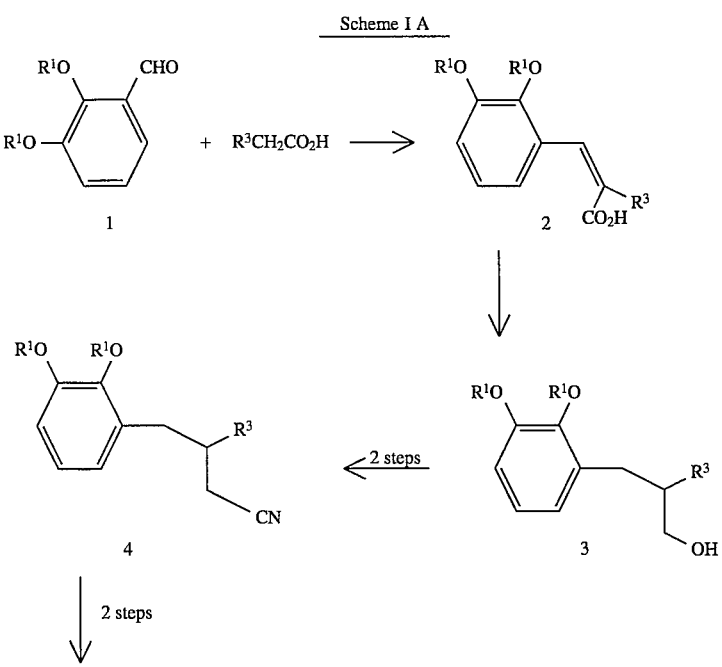

Scheme I A

-continued
Scheme I A
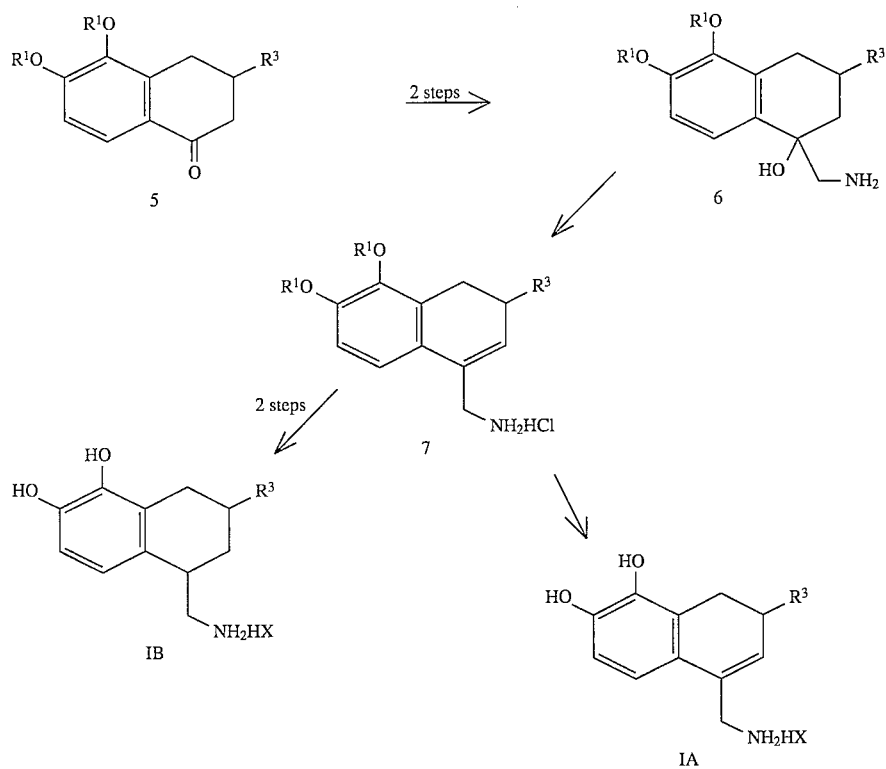
Scheme 1B
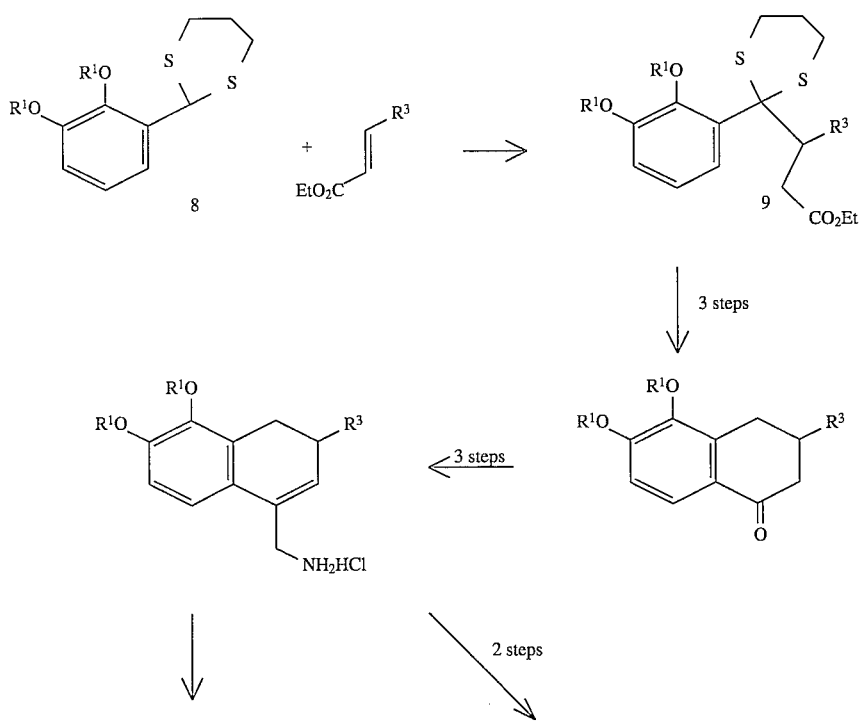

-continued
Scheme 1B
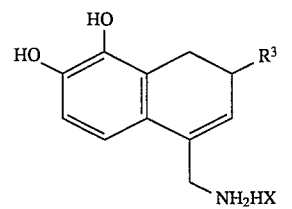
IA
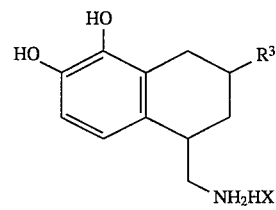
IB
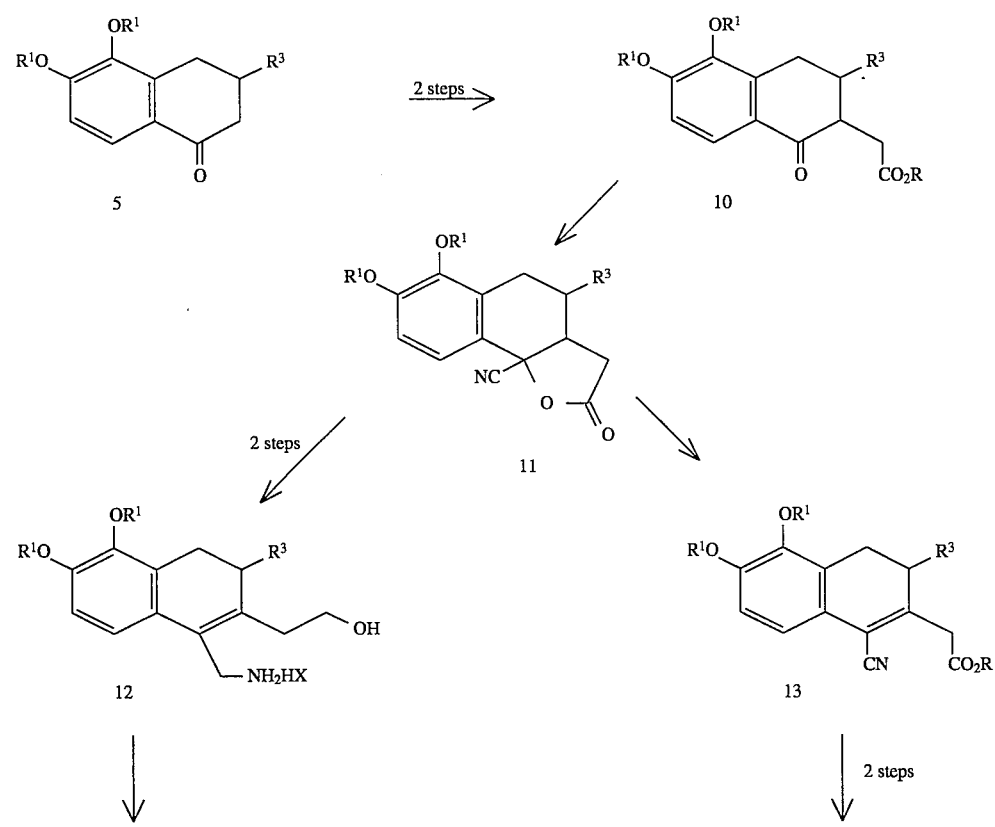
Scheme II

-continued
Scheme II
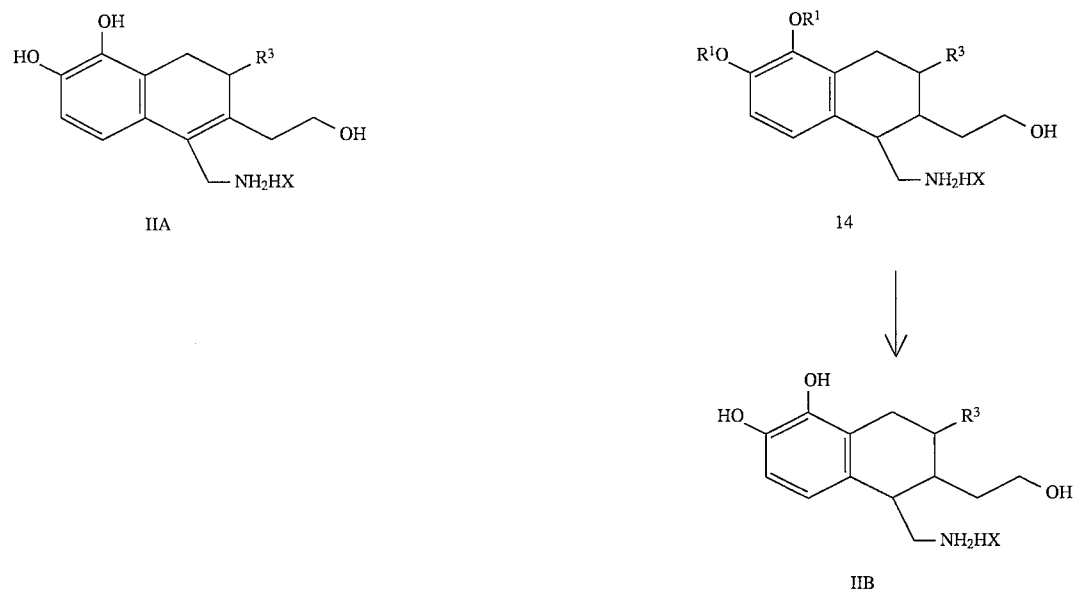
Scheme III
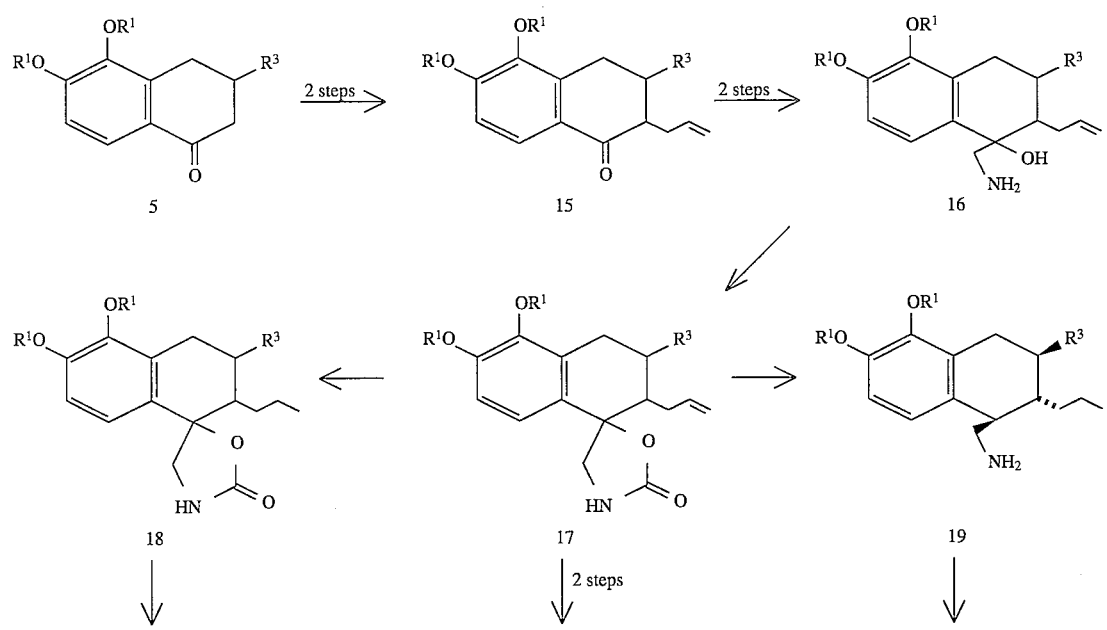

5,591,884
-continued
Scheme III
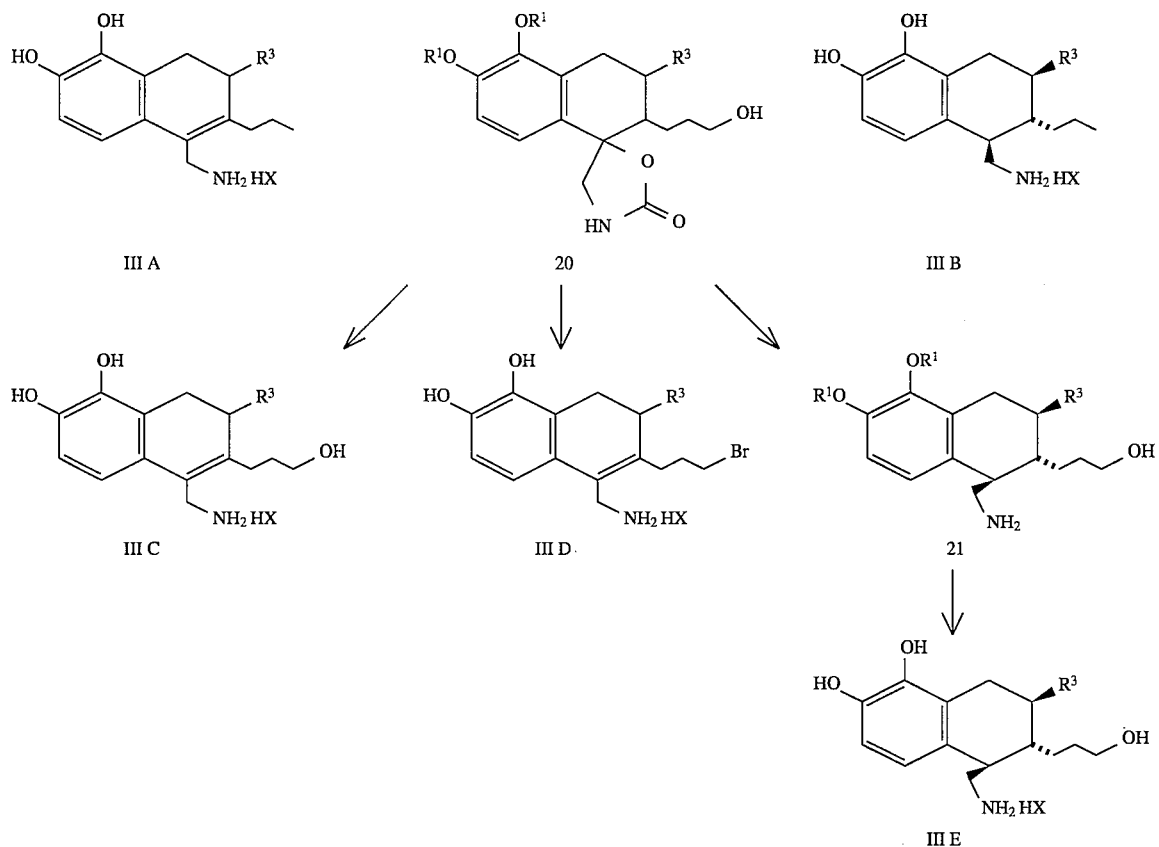
Scheme IV
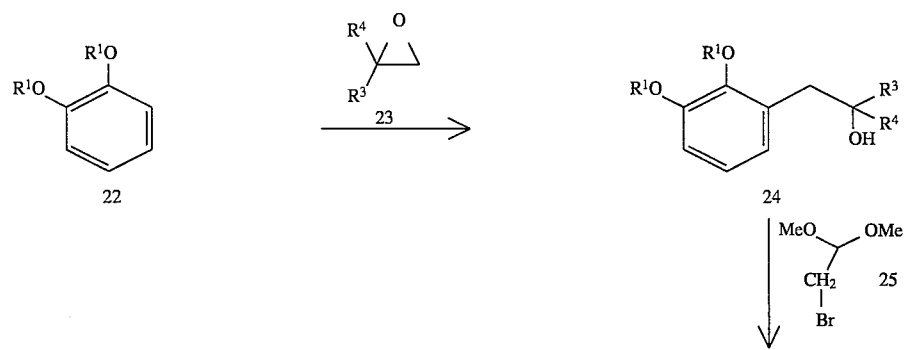

-continued
Scheme IV
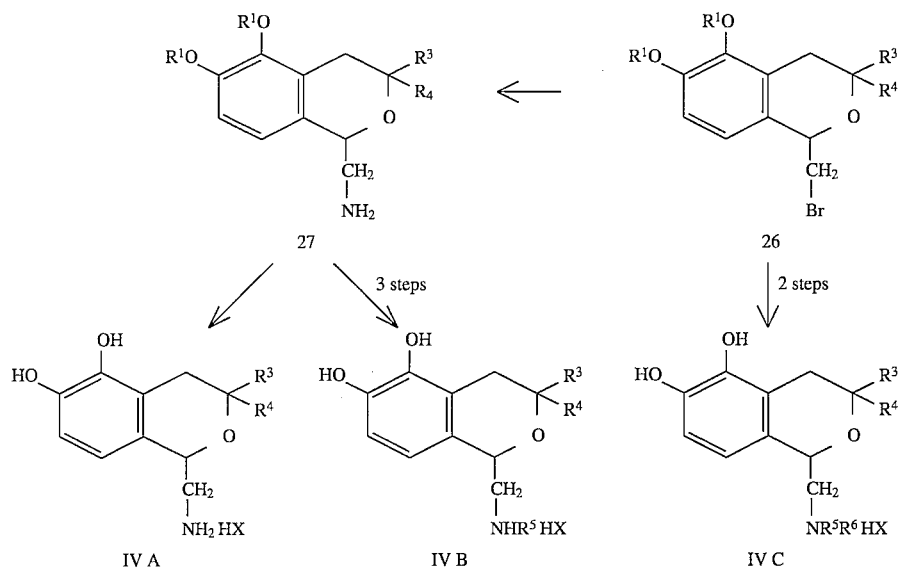
Scheme V
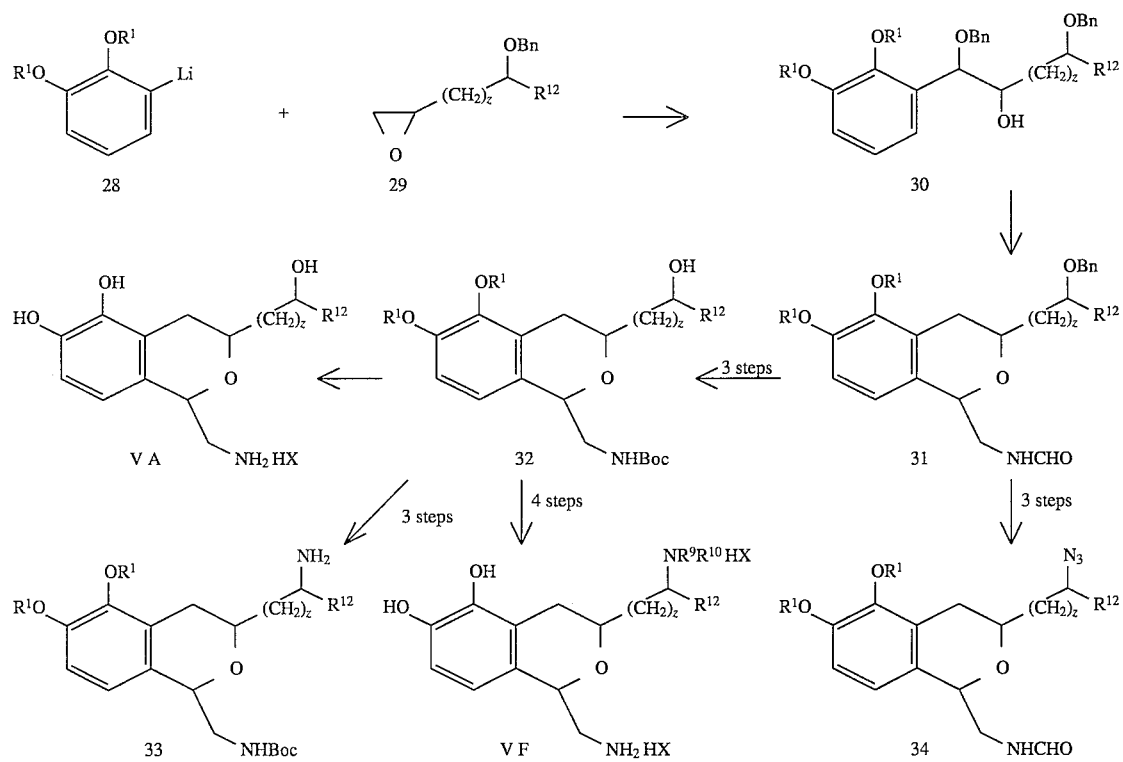

-continued
Scheme V
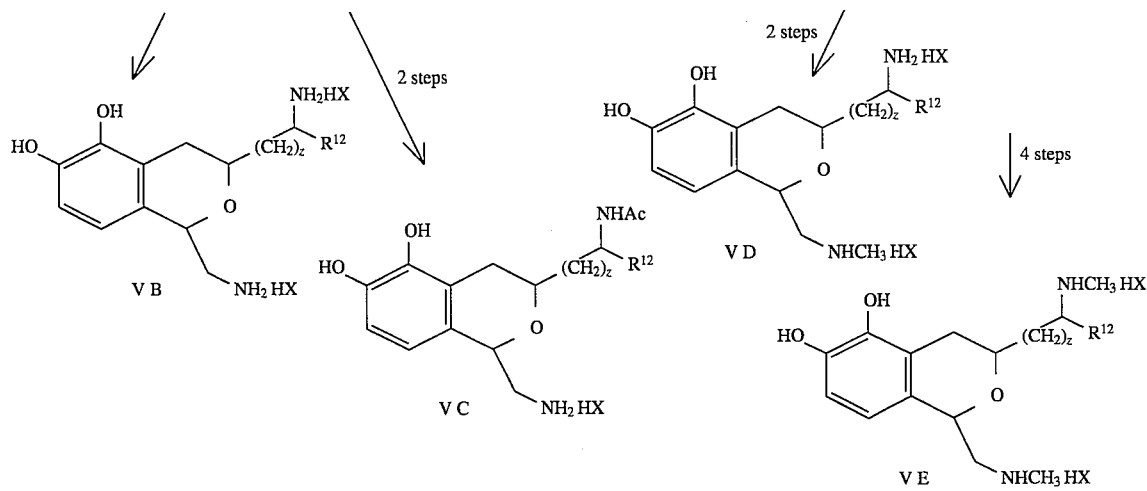
Scheme VIA
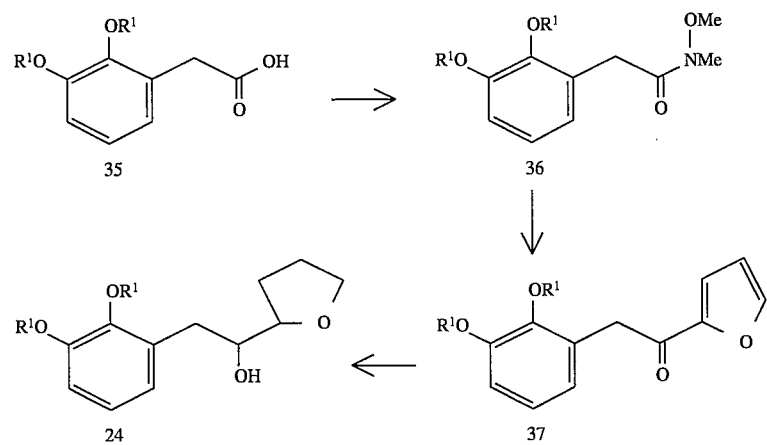
Scheme VIB
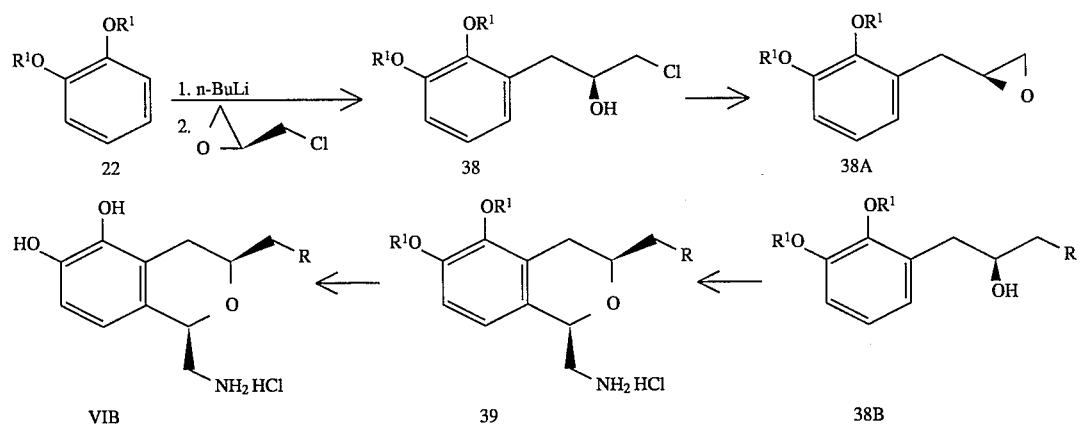

Scheme VIIA
(X, Y = Br or Cl)
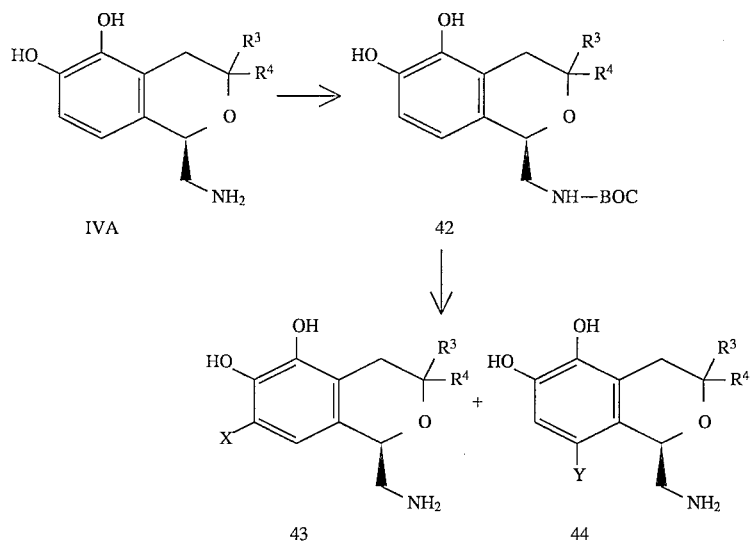
Scheme VIIB
(X, Y = F, Me, or Et)
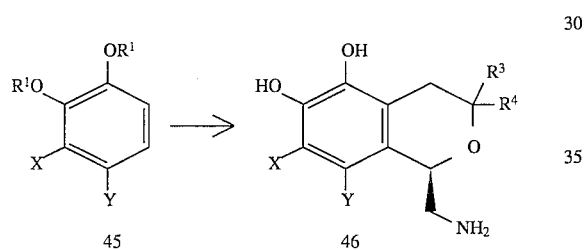
Scheme VIII
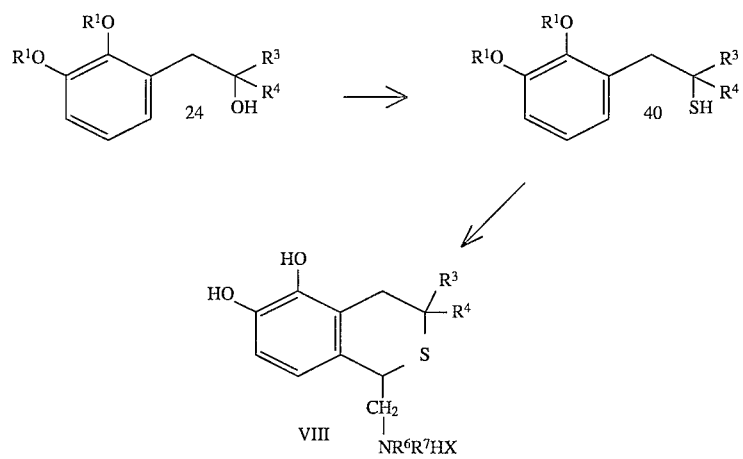

5,591,884
Scheme IX
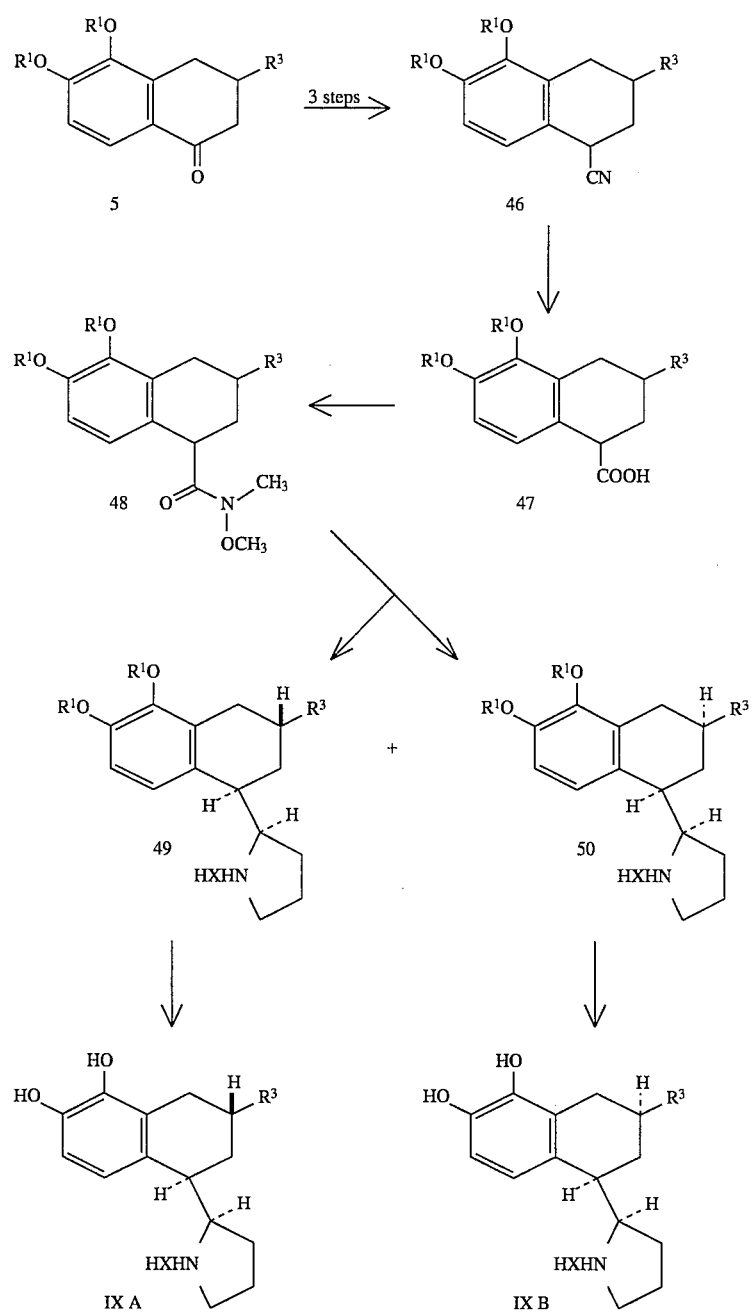

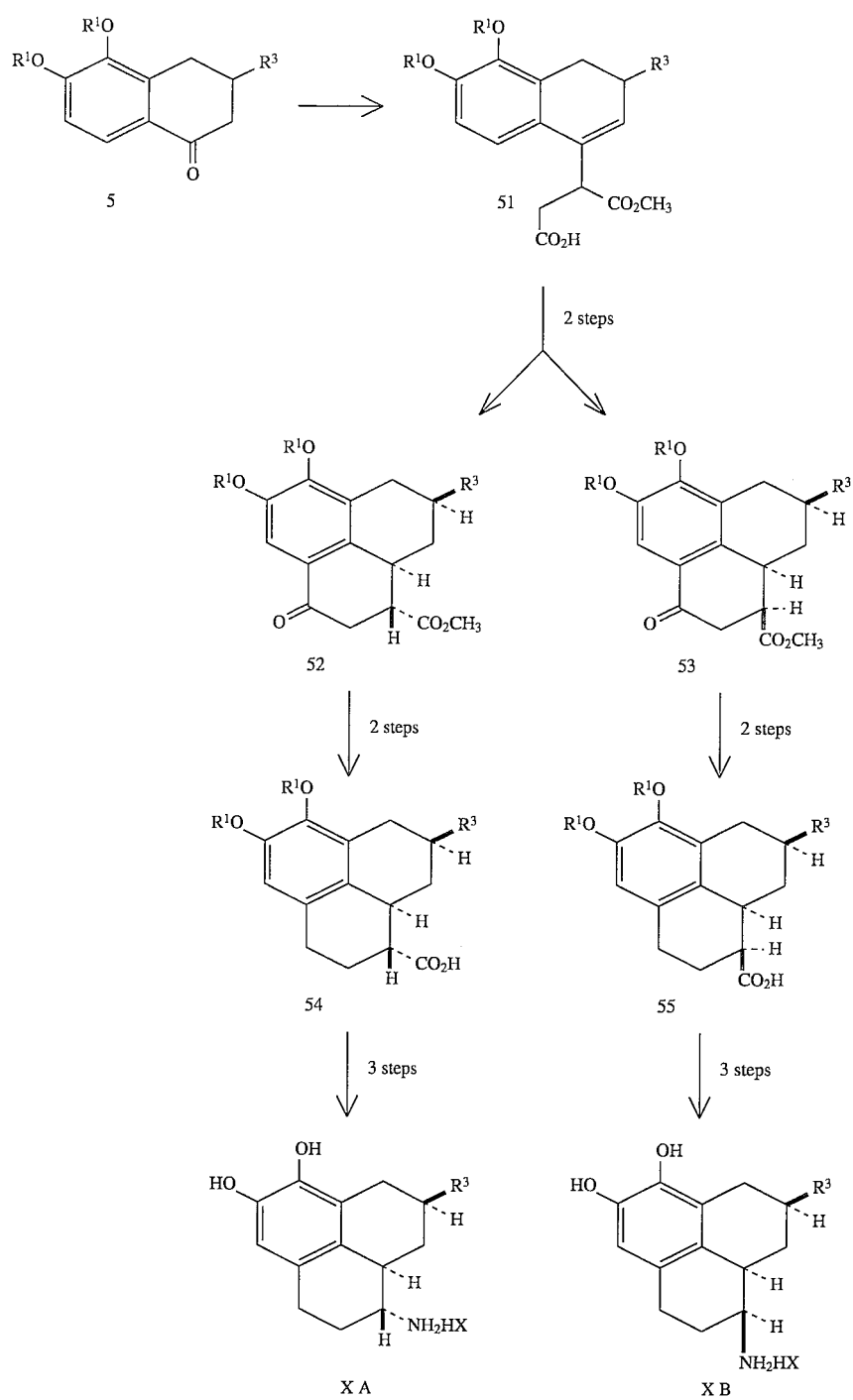

Scheme XI
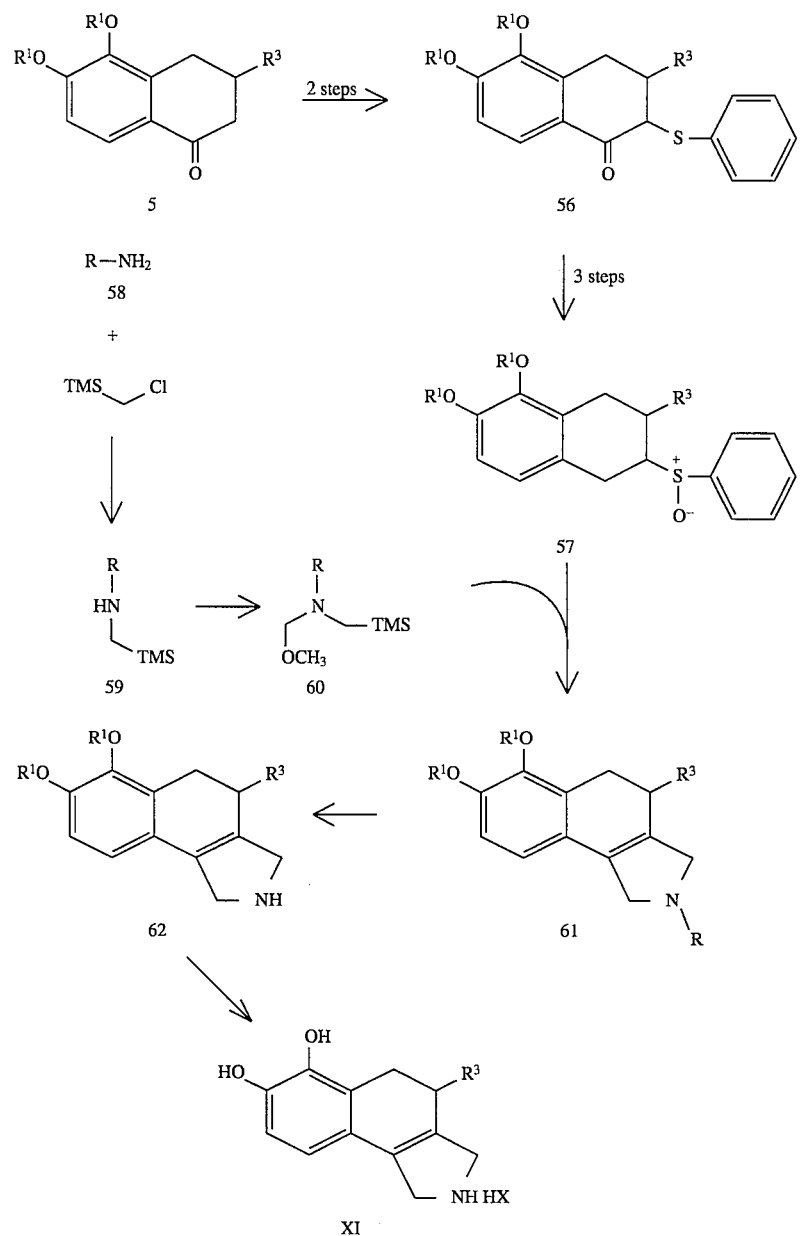

5,591,884
Scheme XII
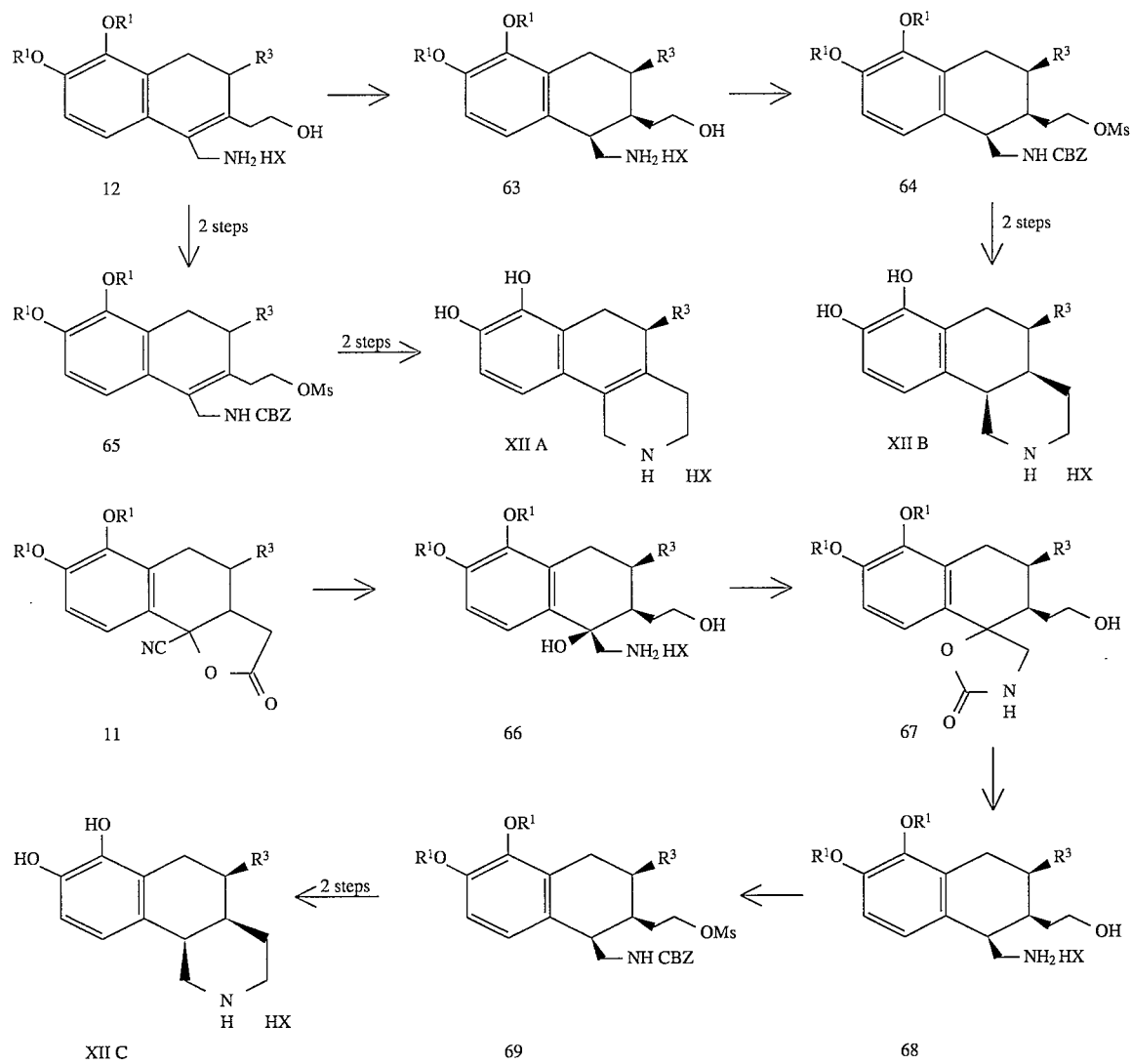
Scheme XIII
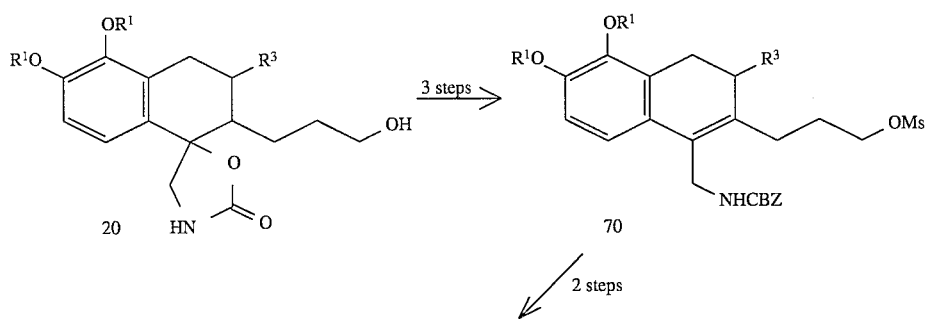

-continued
Scheme XIII
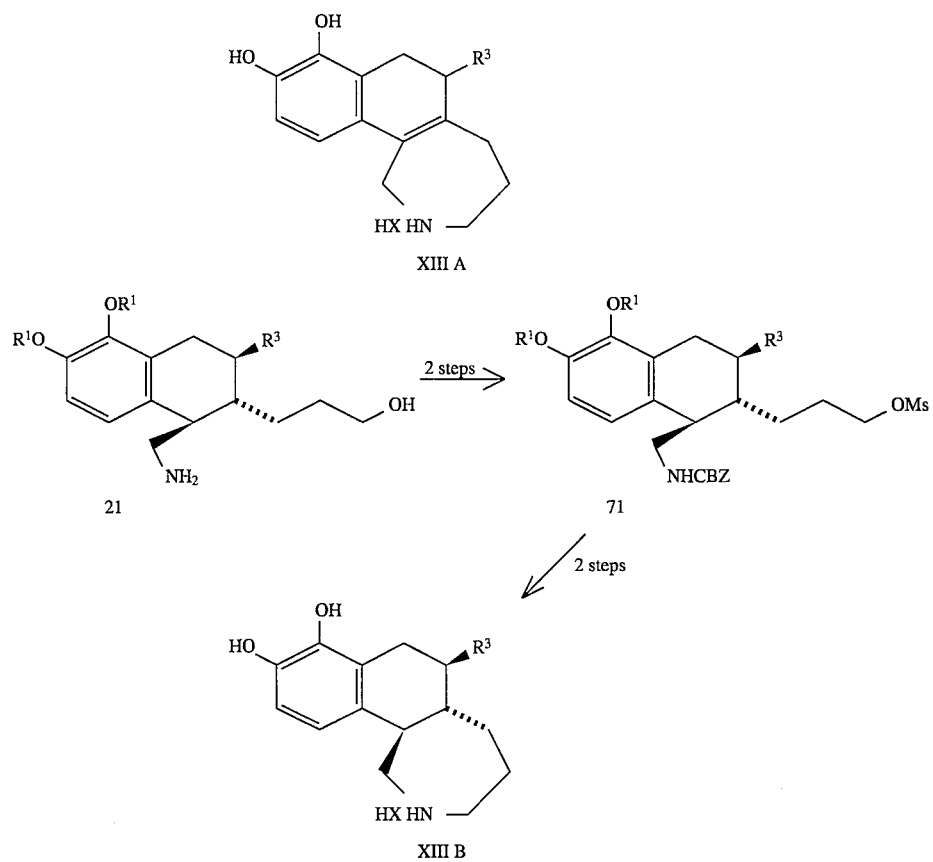
Scheme XIV
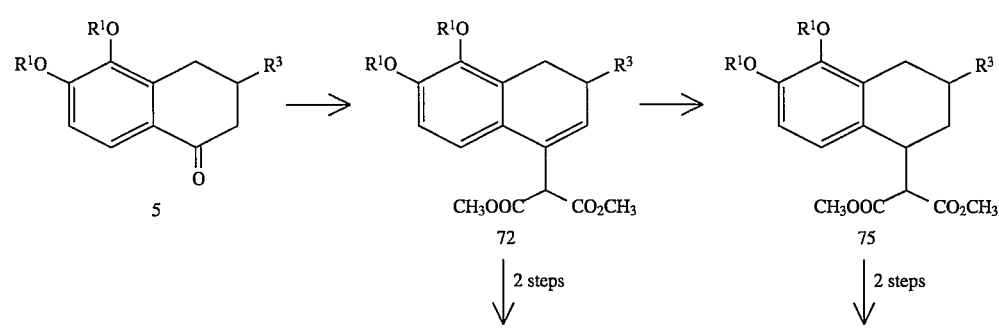

-continued
Scheme XIV
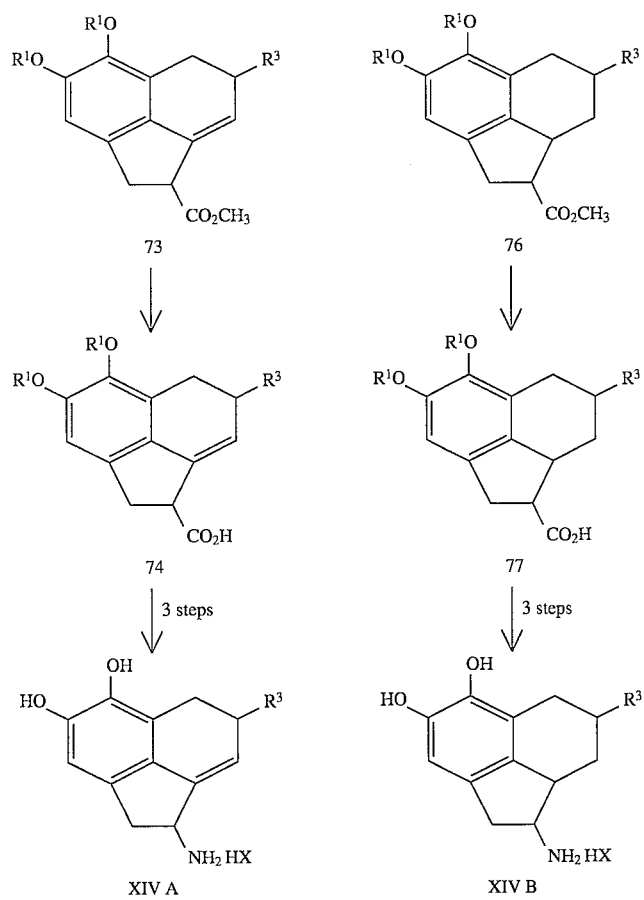
Scheme XV
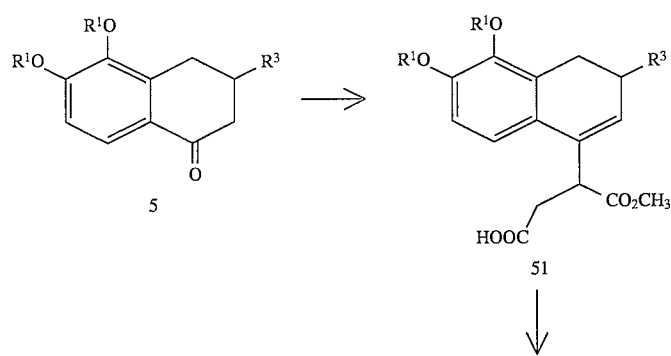

5,591,884
61
-continued
Scheme XV
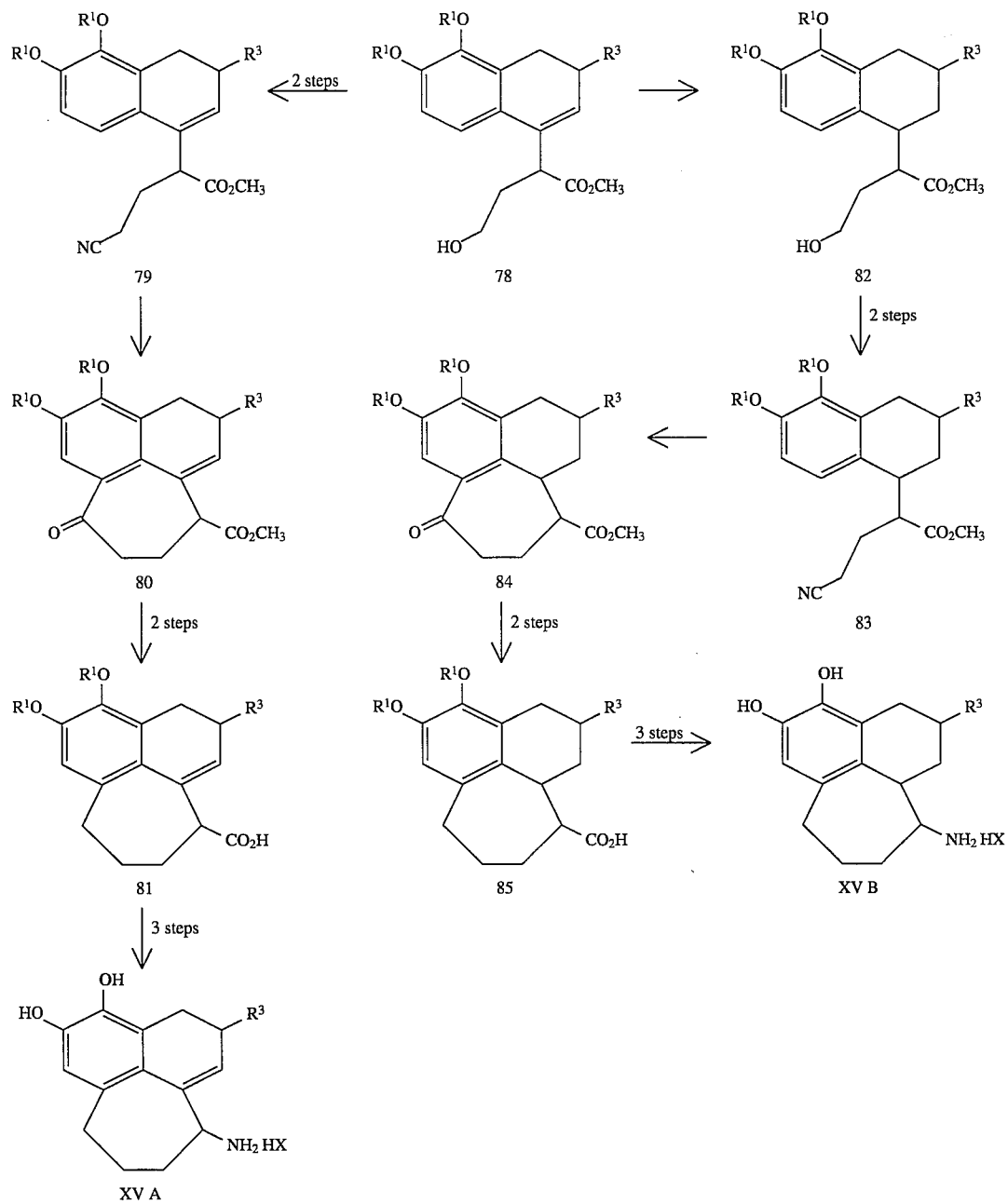
Scheme XVIA
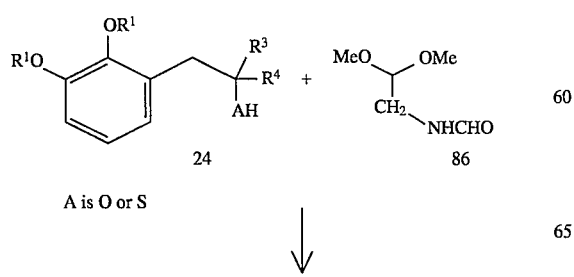
A is O or S
-continued
Scheme XVIA
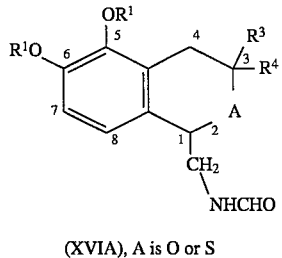
(XVIA), A is O or S

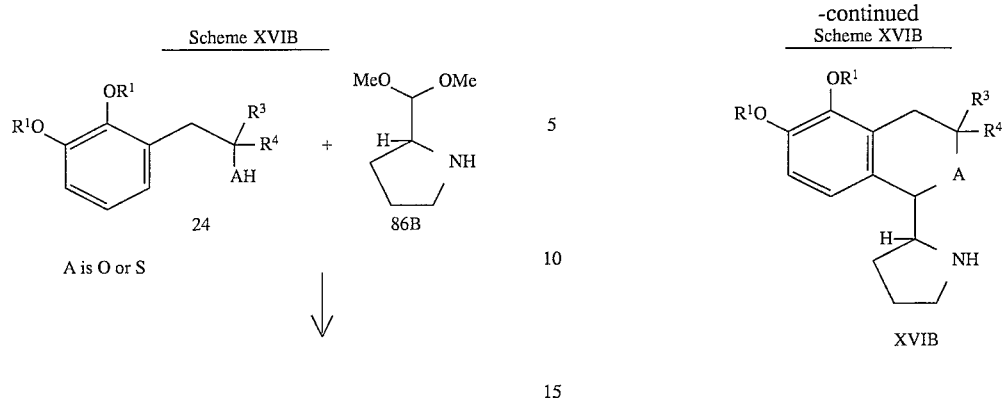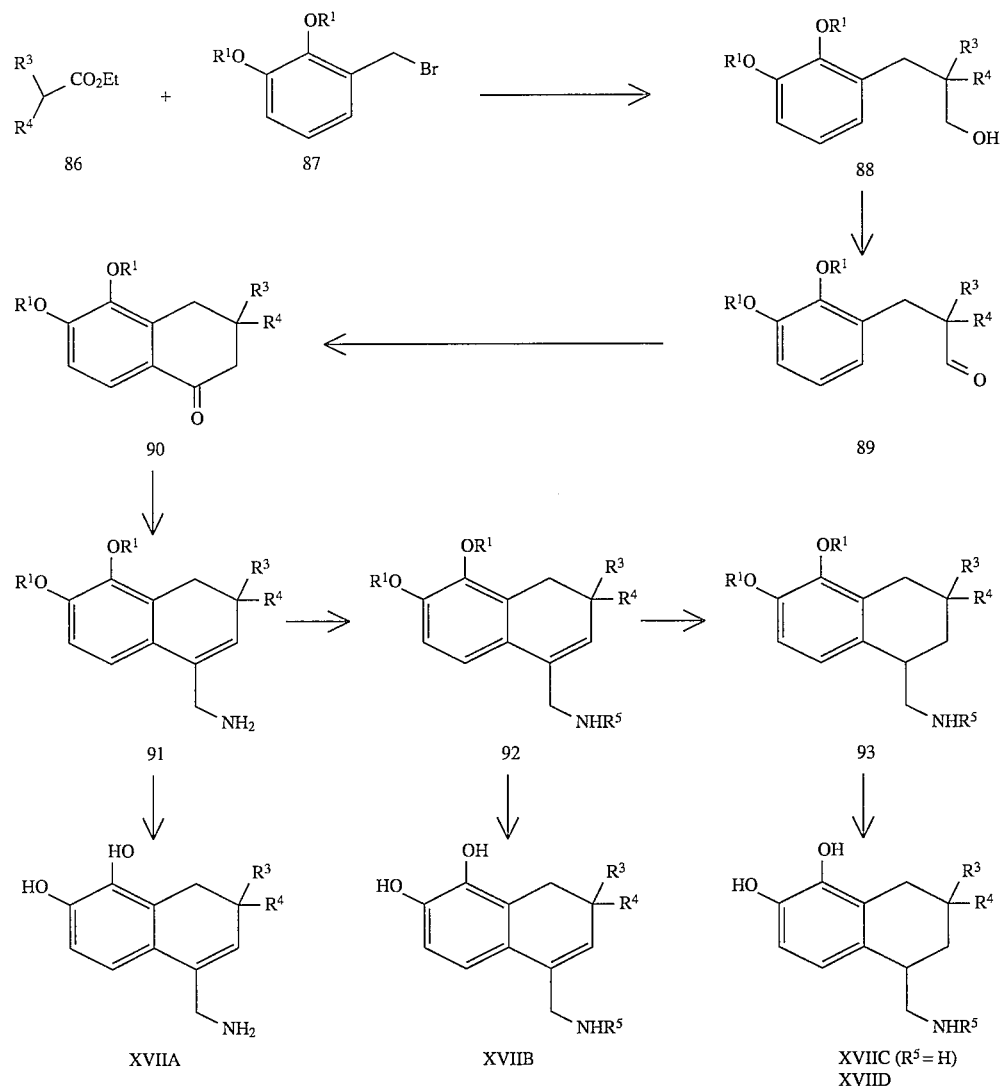

Scheme XVIII

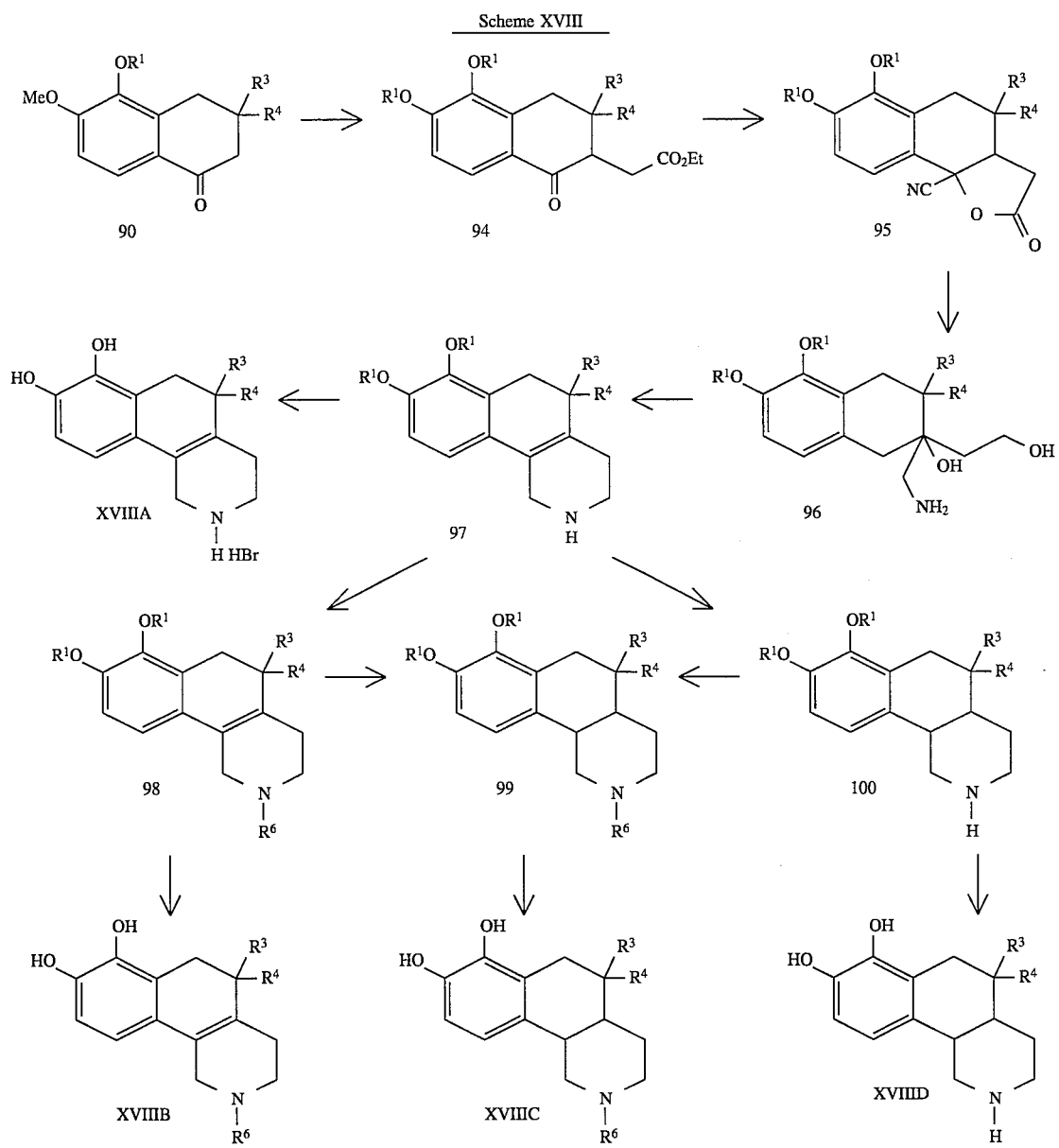

The foregoing may be better understood by reference to the following examples, which are provided for the illustration and not the limitation of the invention.

EXAMPLE 1

5,6-Dimethoxy-3-phenyl-1,2,3,4-tetrahydronaphthalene-1-one

Method A

Step 1: (E,Z)-3-(2',3'-Dimethoxyphenyl)-2-phenylpropenoic acid

A solution of 202 g (1.21 mol) of 2,3-dimethoxybenzaldehyde (commercially available from Aldrich Chemical Co.), 200 g (1.47 mol) of phenyl acetic acid (commercially available from Aldrich Chemical Co.), 600 mL of acetic anhydride and 204 mL (1.46 mol) of triethylamine (TEA) was heated at reflux temperature for 24 h. The reaction mixture was allowed to cool to ambient temperature and 1 L of water was added, followed by the addition of 2 L of ethyl acetate and another 4 L of water. The layers were separated and the organic layer was extracted with saturated aqueous sodium bicarbonate solution. The combined aqueous layers were acidified with concentrated hydrochloric acid and extracted with 4 L of ethyl acetate. The ethyl acetate solution was dried over anhydrous magnesium sulfate, filtered and concentrated in vacuo to give 250 g (72% yield) of the title compound as a 30/70 mixture of the E and Z isomers, m.p. 115°–160° C.; DCI MS: 285 (M+H)$^+$, 302 (M+NH$_4$)$^+$.

Step 2: 3-(2',3'-Dimethoxyphenyl)-2-phenylpropanol

A solution of 15 g (395 mmol) of lithium aluminum hydride (LAH) in 500 mL of tetrahydrofuran (THF) was cooled to 0° C. A solution of (E,Z)-3-(2',3'-dimethoxyphenyl)-2-phenylpropenoic acid (50 g, 176 mmol), from step 1, in 100 mL of THF was added to the LAH solution dropwise over a 30 min period. The reaction mixture was heated at reflux temperature for 2 h and then cooled to 0° C. The reaction was quenched by the sequential addition of 15 mL of water, 15 mL of 15% aqueous sodium hydroxide solution and 45 mL of water. The precipitate was filtered and the filtrate concentrated in vacuo to give 46.6 g (97% yield) of the title compound as an oil; $^1$H NMR (CDCl$_3$) δ: 1.8–0.19 (m, 1H), 2.1–2.2 (m, 1H), 2.7–2.95 (m, 1H), 3.0–3.15 (m, 2H), 3.7–3.8 (m, 1H), 3.8 (s, 3H), 3.83 (s,3H), 6.63 (d, 1H), 6.75 (d, 1H), 6.9 (t, 1H), 7.15–7.4 (m, 5H).

Step 3: 3-(2',3'-Dimethoxyphenyl)-2-phenylpropane 1-methanesulfonate 3-(2',3'-Dimethoxyphenyl)-2-phenylpropanol (41.5 g, 152 mmol), from step 2, and 30.5 g (301 mmol) of TEA were dissolved in 300 mL of THF. Methanesulfonyl chloride (34.5 g, 301 mmol) was added slowly to this solution at 0° C. The reaction mixture was allowed to warm to ambient temperature. After stirring the reaction mixture for 1 h at ambient temperature, it was diluted with 300 mL of diethyl ether and washed with water, dried over anhydrous magnesium sulfate, filtered and concentrated to give 40.8 g (76% yield) of 3-(2',3'-dimethoxyphenyl)-2-phenylpropane 1-methanesulfonate as an oil: $^1$H NMR (CDCl$_3$) δ: 2.7 (s, 3H), 2.96 (dd, 1H), 3.1 (dd, 1H), 3.35–3.45 (m, 1H), 3.78 (s, 3H), 3.82 (s, 3H), 4.35 (m, 2H), 6.62 (dd, 1H), 6.77 (dd, 1H), 6.9 (t, 1H), 7.2–7.35 (m, 5H).

Step 4: 4-(2',3'-Dimethoxylphenyl)-3-phenylbutanenitrile 3-(2',3'-Dimethoxyphenyl)2-phenylpropane 1-methanesulfonate (40.5 g, 116 mmol), from step 3, and 17 g (347 mmol) of sodium cyanide were dissolved in 100 mL of dimethyl sulfoxide (DMSO) and the resultant solution was heated to 80° C. After being stirred at 80° C. for 18 h, the reaction mixture was allowed to cool to ambient temperature, diluted with ethyl acetate and washed sequentially with water and brine. The solvents were removed in vacuo to give 25 g (77% yield) of the title compound as an oil; $^1$H NMR (CDCl$_3$) δ: 2.56 (d, 2H), 3.02 (d, 1H), 3.05 (d, 1H), 3.25–3.35 (m, 1H), 3.72 (s, 3H), 3.75 (s, 3H), 6.65 (dd, 1H), 6.8 (dd, 1H), 6.93 (t, 1H), 7.2–7.4 (m, 5H).

Step 5: 4-(2',3'-Dimethoxyphenyl)-3-phenylbutyric acid 4-(2',3'-Dimethoxyphenyl)-3-phenylbutanenitrile (20 g, 71 mmol), from Step 4, was dissolved in 1.5 L of ethanol. Sodium hydroxide (20 g, 0.5 mol) and 200 mL of water were added and the reaction mixture was heated at reflux temperature for 24 h. The solvent was removed in vacuo and 1 L of water plus 1 L of methylene chloride were added to the residue. The layers were separated and the organic layer discarded. The aqueous layer was acidified with concentrated hydrochloric acid and extracted with 3 L of ethyl acetate. The ethyl acetate solution was dried over anhydrous sodium sulfate, filtered and concentrated in vacuo to give 21 g (98% yield) of the title compound as an oil; $^1$H NMR (CDCl$_3$) δ: 2.6–2.7 (m, 2H), 2.9 (d, 2H), 3.4–3.5 (m, 1H), 3.72 (s, 3H), 3.82 (s, 3H), 6.6 (dd, 1H), 6.73 (dd, 1H), 6.88 (t, 1H), 7.1–7.3 (m, 5H).

Step 6: 5,6-Dimethoxy-3-phenyl-1,2,3,4-tetrahydronaphthalen-1-one 4-(2',3'-Dimethoxyphenyl)-3-phenylbutyric acid (37 g, 123 mmol), from Step 5, was added dropwise to 200 g of polyphosphoric acid heated to 100° C. The resultant mixture was stirred and heated at 100° C. for 0.25 h. A mixture of 100 g of ice and 200 mL of water was added to the reaction mixture. The precipitate which formed was filtered, washed with 3×75 mL of water and dissolved in 300 mL of methylene chloride. The methylene chloride solution was dried over anhydrous magnesium sulfate, filtered and concentrated to give 28 g (81% yield) of 5,6-dimethoxy-3-phenyl-1,2,3,4-tetrahydronaphthalen-1 -one, m.p; 127°–128° C.; $^1$H NMR (CDCl$_3$) δ: 2.75–3.0 (m, 3H), 3.3–3.5 (m, 2H), 3.8 (s, 3H), 3.95 (s, 3H), 6.93 (d, 1H), 7.25–7.4 (m, 5H), 7.9 (d, 1H).

Method B

Step 1: 2-(2',3'-Dimethoxyphenyl)-1,3-dithiane

A solution of 49.5 g (298 mmol) of 2,3-dimethoxybenzaldehyde and 48.4 g (447 mmol) of propane-1,3-dithiol in 800 mL of methylene chloride was cooled to 0° C. Boron trifluoride etherate (7.5 mL, 61 mmol) was added dropwise to the cooled solution and the reaction mixture was stirred at 0° C. for 0.5 h, then at ambient temperature for 18 h. The methylene chloride solution was washed with 2×200 mL of 10% aqueous sodium hydroxide solution, 200 mL of water and 100 mL of brine, dried over anhydrous sodium sulfate and concentrated in vacuo to give 75 g (98% yield) of 2-(2',3'-dimethoxyphenyl)-1,3-dithiane, m.p. 119°–120° C.; $^1$H NMR (CDCl$_3$) δ: 1.8–2.0 (m, 1H), 2.1–2.25 (m, 1H), 2.86 (t,1H) 2.91 (t, 1H), 3.05–3.2 (m, 2H), 3.83 (s, 3H), 3.91 (s, 3H), 5.68 (s, 1H), 6.86 (dd, 1H), 7.07 (t, 1H), 7.19 (dd, 1H).

Step 2: Ethyl 4-(2',3'-dimethoxyphenyl)-4-(1",3"-dithiane)-3-phenylbutyrate

A solution of 2-(2',3'-dimethoxyphenyl)-1,3-dithiane (57 g, 222 mmol), from Step 1, in 273 mL of dry THF was cooled to −78° C. in a dry ice/acetone bath. To this solution was added 92.2 mL of a 2.5M solution of n-butyl lithium in hexane. After the addition was complete the reaction mixture was stirred for 0.75 h at −78° C. 1,3-Dimethyl-2-imidazolidinone (75 mL, 686 mmol), commercially available from Aldrich Chemical Company, was added to the reaction mixture in one portion, followed by 39 g (221 retool) of ethyl cinnamate (commercially available from Aldrich Chemical Company) added dropwise. The reaction mixture was stirred for 1 h at −78° C. then quenched with 50 mL of 10% aqueous acetic acid and allowed to warm to 0° C. The reaction mixture was diluted with 150 mL of diethyl ether and the layers separated. The organic layer was washed with 2×100 mL of saturated aqueous sodium bicarbonate solution, 100 mL of water and 100 mL of brine, dried over anhydrous magnesium sulfate, filtered and concentrated to give a crude oily product. The crude product was crystallized from ethyl acetate/hexane to give 32 g (48% yield) of the title compound, m.p. 125°–126° C. A second crop of crystals yielded an additional 11 g (total yield 59%) of ethyl 4-(2',3'-dimethoxyphenyl)-4-(1",3"-dithiane)-3-phenylbutyrate, m.p. 124.5°–125° C.; $^1$H NMR (CDCl$_3$) δ: 0.8 (t, 3H), 1.75–1.9 (m, 2H), 2.5–2.85 (m, 4H), 3.05–3.25 (m, 2H), 3.7–3.95 (m, 2H), 3.88 (s, 3H), 4.0 (s, 3H), 4.45–4.5 (m, 1H), 6.8–6.9 (m, 2H), 7.0–7.4 (m, 6H).

Step 3: Ethyl 4-(2',3'-dimethoxyphenyl)-3-phenylbutyrate

Ethyl 4-(2',3'-dimethoxyphenyl)-4-(1",3"-dithiane)-3-phenylbutyrate (14.5 g, 39 mmol), from Step 2, and 145 g Raney nickel and 300 mL of absolute ethanol were mixed together and heated at reflux temperature under 1 atmosphere of hydrogen for 3.25 h. The stirring was stopped and the mixture was allowed to cool slightly before the solvent was decanted from the catalyst. An additional 300 mL of absolute ethanol was added to the catalyst and the mixture stirred and heated to reflux. The stirring was again stopped and the reaction mixture was allowed to cool slightly before the solvent was decanted from the catalyst. The combined supernatants were filtered through Celite® filter aid and concentrated in vacuo to give 10.8 g (97% yield) of ethyl 4-(2',3'-dimethoxyphenyl)-3-phenylbutyrate as a clear oil; $^1$H NMR (CDCl$_3$) δ: 1.11 (t, 3H), 3.07 (dd, 1H), 3.35 (dd, 1H), 3.81 (s, 3H), 3.84 (s, 3H), 3.9–4.1 (m, 3H), 6.65 (dd, 1H), 6.77 (dd, 1H), 6.88 (t, 1H), 7.2–7.4 (m, 5H).

Step 4: 4-(2',3'-Dimethoxyphenyl)-3-phenylbutyric acid

Ethyl 4-(2',3'-dimethoxyphenyl)-3-phenylbutyrate (40.3 g, 123 mmol), from Step 3, was dissolved in 400 mL of methanol and 62 mL of 3M aqueous sodium hydroxide solution was added in one portion. The reaction mixture was stirred at ambient temperature for 18 h. The reaction mixture was concentrated and the residue was partitioned between 300 mL of diethyl ether and 200 mL of water. The layers were separated and the aqueous layer was adjusted to pH 6 with 6M aqueous hydrochloric acid solution and extracted with 3×200 mL of diethyl ether. The organic layers were combined, washed with brine, dried over anhydrous magnesium sulfate, filtered and concentrated in vacuo to give 37 g (100% yield) of the title compound as a colorless oil. The $^1$H NMR spectrum was identical to the spectrum reported for the product of Step 5 of Method A, Example 1.

Step 5: 5,6-Dimethoxy-3-phenyl-1,2,3,4-tetrahydronaphthalen-1-one 4-(2',3'-Dimethoxyphenyl)-3-phenylbutyric acid (13.3 g, 44.3 mmol), from Step 4, was treated with 14 mL (216 mmol) of methanesulfonic acid and 200 mL of trifluoroacetic acid at 60° C. for 1.5 h. After cooling the reaction mixture, the trifluoroacetic acid was removed in vacuo and ice water was added to the residue. Methylene chloride was added and the layers were separated. The organic layer was washed with 1N aqueous sodium hydroxide solution, water and brine, dried over anhydrous magnesium sulfate, filtered and concentrated under reduced pressure. The residue was recrystallized three times from methanol to give 9.6 g (77% yield) of 5,6-dimethoxy-3-phenyl-1,2,3,4-tetrahydronaphthalen-1-one, m.p. 126°–128° C.; $^1$H NMR spectrum was identical to the spectrum reported for the product of Step 6 of Method A, Example 1.

EXAMPLE 2

1-Aminomethyl-5,6-dihydroxy-3-phenyl-3,4-dihydronaphthalene

Step 1: 1-Aminomethyl-5,6-dimethoxy-1-hydroxy-3-phenyl-1,2,3,4-tetrahydronaphthalene 5,6-Dimethoxy-3-phenyl-1,2,3,4-tetrahydronaphthalen-1-one (14.6 g, 51.7 mmol), from Example 1, 24 mL of acetonitrile, 10.3 g (104 mmol) of trimethylsilylcyanide, commercially available from Aldrich Chemical Company, and 100 mg of aluminum chloride were mixed together and heated at reflux temperature for 2.5 h. The reaction mixture was cooled and concentrated. The residue was added dropwise to a solution of 4.3 g (113 mmol) of lithium aluminum hydride in 101 mL of diethyl ether. After the reaction mixture was heated at reflux temperature for 2.5 h, 4.3 mL of water was added dropwise, followed by 4.3 mL of 15% aqueous sodium hydroxide solution, followed by a second 4.3 mL of water. The reaction mixture was stirred until a granular precipitate formed. The solid was filtered and washed with 30×80 mL of methylene chloride. The filtrate was concentrated and the resultant solid was triturated with ethyl acetate/hexane to give 11.9 g (73% yield) of the title compound, m.p. 175°–176° C.; $^1$H NMR (d$_6$-DMSO) δ: 2.03 (t, 1H), 2.28 (dt, 1H), 2.65 (dd, 1H), 2.83 (dd, 1H), 2.95–3.1 (m, 2H), 3.28 (dd, 1H), 3.75 (s, 3H), 3.86 (s, 3H), 6.87 (d, 1H), 7.2–7.4 (m, 6H).

Step 2: 1-Aminomethyl-5,6-dimethoxy-3-phenyl-3,4-dihydronaphthalene hydrochloride 1-Aminomethyl-5,6-dimethoxy-1-hydroxy-3-phenyl-1,2,3,4-tetrahydronaphthalene (11.5 g, 37 mmol), from Step 1, was heated at reflux temperature in 300 mL of isopropyl alcohol saturated with hydrochloric acid for 2 h. The resultant solution was concentrated and the solid residue was triturated with hot toluene to give 10.6 g (98% yield) of 1-aminomethyl-5,6-dimethoxy-3-phenyl-3,4-dihydronaphthalene hydrochloride, m.p. 189.5°–190° C.; $^1$H NMR (d$_6$-DMSO) δ: 2.78 (dd, 1H), 3.11 (dd, 1H), 3.2–3.4 (m, 2H+H$_2$O), 3.6 (s, 3H), 3.81 (s, 3H), 3.93 (d, 1H), 6.1 (d, 1H), 6.93 (d, 1H), 7.12 (d, 1H), 7.2–7.4 (m, 5H).

Step 3: 1-Aminomethyl-5,6-dihydroxy-3-phenyl-3,4-dihydronaphthalene hydrobromide (EXAMPLE 2A)

1-Aminomethyl-5,6-dimethoxy-3-phenyl-3,4-dihydronaphthalene hydrochloride (6.0 g, 20.2 mmol), from Step 2, was suspended in 200 mL of methylene chloride and boron tribromide (90.5 mL of 1M solution of BBr$_3$ in methylene chloride) was added dropwise while the reaction mixture was being cooled (to −78° C.) in a dry ice/acetone bath. The reaction mixture was warmed to 0° C. and stirred for 0.5 h, then again cooled to −78° C. in a dry ice/acetone bath. Methanol (50 mL) was added dropwise to the reaction mixture, which was allowed to warm to ambient temperature then concentrated in vacuo. Methanol was added to the residue and the solution was reconcentrated. This residue was dissolved in a small amount of methanol and the methanol solution was added to 700 mL of diethyl ether. The precipitate which formed was filtered, washed with diethyl ether and recrystallized from methanol/ether to give 2.5 g (45% yield) of the title compound, m.p. 223°–225° C. $^1$H NMR (d$_6$-DMSO) δ: 2.68 (dd, 1H), 3.09 (dd, 1H), 3.6–3.7 (m, 1H), 3.9 (s, 2H), 5.97 (d, 1H), 6.69 (m, 2H), 7.2–7.35 (m, 5H), 8.1 (br s, 3H), 8.4 (s, 1H), 9.5 (s, 1H).

Step 4: 1-Aminomethyl-5,6-dihydroxy-3-phenyl-3,4-dihydronaphthalene hydrochloride (Example 2B)

A slurry of 10 g (25 mmol) of 1-aminomethyl-5,6-dimethoxy-3-phenyl-3,4-dihydronaphthalene hydrochloride, from Step 2, in 150 mL of 1,2-dichloroethane was cooled to 10° C. under a nitrogen atmosphere. Boron trichloride was passed through the reaction mixture until 27 g (230 mmol) had been added. The reaction mixture was allowed to warm to ambient temperature and stirred for 18 h. The reaction mixture was then cooled in ice and 100 mL of methanol was added dropwise. The reaction mixture was again allowed to warm to ambient temperature and concentrated in vacuo. Twice, 500 mL portions of methanol were added to the residue and it was reconcentrated. The resultant foam was dissolved in 40 mL of ethanol, filtered and the solution was treated with 40 mL of methylene chloride and 80 mL of heptane. Off-white crystals of 1-aminomethyl-5,6-dihydroxy-3-phenyl-3,4-dihydronaphthalene hydrochloride (5.1 g, 56% yield) were collected by filtration, m.p. 204°–205° C. The $^1$H NMR spectrum was identical to the spectrum for the product of Example 2A.

EXAMPLE 3

5.6-Bis(acetoxy)-1-aminomethyl-3-phenyl-3,4-dihydronaphthalene hydrochloride

A suspension of 7.6 g (25 mmol) of 1-aminomethyl-5,6-dihydroxy-3-phenyl-3,4-dihydronaphthalene hydrochloride (Example 2B) in 400 mL of acetic anhydride saturated with anhydrous hydrogen chloride was stirred at ambient temperature for 48 h. Approximately 2 L of diethyl ether was added and a solid was collected by filtration and washed with diethyl ether. Crystallization of the crude material (6.7 g) was achieved by dissolving the powder in 400 mL of hot ethanol, adding 100 mL of water, filtering the solution hot and allowing it to cool. The white crystals which formed were filtered and dried to give 2.8 g (29% yield) of 5,6-bis(acetoxy)-1-aminomethyl-3-phenyl-3,4-dihydronaphthalene hydrochloride, m.p. 207°–208° C. $^1$H NMR ($d_6$-DMSO) δ: 2.28 (s, 6H), 2.62 (dd, 1H), 2.95 (dd, 1H), 3.7–3.8 (m, 1H), 3.97 (s, 2H), 6.25 (d, 1H), 7.19 (d, 1H), 7.2–7.4 (m, 6H), 8.41 (br s, 3H).

EXAMPLE 4

5,6-Bis(acetoxy)-1-(alanyl-alanyl)aminomethyl-3-phenyl-3,4-dihydronaphthalene hydrochloride (general procedure for preparation of amino prodrugs)

Step 1: 5,6-Bis(acetoxy)-1-(N-t-butoxycarbonyl-alanyl-alanyl)aminomethyl-3-phenyl-3,4-dihydronaphthalene N-t-Butoxycarbonyl-alanyl-alanine (BocAla-Ala) (2.01 g, 7.74 mmol) was added to a stirred solution of 1-aminomethyl-5,6-bis(acetoxy)-3-phenyl-3,4-dihydronaphthalene hydrochloride (3 g, 7.74 mmol), the product of Example 3, in 35 mL of DMF. The resultant solution was cooled to 0° C. To the cold solution was added 1.56 g (8.13 mmol) of 1-(3-dimethylaminopropyl)-3-ethylcarbodiimide hydrochloride (EDCI), followed approximately 10 minutes later by 1.1 g (8.13 mmol) of 1-hydroxybenzotriazole hydrate (HOBT) and, after allowing the HOBT to dissolve, by 1.8 g (16 mmol) of 4-methylmorpholine (NMM). The resultant solution was stirred for 3 h at 0° C. and then stirred overnight at ambient temperature. The reaction mixture was then diluted with 100 mL of water and the resultant milky mixture was extracted with 3×75 mL of ethyl acetate. The combined organic layers were washed successively with 50 mL of 1M aqueous phosphoric acid solution, 50 mL of saturated aqueous sodium bicarbonate solution, 2×50 mL of water and 50 mL of brine. The organic layer was then dried over anhydrous magnesium sulfate, filtered and concentrated in vacuo to a light yellow colored foam. The foam (5.06 g) was purified by flash chromatography using $C_{18}$ODS ($C_{18}$-octadecylsilane) on silica as the solid phase and a 50% solution of 1% aqueous trifluoroacetic acid (TFA) in acetonitrile as the eluent to give 2.03 g (44% yield) of the title compound as a light yellow colored solid, m.p. 114°–116° C.; $^1$H NMR (CDCl$_3$) δ: 1.23 (q, 3H), 1.35 (q, 3H), 1.42 (s, 9H), 2.23 (s, 3H), 2.28 (s, 3H), 2.70 (m, 1H), 2.95 (dd, 1H), 3.68 (m, 1H), 4.05 (q, 1H), 4.2–4.47 (m, 3H), 6.01 (d, 1H), 7.04 (d, 1H), 7.17 (d, 1H), 7.26 (m, 5H).

Step 2: 5,6-Bis(acetoxy)-1-(alanyl-alanyl)aminomethyl-3-phenyl-3,4-dihydronaphthalene hydrochloride 5,6-Bis(acetoxy)-1-(N-t-butoxycarbonyl-alanyl-alanyl)aminomethyl-3-phenyl-3,4-dihydronaphthal hydrochloride (2.00 g, 3.36 mmol) from Step 1 was dissolved in 25 mL of diethyl ether. The resultant solution was cooled and saturated with hydrogen chloride. The solution was stirred at ambient temperature for 3 h. The precipitate was filtered and washed thoroughly with dry diethyl ether. The solid was dried overnight at 60° C. in vacuo to give 1.69 g (95% yield) of the title compound as an off-white solid, m.p. 145°–161° C. (dec); $^1$H NMR (CDCl$_3$) δ: 1.35 (dd, 3H), 1.41 (m, 3H), 2.23 (s, 3H), 2.26 (s, 3H), 2.70 (dt, 1H), 2.95 (dd, 1H), 3.69 (br s, 1H), 3.89 (dq, 1H), 4.17–4.45 (m, 3H), 6.11 (d, 1H), 7.0 (d, 1H), 7.25 (m, 6H), 8.27 (m, 1H). Analysis calculated for $C_{27}H_{33}N_3O_6$+1.3HCl: C, 59.73; H, 6.37; N, 7.74. Found: C, 59.94; H, 6.08; N, 7.64.

EXAMPLE 5

1-Aminomethyl-5,6-bis(trimethylacetoxy)-3-phenyl-3,4-dihydronaphthalene hydrochloride Step 1: N-t-Butyloxycarbonyl-1-aminomethyl-5,6-dihydroxy-3-phenyl-3,4-dihydronaphthalene Triethylamine (7 mL) was added to a solution of 15 g (56 mmol) of 1-aminomethyl-5,6-dihydroxy-3-phenyl-3,4-dihydronaphthalene hydrochloride, from Example 2 in 100 mL of dimethylformamide (DMF). The solution was cooled to 0° C. and a solution of di-t-butyldicarbonate (18 g, 82.5 mmol) in 50 mL of DMF was added over a period of 1 h. After the addition was complete, 250 mL of water was added to the reaction mixture and it was extracted with ethyl acetate. The combined organic layers from the extraction were washed with 1N hydrochloric acid solution and brine, dried over anhydrous magnesium sulfate, filtered and concentrated in vacuo. The brown residue was triturated with boiling hexanes to give 16.7 g (99% yield) of the title compound as an off-white solid, m.p. 175°–177° C., $^1$H NMR δ: 1.45 (s, 9H), 2.74 (dd, 1H), 3.19 (dd, 1H), 3.6–3.7 (m, 1H), 4.1–4.25 (m, 2H), 4.71 (br s, 1H), 5.4 (br s, 1H), 5.88 (d, 1H), 6.0 (br s, 1H), 6.68 (s, 2H), 7.2–7.35 (m, 5H).

Step 2: N-t-Butyloxycarbonyl-1-aminomethyl-5,6-bis(trimethylacetoxy)-3-phenyl-3,4-dihydronaphthalene N-t-Butyloxycarbonyl-1-aminomethyl-5,6-dihydroxy-3-phenyl-3,4-dihydronaphthalene (3 g, 8.16 mmol), from Step 1, and 11 mL of triethylamine were combined and cooled to 0° C. A solution of trimethylacetyl chloride (2.1 mL, 17 mmol) in 13 mL of dioxane was added to the cooled solution dropwise. The reaction mixture was allowed to warm to ambient temperature and stirred at ambient temperature for 2 h. Water (25 mL) was added to the reaction mixture and the pH was adjusted to 4 with concentrated phosphoric acid. The reaction mixture was extracted with diethyl ether. The combined ether extracts were washed with aqueous saturated sodium bicarbonate solution, water and brine, dried over anhydrous magnesium sulfate, filtered and concentrated in vacuo to give 4.26 g (89% yield) of N-t-butyloxycarbonyl-1-aminomethyl-5,6-bis(trimethylacetoxy)-3-phenyl-3,4-dihydronaphthalene as an off-white solid, m.p. 64°–69° C.; $^1$H NMR (CDCl$_3$) δ: 1.3 (s, 9H), 1.34 (s, 9H), 1.45 (s, 9H), 2.68 (dd, 1H), 2.93 (dd, 1H), 3.6–3.75 (m, 1H), 4.1–4.3 (m, 2H), 4.63 (br s, 1H), 6.03 (d, 1H), 6.98 (d, 1H), 7.15–7.35 (m, 6H).

Step 3: 1-Aminomethyl-5,6-bis(trimethylacetoxy)-3-phenyl-3,4-dihydronaphthalene hydrochloride N-t-Butyloxycarbonyl-1-aminomethyl-5,6-bis(trimethylacetoxy)-3-phenyl-3,4-dihydronaphthalene (14 g, 26 mmol), from Step 2, was dissolved in 75 mL of dioxane and saturated with anhydrous hydrogen chloride. The reaction mixture was stirred for 2 h and concentrated in vacuo. The solid residue was dissolved in a minimum amount of methanol and the methanol solution was added dropwise to an excess amount (500 mL) of diethyl ether. The precipitate was filtered, washed with diethyl ether and dried to give 9.1 g (90% yield) of 1-aminomethyl-5,6-bis(trimethylacetoxy)-3-phenyl-3,4-dihydronaphthalene hydrochloride as a white powder, m.p. 210°–212° C.; $^1$H NMR ($d_6$-DMSO) δ: 1.25 (s, 9H), 1.28 (s, 9H), 2.61 (dd, 1H), 2.89 (dd, 1H), 3.75–3.85 (m, 1H), 3.99 (s, 2H), 6.28 (d, 2H), 7.15 (d, 1H), 7.2–7.35 (m, 5H), 7.37 (d, 1H), 8.37 (br s, 3H).

EXAMPLES 6–15

Following the procedures described in Example 4 using the appropriate aminomethyl compound of formula I with both catechol hydroxyl group protected as shown in the table and the appropriate (D) or (L) amino acid or peptide having the N-terminal amino group protected preferably as a carbamate, and more preferably as the t-butoxycarbonyl derivative, Examples 5–14 were prepared as disclosed below in Table 1.

EXAMPLES 16–34

Following the procedures described in Example 15, replacing the trimethylacetyl chloride with R1–Cl. where R1 is as shown in the table, Examples 16–34 were prepared as disclosed below in Table 1.

TABLE 1

Examples 6–15

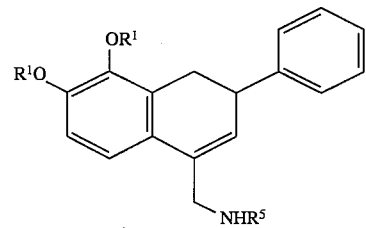

| Ex. # | R1 | R5 | mp °C. | MS[a] (M + H)+ | | C | H | N |
|---|---|---|---|---|---|---|---|---|
| 6 | acetyl | CO₂CH(CH₃)—OCOCH₃ | oil | 499 (M + NH₄)+ | calc: found: | 64.85 64.68 | 5.65 5.99 | 2.91 2.74 |
| 7 | acetyl | γ-L-glutamyl | 142–177 (dec) | 481 | calc: found: | 481.1975[b] 481.1696 | | |
| 8 | acetyl | L-leucyl | 187–192 (dec) | 451 | calc: found: | 62.01 62.39 | 6.30 6.54 | 5.48 5.60 |
| 9 | acetyl | α-L-aspartyl | 150 (dec) | 467 | calc: found: | 57.32 57.44 | 5.33 5.63 | 5.33 5.36 |
| 10 | acetyl | L-alanyl | 150–158 (dec) | 423 | calc: found: | 61.28 61.60 | 5.93 6.03 | 6.15 5.99 |
| 11 | acetyl | D-alanyl | 150–157 (dec) | 423 | calc: found: | 61.06 61.13 | 5.89 6.07 | 6.09 5.94 |
| 12 | acetyl | L-norvalyl | 136 (dec) | 451 | calc: found: | 62.95 62.96 | 6.47 6.50 | 5.79 5.65 |
| 13 | acetyl | L-prolyl | 150–152 (dec) | 449 | calc: found: | 60.31 60.19 | 5.82 5.79 | 5.41 5.51 |
| 14 | acetyl | L-methionyl | 135–142 (dec) | 483 | calc: found: | 59.19 59.14 | 6.00 6.11 | 5.40 5.30 |
| 15 | benzoyl | L-alanyl-L-alanyl | 184–185 (dec) | 618 | calc: found: | 63.55 63.54 | 5.00 4.96 | 5.76 5.72 |
| 16 | benzoyl | H | 173–182 | | calc: found: | * see example 16 detail following table | | |
| 17 | butanoyl | H | 145–150 (dec) | 408 | calc: +0.5 H₂O found: | 66.29 65.98 | 6.90 6.80 | 3.09 2.96 |
| 18 | iso-butanoyl | H | na | 408 | calc: +0.2 H₂O found: | 67.09 6 7.04 | 6.85 6.79 | 3.13 3.11 |
| 19 | methyl succinoyl | H | 116–118 | 496 | calc: found: | 60.96 60.87 | 5.68 5.66 | 2.63 2.72 |
| 20 | propionyl | H | 111–112 | 380 | calc:+ 1.75H₂O found: | 62.20 62.20 | 6.74 6.74 | 2.57 2.26 |
| 21 | —CO—NH-phenyl | H | na | na | calc: found: | na | | |
| 22 | acetyl[c] | H | 252 | 354 | calc: +0.5 H₂O found: | 64.69 63.36 | 6.20 6.10 | 3.59 3.48 |
| 23 | methoxy-carbonyl | H | 135–138 | 384 | calc: +0.5 H₂O found: | 58.81 58.64 | 5.40 5.25 | 3.27 3.25 |
| 24 | isobutyl succinoyl | H | 112–114 | 552 | calc: +0.1 H₂O found: | 63.12 62.74 | 6.53 6.50 | 2.37 2.30 |
| 25 | dimethyl- | H | 100–103 | 410 | calc:+1.1 | 61.95 | 6.33 | 9.42 |

TABLE 1-continued

Examples 6–15

[Structure: naphthalene derivative with OR¹ groups at 5,6 positions, phenyl substituent, and CH₂NHR⁵ group]

| Ex. # | R1 | R5 | mp °C. | MS[a] (M + H)+ | | C | H | N |
|---|---|---|---|---|---|---|---|---|
| | aminocarbonyl | | | | H₂O +0.3 EtOAc found: | 58.83 | 6.29 | 8.19 |
| 26 | trifluormethyl-sulfonyl | H | 128–130 | 532 | calc:+0.1 C₆H₁₄ found: | 40.18 41.07 | 2.84 2.93 | 2.47 2.50 |
| 27 | beta-alanyl | H | 219 | na | calc: found: na | | | |
| 28 | (1,2-carbonyl) | H | 245 (dec) | 294 | calc: +0.1 H₂O found: | 65.56 65.08 | 4.89 4.91 | 4.25 4.17 |
| 29 | ethoxycarbonyl | H | 130–132 | 412 | calc: found: | 61.06 61.21 | 5.90 5.97 | 3.10 3.05 |
| 30 | —CO—NH-benzyl | H | 214–215 | 534 | calc: +0.5 H₂O found: | 69.53 68.11 | 5.66 5.57 | 7.37 7.18 |
| 31 | —CO—NH-methyl | H | 205–206 | 382 | calc: found: | 60.36 59.08 | 5.79 5.93 | 10.06 9.23 |
| 32 | acetyl | CO—O-t-butyl | 161–162 | 469 | calc: found: | 69.16 68.93 | 6.47 6.45 | 3.10 3.10 |
| 33 | p-nitrobenzoyl | H | 150 (dec) | 566 | calc: found: | 61.84 61.55 | 4.01 4.04 | 6.98 6.86 |
| 34 | p-methoxybenzoyl | H | 159–161 | 536 | calc: +1 H₂O found: | 67.17 67.16 | 5.47 5.24 | 2.37 2.35 | a. Mass spectral M/Z (DCI/NH₃)
b. High Resolution mass spectral analysis
c. starting from compound of Example 35 instead of Example 5.
d. structure confirmed by NMR data

EXAMPLE 16

1-Aminomethyl-5,6-bis(benzoyloxy)-3-phenyl-3,4-dihydronaphthalene hydrochloride Following the procedures described in Example 5, replacing methylacetyl chloride with benzoyl chloride and 1-aminomethyl-5,6-dihydroxy-3-phenyl-3,4-dihydronaphthalene hydrochloride with the compound of Example 15, the title compound was prepared. m.p. 173°–182° C.; ¹H NMR (CD₃OD) δ: 2.88 (t, 1H), 3.05 (dd, 1H), 3.65–3.8 (m, 2H), 4.0–4.1 (br s, 1H+CH3OH), 6.35 (d, 1H), 7.05–7.35 (m, 10H), 7.35–7.55 (m, 3H), 7.9–8.0 (m, 4H), 8.5–8.65 (br s, 3H).

EXAMPLE 35

[1,3-cis]1-Aminomethyl-5,6-dihydroxy-3-phenyl-1,2,3,4-tetrahydronaphthalene hydrobromide Step 1: [1,3-cis]1-Aminomethyl-5,6-dimethoxy-3-phenyl-1,2,3,4-tetrahydronaphthalene hydrochloride To 0.2 g (0.67 mmol) of 1-aminomethyl-5,6-dimethoxy-3-phenyl-3,4-dihydronaphthalene hydrochloride, from Step 2, of Example 2, was added 0.05 g of 10% palladium supported on carbon. The reaction mixture was sealed under hydrogen and stirred overnight at ambient temperature. The reaction mixture was flushed with nitrogen before it was filtered through Celite® filter aid and washed with 15 mL of absolute ethanol and 15 mL of methylene chloride. The filtrate was concentrated to give 0.2 g (100% yield) of [1,3-cis]1-aminomethyl-5,6-dimethoxy-3-phenyl-1,2,3,4-tetrahydronaphthalene hydrochloride, m.p. 230°–231° C.; ¹H NMR (d₆-DMSO) δ: 2.15–2.25 (m, 1H), 2.5–2.65 (m, 1H), 2.8–2.95 (m, 2H), 3.0–3.1 (m, 1H), 3.1–3.4 (m, 1H), 3.45–3.5 (m, 1H), 3.66 (s, 3H), 3.78 (s, 3H), 6.95 (d, 1H), 7.12 (d, 1H), 7.2–7.3 (m, 1H), 7.35–7.45 (m, 4H), 8.0 (br s, 3H).

Step 2: [1.3-cis]1-Aminomethyl-5,6-dihydroxy-3-phenyl-1,2,3,4-tetrahydronaphthalene hydrobromide

[1,3-cis]1-Aminomethyl-5,6-dimethoxy-3-phenyl-1,2,3,4-tetrahydronaphthalene hydrochloride (0.2 g, 0.67 mmol), from Step 1, was suspended in 13 mL of methylene chloride and the suspension was cooled to −78° C. in a dry ice/ acetone bath. Boron tribromide (3 mL of a 1M solution in methylene chloride, 3 mmol) was added and the reaction mixture was allowed to warm to ambient temperature, kept at ambient temperature for 1.5 h then cooled to −78° C. Methanol (3 mL) was added to the reaction mixture and it was again allowed to warm to ambient temperature then concentrated in vacuo. The residue was redissolved in methanol and reconcentrated. The residue was again redissolved in methanol and the methanol solution was added to a large excess of diethyl ether. The resultant precipitate was filtered and recrystallized from ethanol/diethyl ether to give 0.14 g (64% yield) of the title compound as a white powder, m.p. 256°–259° C.; $^1$H NMR (d$_6$-DMSO) δ: 1.63 (q, 1H), 2.1–2.25 (m, 1H), 2.4–2.5 (m, 1H), 2.75–2.95 (m, 2H), 3.02 (dd, 1H), 3.15–3.3 (m, 1H), 3.4–3.5 (m, 1H), 6.68 (s, 2H), 7.2–7.3 (m, 1H), 7.3–7.4 (m, 4H), 7.8 (br s, 3H), 8.2 (br s, 1H), 9.1 (br s, 1H).

EXAMPLE 36

1-Aminomethyl-3-cyclohexyl-5,6-dihydroxy-3,4-dihydronaphthalene hydrobromide

Step 1: Ethyl 3-cyclohexylpropenoate

Sodium hydride (2.6 g, 108 mmol) was added to 100 mL of THF and 19.8 mL (98.9 mmol) of triethylphosphonoacetate, commercially available from Aldrich Chemical Company, was added dropwise at 0° C. The reaction mixture was stirred for 1 h at ambient temperature and 12.1 mL (99.9 mmol) of cyclohexanecarboxaldehyde, commercially available from Aldrich Chemical Company, was added. The reaction mixture was heated at reflux temperature for 15 min then cooled and filtered. The filtrate was concentrated under reduced pressure and the product was distilled at 140° C. (15 Torr) to give 15.2 g (84% yield) of ethyl 3-cyclohexylpropenoate as a clear liquid; $^1$H NMR (CDCl$_3$) δ: 1.1–1.4 (m, 6H), 1.3 (t, 3H), 1.6–1.8 (m, 5H), 2.05–2.2 (m, 1H), 4.2 (q, 2H), 5.75 (d, 1H), 6.92 (d, 1H).

Step 2: 1-Aminomethyl-3-cyclohexyl-5,6-dimethoxy-3,4-dihydronaphthalene hydrochloride 2-(2',3'-Dimethoxyphenyl)-1,3-dithiane, from Step 1 of Example 1, Method B, and ethyl 3-cyclohexylpropenoate, from Step 1 of this Example, were condensed as described in Step 2 of Example 1, Method B. The adduct was treated with Raney nickel and sodium hydroxide to give the corresponding acid. The acid was cyclized with polyphosphoric acid as described in Step 6 of Example 1, Method A, to give 3-cyclohexyl-5,6-dimethoxy-1,2,3,4-tetrahydronaphthalen-1-one. This ketone was treated with trimethylsilylcyanide in the presence of aluminum chloride and reduced with lithium aluminum hydride as described in Step 1 of Example 2 to give 1-aminomethyl-5,6-dimethoxy-1-hydroxy-3-cyclohexyl-1,2,3,4-tetrahydronaphthalene. The hydroxy group was eliminated by treatment with anhydrous hydrogen chloride in isopropyl alcohol as described in Step 2 of Example 2 to give 1-aminomethyl-3-cyclohexyl-5,6-dimethoxy-3,4-dihydronaphthalene hydrochloride, m.p. 178°–179° C.; $^1$H NMR (d$_6$-DMSO) δ: 1.0–1.4 (m, 7H), 1.5–1.9 (m, 6H), 2.0–2.2 (m, 1H), 2.5 (dd, 1H), 2.7 (dd, 1H), 3.6 (s, 3H), 3.81 (s, 3H), 5.8 (d, 1H), 6.6 (m, 2H).

Step 3: 1-Aminomethyl-3-cyclohexyl-5,6-dihydroxy-3,4-dihydronaphthalene hydrobromide 1-Aminomethyl-3-cyclohexyl-5,6-dimethoxy-3,4-dihydronaphthalene hydrochloride (2.7 g, 8.9 mmol), from Step 2, was dissolved in 72 mL of methylene chloride and cooled to −78° C. Boron tribromide (36 mL of a 1M solution in methylene chloride) was added and the reaction mixture was warmed to 0° C. for 1 h. The reaction mixture was cooled again to −78° C. and 30 mL of methanol was added. After stirring at ambient temperature for 1 h, the reaction mixture was concentrated, diluted with methanol and reconcentrated. The residue was dissolved in methanol and the methanol solution was added dropwise to an excess amount of diethyl ether. The precipitate was filtered and recrystallized from ethanol/ether to give 2.2 g 79% yield) of the title compound, m.p. 212°–213° C.; $^1$H NMR (d$_6$-DMSO) δ: 1.0–1.4 (m, 7H), 1.55–1.9 (m, 6H), 2.05–2.15 (m, 1H), 2.47 (dd, 1H), 2.74 (dd, 1H), 5.83 (d, 1H), 6.60 (m, 2H).

EXAMPLE 37

[1R, 3S]1-Aminomethyl-5,6-dihydroxy-1,2,3,4-tetrahydronaphthalene hydrobromide

Step 1: [1R, 3S]1-Aminomethyl-3-cyclohexyl-5,6-dimethoxy-1,2,3,4-tetrahydronaphthalene hydrochloride 1-Aminomethyl-3-cyclohexyl-5,6-dimethoxy-3,4-dihydronaphthalene hydrochloride (1 g, 3.3 mmol), from Step 2 of Example 36, was dissolved in 20 mL of ethanol and 0.25 g of 10% palladium on carbon was added to the ethanol solution. The reaction mixture was sealed under one atmosphere of hydrogen and shaken at ambient temperature for 24 h. The reaction mixture was filtered to remove the catalyst and concentrated to give 1 g (100% yield) of the title compound. m.p. 282°–283° C.; $^1$H NMR (d$_6$-DMSO) δ: 1.0–1.5 (m, 8H), 1.5–1.9 (m, 5H), 2.0–2.2 (m, 2H), 2.7–3.1 (m, 3H), 3.3–3.4 (m, 1H), 3.8 (s, 3H), 3.9 (s, 3H), 6.4–6.8 (m, 2H).

Step 2: [1R, 3S]1-Aminomethyl-3-cyclohexyl-5,6-dihydroxy-1,2,3,4-tetrahydronaphthalene hydrobromide

[1R, 3S]1-Aminomethyl-3-cyclohexyl-5,6-dimethoxy-1,2,3,4-tetrahydronaphthalene hydrochloride (0.7 g, 2.3 mmol), from Step 1, was suspended in 20 mL of methylene chloride at −78° C. Boron tribromide (9.7 mL of a 1M solution in methylene chloride, 9.7 mmol) was added and the reaction mixture was allowed to warm to ambient temperature. After stirring at ambient temperature for 1 h, the reaction mixture was cooled to −78° C. and 10 mL of methanol was added. The reaction mixture was again allowed to warm to ambient temperature and stirred at ambient temperature for 1 h. The solvent was removed in vacuo and methanol was added to the residue. The methanol solution was concentrated and the residue dissolved in a minimal amount of methanol and added dropwise to a large excess of diethyl ether. The precipitate was filtered and recrystallized from ethanol/diethyl ether to give 0.48 g (65% yield) of [1R, 3S]1-aminomethyl-3-cyclohexyl-5,6-dihydroxy-1,2,3,4-tetrahydronaphthalene hydrobromide, m.p. 203°–204° C.: $^1$H NMR (d$_6$-DMSO) δ: 0.9–1.5 (m, 8H), 1.6–1.9 (m, 5H), 2.0–2.1 (m, 2H), 2.7–3.0 (m, 3H), 3.3–3.4 (m, 1H), 6.5–6.7 (m, 2H).

EXAMPLES 38–43

Following the synthesis outlined in Example 36, using the appropriate aldehyde, Examples 38–43 were made, as their hydrochloride salts, as disclosed in Table 2. The structure of each was continued by melting point (m.p.), elemental analysis and mass spectra as designated. Examples 42 and 43, as disclosed in Table 2, were prepared, using the appropriate aldehyde, following sequentially the procedures described in Examples 37 and 38, as their hydrochloride salts. The structure of each was confirmed by melting point (m.p.), elemental analysis and mass spectra as designated.

TABLE 2

Examples 38–43

| Example # | Compound* | Aldehyde | m.p. °C. | MS** | Elemental Analysis C H N |
|---|---|---|---|---|---|
| 38 | [structure: tetrahydronaphthalene with OH, HO substituents, 3-hydroxyphenyl group, CH₂NH₂·HCl] | 3-methoxybenzaldehyde | 210 | 284 | calc: 54.05 5.20 3.71 +3/4 H₂O Found: 53.95 4.97 3.86 |
| 39 | [structure: tetrahydronaphthalene with OH, HO substituents, 4-hydroxyphenyl group, CH₂NH₂·HCl] | 4-methoxybenzaldehyde | 223–6 | 284 | calc: 55.78 5.01 3.83 +0.1 H₂O Found: 55.64 5.25 3.74 |
| 40 | [structure: tetrahydronaphthalene with OH, HO substituents, 2-naphthyl group, CH₂NH₂·HCl] | 2-naphthaldehyde | >225 | | calc: Found: na*** |
| 41 | [structure: tetrahydronaphthalene with OH, HO substituents, 1-naphthyl group, CH₂NH₂·HCl] | 1-naphthaldehyde | 192–8 | 318 | calc: Found: na*** |
| 42 | [structure: tetrahydronaphthalene with OH, HO substituents, 3-hydroxyphenyl group, CH₂NH₂·HCl] | 3-methoxybenzaldehyde | 250° C. | 286 | calc: 53.13 5.77 3.65 +1 H₂O Found: 52.97 5.53 4.03 |

TABLE 2-continued

Examples 38–43

| Example # | Compound* | Aldehyde | m.p. °C. | MS** | Elemental Analysis C | H | N |
|---|---|---|---|---|---|---|---|
| 43 | [structure: 5,6-dihydroxy-2-(naphthalen-2-yl)-1-aminomethyl-3,4-dihydronaphthalene hydrochloride] | [2-naphthaldehyde] | 190-6 | 320 | calc:<br>Found: na*** | | |

*all compounds 1–3 cis unless indicated otherwise
**DCl MS (M + H)+
***structure confirmed by NMR data

EXAMPLE 44

1-Aminomethyl-5,6-dihydroxy-2-(2'-hydroxy-1'-ethyl)-3-phenyl-3,4-dihydronaphthalene hydrobromide Step 1: 2-(Carboethoxy)methyl-5,6-dimethoxy-3-phenyl-1,2,3,4-tetrahydronaph-thalen-1-one To a solution of 5,6-dimethoxy-3-phenyl-1,2,3,4-tetrahydronaphthalen-1-one (5 g, 17.7 mmol, 1.0 equivalents), the product of Example 1, in 150 mL of dry THF cooled to −78° C., was added 19.5 mL of lithium bis(trimethylsilyl)amide (1M solution in THF, 19.5 mmol, 1.1 equivalent). The resultant solution was stirred at −78° C. for 1 h and then ethyl bromoacetate (2.2 mL, 19.5 mmol, 1.1 equivalent) was added in one portion. The reaction solution was then allowed to warm to ambient temperature and was stirred for 3 h. The reaction was quenched by the addition of 50 mL of saturated ammonium chloride solution. The resultant light yellow colored THF layer was separated and evaporated to an oil. The oil was taken up into 200 mL of methylene chloride and the methylene chloride solution was washed with 2×50 mL of water and 50 mL of brine, dried over anhydrous magnesium sulfate, filtered and concentrated in vacuo. The residue was chromatographed on silica gel eluted with ethyl acetate/hexane (1:6) to give 5.4 g (83% yield) of the title compound as a white solid; $^1$H NMR (CDCl$_3$) δ: 1.2 (t, 3H, J=7.5 Hz), 2.45 (m, 2H), 3.03 (m, 1H), 3.30 (m, 2H), 3.43 (m, 1H), 3.78 (s, 3H), 3.93 (s, 3H), 4.07 (m, 2H), 6.92 (d, 1H, J=9.0 Hz), 7.32 (m, 5H), 7.89 (d, 1H, J=9.0 Hz).

Analysis calculated for C$_{22}$H$_{24}$O$_5$: C, 71.72; H, 6.57. Found: C, 71.39; H, 6.63.

Step 2: 9b-Cyano-6,7-dimethoxy-2-oxo-4-phenyl-2,3,3a,4,5,9b-hexahydronaphtho[1.2b]furan To a solution of 2-(carboethoxy)methyl-5,6-dimethoxy-3-phenyl-1,2,3,4-tetrahydronaphthalen-1-one (1.0 g, 2.7 mmol, 1.0 equivalent) from Step 1, in 10 mL of anhydrous toluene at ambient temperature was added 5.4 mL of diethylaluminum cyanide (1M solution in toluene, 5.4 retool, 2.0 equivalents). The resultant solution was stirred at ambient temperature for 1 h and then poured with vigorous stirring into a mixture of 15 mL of concentrated hydrochloric acid and 70 mL of ice water. The organic layer was diluted with 75 mL of methylene chloride and then separated from the aqueous layer. The organic layer was washed with 25 mL of 2M anhydrous hydrochloric acid solution, 25 mL of water and 25 mL of brine, dried over anhydrous magnesium sulfate, filtered and concentrated to give 1 g (105% crude yield) of the title compound as an oily residue. The crude product was carried on to the next step without purification; $^1$H NMR (CDCl$_3$) δ: 2.45 (d, 1H, J=18.0 Hz), 2.72 (m, 2H), 3.05 (m, 1H), 3.23 (m, 1H), 3.37 (m, 1H), 3.79 (s, 3H), 3.94 (s, 3H), 7.0 (d, 1H), 7.30 (m, 5H), 7.52 (d, 1H, J=9.0 Hz).

Step 3: 1-Aminomethyl-5,6-dimethoxy-2-(2'-hydroxy-1'-ethyl)-3-phenyl-3,4-dihydronaphthalene hydrochloride To a stirred solution of 9b-cyano-6,7-dimethoxy-2-oxo-4-phenyl-2,3,3a,4,5,9b-hexahydronaphtho[1,2b]furan (1.0 g, 2.86 mmol, 1.0 equivalent); from Step 2, in 30 mL of anhydrous THF, was added lithium aluminum hydride (0.22 g, 5.7 mmol, 2.0 equivalents) from a solid addition funnel. After the addition was complete, the reaction mixture was heated at reflux for 3 h. The reaction mixture was then cooled poured into a 250 mL Erlenmeyer flask and was diluted with 50 mL of anhydrous THF. The reaction was quenched by the addition of excess sodium sulfate decahydrate. The resultant suspension was filtered through Celite® filter aid and the filter cake was washed with 100 mL of hot THF. The filtrate was concentrated to a light amber colored foam. This foam was dissolved in a solution of 3M anhydrous hydrochloric acid in isopropanol and the resultant solution was heated at reflux for 18 h. The solution was then concentrated in vacuo. The residue was triturated with methylene chloride/diethyl ether (1:1) to give 250 mg (25% yield) of the title compound; $^1$H NMR (CDCl$_3$) δ: 2.03 (m, 1H), 2.63 (m, 1H), 3.12 (m, 2H), 3.37 (s, 3H), 3.52 (m, 3H), 3.71 (s, 3H), 3.80 (m, 1H), 4.18 (m, 2H), 5.28 (br s, 1H), 6.23 (d, 1H, J=8 Hz), 6.95–7.4 (m, 6H).

Analysis calculated for C$_{21}$H$_{26}$ClNO$_3$+1.5 H$_2$O: C, 54.16; H, 6.40; N, 2.87. Found: C, 54.15; H, 6.01; N, 3.01.

Step 4: 1-Aminomethyl-5,6-dihydroxy-2-(2'-hydroxy-1'-ethyl)-3-phenyl-3,4-dihydronaphthalene hydrobromide To a solution of 1-aminomethyl-5,6-dimethoxy-2-(2'-hydroxy-1'-ethyl)-3-phenyl-3,4-dihydronaphthalene hydrochloride (60 mg, 0.177 mmol, 1.0 equivalent), from Step 3, in 2 mL of anhydrous methylene chloride cooled to −78° C. was added 350 μL of boron tribromide (1.0M solution in methylene chloride, 0.35 mmol, 2.0 equivalents). The resultant solution was allowed to warm to ambient temperature gradually over a period of 2 h and then it was again cooled to −78° C. and quenched by the addition of 20 mL of anhydrous methanol. The solid was filtered and recrystallized from a mixture of methanol, methylene chloride and diethyl ether to give 50 mg (80% yield) of the title compound as a white powder, m.p. 252°–255° C.; DCI MS M/Z: 312 (M+H)$^+$; I.R. (KBr): 3400, 1600, 1490, 1280, 1200, 700 cm$^{-1}$; $^1$H NMR (CD$_3$OD) δ: 2.22 (m, 1H), 2.75 (m, 1H), 2.93 (m, 1H), 3.30 (m, 1H), 3.70 (m, 3H), 4.13 (d, 1H, J=12 Hz), 4.28 (d, 1H, J=13.5 Hz), 6.70 (d, 1H, J=7.5 Hz), 6.85 (d, 1H, J=7.5 Hz), 7.10 (m, 5H). Analysis calculated for C$_{19}$H$_{22}$BrNO$_3$+0.5 CH$_2$Cl$_2$: C, 53.87; H, 5.33; N, 3.22. Found: C, 53.54; H, 5.24; N, 3.21.

EXAMPLE 45

[1-2-trans]1-Aminomethyl-5,6-dihydroxy-2-(2'-hydroxy-1'-ethyl)-3-phenyl-1,2,3,4-tetrahydronaphthalene formic acid salt Step 1: [1-2-trans]2-(Carboethoxy)methyl-1-cyano-5,6-dimethoxy-3-phenyl -3,4dihydronaphthalene 9b-Cyano-6,7-dimethoxy-2-oxo-4-phenyl-2,3,3a,4,5,9b-hexahydro-naphtho[1,2b]furan (5.0 g, 14.31 mmol, 1.0 equivalents), the product of Step 2 of Example 44, was dissolved in 120 mL of a solution of 2M anhydrous hydrochloric acid in ethanol and the resultant solution was heated at reflux for 2 h. The solvent was evaporated in vacuo and the residue was dissolved in 120 mL of methylene chloride. The methylene chloride solution was washed with 2×25 mL of saturated aqueous sodium bicarbonate solution, 25 mL of water and 25 mL of brine, dried over anhydrous magnesium sulfate, filtered and concentrated in vacuo to give 5 g (93% yield) of the title compound as a colorless oil; $^1$H NMR (CDCl$_3$) δ: 1.22 (t, 3H, J=7.5 Hz), 3.24 (m, 3H), 3.54 (s, 3H), 3.70 (d, 1H, J=15 Hz), 3.58 (s, 3H), 3.90 (m, 1H), 4.08 (m, 2H), 6.82 (d, 1H, J=7.0 Hz), 7.03 (m, 2H), 7.20 (m, 3H), 7.30 (d, 1H, J=7.0 Hz).

Step 2 : [1-2-trans]1-Aminomethyl-5,6-dimethoxy-2-(2'-hydroxy-1'-ethyl)-3-phenyl-1,2,3,4-tetrahydronaphthalene To a stirred solution of 2-(carboethoxy)methyl-1-cyano-5,6-dimethoxy-3-phenyl-3,4-dihydronaphthalene (2 g, 5.3 mmol, 1.0 equivalent), from Step 1, in 50 mL of anhydrous methanol at ambient temperature, was added 5.13 g (212 mmol, 40 equivalents) of magnesium powder. The resultant mixture was stirred at ambient temperature for 2 h and then it was cooled to 0° C. The reaction was quenched by the slow addition of 150 mL of 2N aqueous hydrochloric acid solution. The aqueous solution was extracted with 4×50 mL of methylene chloride. The combined organic layers were washed with 50 mL of water and 50 mL of brine, dried over anhydrous magnesium sulfate, filtered and concentrated to a colorless oil. The oil was dissolved in 75 mL of anhydrous THF. To this solution at 0° C. was added 0.4 g (10.5 mmol, 2.0 equivalents) of lithium aluminum hydride. The resultant mixture was heated at reflux for 4 h and then diluted with 100 mL of anhydrous THF. The reaction was quenched by the addition of sodium sulfate decahydrate. The reaction mixture was then filtered through Celite® filter aid and the filter cake washed thoroughly with hot THF. The filtrate was concentrated in vacuo. The residue was chromatographed on silica gel eluted with methylene chloride/methanol/ammonium hydroxide (89:9:1) to give 1.15 g (63% yield) of the title compound as a 1:1 mixture of diastereomers; $^1$H NMR (CDCl$_3$) δ: 1.15–1.5 (m, 4H), 1.67 (m, 1H), 1.90 (m, 1H), 2.20 (m, 1H), 2.35 (m, 1H), 2.45 (m, 1H), 2.55–3.05 (m, 6H), 3.18 (m, 4H), 3.50 (m, 4H), 3.73 (s, 3H), 3.75 (m, 1H), 3.83 (s, 3H), 3.87 (s, 6H), 6.80 (m, 2H), 6.92 (m, 2H), 7.2–7.4 (m, 10H).

Step 3: [1-2-trans]1-Aminomethyl-5,6-dihydroxy-2-(2'-hydroxy-1'-ethyl)-3-phenyl-1,2,3,4-tetrahydronaphthalene formic acid salt A stirred solution of 1-aminomethyl-5,6-dimethoxy-2-(2'-hydroxy-1'-ethyl)-3-phenyl-1,2,3,4-tetrahydronaphthalene (0.6 g, 1.76 mmol, 1.0 equivalents), from Step 2, in 18 mL of anhydrous methylene chloride cooled to −78° C., was added 3.52 mL of boron tribromide (1M solution in methylene chloride, 3.52 mmol, 2.0 equivalents). The resultant reaction mixture was stirred at −78° C. for 1 h and then it was allowed to warm to ambient temperature. The reaction mixture was stirred at ambient temperature for 1 h and cooled again to −78° C. The reaction was quenched by the addition of 50 mL of anhydrous methanol. The resultant solution was stirred at ambient temperature for 1 h and then concentrated in vacuo. The residue was chromatographed on silica gel eluted with ethyl acetate/formic acid/water (18:1:1) to give the title compound as a light tan colored powder, m.p. 190° C. (dec); DCI MS M/Z: 312 (M+H)$^+$; I.R. (KBr): 3400, 3240, 1600, 1490, 1290, 1050, 700 cm$^{-1}$; $^1$H NMR (CD$_3$OD) δ: 1.21 (m, 1H), 1.50 (m, 2H), 1.67 (m, 1H), 2.15 (m, 1H), 2.22 (m, 1H), 2.53 (m, 1H), 2.63 (m, 1H), 3.10 (m, 8H), 3.43 (m, 2H), 3.50 (m, 2H), 7.6 (m, 2H), 7.72 (m, 2H), 7.23 (m, 4H), 7.35 (m, 6H), 8.51 (s, 2H). Analysis calculated for C$_{19}$H$_{23}$NO$_3$+2.5 HCO$_2$H: C, 56.96; H, 6.37; N, 2.45. Found: C, 56.72; H, 6.08; N, 3.30.

EXAMPLE 46

1-Aminomethyl-5,6-dihydroxy-3-phenylnaphthalene hydrochloride

Step 1: 1-(N-t-Butoxycarbonyl)aminomethyl-5,6-bis(acetoxy)-3-phenyl-3,4-dihydronaphthalene hydrochloride Triethylamine (0.33 mL, 2.37 mmol) was added to a cold solution of 1 g (2.58 mmol) of 1-aminomethyl-5,6-bis(acetoxy)-3-phenyl-3,4-dihydronaphthalene hydrochloride, the product of Example 3, in 10 mL of DMF. The resultant solution was added dropwise to a solution of 1.27 mL (5.52 mmol) of trimethylacetic anhydride (commercially available from Aldrich Chemical Co.) in 2 mL of DMF. The solution was allowed to stir at 0° C. for approximately 0.5 h and then at ambient temperature for 3 h. Water (25 mL) was added and the resultant mixture was extracted with ethyl acetate. The combined organic layers were washed successively with 2 ×15 mL of 1N aqueous hydrochloric acid solution, 2×15 mL of water and 15 mL of brine, dried over anhydrous magnesium sulfate and concentrated in vacuo. The residue was purified by flash chromatography on silica gel eluted with hexane/ethyl acetate (3:1) to give 0.84 g (72% yield) of the title compound; DCI MS M/Z: 469 (M+NH$_4$)$^+$; $^1$H NMR (CDCl$_3$) 67 :1.45 (s, 9H), 2.25 (s, 3H), 2.28 (s, 3H), 2.63–2.78 (m, 1H), 2.91–3.03 (m, 1H), 3.63–3.74 (m, 1H), 4.08–4.34 (m, 2H), 4.65 (br s, 1H), 6.02 (d, 1H), 7.05 (d, 1H), 7.22–7.37 (m, 6H).

Step 2: 5,6-Bis(acetoxy)-1-(N-t-butoxycarbonyl)aminomethyl-3-phenylnaphthalene

To a solution of 1.59 g (3.52 mmol) of 5,6-bis(acetoxy)-1-(N-t-butoxycarbonyl)aminomethyl-3-phenyl-3,4-dihydronaphthalene, from Step 1, in 50 mL of toluene was added 0.80 g (3.52 mmol) of 2,3-dichloro-5,6-dicyano-1,4-benzoquinone as a solid. The reaction mixture was heated to 70° C. under a nitrogen atmosphere and allowed to stir overnight. After cooling the reaction mixture to ambient temperature, the orange colored mixture was filtered through a bed of Celite® filter aid. The filtrate was concentrated in vacuo. The residue was taken up in 50 mL of methylene chloride and the methylene chloride solution was washed with 2×25 mL of 1M aqueous phosphoric acid solution, 2×25 mL of aqueous sodium bicarbonate solution, 25 mL of water and 25 mL of brine, dried over anhydrous sodium sulfate, filtered and concentrated in vacuo. The residue was purified on a silica gel column eluted with 3:1 hexane/ethyl acetate to give 0.77 g (49% yield) of the title compound as a white solid; $^1$H NMR (CDCl$_3$) δ: 1.47 (s, 9H), 2.35 (s, 3H), 2.47 (s, 3H), 4.81 (d, 2H), 4.89 (br s, 1H), 7.36–7.43 (m, 5H), 7.64–7.71 (m, 2H), 7.94 (d, 1H), 8.01 (d, 1H).

Step 3: 5,6-Bis(acetoxy)-1-aminomethyl-3-phenylnaphthalene hydrochloride 5,6-Bis(acetoxy)-1-(N-t-butoxycarbonyl)aminomethyl-3-phenylnaphthalene (300 mg, 0.67 mmol) from Step 2 was dissolved in 10 mL of dioxane saturated with anhydrous hydrogen chloride. The resultant solution was stirred for 2 h at ambient temperature and concentrated in vacuo. The solid residue was recrystallized from ethanol/hexane to give 130 mg (50% yield) of the title compound as a white solid; DCI MS M/Z: 350 (M+H)$^+$, 367 (M+NH$_4$)$^+$; $^1$H NMR (d$_6$-DMSO) δ: 2.36 (s, 3H), 2.51 (m, 3H+DMSO), 4.65 (s, 2H), 7.44–7.51 (m, 1H), 7.54–7.61 (m, 3H), 7.78 (d, 2H), 8.07 (s, 1H), 8.13–8.19 (m, 2H), 8.39 (br s, 3H).

Step 4: 1-Aminomethyl-5,6-dihydroxy-3-phenylnaphthalene hydrochloride 5,6-Bis(acetoxy)-1-aminomethyl-3-phenylnaphthalene hydrochloride (130 mg, 0.34 mmol) from Step 3 was dissolved in 10 mL of methanol saturated with hydrogen chloride. The resultant solution was stirred at ambient temperature for 3 h and then concentrated in vacuo. The solid residue was dissolved in a minimal amount of ethanol. The ethanol solution was added slowly to 30 mL of dry diethyl ether and the precipitate was collected by filtration. The solid was dried at 60° C. in vacuo to give 77 mg (76% yield) of the title compound as a white solid, m.p. 205–°212° C. (dec); DCI MS M/Z: 266 (M+H)$^+$, 283 (M+NH$_4$)+; $^1$H NMR (d$_6$-DMSO) δ: 4.50 (d, 2H), 7.28 (d, 1H), 7.36–7.60 (m, 4H), 7.77 (s, 1H), 7.83 (d, 2H), 8.35 (s, 1H), 8.49 (br s, 3H), 9.22 (br s, 1H), 9.60 (br s, 1H).

EXAMPLE 47

[1,3-cis]-1-Bromomethyl-3-t-butyl-5,6-cyclohexylidenedioxy-3,4-dihydro-1H-2-benzopyran Step 1: Epoxide Synthesis t-Butyl ethylene oxide, the epoxide used in the synthesis of [1,3-cis]1-bromomethyl-3-t-butyl-5,6-cyclohexylidenedioxy-3,4-dihydro-1H-2-benzopyran, is commercially available. Epoxides necessary for the synthesis of other benzopyran derivatives of the present invention which are not commercially available were synthesized by either Method A, Method B or Method C described below.

Method A: 1-Cyclohexyl ethylene oxide

Sodium hydride (4.5 g, 187.5 mmol) and trimethylsulfoxonium iodide (41.25 g, 187.5 mmol) were combined in a 3-neck flask equipped with a mechanical stirrer and an addition funnel. Dimethyl sulfoxide (DMSO) was added slowly, over a 30 min period, until 200 mL had been added. Gas was evolved throughout the addition. A solution of cyclohexane carboxaldehyde (21.8 mL, 180 mmol) in 50 mL of DMSO was added dropwise to the reaction mixture over a 15 min period. The reaction mixture was heated to 55° C. and stirred at 55° C. for 30 min. The reaction mixture was cooled to ambient temperature and poured into 500 mL of water. The aqueous solution was extracted with 3×100 mL of diethyl ether. The combined ether extracts were washed with water and brine, dried over anhydrous magnesium sulfate and concentrated in vacuo. The crude product was distilled (44° C., 0.1 mm) to give 14 g (62% yield) of 1-cyclohexyl ethylene oxide as a clear colorless liquid.

Method B: 1-Benzyl ethylene oxide

A solution of m-chloroperbenzoic acid (mCPBA; 17 g, 0.1 mol) in 120 mL of methylene chloride was added (at ambient temperature) dropwise to a solution of allyl benzene (10 g, 85 mmol) in 200 mL of methylene chloride. After the reaction mixture was stirred for 5 h with a mechanical stirrer, 5 additional grams of m-CPBA were added and the reaction mixture stirred for another 2 h. The reaction mixture was then diluted with 200 mL of ether, washed with 2×100 mL of aqueous sodium bisulfite solution, 1×100 mL of aqueous sodium bicarbonate solution and 1×100 mL of brine. The organic solution was dried over anhydrous magnesium sulfate, filtered and concentrated in vacuo. The residue was purified by bulb-to-bulb distillation (60° C., 0.1 mm) to give 8.5 g (77% yield) of 1-benzyl ethylene oxide as a clear colorless liquid.

Method C: [1R]1-(1-Adamantyl)ethylene oxide

The title compound was prepared as described in Example 179, Steps 1–3, below.

Step 2: 3,3-Dimethyl-1-(spiro-[(1,3-benzodioxole)-2'-cyclohexane])-2-butanol n-Butyl lithium (12.6 mL of 2.5M solution in hexane, 32 mmol) was added to a solution of spiro[1,3-benzodioxole)-2,1'-cyclohexane](5 g, 26.3 mmol), prepared as described by Boeckmann and Schill in *Chemische Berichte*, 110:703 (1977), in 40 mL of THF at 0° C. After 4 h, 3,3-dimethyl-1,2-epoxybutane (2.5 g, 25 mmol), commercially available from Aldrich Chemical Company, was added dropwise and the reaction mixture was warmed to 25° C. After 3 h at 25° C., the reaction mixture was poured into saturated aqueous ammonium chloride solution and extracted with 3×75 mL of diethyl ether. The combined ether extracts were washed with 50 mL of aqueous ammonium chloride solution and 50 mL of brine, dried over anhydrous magnesium sulfate, filtered and concentrated in vacuo to an oil. The oil was purified on silica gel eluted with 10% ethyl acetate in hexane to give 3.5 g (48% yield) of the title compound as a viscous oil. DCI MS: 308 (M+NH$_4$)$^+$. $^1$H NMR (d$_6$-DMSO) δ: 0.89 (s, 9H), 1.4–1.9 (m, 10H), 2.27 (dd, 1H, J=14.4, 9.3 Hz), 2.75 (dd, 1H, J=14.4, 3.0 Hz), 3.3 (m, 1H), 4.38 (d, 1H, J=6.3 Hz), 6.18 (m, 3H).

Step 3A: [1,3-cis]-1-Bromomethyl-3-t-butyl-5,6-cyclohexylidenedioxy-3,4-dihydro-1H 2-benzopyran Boron trifluoride etherate (2.88 mL, 23.5 mmol) was added dropwise to a stirred solution of the product of Step 2 (3.4 g, 11.7 mmol) and bromoacetaldehyde dimethyl acetal (1.4 mL, 11.7 mmol) in 15 mL of methylene chloride at −25° C. The reaction mixture was allowed to warm to 0° C. After 1 h at 0° C., the reaction mixture was diluted with 20 mL of diethyl ether and poured into 50 mL of aqueous sodium carbonate solution. The resultant mixture was extracted with 3×50 mL of diethyl ether. The combined ether extracts were washed with aqueous sodium bicarbonate solution and brine, dried over anhydrous magnesium sulfate, filtered and concentrated under reduced pressure. The residue was purified by column chromatography on silica gel eluted with 2.5% ethyl acetate in hexane to give 2.85 g (61% yield) of the title compound as a colorless solid, m.p. 113°–114° C. DCI MS: 414 (M+NH$_4$)$^+$. $^1$H NMR (CDCl$_3$) δ: 1.0 (s, 9H), 1.4–1.95 (m, 10H), 2.6 (m, 2H), 3.28 (dd, 1H, J=9.3, 5.4 Hz), 3.52 (dd, 1H, J=1.25, 7.5 Hz), 3.85 (dd, 1H, J=11.25, 3.0 Hz), 4.87 (m, 1H), 6.5 (d, 1H, J=9.0 Hz), 6.6 (d, 1H, J=9.0 Hz).
Alternate Step 3B: [1,3-cis]-1-(2-Bromoethyl)-3-t-butyl-5,6-cyclohexylidenedioxy-3,4-dihydro-1H-2-benzopyran The title compound was prepared following the procedure described in Step 3 above and using 3-bromopropionaldehyde dimethyl acetal instead of bromoacetaldehyde dimethyl acetal.

EXAMPLE 48

[1,3-cis]1-Aminomethyl 3-t-butyl-5,6-dihydroxy-3,4-dihydro-1H-2-benzopyran hydrochloride Step 1: [1,3-cis]1-Azidomethyl-3-t-butyl-5,6-cyclohexylidenedioxy-3,4-dihydro-1H-2-benzopyran Lithium azide (1.6 g, 31 mmol) was added to a solution of the product of Example 47 (2.5 g, 6.35 mmol) in 12 mL of dimethylformamide (DMF) at 25° C. The reaction mixture was heated at 75° C. for 2 h then cooled and poured into 50 mL of water. The aqueous solution was extracted with 3×50 mL of diethyl ether. The combined ether extracts were washed with 50 mL of water. 50 mL of brine, dried over anhydrous magnesium sulfate, filtered and concentrated in vacuo. The residue was purified by column chromatography on silica gel eluted with 2.5% ethyl acetate in hexane to give 1.56 g (69% yield) of the title compound as a colorless syrup; MS DCI: 358 (M+H)$^+$, 375 (M+NH$_4$)$^+$; $^1$H NMR (CDCl$_3$) δ: 1.1 (s, 9H), 1.4–1.95 (m, 10H), 2.6 (m, 2H), 3.3 (dd, 1H, J=8.7, 6.0 Hz), 3.42 (dd, 1H, J=13.5, 7.5 Hz), 3.52 (dd, 1H, J=13.5, 3.0 Hz), 4.9 (m, 1H), 6.42 (d, 1H, J=9.0 Hz), 6.59 (d, 1H, J=9.0 Hz).
Step 2: [1,3-cis]1-Aminomethyl-3-t-butyl-5,6-cyclohexylidenedioxy-3,4-dihydro-3,4-dihydro-1H-2-benzopyran hydrochloride Lithium aluminum hydride (LAH) solution (4.2 mL of 1M solution in ether, 4.2 mmol) was added dropwise to a solution of [1,3-cis]1-azidomethyl-3-t-butyl-5,6-cyclohexylidenedioxy-3,4-dihydro-1H-2-benzopyran (1.5 g, 4.2 mmol) in 25 mL of dry diethyl ether at 0° C. After 15 min, the reaction mixture was allowed to warm to 25° C. and was stirred at 25° C. for 1 h. The reaction mixture was cooled to 0° C. and the reaction was quenched by the sequential addition of. 0.16 mL of water, 0.16 mL of 15% aqueous sodium hydroxide solution and 0.48 mL of water. The precipitate was removed by filtration and washed with ether. The filtrate was concentrated in vacuo. The crude amine product was dissolved in 15 mL of diethyl ether and diethyl ether saturated with hydrogen chloride was added in excess. The solid was collected by vacuum filtration, washed with diethyl ether and dried to give 1.48 g (96% yield) of the title compound as a colorless solid, m.p. 164°–167° C.; DCI MS: 332 (M+H)$^+$; $^1$H NMR (d$_6$-DMSO) δ: 1.0 (s, 9H), 1.4–1.9 (m, 10H), 2.6 (m, 2H), 2.9 (dd, 1H, J=14.7, 10.5 Hz), 3.2 (m, 2H), 3.5 (dd, 1H, J=14.7, 3.0 Hz), 4.82 (br d, 1H, J=8 Hz), 6.7 (m, 2H), 7.9 (br s, 2H).
Step 3: [1,3-cis]1-Aminomethyl-3-t-butyl-5,6-dihydroxy-3,4-dihydro-1H-2-benzopyran hydrochloride A solution of [1,3-cis]1-aminomethyl-3-t-butyl-5,6-cyclohexylidenedioxy-3,4-dihydro-1H-2-benzopyran hydrochloride, from Step 1, (1 g, 2.72 mmol) in 15 mL of ethanol was saturated with anhydrous hydrogen chloride. The solution was heated to reflux temperature. After 2 h at reflux temperature the solution was concentrated to approximately 2 mL. A solid was precipitated with diethyl ether, filtered, washed with diethyl ether and dried in a vacuum oven at 80° C. to give 630 mg (81% yield) of the title compound as a colorless powder, m.p. 258° C.; IR 3200, 1620, 1490, 1300, 1060 cm$^{-1}$; DCI MS: 252 (M+H)$^+$; $^1$H NMR (d$_6$-DMSO) δ: 1.0 (s, 9H), 2.38 (dd, 1H, J=16.5, 12 Hz), 2.63 (dd, 1H, J=16.5, 2.8 Hz), 2.85 (m, 1H), 3.22 (dd, 1H, J=12.0, 4.2 Hz), 3.45 (m, 1H), 4.8 (br d, 1H, J=7.5 Hz), 6.5 (d, 1H, J=7.8 Hz), 6.65 (d, 1H, J=7.8 Hz), 7.9 (br s, 2H), 8.46 (br s, 1H), 9.22 (br s, 1H). Analysis calculated for C$_{14}$H$_{22}$ClNO$_3$: C, 58.43; H, 7.70; N, 4.9. Found: C, 58.37; H 7.69; N, 4.77.

EXAMPLES 49–106

Following the synthesis outlined in Examples 47 and 48, using the appropriate epoxide and the appropriate aldehyde diacetal, Examples 49–106 were made as disclosed in Table 3. The structure of each was confirmed by melting point (m.p), elemental analysis and mass spectra as designated.

TABLE 3

Examples 49-106

| Ex. No. | Compound* | Epoxide | mp °C. | MS* | Elemental Analysis C H N |
|---|---|---|---|---|---|
| 49 | [HO, HO-phenyl with CH2-CH(O-)-CH2-Ph and CH2-NH2] | benzyl epoxide | 1 146 | 272 | c: 60.60 6.05 4.42<br>f: 60.63 6.27 4.20 |
| 50 | [HO, HO-phenyl with cyclohexylmethyl ether chain] | cyclohexylmethyl epoxide | 2 225 | 278 | c: 61.24 7.71 4.46<br>f: 61.23 7.83 4.34 |
| 51 | [HO, HO-phenyl with ethyl ether chain] | ethyl epoxide | 1 204–6 | 224 | c: 55.50 6.99 5.39<br>f: 55.85 7.15 5.31 |
| 52 | [HO, HO-phenyl with spirocyclohexyl ether chain] | spiro cyclohexane epoxide | 2 234 | 264 | c: 60.10 7.40 4.67<br>f: 60.20 7.53 4.63 |

TABLE 3-continued

Examples 49-106

| Ex. No. | Compound* | Epoxide** | | mp °C. | MS*** | Elemental Analysis C H N |
|---|---|---|---|---|---|---|
| 53 | [structure with 4-hydroxyphenoxy group, dihydroxyphenyl, pyran, NH₂] | [4-OMe phenoxymethyl epoxide] | 3 | 220-1 | 332 | c: 58.78 6.03 3.81<br>f: 58.39 6.20 3.71 |
| 54**** | [structure with phenyl, dihydroxyphenyl, pyran, NH₂] | [styrene oxide] | 1 | 158<br>[alpha]$_D$ = −116.5°<br>(c = 0.405, 1N HCl) | 272 | c: 60.60 6.05 4.42<br>f: 60.63 6.27 4.20 |
| 55 | [structure with phenoxy, dihydroxyphenyl, pyran, NH₂] | [phenoxymethyl epoxide] | 3 | 230 | 302 | c: 60.45 5.97 4.15<br>f: 60.34 6.04 4.02 |
| 56 | [structure with biphenyloxy, dihydroxyphenyl, pyran, NH₂] | [2-phenylphenoxymethyl epoxide] | 3 | 205 | 378 | c: 66.74 5.85 3.38<br>f: 66.54 5.88 3.37 |

TABLE 3-continued

Examples 49–106

| Ex. No. | Compound* | Epoxide | mp °C. | MS* | Elemental Analysis C H N |
|---|---|---|---|---|---|
| 57 | (3,4-dihydroxyphenyl ethylamine coupled with 4-tert-butylphenoxy glycidyl ether) | 4-tert-butylphenoxymethyl oxirane | 3 217 | 358 | c: 64.03 7.16 3.56<br>f: 63.90 7.18 3.51 |
| 58 | (3,4-dihydroxyphenyl ethylamine coupled with 4-bromophenoxy glycidyl ether) | 4-bromophenoxymethyl oxirane | 3 225 | 380 | c: 49.00 4.60 3.36<br>f: 49.03 4.65 3.33 |
| 59 | (3,4-dihydroxyphenyl ethylamine coupled with adamantyl oxirane) | Adam-oxirane | 3 250 | 330 | c: 65.65 7.71 3.83<br>f: 65.59 7.83 3.73 |

*As the HCl salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCI MS (M + H)+
****Prepared by the procedure described in Examples 47, 48 and old 130 using (–)-B-chlorodiiidopinocamphorylborane TABLE 3-continued Examples 49-106

| Ex. No. | Compound* | Epoxide | mp °C. | MS* | Elemental Analysis C H N |
|---|---|---|---|---|---|
| 60 | (structure) | (benzyl epoxide) | 3 242 | 286 | c: 63.45 6.26 4.35<br>f: 63.32 6.30 4.27 |
| 61 | (structure) | (phenethyl epoxide) | 3 215 | 300 | c: 64.38 6.60 4.17<br>f: 64.33 6.65 4.06 |
| 62 | (structure) | (styrene oxide) | 1 241 | 350 | c: 49.70 4.43 3.62<br>f: 49.77 4.44 3.58 |
| 63 | (structure) | (cyclohexylmethyl epoxide) | 2 162–3 | 358 | c: 73.90 8.74 3.92<br>f: 73.82 8.74 3.67 |

TABLE 3-continued

Examples 49–106

| Ex. No. | Compound* | Epoxide | mp °C. | MS* | Elemental Analysis C H N |
|---|---|---|---|---|---|
| 64 | (3,4-dihydroxyphenyl structure with octyl and NH₂) | octyl epoxide | 1  200 | 308 | c: 62.87 8.79 4.07<br>f: 62.80 8.69 4.03 |
| 65 | (3,4-dihydroxyphenyl structure with decyl and NH₂) | decyl epoxide | 1  193 | 336 | c: 64.58 9.21 3.77<br>f: 64.74 9.13 3.69 |
| 66 | (3,4-dihydroxyphenyl structure with alkenyl and NH₂) | alkenyl epoxide | 3  203 | 278 | c: 60.08 7.77 4.37<br>f: 60.34 7.77 4.34<br>+1/3H₂O |
| 67 | (3,4-dihydroxyphenyl structure with ethyl and NH₂) | ethyl epoxide | 1  240 | 224 | c: 55.49 6.99 5.39<br>f: 55.16 6.86 5.29 |

*As the HBr salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCI MS (M + H)+
****Prepared by the procedure described in Examples 47, 48 and old 130 using (−)-B-chlorodiidopinocamphorylborane TABLE 3-continued Examples 49–106

| Ex. No. | Compound* | Epoxide | mp °C. | MS* | Elemental Analysis C H N |
|---|---|---|---|---|---|
| 68 | (structure: hexyl-substituted chromane with NH₂ and two OH on phenyl) | hexyl-epoxide | 1  205 | 280 | c: 59.71  8.34  4.35<br>f: 59.41  8.14  4.25<br>+1/3H₂O |
| 69 | (structure: 4-bromophenyl chromane with NH₂, two OH) | 4-Br-phenyl epoxide | 2  222 | 350 | c: 49.70  4.43  3.62<br>f: 50.19  4.49  3.60 |
| 70**** | (structure: 3-hydroxyphenyl chromane with NH₂, two OH) | 3-phenoxyphenyl epoxide | 2  265 | 324 | c: 58.53  5.68  4.26<br>f: 58.72  5.57  4.15<br>+1/4H₂O |
| 71 | (structure: diphenylmethyl chromane with NH₂, two OH) | diphenylmethyl epoxide | 2  250 | 362 | c: 69.43  6.08  3.52<br>f: 69.17  6.22  3.41 |

TABLE 3-continued

Examples 49–106

| Ex. No. | Compound* | Epoxide | mp °C. | MS* | Elemental Analysis C H N |
|---|---|---|---|---|---|
| 72 | (structure) | (structure) | 2  259 | 280 | c: 60.84  8.30  4.43<br>f: 59.80  8.14  4.29 |
| 73 | (structure) | (structure) | 1  212 | 250 | c: 57.04  7.18  4.75<br>f: 57.44  6.98  4.52<br>+1/2H$_2$O |
| 74 | (structure) | (structure) | 2  234 | 306 | c:<br>f: na |
| 75 | (structure) | (structure) | 3  227 | 316 | c: 59.91  6.42  3.88<br>f: 59.94  6.05  3.89<br>+1/2H$_2$O |

*As the HBr salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCI MS (M + H)+;
****the benzyl protecting group was removed byy hydrogenolysis prior to removal of the cyclohexylidene group from the catechol, TABLE 3-continued Examples 49–106

| Ex. No. | Compound* | Epoxide | mp °C. | MS* | Elemental Analysis C H N |
|---|---|---|---|---|---|
| 76 | (cyclooctyl-substituted chroman with NH₂ and two OH groups) | (cyclooctylmethyl epoxide) 2 | >250 | 306 | c: 63.23 8.25 4.10<br>f: 62.99 8.16 4.00 |
| 77 | (benzyloxyethyl-substituted chroman with NH₂ and two OH groups) | (benzyloxyethyl epoxide) 3 | 222 | 316 | c: 60.88 6.72 3.74<br>f: 60.64 6.52 3.85<br>+1/2H₂O |
| 78 | (cyclopentylmethyl-substituted chroman with NH₂ and two OH groups) | (cyclopentylmethyl epoxide) 3 | >230 | 278 | c: 61.23 7.71 4.46<br>f: 61.26 7.71 4.44 |
| 79 | (butyl-substituted chroman with NH₂ and two OH groups) | (butyl epoxide) 1 | 215 | 252 | c: 58.43 7.71 4.87<br>f: 58.38 7.58 4.77 |

TABLE 3-continued

Examples 49–106

| Ex. No. | Compound* | Epoxide | mp °C. | MS* | Elemental Analysis C H N |
|---|---|---|---|---|---|
| 80 | (4-iodophenyl chromane aminomethyl with HO, HO substituents) | (4-iodophenyl glycidyl) | 2 257–9 | 398 | c: 43.86 4.03 3.20<br>f: 43.73 3.93 3.15<br>+1/2H$_2$O |
| 81 | (cyclohexyl chromane aminomethyl with HO, HO, Br substituents) | (cyclohexylmethyl epoxide) | 2 233 | 357 | c: 48.93 5.90 3.57<br>f: 49.18 5.86 3.51 |
| 82 | (3-methoxyphenyl chromane aminomethyl with HO, HO substituents) | (3-methoxyphenyl glycidyl) | 2 250–1 (dec) | 302 | c: 60.44 5.97 4.15<br>f: 60.23 6.01 6.01 |
| 83 | (4-methoxyphenyl chromane aminomethyl with HO, HO substituents) | (4-methoxyphenyl glycidyl) | 2 257 (dec) | 316 | c: 61.45 6.30 3.98<br>f: 61.20 6.30 3.91 |

TABLE 3-continued

Examples 49–106

| Ex. No. | Compound* | Epoxide | mp °C. | MS* | Elemental Analysis C H N |
|---|---|---|---|---|---|
| 84 | (3,4-dihydroxyphenyl chroman with Adam, NH₂) | Adam-epoxide | 3  267-9 | 330 | c: 62.77 8.38 3.32<br>f: 62.56 8.02 3.15<br>+½Et₂O + 1H₂O |
| 85 | (3,4-dihydroxyphenyl chroman with Adam, NH₂) | Adam-epoxide | 4  145 (dec) | 330 | c: 63.06 7.85 3.68<br>f: 63.25 7.73 3.35<br>+0.8H₂O |
| 86 | (3,4-dihydroxyphenyl with adamantyl, NH₂) | adamantyl-epoxide | 4  210 | 330 | c: 63.06 7.85 3.68<br>f: 63.16 7.70 3.58 |
| 87 | (3,4-dihydroxyphenyl chroman with isoindolinone, NH₂) | isoindolinone-epoxide | 3  254 (dec) | 341 | c: 56.46 5.42 6.93<br>f: 56.70 5.44 6.75<br>+0.76HCl |

*As the HBr salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCl MS (M + H)+
****Prepared by the procedure described in Examples 47, 48 and old 130 using (−)-B-chlorodiidopinocamphorylborane TABLE 3-continued Examples 49-106

| Ex. No. | Compound* | Epoxide | mp °C. | MS* | Elemental Analysis C H N |
|---|---|---|---|---|---|
| 88 | (structure) | (cyclohexyl-CH2-epoxide), 3 | 251-2 | 292 | c: 62.28 7.99 4.27<br>f: 62.75 7.83 4.21 |
| 89 | (structure) | (isobutyl-epoxide), 3 | 235-6 | 252 | c: 58.43 7.71 4.87<br>f: 58.48 7.71 4.66 |
| 90 | (structure) | Adam-epoxide, 2 | na | 344 | c:<br>f: na |
| 91 | (structure) | (cyclohexyl-ethyl-epoxide), 3 | 244-5 (dec) | 306 | c: 62.42 8.29 4.04<br>f: 62.71 8.20 4.08 |

TABLE 3-continued

Examples 49–106

| Ex. No. | Compound* | Epoxide | mp °C. | MS* | Elemental Analysis C H N |
|---|---|---|---|---|---|
| 92 | [structure: phenol with OH, OH, and side chain ending in NH₂, with ether-linked amide-ester] | [epoxide structure with ester linkage and N] 3 | >260 (dec) | 339 | c: 50.07 6.30 7.30<br>f: 49.95 6.10 7.30 |
| 93 | [structure: dihydroxyphenyl with cycloheptane spiro ether, CH₂NH₂ side chain] | [cycloheptane spiro epoxide] 2 | 239 | 278 | c: 61.24 7.71 4.46<br>f: 61.51 7.87 4.38 |
| 94 | [structure: dihydroxyphenyl with cyclooctane spiro ether, CH₂NH₂ side chain] | [cyclooctane spiro epoxide] 2 | 228 | 292 | c:<br>f: na |

*As the HBr salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCI MS (M + H)+
****Prepared by the procedure described in Examples 47, 48 and old 130 using (−)-B-chlorodiidopinocamphorylborane TABLE 3-continued Examples 49–106

| Ex. No. | Compound* | Epoxide | mp °C. | MS* | Elemental Analysis C H N |
|---|---|---|---|---|---|
| 95 | (structure with spiro tetrahydropyran, dihydrobenzofuran-type, HO, HO, NH₂) | (spiro tetrahydropyran epoxide) | 2 >260 | 266 | c: 55.72 6.68 4.64<br>f: 56.06 6.78 4.63 |
| 96 | (phenyl-substituted dihydrobenzofuran with HO, HO, NH₂) | (styrene oxide) | 1 171–4 | 272 | c: 61.54 5.97 4.48<br>f: 61.74 6.23 4.15<br>+1/4H₂O |
| 97 | (PETTF-substituted dihydrobenzofuran with HO, HO, NH₂) | PETTF-epoxide | 3 na | 402 | c: 50.85 4.56 3.12<br>f: 50.74 4.22 3.50<br>+0.3HCl |
| 98 | (4-CF₃-phenyl dihydrobenzofuran with HO, HO, NH₂) | (4-CF₃-benzyl epoxide) | 3 >225 (dec) | 340 | c: 52.01 4.32 3.47<br>f: 52.31 4.49 3.59<br>+0.4HCl |

TABLE 3-continued

Examples 49-106

| Ex. No. | Compound* | Epoxide | mp °C. | MS* | Elemental Analysis C H N |
|---|---|---|---|---|---|
| 99 | (3,4-dihydroxyphenyl-CH2-pyran-CH2-NH2 with 3-CF3-phenyl) | 3-CF3-benzyl epoxide | 3 >220 (dec) | 340 | c: 340.1167**** f: 340.1161 |
| 100 | (3,4-dihydroxyphenyl-CH2-pyran-CH2-NH2 with neopentyl) | neopentyl epoxide | 4 255 | 252 | c: 58.43 7.71 4.87 f: 58.20 7.58 4.67 |
| 101 | (3,4-dihydroxyphenyl-CH2-pyran-CH2-NH2 with allyl) | allyl epoxide | 3 204 (dec) | 272 | c: 57.46 6.68 5.15 f: 56.18 5.93 4.92 |
| 102 | (3,4-dihydroxyphenyl-CH2-pyran-CH2-NH2 with neopentyl) | neopentyl epoxide | 1 268 (dec) | na | c: 252.1601**** f: 252.1600 |

*As the HBr salt unless indicated otherwise (FB = free base); all compounds 1–3 cis unless indicated otherwise
**1 = commercially available, 2 = synthesized by method A of Example 47, 3 = synthesized by Method B of Example 47; 4 = synthesized by Method C of Example 47.
***DCl MS (M + H)+
****Prepared by the procedure described in Examples 47, 48 and old 130 using (−)-B-chlorodiidopinocamphorylborane;
*****High resolution mass spectrometry.

TABLE 3-continued

Examples 49-106

| Ex. No. | Compound* | Epoxide | mp °C. | MS* | Elemental Analysis C H N |
|---|---|---|---|---|---|
| ****High resolution mass spectrometry | | | | | |
| 103 | (structure: HO, HO, F phenyl with Adam-pyran-NH₂) | Adam-epoxide | 4  211-4 | 348 | c: 59.77 7.27 3.49<br>f: 59.77 6.89 3.54<br>+HCl + H₂O |
| 104 | (structure: HO, HO phenyl with t-Bu-pyran-NH₂) | t-Bu-epoxide | 2  197 | 266 | c: 59.70 8.02 4.64<br>f: 59.85 8.06 4.57 |
| 105 | (structure: HO, HO phenyl with methyl-allyl-pyran-NH₂) | methyl-vinyl-epoxide | 3  249-51 | 250 | c:<br>f: na |
| 106 | (structure: HO, HO, F phenyl with Adam-pyran-NH₂) | Adam-epoxide | 3  206-10 | 348 | c: 58.46 7.36 3.41<br>f: 58.32 7.20 3.22<br>+HCl + 1.5H₂O |

*As the HBr salt unless indicated otherwise (FB = free base); all compounds 1-3 cis unless indicated otherwise
**1 = commercially available, 2 = synthesized by method A of Example 47, 3 = synthesized by Method B of Example 47; 4 = synthesized by Method C of Example 47.
***DCI MS (M + H)+

EXAMPLE 107

1- Aminomethyl -8-bromo-adamantyl-5,6-dihydroxy-3,4-dihydro-1H-2-benzopyran hydrobromide Starting with the compound of Example 59, protecting the amino group with BOC and reacting 2.00 g (4.66 mmol) of the BOC-protected compound with 0.746 g (4.66 mmol) of bromine in methylene chloride at 0° C. for 3 hours, followed by quenching with sodium bisulfite, extraction with methylene chloride and purification by chromatography on silica gel, the title compound was prepared. mp 210° C. (dec). anal. calc. for $C_{20}H_{26}BrNO_3 \cdot 0.8HBr \cdot 0.5EtOH$: C, 50.83; H, 5.99: N, 2.85; found: C, 51.03; H, 6.22; N, 2.76.

EXAMPLE 108

[1,3-cis]1-(1S-(1-Amino)ethyl)-5,6-dihydroxy-3-phenyl-3,4-dihydro-1H-2-benzopyran Following the synthesis outlined in Example 47, replacing the bromoacetaldehyde dimethyl ketal with N-Cbz-alaninal, the compound of Example 108 was prepared. mp 272°–4° C. MS: 286. anal. calc.+HCl+$H_2O$: C, 60.09; H, 6.50: N, 4.12; found: C, 60.34; H, 6.32; N, 4.01.

EXAMPLE 109

[1,3-cis]1-Aminomethyl-5,6-dihydroxy-3-(2'-tetrahydrofuranyl)-3,4-dihydro-1H-2-benzopyran hydrobromide Step 1: 1-(2',3'-Dimethoxyphenyl)-N-methoxy-N-methylacetamide Oxalyl chloride (0.45, 5.1 mmol) and 2–3 drops of N,N-dimethylformamide (DMF) were added to a chilled (0° C.) solution of 2,3-dimethoxyphenylacetic acid in 25 mL of THF. The resultant solution was allowed to warm to ambient temperature over a 4 h period. The solvent was removed in vacuo and the residue was dissolved in 50 mL of chloroform. N-methoxy-N-methyl-hydroxylamine hydrochloride (0.55 g, 5.61 mmol) was added and the resultant solution was chilled to 0° C. Pyridine (0.91 mL, 11.23 mmol) was added and the solution was stirred for 2 h at 0° C. The solution was then washed twice with brine, dried over anhydrous magnesium sulfate, filtered and concentrated in vacuo to an oil. The oil was purified by column chromatography on silica gel eluted with 20% ethyl acetate in hexane to give 0.65 g (53% yield) of the title compound as an oil; MS DCI: 240 (M+H)$^+$, 257 (M+NH$_4$)$^+$; $^1$H NMR (CDCl$_3$) δ: 3.21 (s, 3H), 3.68 (s, 3H), 3.80–3.84 (m, 5H), 3.87 (s, 3H), 6.80–6.87 (m, 2H), 6.98–7.4 (m, 1H).

Step 2: 2-(2',3'-Dimethoxyphenyl)-1-furanylethanone n-Butyl lithium (1.87 mL, 3.76 mmol of a 1.75M solution in hexanes) was added to a chilled (0° C.) solution of furan (0.2 mL, 2.72 mmol) in 5 mL of THF. The mixture was allowed to warm to ambient temperature over a 4 h period. The mixture was then chilled again to 0° C. and a solution of 0.65 g (2.72 mmol) of 1-(2',3'-dimethoxyphenyl)-N-methoxy-N-methyl-acetamide, from Step 1, was added. The reaction mixture was allowed to warm to ambient temperature over a 2 h period and was then quenched with a saturated aqueous ammonium chloride solution. The mixture was extracted with ethyl acetate and the extracts were washed once each with saturated aqueous ammonium chloride and brine. The extracts were dried over anhydrous magnesium sulfate, filtered and concentrated in vacuo to give 0.5 g (75% yield) of the title compound as an oil; MS DCI: 247 (M+H)$^+$, 264 (M+NH$_4$)$^+$; $^1$H NMR (CDCl$_3$) δ: 3.80 (s, 3H), 3.85 (s, 3H), 4.15 (s, 2H), 6.51–6.53 (m, 1H), 6.82–6.88 (m, 3H), 6.99–7.05 (m, 1H), 7.25–7.28 (m, 1H).

Step 3: 2-(2',3'-Dimethoxyphenyl)-1-tetrahydrofuranyl ethanol

A solution of 450 mg (1.8 mmol) of 2-(2',3'-dimethoxyphenyl)-1-furanylethanone, from Step 2, and 20% palladium on carbon (225 mg) in 75 mL of methanol was shaken under 4 atmospheres of hydrogen until hydrogen uptake ceased. The solution was filtered and concentrated in vacuo to give 320 mg (69% yield) of the title compound as an oily solid. This product was carried on without purification to the next step.

Step 4: 1-Aminomethyl-3-(2'-tetrahydrofuranyl)-5,6-dihydroxy-3,4-dihydro-1H-2-benzopyran hydrobromide 2-(2',3'-Dimethoxyphenyl)-1-tetrahydrofuranyl ethanol, from Step 3, was converted to the title compound using the procedures described in Step 3 of Example 47 and Steps 1 and 2 of Example 48. The dimethoxy protecting groups were removed with boron tribromide by the procedures described in Step 3 of Example 2 to afford the title compound, m.p.>250° C.; FAB MS (M/Z): 266 (M+H)$^+$; $^1$H NMR (d$_6$-DMSO) δ: 1.75–1.93 (m, 4H), 2.37–2.47 (m, 1H), 2.50–2.60 (m, 1H), 2.60–2.68 (m, 1H), 2.71–2.79 (m, 1H), 3.65–3.72 (m, 1H), 3.76–3.84 (m, 2H), 3.90–4.00 (m, 1H), 4.84–4.91 (m, 1H), 6.48 (d, 1H), 6.68 (d, 1H), 7.72–7.84 (m, 2H), 8.41–8.49 (m, 1H), 9.20–9.28 (m, 1H). High resolution mass spectral analysis calculated for $C_{14}H_{20}NO_4$: 266.132. Found: 266.1391

EXAMPLE 110

[1,3-cis]1-Aminomethyl-5,6-dihydroxy-3-(3'-prop-1'-ynyl)3,4-dihydro-1H-2-benzopyran hydrochloride Step 1: 3-(Spiro-[(1,3-benzodioxole)-2,1'-cyclohexane])-propene oxide n-Butyl lithium (30 mL of 2.5M solution in hexane, 75 mmol) was added dropwise to a solution of spiro[1,3-benzodioxole)-2,1'-cyclohexane](5 g, 26.3 mmol), prepared as described by Boeckmann and Schill in *Chemische Berichte* 110:703 (1977), in 125 mL of anhydrous THF at 0° C. The solution was stirred at 0° C. for 2 h and then a solution of 4.8 g (52 mmol) of epichlorohydrin in 10 mL of THF was added via cannula over a 15 minute period. The reaction mixture was heated to ambient temperature and stirred for 60 minutes at ambient temperature and heated at 65° C. for 75 minutes. The reaction mixture was cooled to ambient temperature and poured into 150 mL of water. The aqueous layer was extracted with 2×75 mL of diethyl ether. The combined ether layers were washed with 75 mL of saturated sodium bicarbonate and brine, dried over anhydrous magnesium sulfate, filtered and concentrated in vacuo to an amber colored oil. The oil was purified by flash chromatography on silica gel eluted with 8% ethyl acetate in hexane to give 6.81 g (53% yield) of the title compound as a clear oil.

Step 2: 1-(Spiro-[(1,3-benzodioxole)-2,1'-cyclohexane])-4-pentyn-2-ol

Crude 3-(spiro-[(1,3-benzodioxole)-2,1'-cyclohexane])-propene oxide (8.29 g, 33.7 mmol), from Step 1, was added to a chilled (0° C.) suspension of lithium acetylideethylenediamine complex (4.65 g, 45.5 mmol of a 90% solid) in 50 mL of methyl sulfoxide. The mixture was allowed to warm to ambient temperature over a 3 h period during which the mixture became a homogeneous solution. The reaction was quenched with 50 mL of water and the aqueous layers were washed with water and brine, dried over anhydrous magnesium sulfate filtered and concentrated in vacuo to an oil. The oil was purified by column chromatography on silica gel eluted with 15% ethyl acetate in hexane to give 2.08 g (23% yield) of the title compound as an oil; MS DCI: 273 (M+H)$^+$, 290 (M+NH$_4$)$^+$; $^1$H NMR (CDCl$_3$) δ: 1.45–1.55 (m, 2H), 1.67–1.77 (m, 4H), 1.85–1.95 (m, 4H), 2.09 (t, 1H), 2.28 (d, 1H), 2.32–2.50 (m, 2H), 2.80–2.93 (m, 2H), 4.00–4.15 (m, 1H), 6.62–6.77 (m, 3H).

Step 3: 1-Aminomethyl-5,6-dihydroxy-3-(3'-prop-1'-ynyl)-3,4-dihydro-1H-2-benzopyran hydrochloride 1-(Spiro-[(1,3-benzodioxole)-2,1'-cyclohexane])-4-pentyn-2-ol, from Step 2, was converted to the title compound using the procedures described in Step 3 of Example 47 and Steps 1–3 of Example 48 to afford the title compound, m.p.>250° C.; DCI MS (M/Z): 234 (M+H)$^+$; 1H NMR (d$_6$-DMSO) δ: 2.34–2.47 (m, 1H), 2.52–2.57 (m, 1H), 2.57–2.68 (m, 1H), 2.84–2.92 (m, 2H), 2.95 (t, 1H), 3.39–3.47 (m, 1H), 3.71–3.81 (m, 1H), 4.87–4.91 (m, 1H), 6.2 (d, 1H), 6.69 (d, 1H), 7.88 (s, 2H), 8.53 (s, 1H), 9.31 (s, 1H). Analysis calculated for C$_{13}$H$_{16}$ClNO$_3$: C, 57.89; H, 5.98; N, 5.19. Found: C, 57.73; H, 6.15; N, 5.09.

EXAMPLE 111

[1,3-cis]3-Cyclohexyl-5,6-dihydroxy-1-methylaminomethyl-3,4-dihydro-1H-2-benzopyran hydrochloride

[1,3-cis]-1-Aminomethyl-3-cyclohexyl-5,6-cyclohexylidenedioxy-3,4-dihydro-1H-2-benzopyran hydrochloride (synthesized as described in Steps 1 and 2 of Example 48 for [1,3-cis]-1-aminomethyl-3-t-butyl-5,6-cyclohexylidenedioxy-3,4-dihydro-1H-2-benzopyran hydrochloride) (0.82 g, 2.3 mmol) was partitioned between methylene chloride and saturated aqueous sodium bicarbonate solution. The methylene chloride layer was concentrated under reduced pressure and the residue was dissolved in 25 mL of ethyl formate. The ethyl formate solution was heated to reflux temperature. After 1 h at reflux temperature, the reaction mixture was concentrated to a white solid. The solid was dissolved in 15 mL of THF and 175 mg (4.6 mmol) of lithium aluminum hydride (LAH) was added. The reaction mixture was heated at reflux temperature for 3 h then cooled to 0° C. The reaction was quenched by the sequential addition of 0.175 mL of water. 0.175 mL of 15% aqueous sodium hydroxide solution and 0.525 mL of water. The reaction mixture was filtered and the filter cake washed with diethyl ether. The filtrate was concentrated in vacuo. The residue was dissolved in 20 mL of ethanol and the alcohol solution was saturated with anhydrous hydrogen chloride then heated at reflux temperature for 2 h. The ethanol was evaporated down to approximately 2 mL and ether was added until a solid precipitate was formed. The solid was filtered, washed with diethyl ether and dried to give 504 mg (67% yield) of the title compound as a colorless powder, m.p. 244° C.; DCI MS: 292 (M$^+$H)$^+$. Analysis calculated for C$_{17}$H$_{26}$ClNO$_3$: C, 62.28; H, 7.99; N, 4.27. Found: C, 62.24: H, 7.90; N, 4.21.

EXAMPLE 112

[1R,3S]3-t-Butyl-5,6-dihydroxy-1-methylaminomethyl-3,4-dihydro-1H-2-benzopyran hydrochloride Following the synthesis outlined in Example 111 and starting with [1R,3S]1-aminomethyl-3-t-butyl-5,6-cyclohexylidenedioxy-3,4-dihydro-1H-2-benzopyran hydrochloride from Step 2 of Example 48, [1R,3S]3-t-butyl-5,6-dihydroxy-1-methylaminomethyl-3,4-dihydro-1H-2-benzopyran hydrochloride was prepared, m.p. 246° C.; DCI MS: 266 (M+H)+.

Analysis calculated for C$_{15}$H$_{23}$ClNO$_3$: C,59.70; H, 8.00; N, 4.64. Found: C, 59.64; H, 8.10: N. 4.45.

EXAMPLE 113

[1,3-cis]1-(N-Allyl)aminomethyl-3-cyclohexyl-5,6-dihydroxy-3,4-dihydro-1H-2-benzopyran hydrochloride Step 1: [1,3-cis]1-(N-Allyl)aminomethyl-3-cyclohexyl-5,6-cyclohexylidenedioxy-3,4-dihydro-1H-2-benzopyran

[1,3-cis]1-Bromomethyl-3-cyclohexyl-3,4-dihydro-5,6-dihydroxy-1H-2-benzopyran (1.1 g, 2.6 mmol) (prepared as described in Example 47, using cyclohexyl ethylene oxide) and dissolved in 10 mL of allyl amine. The reaction mixture was heated at reflux temperature for 5 h then concentrated in vacuo. The residue was dissolved in 50 mL of ethyl acetate. The solution was washed with 2×25 mL of aqueous sodium bicarbonate solution and 1×25 mL of brine, dried over anhydrous sodium sulfate, filtered and concentrated in vacuo. The residue was purified by column chromatography on silica gel eluted with 30% ethyl acetate in hexane to give 928 mg (90% yield) of the title compound as a colorless oil; DCI MS: 398 (M+H)$^{30}$; $^1$H NMR (CDCl$_3$) δ: 1.0 (m, 20H), 2.05 (m, 1H, J=11.0 Hz), 2.4 (br s, 1H), 2.5 (dd, 1H, J=13.5, 9.0 Hz), 2.7 (dd, 1H, J=13.5, 2.8 Hz), 282 (dd, 1H, J=10.0, 7.5 Hz), 3.18 (dd, 1H, J=10.0, 3.0 Hz), 3.48 (m, 3H), 4.7 (br d, 1H, J=7.5 Hz), 5.2 (m, 2H), 5.95 (m, 1H), 6.5 (d, 1H, J=6.3 Hz), 6.58 (d, 1H, J=6.3 Hz).

Step 2: [1,3-cis]1-(N-Allyl)aminomethyl-3-cyclohexyl-3,4-dihydro-5,6-dihydroxy-1H-2-benzopyran hydrochloride

[1,3-cis]1-(N-Allyl)aminomethyl-3-cyclohexyl-3,4-dihydro-5,6-cyclohexylidenedioxy-1H-2-benzopyran (920 mg, 2.3 mmol), from Step 1, was dissolved in 15 mL of ethanol saturated with anhydrous hydrogen chloride. The acidic solution was heated at reflux temperature for 2 h then concentrated to ~2 mL. Diethyl ether was added and the precipitate was filtered, washed with diethyl ether and dried to give 590 mg (72% yield) of the title compound as an off-white powder, m.p. 217°–219° C.; DCI MS: 318 (M+H)$^+$. Analysis calculated for C$_{19}$H$_{28}$ClNO$_3$: C, 64.49; H, 7.98; N, 3.96. Found: C, 64.34; H, 8.02; N, 3.82.

EXAMPLES 114–148

Following the syntheses described in Examples 47 and 113, using the appropriate epoxide and the appropriate amine, Examples 114–131 were prepared as disclosed in Table 4.

Examples 123, 124 and 127 were prepared by replacing the bromoacetaldehyde dimethyl acetal of Example 47 step 3 with the appropriate Z-protected prolinal dimethyl acetal as indicated, followed by deprotection. The chiral prolinals were prepared from the chiral amino acid alcohols following the procedures given in *Chem. Pharm. Bull* (1982), 30, 1921 and *Tetrahedron Letters* (1986), 27, 6111.

Examples 132–146 were prepared by the procedures described in Examples 47, 48 and 111. Examples 147 and 148 were prepared were prepared by the procedures described in Examples 47, 48 and 111, repeating the procedure of Example 111 in order to place the second methyl group on the amino function. The structure of each was confirmed by melting point, mass spectra and elemental analysis as designated.

TABLE 4

Examples 114-148

| Ex. No. | Compound* | Amine | mp °C. | MS** | Elemental Analysis C H N |
|---|---|---|---|---|---|
| 114 | (structure with cyclohexyl, catechol, NH-cyclopropyl, HCl) | cyclopropyl-NH$_2$ | 200 | 318 | c: 64.49 7.97 3.96<br>f: 64.43 8.02 3.88 |
| 115 | (structure with cyclohexyl, catechol, pyrrolidine, HCl) | cyclopentyl-NH$_2$ | 240-2 | 332 | c: 65.29 8.22 3.81<br>f: 65.26 8.26 3.73 |
| 116 | (structure with cyclohexyl, catechol, NH-CH$_2$CH$_2$CH$_2$OH) | HO-CH$_2$CH$_2$CH$_2$-NH$_2$ | 116 | 336 | c: 59.91 8.20 3.67<br>+1/2 H$_2$O<br>f: 60.13 8.02 3.61 |
| 117 | (structure with Adam, catechol, NH-allyl) | CH$_2$=CH-CH$_2$-NH$_2$ | 225 | 370 | c: 68.05 7.95 3.45<br>f: 68.00 7.91 3.36 |
| 118 | (structure with cyclohexyl, catechol, NH-propargyl) | HC≡C-CH$_2$-NH$_2$ | 211-2 | 316 | c: 64.86 7.45 3.98<br>f: 64.58 7.59 3.82 |

TABLE 4-continued
Examples 114–148
| | | | | | |
|---|---|---|---|---|---|
| 119 | 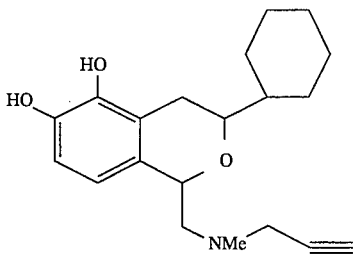 | 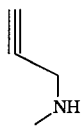 | 216–8 | 330 | c: 64.85 7.75 3.78<br>f: 65.13 7.68 3.72 |
| 120 | 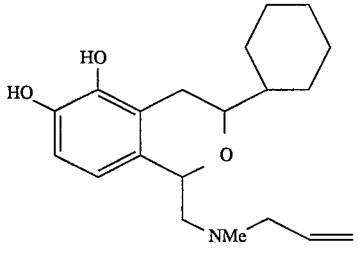 | 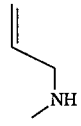 | 172–3 | 332 | c: 65.29 8.22 3.81<br>f: 65.35 8.36 3.77 |
| 121 | 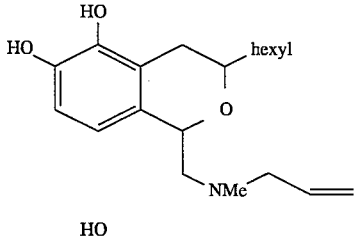 | 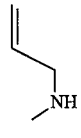 | 144–6 | 334 | c: 64.94 8.72 3.79<br>f: 64.68 8.70 3.73 |
| 122 | 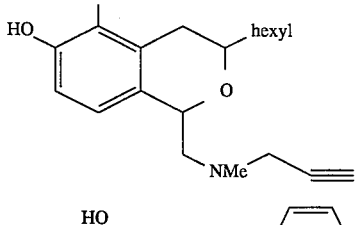 | 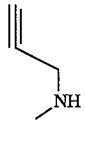 | 141–2 | 332 | c: 65.29 8.22 3.81<br>f: 65.22 8.17 3.79 |
| 123 | 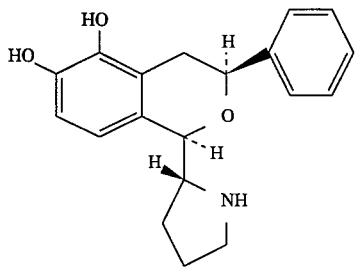 | 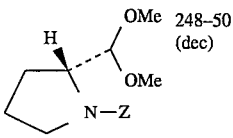 | 248–50<br>(dec) | 312 | c: 63.15 6.56 3.88<br>f: 63.29 6.16 3.87 |
| 124 | 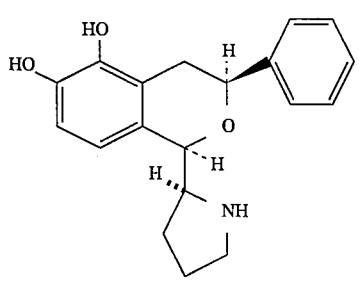 | 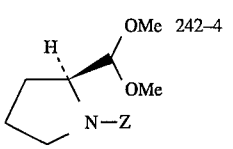 | 242–4 | 312 | c: 65.61 6.38 4.03<br>+1 HCl<br>f: 65.21 6.48 3.95 |

TABLE 4-continued

Examples 114–148

| | Structure | Amine | mp | MW | Analysis |
|---|---|---|---|---|---|
| 125 | (3,4-dihydroxyphenyl-CH2-CH(butyl)-O-... -CH(CH3)-CH2-NH-allyl) | allylamine | 152–5 | 292 | c: 62.47 7.71 4.29<br>f: 62.43 8.04 4.24 |
| 126 | (3,4-dihydroxyphenyl-CH2-CH(Ph)-O-... -CH(CH3)-CH2-NH-allyl) | allylamine | 215–222 (dec) | 312 | c: 60.53 6.10 3.72<br>+0.8 HCl<br>f: 60.43 5.89 3.66 |
| 127 | (3,4-dihydroxyphenyl-CH2-CH(Ph)-O-... -CH(CH3)-CH(H)-NH-pyrrolidine) | pyrrolidine with CH(OMe)2, N-Z | 220 (dec) | 312 | c: 62.97 6.23 3.87<br>+0.4 HCl<br>f: 62.89 6.10 3.85 |
| 128 | (3,4-dihydroxyphenyl-CH2-CH(tBu)-O-... -CH(CH3)-NH-ethyl) | ethylamine | 123 | 280 | c: 60.85 8.30 4.44<br>f: 60.85 8.31 4.36 |
| 129 | (3,4-dihydroxyphenyl-CH2-CH(tBu)-O-... -CH(CH3)-NH-allyl) | allylamine | 165 | 292 | c: 61.94 8.01 4.25<br>+0.1 H2O<br>f: 61.78 8.05 4.20 |
| 130 | (3,4-dihydroxyphenyl-CH2-CH(Ph)-O-... -CH2-NH-allyl) | allylamine | 180–83 | 312 | c: 64.93 6.34 3.98<br>+0.1 HCl<br>f: 64.68 6.33 3.98 |
| 131 | (3,4-dihydroxyphenyl-CH2-CH(tBu)-O-... -CH(CH3)-NH-propyl) | propylamine | 118 | 374 | c: 61.90 8.56 4.27<br>f: 62.24 8.34 4.24 |

TABLE 4-continued

Examples 114–148

| Ex. No. | Compound* | mp °C. | MS** | Elemental Analysis C H N |
|---|---|---|---|---|
| 132 | (structure) | 221 | 264 | c: 59.03 7.46 4.59 +0.3 H₂O  f: 59.20 7.32 7.49 |
| 133 | (structure) | >260 | 239 | c: 46.31 6.48 9.00  f: 46.04 6.03 8.08 |
| 134 | (structure, Adam) | 264 | 344 | c: 66.39 7.96 3.69  f: 66.31 7.94 3.57 |
| 135 | (structure, butyl) | 194–6 | 266 | c: 59.69 8.02 4.64  f: 59.24 7.94 4.46 |
| 136 | (structure, 4-F-phenyl) | >260 | 304 | c: 57.07 5.92 3.92  f: 56.79 5.73 3.61 |
| 137 | (structure, 4-OMe-benzyl) | >260 (dec) | 330 | c: 59.45 6.83 3.65  f: 59.25 6.43 3.56 |
| 138 | (structure, phenyl) | 250–2 | 286 | c: 63.40 6.30 4.40  f: 63.00 6.30 4.30 |

TABLE 4-continued

Examples 114–148

| | | | | |
|---|---|---|---|---|
| 139 | (structure: 2,3-dihydroxyphenyl with CH2-CH(O-adamantyl)- and CH(CH3)-CH2-NH-CH3 substituents) | na | 358 | c: 66.25 8.46 3.36 +0.5 EtOH<br>f: 66.30 8.39 3.36 |
| 140 | (structure: 2,3-dihydroxyphenyl chroman with cyclohexylmethyl and CH(CH3)-NH-CH3) | 209–10 | 306 | c: 63.24 8.25 4.10<br>f: 62.97 8.17 4.02 |
| 141 | (structure: with spiro cycloheptyl) | 145 | 292 | c: 62.28 7.99 4.27<br>f: 62.16 7.84 4.26 |
| 142 | (structure: with spiro cyclooctyl) | 194 | 306 | c: 306.2069***<br>f: 306.2076 |
| 143 | (structure: with spiro tetrahydropyran) | 247 | 280 | c: 57.05 7.02 4.44<br>f: 56.72 6.84 4.30 |
| 144 | (structure: with pentyl) | na | 280 | c: 60.85 8.30 4.44<br>f: 60.74 8.13 4.43 |
| 145 | (structure: fluoro-dihydroxyphenyl with adamantyl, stereochem H) | >250 | 362 | c: 58.07 6.96 3.22 +2 HCl<br>f: 57.71 7.18 2.92 |

TABLE 4-continued

Examples 114–148

| | | | | |
|---|---|---|---|---|
| 146 | 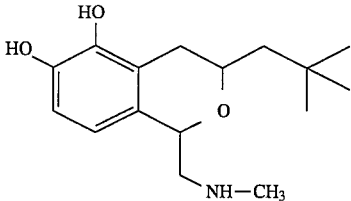 | 185 | 280 | c: 60.85 8.30 4.44<br>f: 61.14 8.14 4.24 |
| 147 | 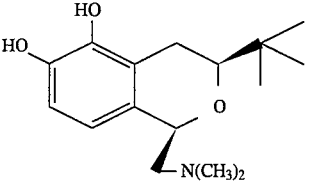 | 223 | 280 | c: 60.85 8.30 4.44<br>f: 60.65 8.21 4.33 |
| 148 | 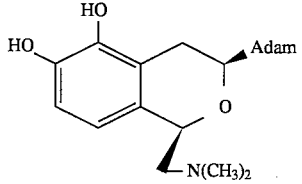 | dec | 358 | c:<br>f:   na |
| 148A | 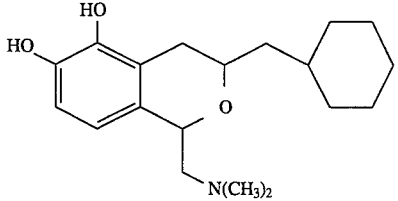 | 215 | 320 | c: 64.12 8.50 3.94<br>f: 63.95 8.48 3.84 |

*As the HCl salt unless indicated otherwise (FB = free base); Adam=adamantyl; all compounds 1–3 cis unless indicated otherwise
***DCl MS(M + H)+
***High Resolution mass spectrometry

EXAMPLE 149

5,6-Dihydroxy-1-(N-methyl)aminomethyl-3-phenyl-3,4-dihydronaphthalene

1-Aminomethyl-5,6-dimethoxy-3-phenyl-3,4-dihydronaphthalene, the product of Step 2 of Example 2, was N-methylated as described in Example 111 and deprotected as described in Step 4 of Example 2 to give the title compound as its hydrochloride salt, m.p. 131°–133° C.; DCI MS: 282 (M+H)$^+$. Analysis calculated for $C_{18}H_{20}ClNO_2$: C, 68.03; H, 6.34; N, 441. Found: C, 67.64: H, 6.54; N, 4.31.

EXAMPLE 150

[1,3-cis]5,6-Dihydroxy-1-(N-methyl)aminomethyl-3-phenyl-1,2,3,4-tetrahydro-naphthalene

[1,3-cis]1-Aminomethyl-5,6-dimethoxy-3-phenyl-1,2,3,4-tetrahydro-naphthalene, the product of Step 1 of Example 35, was N-methylated as described in Example 111 and deprotected as described in Step 4 of Example 2 to give the title compound as its hydrochloride salt, m.p. 211°213° C.; DCI MS: 284 (M+H)$^+$. Analysis calculated for $C_{18}H_{22}ClNO_2$: C, 65.75; H, 7.05; N, 4.26. Found: C, 65.54; H, 6.89; N, 4.04.

EXAMPLES 151–153

Following the synthesis described in Examples 1A and 2, the 1-aminomethyl precursors to Examples 151–153 were prepared with the catechol hydroxyl groups protected as dimethyl ethers. The 1-aminomethyl compounds were N-acylated. The N-acyl derivatives reduced as described in Example 111 and deprotected as described in Step 4 of Example 2, using the appropriate acylating agent and lithium aluminum hydride (LAH) as the reducing agent to give Examples 151–153 as their hydrochloride salts unless otherwise noted. In the case of Example 152, the acylation/reduction sequence was repeated to give the dialkylamino derivative. Examples 151–153 are disclosed in Table 5. The structure of each was confirmed by melting point (m.p.), elemental analysis and mass spectra, as designated.

TABLE 5

Examples 151–153

| Ex. No. | Compound* | Acyl chloride | mp °C. | MS** | High Resolution Mass Spectrum |
|---|---|---|---|---|---|
| 151 | HO, HO — benzopyran with CH₂-CH(Ph) linkage, O, and NH-propyl substituent | PhCH₂CH₂C(=O)Cl | 198 | 310 | c: 309.1725 f: 309.1722 |
| 152 | HO, HO — benzopyran, MeSO₄·salt, N(propyl)(propyl) | PhCH₂CH₂C(=O)Cl | na | 352 | c: 351.2196 f: 351.2203 |
| 153 | HO, HO — benzopyran with NH-ethyl | PhCH₂CH₂C(=O)Cl | 122 | 296 | c: 295.1572 f: 295.1571 |

*As the HCl salt unless indicated otherwise (FB = free base); all compounds 1–3 cis unless indicated otherwise
***DCl MS (M + H)+
***High Resolution mass spectrometry

EXAMPLE 154

[1,3-cis]1,3-Bis(aminomethyl)-3,4-dihydro-5,6-dihydroxy-1H-2-benzopyran dihydrochloride Step 1: 1-Benzyloxy-3-(spiro-[(1,3-benzodioxole)-2,1'-cyclohexane])-2-propanol Glycidol (3.1 g, 42 mmol) was added dropwise to a suspension of sodium hydride (1.0 g, 42 mmol) in 25 mL of dry dimethyl formamide (DMF) at 0° C. After stirring the suspension for 30 min at 0° C., 7.1 g (42 mmol) of benzyl bromide was added dropwise and the reaction mixture was stirred at 0° C. for 40 min. The reaction mixture was then diluted with 75 mL of diethyl ether, transferred to a separatory funnel and washed with 2×30 mL of 2N aqueous sulfuric acid solution, 2×30 mL of water and saturated aqueous sodium bicarbonate solution. The organic solution was dried over anhydrous magnesium sulfate, filtered and concentrated at reduced pressure to give 5.3 g of the protected epoxy alcohol as an oil.

N-Butyl lithium (18.5 mL of 2.5M solution in hexane, 46 mmol) was added to a solution of spiro[(1,3-benzodioxole)-2,1'-cyclohexane](7.4 g, 39 mmol) in 75 mL of THF at 0° C. After 4 h, the protected glycidol (5.3 g, 32 mmol) in 10 mL of THF was added dropwise and the reaction mixture was allowed to warm to ambient temperature. After 1.5 h, the reaction mixture was poured into 10% aqueous ammonium chloride solution and extracted with 2×50 mL of diethyl ether. The combined ether extracts were washed with ammonium chloride solution, dried over anhydrous magnesium sulfate, filtered and concentrated in vacuo. The residue was purified by column chromatography on silica gel eluted with 20% ethyl acetate in hexane to give 4.4 g (38% yield) of the title compound as a colorless oil. DCI MS: 372 (M+NH₄)+, 355 (M+H)+. ¹H NMR (CDCl₃) δ: 1.4–1.9 (m, 10H), 2.46 (d, 1H, J=3.9 Hz), 2.79 (d, 2H, J=7.0 Hz), 3.4 (dd, 1H, J=9.9, 7.2 Hz), 3.52 (dd, 1H, J=9.9, 3.0 Hz), 4.12 (m, 1H), 4.54 (s, 2H), 6.6–6.73 (m, 3H), 7.34 (m, 5H).

Step 2: [1,3-cis]3-Benzoxymethyl-1-bromomethyl-5,6-cyclohexylidenedioxy-3,4-dihydro-1H-2-benzopyran A solution of 1-benzyloxy-3-(spira-[(1,3-benzodioxole)-2,1'-cyclohexane])-2-propanol (4.3 g, 12 mmol), from Step 1, and bromoacetaldehyde dimethyl acetal (1.7 mL, 14 mmol) in 25 mL of methylene chloride was cooled to 0° C. Boron trifluoride etherate (3.6 mL, 29 mmol) was added dropwise and the reaction mixture was stirred for 1.5 h. The resultant dark brown solution was poured into 50 mL of 10% aqueous sodium carbonate solution and the aqueous solution was extracted with 3×50 mL of diethyl ether. The combined ether extracts were washed with saturated aqueous sodium bicarbonate solution and brine, dried over anhydrous magnesium sulfate, filtered and concentrated under reduced pressure. The residue was purified by column chromatography on silica gel eluted with 20% ethyl acetate in hexane to give 4.2 g (75%) of the title compound as a colorless syrup; DCI MS: 476 (M+NH$_4$)$^+$. $^1$H NMR (CDCl$_3$) δ: 1.45–1.95 (m, 10H), 2.57 (dd, 1H, J=16.5, 11.4 Hz), 2.71 (dd, 1H, J=16.5, 3 Hz), 3.59 (dd, 1H, J=11.4, 6 Hz), 3.63 (dd, 1H, J=10.8, 4.2 Hz), 3.73 (dd, 1H, J=10.8, 6 Hz), 3.87 (dd, 1H, J=11.4, 2.7), 4.65 (d, 1H, J=12 Hz), 4.72 (d, 1H, J=12 Hz), 5.0 (m, 1H), 6.52 (d, 1H, J=8.4 Hz), 6.62 (d, 1H, J=8.4 Hz), 7.42–7.25 (m, 5H).

Step 3: [1,3-cis]1-Bromomethyl-3-hydroxymethyl-5,6-cyclohexylidenedioxy-3,4-dihydro-1H-2-benzopyran 5% Platinum on carbon (1.0 g) was added to a solution of [1,3-cis]3-benzyloxymethyl-1-bromomethyl-5,6-cyclohexylidenedioxy-3,4-dihydro-1H-2-benzopyran (4.0 g, 8.7 mmol), from Step 2, in 150 mL of methanol and 5 mL of ethyl acetate. The reaction mixture was sealed under 4 atmospheres of hydrogen and shaken overnight. The reaction mixture was filtered to remove the catalyst and concentrated to a light brown oil. The oil was purified by column chromatography on silica gel eluted with 30% ethyl acetate in hexane to give 2.2 g (68% yield) of the title compound as a white foam. $^1$H NMR (CDCl$_3$) δ: 1.4–1.95 (m, 10H), 2.25 (dd, 1H, J=8.4, 4.5 Hz), 2.62 (d, 2H, J=7.5 Hz), 3.57 (dd, 1H, J=11.4, 6.9 Hz), 3.65–3.9 (m, 4H), 4.98 (m, 1H), 6.52 (d, 1H, J=8.4 Hz), 6.63 (d, 1H, J=8.4 Hz).

Step 4: 1-Azidomethyl-5,6-cyclohexylidenedioxy-3-hydroxymethyl-3,4-dihydro-1H-2-benzopyran Lithium azide (1.0 g, 20 mmol) was added to a solution of [1,3-cis]1-bromomethyl-5,6-cyclohexylidenedioxy-3-hydroxymethyl-3,4-dihydro-1H-2-benzopyran (2.17 g, 5.87 mmol), from Step 3, in 20 mL of DMF. The reaction mixture was heated to 70° C. for 1.5 h then cooled to ambient temperature and poured into 50 mL of diethyl ether and 50 mL of water. The layers were separated and the aqueous layer was extracted with 2×50 mL of diethyl ether. The combined ether layers were washed with saturated aqueous sodium bicarbonate solution, dried over anhydrous magnesium sulfate, filtered and concentrated in vacuo. The residue was purified by column chromatography on silica gel eluted with 25% ethyl acetate in hexane to give 1.38 g (70% yield) of the title compound as a colorless glass. $^1$H NMR (CDCl$_3$) δ: 1.45–1.95 (m, 10H), 2.14 (dd, 1H, J=9.0, 4.8 Hz), 2.63 (d, 2H, 7.5 Hz), 3.5 (dd, 1H, J=13.5, 7.0 Hz), 3.62 (dd, 1H, J=13.5, 2.7 Hz), 3.65–3.9 (m, 3H), 5.02 (m, 1H), 6.45 (d, 1H, J=8.4 Hz), 6.61 (d, 1H, J=8.4 Hz).

Step 5: [1,3-cis]1,3-Bis(azidomethyl)-5,6-cyclohexylidenedioxy-3,4-dihydro-1H-2-benzopyran Methanesulfonyl chloride (0.128 mL, 1.65 mmol) was added dropwise to a solution of 1,3-cis 1-azidomethyl-5,6-cyclohexylidenedioxy-3-hydroxymethyl-3,4-dihydro-1H-2-benzopyran (500 mg, 1.5 mmol), from Step 4, and 0.314 mL (2.25 mmol) of triethylamine (TEA) in 15 mL of methylene chloride at 0° C. After stirring for 30 min at 0° C., the reaction mixture was transferred to a separatory funnel and diluted with diethyl ether. The layers were separated and the organic layer was washed with 2×20 mL of water, 2×15 mL of 1N aqueous hydrochloric acid solution and brine, dried over magnesium sulfate, filtered and concentrated under reduced pressure to yield a white foam. The foam was dissolved in 20 mL of DMF and 440 mg (9 mmol) of lithium azide was added. The reaction mixture was heated to 80° C. and stirred at 80° C. for 4 h then cooled and poured into 50 mL of water. The aqueous solution was extracted with 3×30 mL of diethyl ether and the combined ether extracts were washed with 30 mL of water and brine, dried over anhydrous magnesium sulfate and concentrated under reduced pressure. The residue was purified on silica gel eluted with diethyl ether to give 450 mg (84% yield) of the title compound as a pale yellow oil; DCI MS: 374 (M+NH$_4$)$^+$. $^1$H NMR (CDCl$_3$) δ: 1.45–1.95 (m, 10H), 2.67 (m, 2H), 3.38 (dd, 1H, J=13.5, 3.9 Hz), 3.5 (m, 2H), 3.7 (dd, 1H, J=13.5, 2.7 Hz), 3.9 (m, 1H), 5.0 (m, 1H), 6.47 (d, 1H, J=8.7 Hz), 6.62 (d, 1H, J=8.7 Hz).

Step 6: [1,3-cis]1,3-Bis(aminomethyl)-5,6-cyclohexylidenedioxy-3,4-dihydro-1H-2-benzopyran Lithium aluminum hydride (2.4 mL of 1.0M solution in diethyl ether, 2.4 mmol) was added dropwise to a solution of [1,3-cis]1,3-bis(azidomethyl)-5,6-cyclohexylidenedioxy-3,4-dihydro-1H-2-benzopyran (430 mg, 1.2 mmol), from Step 5, in 10 mL of anhydrous diethyl ether at 0° C. The reaction mixture was allowed to warm to ambient temperature and stirred for 45 min. The reaction was then quenched by the sequential addition of 91 µL of water, 91 µL of 15% aqueous sodium hydroxide solution and 273 µL of water. The solution was dried over anhydrous magnesium sulfate, filtered and concentrated in vacuo to give 212 mg (85% yield) of the title compound as a colorless glass; $^1$H NMR (CDCl$_3$) δ: 1.4–1.95 (m, 14H), 2.5 (dd, 1H, J=17.1 Hz), 2.65 (dd, 1H, J=17.1, 3 Hz), 2.9 (m, 2H), 3.0 (dd, 1H, J=13.8, 6 Hz), 3.21 (dd, 1H, J=13.8, 2.4 Hz), 3.66 (m, 1H), 4.7 (m, 1H), 6.51 (d, 1H, J=8.4 Hz), 6.61 (d, 1H, J=8.4 Hz).

Step 7: [1,3-cis]1,3-Bis(aminomethyl)-3,4-dihydro-5,6-dihydroxy-1H-2-benzopyran dihydrochloride Absolute ethyl alcohol was saturated with anhydrous hydrogen chloride and added to 212 mg (0.96 mmol) of [1,3-cis]1,3-bis(aminomethyl)-5,6-cyclohexylidenedioxy-3,4-dihydro-1H-2-benzopyran from Step 6. The solution was heated to reflux temperature. After 45 min at reflux temperature, a precipitate formed and the volume of the reaction mixture was reduced to 5 mL. Diethyl ether was added until precipitation was complete and the precipitate was collected by vacuum filtration. The solid was washed with diethyl ether and dried in a vacuum oven at 80° C. overnight to give 280 mg (96% yield) of the title compound as a fine white powder, m.p.>260° C.; IR 3320, 3040, 1590, 1500, 1290 cm$^{-1}$; DCI MS: 225 (M+H)$^+$; $^1$H NMR (d$_6$-DMSO) δ: 2.38 (dd, 1H, J=16.5, 12 Hz), 2.76 (m, 2H), 2.97 (m, 1H), 3.52 (m, 2H), 3.9 (m, 1H), 4.83 (m, 1H), 6.54 (d, 1H, 8.1 Hz), 6.7 (d, 1H, J=8.1 Hz), 8.25 (br s, 6H), 8.6 (s, 1H), 9.4 (s, 1H). Analysis calculated for C$_{11}$H$_{18}$Cl$_2$N$_2$O$_3$: C, 44.46; H, 6.11; N, 9.43. Found: C, 44.70; H, 6.04; N, 9.22.

EXAMPLE 155

[1,3-cis]1-Aminomethyl-3,4-dihydro-5,6-dihydroxy-3-hydroxymethyl-1H-2-benzopyran hydrochloride Step 1: [1,3-cis]1-Aminomethyl-5,6-cyclohexylidenedioxy-3,4-dihydro-3-hydroxymethyl-1H-2-benzopyran Lithium aluminum hydride (1.1 mL of 1.0M solution in diethyl ether, 1.1 mmol) was added dropwise to a solution of 370 mg (1.1 mmol) of 1-azidomethyl-5,6-cyclohexylidenedioxy-3,4-dihydro-3-hydroxymethyl-1H-2-benzopyran, the product of Step 4 of Example 154, in 10 mL of anhydrous diethyl ether at 0° C. The reaction mixture was allowed to warm to ambient temperature and stirred for 40 min. The reaction mixture was cooled to 0° C. and quenched by the sequential addition of 42 µL of water, 42 µL of 15% aqueous sodium hydroxide solution and 126 µL of water. The solution was dried over anhydrous magnesium sulfate and filtered. The filtrate was concentrated in vacuo to give 263 mg (77% yield) of the title compound as a white powder; DCI MS: 306 (M+H)$^+$; $^1$H NMR (CDCl$_3$) δ: 1.4–1.95 (m, 13H), 2.6 (m, 2H), 3.03 (dd, 1H, J=13.5, 5.7 Hz), 3.23 (dd, 1H, J=13.5, 2.7 Hz), 3.7 (dd, 1H, J=11.7, 7.5 Hz), 3.77–3.9 (m, 2H), 6.52 (d, 1H, J=8.4 Hz), 6.62 (d, 1H, J=8.4 Hz).

Step 2: [1,3-cis]1-Aminomethyl-3,4-dihydro-5,6-dihydroxy-3-hydroxymethyl-1H-2-benzopyran hydrochloride Absolute ethyl alcohol was saturated with anhydrous hydrogen chloride and added to a suspension of 256 mg (0.83 mmol) of [1,3-cis]1-aminomethyl-5,6-cyclohexylidenedioxy-3,4-dihydro-3-hydroxymethyl-1H-2-benzopyran from Step 1 in 2 mL of ethanol. The reaction mixture was heated to reflux temperature. After 1.5 h at reflux temperature, a precipitate had formed. The solvents were evaporated down under reduced pressure to approximately 5 mL. Diethyl ether was added until the precipitation was complete and the solid was collected by vacuum filtration, washed with diethyl ether and dried in a vacuum oven at 80° C. overnight to give 160 mg (73% yield) of the title compound as an off-white powder, m.p. 235° C.; DCI MS: 226 (M+H)$^+$; IR: 3200, 1590, 1500, 1295, 1050 cm$^{-1}$; $^1$H NMR (d$_6$-DMSO) δ: 2.28 (dd, 1H, J=16.8, 11.4 Hz), 2.66 (dd, 1H, J=16.8, 3.0 Hz), 2.83 (dd, 1H, J=12.3, 9.3 Hz), 3.45–3.7 (m, 4H), 4.8 (m, 2H), 6.51 (d, 1H, J=8.4 Hz), 6.67 (d, 1H, J=8.4 Hz), 8.05 (br s, 3H), 8.48 (br s, 1H), 9.3 (br s, 1H). Analysis calculated for C$_{11}$H$_{16}$ClNO$_4$: C, 50.48; H, 6.16; N, 5.35. Found: C, 50.64; H, 6.24; N, 5.20.

EXAMPLE 156

[1,3-cis]1-Aminomethyl-3,4-dihydro-5,6-dihydroxy-3-pyrrolidinylmethyl-1H-2-benzopyran dihydrochloride Step 1; [1R, 3S]1-Azidomethyl-5,6-cyclohexylidenedioxy-3,4-dihydro-3-pyrrolidinylmethyl-1H-2-benzopyran Methanesulfonyl chloride (0.146 mL, 1.89 mmol) was added dropwise to a solution of 0.57 g (1.72 mmol) of [1 R, 3 S]1-azidomethyl-5,6-cyclohexylidene-dioxy-3,4-dihydro-3-hydroxymethyl-1H-2-benzopyran, the product of Step 4 of Example 154, and 0.36 mL (2.58 mmol) of triethylamine in 15 mL of methylene chloride at 0° C. The reaction mixture was stirred for 30 min at 0° C. then transferred to a separatory funnel and diluted with 45 mL of diethyl ether. The layers were separated and the organic layer was washed with 2×20 mL of water, 2 ×20 mL of 1N hydrochloric acid and 20 mL of brine, dried over anhydrous magnesium sulfate, filtered and concentrated under reduced pressure to 405 mg of white foam. The foam was dissolved in 20 mL of dimethyl formamide (DMF) and an excess amount of pyrrolidine was added to this solution. The reaction mixture was heated at 95° C. for 2.5 h then poured into 75 mL of water. The aqueous solution was extracted with 3×40 mL of diethyl ether. The combined ether extracts were washed with 2×30 mL of water and brine, dried over anhydrous magnesium sulfate, filtered and concentrated in vacuo. The residue was purified by column chromatography on silica gel eluted with 10% methanol in methylene chloride to give 210 mg (55% yield) of the title compound as a white foam; DCI MS: 385 (M+H)$^+$; $^1$H NMR (CDCl$_3$) δ: 1.4–1.9 (m, 14H), 2.5–2.9 (m, 8H), 3.45 (dd, 1H, J=13.2, 6.6 Hz), 3.68 (dd, 1H, J=13.2, 2.4 Hz), 3.9 (m, 1H), 4.97 (m, 1H), 6.45 (d, 1H, J=8.1 Hz), 6.6 (d, 1H, J=8.1 Hz).

Step 2: [1,3-cis]1-Aminomethyl-5,6-cyclohexylidenedioxy-3,4-dihydro-3-pyrrolidinylmethyl-1H-2-benzopyran Lithium aluminum hydride (0.52 mL of a 1.0M solution, 0.52 mmol) was added dropwise to a solution of 20 mg (0.52 mmol) of 1,3-cis 1-azidomethyl-5,6-cyclohexylidenedioxy-3,4-dihydro-3-pyrrolidinylmethyl-1H-2-benzopyran, from Step 1, in 10 mL of anhydrous diethyl ether at 0° C. The reaction mixture was allowed to warm to ambient temperature and it was stirred at ambient temperature for 40 min. The reaction mixture was then cooled to 0° C. and quenched by the sequential addition of 20 μL of water, 20 μL of 15% aqueous sodium hydroxide solution and 60 μL of water. The resultant solution was dried over anhydrous magnesium sulfate and the precipitate filtered. Diethyl ether saturated with anhydrous hydrogen chloride was then added dropwise to the filtrate to precipitate the hydrochloride salt of [1,3-cis]1-aminomethyl-5,6-cyclohexylidenedioxy-3,4-dihydro-3-pyrrolidinylmethyl-1H-2-benzopyran which was collected by vacuum filtration yielding 220 mg (98% yield) of the title compound as its hydrochloride salt, a white solid; DCI MS: 359 (M+H)$^+$.

Step 3: [1,3-cis]1-Aminomethyl-5,6-dihydroxy-3-pyrrolidinylmethyl-1H-2-benzopyran dihydrochloride.

Absolute ethanol (10 mL) was saturated with anhydrous hydrogen chloride and added to 187 mg (0.44 mmol) of the product of Step 2, [1,3-cis]1-aminomethyl-5,6-cyclohexylidenedioxy-3,4-dihydro-3-pyrrolidinylmethyl-1H-2-benzopyran. The reaction mixture was heated to reflux temperature. After 2 h at reflux temperature, a precipitate formed and the reaction mixture was cooled to ambient temperature. The volume of the reaction mixture was reduced under reduced pressure to approximately 5 mL. Diethyl ether was added to the concentrate to precipitate the product which was collected by vacuum filtration and washed with diethyl ether. The solid was dried in a vacuum oven at 80° C. overnight to give 146 mg (96% yield) of the title compound as a fine white powder, m.p.>280° C.; IR 3400, 3200, 2960, 1510, 1295 cm$^{-1}$; DCI MS: 279 (M+H)$^+$; $^1$H NMR (D$_6$-DMSO) δ: 2.0 (m, 4H), 2.33 (dd, 1H, J=16.2, 10.8 Hz), 3.1 (m, 2H), 3.4 (m, 2H), 3.6 (m, 3H), 4.05 (m, 1H), 4.93 (m, 1H), 6.54 (d, 1H, J=8.7 Hz), 6.7 (d, 1H, J=8.7 Hz), 8.4 (br s, 3H), 8.6 (s, 1H), 9.4 (s, 1H), 10.6 (br s, 1H).

Analysis calculated for C$_{15}$H$_{24}$Cl$_2$N$_2$O$_3$: C, 51.29; H, 6.89; N, 7.97. Found: C, 50.94; H, 6.82; N, 7.76.

EXAMPLES 157–160

Following the synthesis described in Example 156, using 3-(benzyloxy)propylene oxide and the appropriate alkyl or cycloalkyl amine, Examples 157 and 158 were prepared as disclosed in Table 6, as their dihydrochloride salts. Following the procedures described in Examples 154 and 155, using 4-(benzyloxy)butylene oxide, Examples 159 and 160 were prepared as disclosed in Table 6. The structure of each was confirmed by melting point, mass spectra and elemental analysis as designated.

TABLE 6

Examples 157–160

| Ex. No. | Compound* | Amine | mp °C. | MS** | Elemental Analysis C H N |
|---|---|---|---|---|---|
| 157 | [structure: dihydroxy chroman with CH2NH2 and piperazine-N-morpholine-like substituent] | O(CH2CH2)2NH (morpholine) | 255 | 295 | c: 49.06 6.59 7.63<br>f: 49.05 6.68 7.42 |
| 158 | [structure: dihydroxy chroman with CH2NH2 and piperidinylmethyl substituent] | piperidine NH | 265 | 293 | c: 52.61 7.17 7.67<br>f: 52.8 7.21 7.53 |
| 159 | [structure: dihydroxy chroman with CH2NH2 and CH2CH2NH2 side chain] | | >250 | 239 | c: 46.52 6.72 8.68<br>+1/4 EtOH<br>f: 46.45 6.59 8.40 |
| 160 | [structure: dihydroxy chroman with CH2NH2 and CH2CH2OH side chain] | | 224 | 240 | c: 51.93 6.61 5.05<br>+0.1 H2O<br>f: 51.79 6.52 4.75 |

*all compounds 1–3 cis unless indicated otherwise
**DCI MS (M + H)+

EXAMPLES 161–172

Following the synthesis illustrated in Scheme V using the appropriate acylating agent Examples 161–172 were prepared as disclosed in Table 7, as their hydrochloride salts. The structure of each was confirmed by melting point, mass spectra and elemental analysis as designated.

TABLE 7

Examples 161–169

| Ex. No. | Compound* | Acyl chloride | mp °C. | MS** | Elemental Analysis C H N |
|---|---|---|---|---|---|
| 161 | [structure: dihydroxy chroman with CH2NH2 and NHC(O)CH3 side chain] | ClC(O)CH3 | >260 | 267 | c:<br>f: na |

TABLE 7-continued

Examples 161–169

| Ex. No. | Compound* | Acyl chloride | mp °C. | MS** | Elemental Analysis C H N |
|---|---|---|---|---|---|
| 162 | (structure: dihydroxyphenyl chroman with N-acetyl, pentyl, CH₂NH₂) | ClC(O)CH₃ | 175 | 337 | c: 57.65 8.14 7.07 +1/2 EtOH<br>f: 58.05 7.82 6.78 |
| 163 | (structure: dihydroxyphenyl chroman with N-acetyl, pentyl, CH₂NH₂) | ClC(O)CH₃ | 183–4 | 337 | c: 55.30 7.98 7.17 +1 H₂O<br>f: 55.17 7.61 7.13 |
| 164 | (structure: dihydroxyphenyl chroman with N-benzoyl, CH₂NH₂) | ClC(O)Ph | 188 | 329 | c: 55.82 6.12 7.23 +1.25 H₂O<br>f: 56.00 6.00 7.01 |
| 165 | (structure: dihydroxyphenyl chroman with N-chloroacetyl, pentyl, CH₂NH₂) | ClC(O)CH₂Cl | 165 | 371 | c: 53.08 6.93 6.88<br>f: 52.71 6.86 6.70 |
| 166 | (structure: dihydroxyphenyl chroman with N-pivaloyl, CH₂NH₂) | ClC(O)C(CH₃)₃ | >250 | 309 | c: 51.38 6.95 7.49 +0.8 HCl<br>f: 51.48 6.88 7.37 |
| 167 | (structure: dihydroxyphenyl chroman with N-(4-bromobenzoyl), CH₂NH₂) | ClC(O)C₆H₄Br | 235 | 408 | c: 48.23 4.61 6.25 +1/4 H₂O<br>f: 48.09 4.59 6.12 |

TABLE 7-continued

Examples 161–169

| Ex. No. | Compound* | Acyl chloride | mp °C. | MS** | Elemental Analysis C H N |
|---|---|---|---|---|---|
| 168 | (structure) | (structure) | >250 | 319 | c: 53.49 5.47 7.80 +1/4 H$_2$O f: 53.43 5.52 7.59 |
| 169 | (structure) | (structure) | >250 | 295 | c: 53.73 7.06 8.35 +1/4 H$_2$O f: 53.69 6.90 8.06 |
| 170 | (structure) | (structure) | >250 | 330 | c: 48.58 5.52 10.00 +0.1 H$_2$O f: 48.98 5.66 9.70 |
| 171 | (structure) | (structure) | >250 | 295 | c: 54.18 7.76 7.43 +1 EtOH f: 54.07 7.70 7.28 |
| 172 | (structure) | (structure) | 234 | 281 | c: 49.06 6.50 7.43 f: 49.03 6.35 7.48 |

*all compounds 1–3 cis unless indicated otherwise;
**DCl MS (M + H)+

EXAMPLES 173–175

Following the synthesis described in Examples 154 and 155, using 4-(benzyloxy)butylene oxide and the procedure for N-methylation described in Example 111, Examples 173–175 were prepared as shown below in Table 8, as their hydrochloride salts. The structure of each was confirmed by melting point, mass spectra and elemental analysis as designated.

TABLE 8

173-175

| Ex. No. | Compound* | mp °C. | MS** | Elemental Analysis C H N |
|---|---|---|---|---|
| 173 | HO-, HO-, phenyl-CH2-CH(O-)-CH2-NH2, with CH2-NHCH3 branch forming ring | >246 | 253 | c: 47.61 7.04 8.29 +0.4 MeOH f: 47.93 6.83 7.89 |
| 174 | HO-, HO-, phenyl-CH2-CH(O-)-CH2-OH, with CH2-NHCH3 branch forming ring | >243 | 254 | c: 53.88 6.96 4.83 f: 53.62 6.99 4.90 |
| 175 | HO-, HO-, phenyl-CH2-CH(O-)-NHCH3, with CH2-NHCH3 branch forming ring | >260 | 253 | c: 45.55 6.50 7.99 +0.3 CH2Cl2 f: 45.55 6.29 8.37 |

*all compounds 1–3 cis unless indicated otherwise;
**DCl MS (M + H)+

EXAMPLE 176

[1,3-cis]1-Aminomethyl-3-cyclohexyl-6,7-dihydroxy-1,3,4,5-tetrahydro-2-benzoxepin hydrochloride Step 1: Spiro[(4-methyl-1,3-benzodioxole)-2,1'-cyclohexane]

A catalytic amount of p-toluenesulfonic acid (approximately 50 mg) was added to a solution of 2,3-dihydroxytoluene (10g, 80.7 mmol) and cyclohexanone (8.3 mL, 81 mmol) in mL of cyclohexane. The reaction mixture was heated to reflux temperature and the water produced in the condensation reaction was removed using a Dean Stark trap. After 6 h, the solution was concentrated to approximately 50 mL and purified on a silica gel column (10 cm×6 cm) eluted with hexane to give 14 g of the title compound as a colorless liquid; $^1$H NMR (CDCl$_3$) δ: 1.5 (m, 2H), 1.7 (m, 4H), 1.9 (m, 4H), 2.2 (s, 3H), 6.6 (m, 3H).

Step 2: 1-Cyclohexyl-2-(2',3'-cyclohexylidenedioxy-4'-methylphenyl)ethanol and 1-Cyclohexyl-3-(2',3'-cyclohexylidenedioxyphenyl)-1-propanol N-Butyl lithium (23 mL of a 2.1M solution in hexane, 49 mmol) was added dropwise to a solution of spiro[(4-methyl-1,3-benzodioxole)-2,1'-cyclohexane](9 g, 44 mmol), from Step 1, in 60 mL of THF at 0° C. The reaction mixture was allowed to warm to 25° C. and stirred at ambient temperature for 4 h. The reaction mixture was then cooled to 0° C and 1cyclohexylethylene oxide was added. The reaction mixture was stirred for 2 h at 25° C. and 30 min at 50° C. then poured into 100 mL of saturated aqueous ammonium chloride solution and extracted with 3×100 mL of diethyl ether. The combined ether extracts were washed with water and brine, dried over anhydrous magnesium sulfate, filtered and concentrated in vacuo. The title compounds were separated by column chromatography on silica gel eluted with 5% ethyl acetate in hexane to give 5.12 g (35% yield) of 1-cyclohexyl-2-(2',3'-cyclohexylidenedioxy-4'-methylphenyl)ethanol and 3.63 g (25% yield) of 1-cyclohexyl-3-(2', 3'-cyclohexylidenedioxyphenyl)-1-propanol.

Step 3: [1,3-cis]1-Bromomethyl-3-cyclohexyl-6,7-cyclohexylidenedioxy-1,3,4,5-tetrahydro-2-benzoxepin hydrochloride Boron trifluoride etherate (1.47 mL, 12 mmol) was added dropwise to a solution of 2 g (6.06 mmol) of 1-cyclohexyl-3-(2',3'-cyclohexylidenedioxy-phenyl)-1-propanol from Step 2 and bromoacetaldehyde dimethyl acetal (0.716 mL, 6.06 mmol) in 30 mL of methylene chloride at −20° C. The temperature of the reaction mixture was maintained between −10° C. and −5° C. for 1 h. The reaction mixture was then diluted with 100 mL of diethyl ether and washed with 2×50 mL of aqueous sodium carbonate solution and 50 mL of brine. The organic solution was dried over anhydrous magnesium sulfate, filtered and concentrated in vacuo. The residue was purified by column chromatography on silica gel eluted with 2% ethyl acetate in hexane to give 1.2 g (46% yield) of the title compound as a colorless foam.

Step 4: [1,3-cis]1-Aminomethyl-3-cyclohexyl-6,7-cyclohexylidenedioxy-1,3,4,5-tetrahydro-2-benzoxepin hydrochloride Lithium azide (590 mg, 12 mmol) was added to a solution of 1.05 g (2.4 mmol) of [1,3-cis]1-bromomethyl-3-cyclohexyl-6,7-cyclohexylidenedioxy-1,3,4,5-tetrahydro-2-benzoxepane hydrochloride, from Step 3, in 10 mL of DMF at 25° C. The reaction mixture was heated to 65° C., stirred at 65° C. for 2.5 h, cooled to ambient temperature and poured into 100 mL of water. The aqueous solution was extracted with 3×50 mL of diethyl ether. The combined ether extracts were washed with 75 mL of water and 75 mL of brine, dried over anhydrous magnesium sulfate, filtered and concentrated in vacuo. The residue was purified by column chromatography on silica gel eluted with 2% ethyl acetate in hexane to give 850 mg (89% yield) of [1,3-cis]-1-azidomethyl-3-cyclohexyl-6,7-cyclohexylidenedioxy-1,3,4,5-tetrahydro-2-benzoxepin hydrochloride. This azide intermediate was dissolved in 25 mL of diethyl ether and lithium aluminum hydride (2.1 mL of a 1M solution in diethyl ether) was added to the solution at 0° C. After warming the reaction mixture to ambient temperature and stirring for 1 h, the reaction mixture was cooled to 0° C. and the reaction quenched by the sequential addition of 80 μL of water, 80 μL of 15% aqueous sodium hydroxide solution and 240 μL of water. The precipitate was filtered and washed with diethyl ether. The filtrate was concentrated and the residue redissolved in diethyl ether. The ether solution was treated with diethyl ether saturated with anhydrous hydrogen chloride. The precipitate was collected by vacuum filtration and dried to give 770 mg (90% yield) of the title compound as a colorless solid, m.p. 250° C.; DCI MS: 372 (M+H)$^+$; $^1$H NMR (CDCl$_3$) δ: 0.9–1.9 (m, 23H), 2.7 (m, 1H), 3.02 (m, 1H), 3.3 (t, 1H, J=11.4 Hz), 3.52 (m, 2H), 4.97 (dd, 1H, J=11.4, 2.9 Hz), 6.45 (d, 1H, J=7.5 Hz), 6.5 (d, 1H, J=7.5 Hz), 8.5 (br s, 2H).

Step 5: [1,3-cis]1-Aminomethyl-3-cyclohexyl-6,7-dihydroxy-1,3,4,5-tetrahydro-2-benzoxepin hydrochloride

[1,3-cis]1-Aminomethyl-3-cyclohexyl-6,7-cyclohexylidenedioxy-1,3,4,5-tetrahydro-2-benzoxepin hydrochloride (200 mg, 0.49 mmol), from Step 4, was added to a 1N solution of anhydrous hydrogen chloride in ethyl alcohol. The reaction mixture was heated to 50° C. and monitored by TLC analysis. After two hours the solution was concentrated to approximately 1 mL and the residue triturated with diethyl ether. The solid was collected by vacuum filtration, washed with diethyl ether and dried to give 62 mg (40% yield) of the title compound as a colorless powder, m.p. 216°–219° C.; DCI MS: 292 (M+H)$^+$. Analysis calculated for C$_{17}$H$_{26}$ClNO$_3$: C, 62.28; H, 7.99; N, 4.27. Found: C, 62.22; H, 8.05; N, 4.14.

EXAMPLE 177

[1,3-cis]1-Aminomethyl-3-cyclohexyl-3,4-dihydro-5,6-dihydroxy-7-methyl-1H-2-benzopyran hydrochloride 1-Cyclohexyl-2-(2',3'-cyclohexylidenedioxy-4'-methylphenyl)ethanol, from Step 2 of Example 176, was converted to the title compound by the procedures described in Example 176 above, Steps 3–5, m.p. 168°–170° C.; DCI MS: 292 (M+H)$^+$. Analysis calculated for C$_{17}$H$_{26}$ClNO$_3$+½H$_2$O: C, 60.61; H, 8.077; N, 4.16. Found: C, 60.39; H, 7.92; N, 4.12.

EXAMPLE 178

[1S,3R]1-Aminomethyl-3-phenyl-5,6-dihydroxy-1H-2-benzopyran hydrochloride

Step 1: 2-(2',3'-Cyclohexylidenedioxyphenyl)-1-phenylethanone

A solution of 15.5 g (50 mmol) of 2-(2',3'-cyclohexylidenedioxyphenyl)-1-phenylethanol prepared from styrene oxide (commercially available from Aldrich Chemical Company) by the procedure described in Step 2 of Example 47, in 60 mL of methylene chloride was added dropwise to a mixture of 60 g (28 mmol) of pyridinium chlorochromate (PCC) and 35 g of Celite® filter aid in 300 mL of methylene chloride at ambient temperature. After 4 h, the reaction mixture was diluted with 200 mL of diethyl ether and filtered through silica gel. The chromium-containing residue was washed several times with diethyl ether. The filtrate was concentrated under reduced pressure to give 14 g (90% yield) of the title compound as a yellow syrup; DCI MS: 326 (M+NH4)$^+$, 309 (M+H)$^+$; $^1$H NMR (CDCl$_3$) δ: 1.4–1.9 (m, 10H), 4.2 (s, 2H), 6.7 (m, 3H), 7.42 (m, 2H), 7.53 (m, 1H), 8.05 (m, 2H).

Step 2: [1R]2-(2',3'-cyclohexylidenedioxyphenyl)-1-phenylethanol

A solution of 754 mg (2.45 mmol) of 2-(2',3'-cyclohexylidenedioxyphenyl)-1-phenylethanone, from Step 1, in 1 mL of THF was added to a solution of 936 mg (2.9 mmol) of (−) B-chlorodiisopinocampheylborane (commercially available from Aldrich Chemical Company) in 3 mL of THF at −20° C. After storing the resultant solution for 12 h at −15° C., the solvent was evaporated, the residue was dissolved in 15 mL of diethyl ether and 565 mg of diethanolamme was added. The mixture was stirred for 30 min. The precipitate was removed by filtration through Celite® filter aid. The filtrate was concentrated and the residue purified by column chromatography on silica gel eluted with methylene chloride/hexane/diethyl ether (100:20:1) to give 546 mg (72% yield) of the title compound; DCI MS: 328 (M+NH$_4$)$^+$; $^1$H NMR (CDCl$_3$) δ: 1.4–1.9 (m, 10H), 2.3 (br s, 1H), 3.0 (m, 2H), 4.98 (dd, 1H, J=7.5, 5.0 Hz), 6.62 (m, 3H), 7.3 (m, 5H).

Step 3: [1S,3R]1-Aminomethyl-3,4-dihydro-5,6-dihydroxy-3-phenyl-1H-2-benzopyran hydrochloride

[1R]2-(2',3'-Cyclohexylidenedioxyphenyl)-3-phenylethanol was converted to [1S,3R]1-aminomethyl-3,4-dihydro-5,6-dihydroxy-3-phenyl-1H-2-benzopyran by the procedures detailed in Step 3 of Example 47 and Steps 1–3 of Example 48, m.p. 158°–160° C.; [alpha]D=110° (c 0.52, 1N HCl); DCI MS: 272 (M+H)$^+$. Analysis calculated for C$_{16}$H$_{18}$ClNO$_3$: C, 60.60; H, 6.05; N, 4.42. Found: C, 60.71; H, 6.2; N, 4.31.

EXAMPLE 179

[1R,3S]3-Adamantyl-1-aminomethyl-3,4-dihydro-5,6-dihydroxy-1H-2-benzopyran hydrochloride Step 1: 1-Aza-2-boro-3-oxa-1,4,4-triphenyl-bicyclo[3.3.0]octane Diphenyl-(2R-2'-pyrrolidinyl)methanol (610 mg, 2.41 mmol) and phenylboronic acid (294 mg, 2.41 mmol) were taken up in 25 mL of toluene. The diphenyl-(2R-2'-pyrrolidinyl)methanol was prepared as described by E. J. Corey et al. in *J American Chem Soc*. 109:5551–53 (1987). The reaction mixture was heated at reflux temperature for 4 h under a nitrogen atmosphere using a Dean Stark trap filled with 4 Å molecular sieves to remove water. The reaction was then cooled and concentrated in vacuo to afford the title compound as a colorless oil. The product was carried on to the next step without purification.

Step 2: [1R]1-(1'-adamantyl)-2-bromo-1-hydroxyethane

Diborane in THF (5.2 mL of 1.0M THF solution, 5.2 mmol) was added dropwise over a period of 10 min to a solution of 2.22 g (8.63 mmol) of 1-adamantyl-bromomethyl ketone (commercially available from Aldrich Chemical Co.) and 2.1 mL of a 0.2M solution in THF (0.43 mmol) of 1-aza-2-boro-3-oxa-1,4,4-triphenyl-bicyclo[3.3.0]octane, from Step 1, in 16 mL of anhydrous THF. The reaction mixture was stirred for 10 min at ambient temperature and then cooled to ~0° C. in an ice bath and then the reaction was quenched by the careful addition of 3 mL of methanol. Diethyl ether saturated with hydrogen chloride (2 mL) was added and the solution was allowed to warm to ambient temperature. The solution was stirred at ambient temperature for 0.5 h and then it was poured into 100 mL of diethyl ether and 100 mL of water. The organic layer was washed with 1N aqueous hydrochloric acid solution, aqueous saturated sodium bicarbonate and brine, dried over anhydrous magnesium sulfate, filtered and concentrated under reduced pressure to give 216 mg (96% yield) of the title compound as a white solid.

Step 3: [1R]1-(1'-adamantyl)-ethylene oxide

A 15% aqueous solution of sodium hydroxide was added to a solution of 1.9 g (7.34 mmol) of [1R]1-(1'-adamantyl)-2-bromo-1-hydroxyethane, from Step 2, in 50 mL of diethyl ether The mixture was stirred vigorously at ambient temperature for ~18 h. The mixture was then diluted with 100 mL of diethyl ether and 50 mL of water. The aqueous layer was extracted with 50 mL of diethyl ether. The combined organic layers were washed with 2×50 mL of water and 50 mL of brine, dried over anhydrous magnesium sulfate, filtered and concentrated under reduced pressure to afford 1.3 g of the title compound. The product was carried on to the next step without purification.

Step 4: [1S]1-(1'-Adamantyl)-2-(spiro-[(1,3-benzodioxole)-2,1'-cyclohexane])-1-ethanol n-Butyl lithium (6.7 mL of a 1.48M solution in hexane, 9.9 mmol) was added over a 10 min period to a solution of spiro[(1,3-benzodioxole)-2,1'-cyclohexane] in 14 mL of THF at 0° C. The reaction mixture was allowed to warm to ambient temperature over a 0.5 h period and then it was stirred for 3.5 h at ambient temperature. The reaction mixture was cooled to −78° C. and a solution of 1.2 g (6.74 mmol) of [1R]1-(1'-adamantyl)-ethylene oxide, from Step 3, in 5 mL of THF was added. Boron trifluoride etherate (1.15 mL, 9.44 mmol) was then added dropwise over a 7 min period. After 30 minutes, 25 mL of aqueous saturated sodium bicarbonate solution was added, followed by 25 mL of ethyl acetate. The reaction mixture was allowed to warm to ambient temperature and transferred to a separatory funnel. Ethyl acetate (50 mL) and saturated aqueous sodium bicarbonate solution (25 mL) were added to the funnel and the layers were separated. The aqueous layer was extracted with ethyl acetate. The combined organic layers were washed with 2×50 mL of aqueous sodium bicarbonate solution and brine, dried over anhydrous magnesium sulfate and concentrated under reduced pressure to an oil. The crude product was dissolved in 20 mL of methanol and the solution was cooled to 0° C. The precipitate was collected by filtration and washed with cold methanol to give 2.21 g (89% yield) of the desired product. The title compound was recrystallized from methanol to give 1.6 g of the title compound, m.p. 72°–73° C.; [alpha]$_D$=−27.75° (c 1.63, CHCl$_3$); DCI MS 386 (M+NH$_4$)$^+$. $^1$H NMR (CDCl$_3$) δ: 0.9 (q, 0.25H, J=6 Hz, MeOH solvate), 1.5–2.1 (m, 25H), 2.5 (dd, 1H, J=13.5, 10.5 Hz), 2.87 (dd, 1H, J=13.5, 2.0 Hz), 3.3 (m, 1H), 3.5 (d, 0.75H, J=6 Hz, MeOH solvate). Analysis calculated for C$_{24}$H$_{32}$O$_3$+0.25MeOH: C, 77.35; H, 8.83. Found: C, 77.09; H, 8.77.

Step 5: [1R,3S]3-(1'-Adamantyl)-5,6-cyclohexylidenedioxy-3,4-dihydro-1-(N-formyl)aminomethyl-1H-2-benzopyran Trimethylsilyltriflate (73 μL, 0.38 mmol) was added to a mixture of 3.5 g (9.5 mmol) of [1 S]1-(1'-adamantyl)-2-(spiro-[(1,3-benzodioxole)-2,1'-cyclohexane])-1-ethanol, from Step 4, and N-formylacetaldehyde dimethyl acetal (2 g, 15.2 mmol) in 20 mL of acetonitrile. The reaction mixture was heated at a gentle reflux for 2 h and an additional 50 μL (0.26 mmol) of trimethylsilyltriflate was added. A precipitate formed and after 4 h the reaction mixture was cooled to 0° C. The precipitate was collected by filtration, washed with cold acetonitrile and dried to afford 2.92 g (70% yield) of the title compound as colorless crystals, m.p. 220°–221° C.; [alpha]$_D$=−33.15° (c 1.63, CHC$_3$); DCI MS: 438 (M+H)$^+$. $^1$H NMR (d$_6$-DMSO) δ: @140° C. 1.5–2.05 (m, 25H), 2.5 (m, 2H), 2.8 (m, 1H), 3.1 (dd, 1H, J=7.5, 3.0 Hz), 3.32 (m, 1H) 3.71 (br s, 1H), 4.65 (br s, 1H), 6.6 (m, 2H), 8.05 (br s, 1H).

Step 6: [1R,3S]3-(1'-Adamantyl)-1-aminomethyl-5,6-cyclohexylidenedioxy-3,4-dihydro-1H-2-benzopyran

[1R,3S]3-(1'-Adamantyl)-5,6-cyclohexylidenedioxy-3,4-dihydro-1-(N-formyl)aminomethyl-1H-2-benzopyran (2.8 g, 6.41 mmol) was mixed together with 20 mL of 15% aqueous sodium hydroxide solution, 30 mL of methanol and 20 mL of THF. The mixture was heated at ~50° C. for 3 h and then it was concentrated in vacuo to ~30 mL. The concentrated mixture was diluted with 150 mL of ethyl acetate/methylene chloride (2:1) and 50 mL of water. The organic layer was washed with 2×50 mL of water and 50 mL of brine. The combined aqueous layers were extracted with ethyl acetate/methylene chloride (2:1) and discarded. The combined organic layers were dried over anhydrous magnesium sulfate, filtered and concentrated in vacuo to give 2.64 g of the title compound as a light tan colored foam. The product was carried on to the next step without purification.

Step 7: [1R,3S]3-(1'-Adamantyl)-1-aminomethyl-3,4-dihydro-5,6-dihydroxy-1H-2-benzopyran hydrochloride A solution of hydrochloric acid in 10:1 THF/water (20 mL of a 4N solution) was added to [1R,3S]3-(1'-adamantyl)-1-aminomethyl-5,6-cyclohexylidenedioxy-3,4-dihydro-1H-2-benzopyran (1.1 g, 2.7 mmol) from Step 6, and the reaction mixture was heated at reflux temperature for 3 h. The reaction mixture was cooled to 0° C. and 10 mL of diethyl ether was added. At the onset of crystallization an additional 10 mL of diethyl ether was added. After 30 min the precipitate was removed by filtration, washed with diethyl ether and dried to give 0.81 g (82% yield) of the title compound as a colorless solid; DCI MS: 330 (M+H)$^+$. $^1$H NMR (CD$_3$OD) δ: 1.65–2.05 (m, 15H), 2.6 (dd, 1H, J=16.5, 12.0 Hz), 2.72 (dd, 1H, J=16.5, 3.0 Hz), 3.08 (dd, 1H, J=12.6, 7.5 Hz), 3.15 (dd, 1H, J=12.0, 3.0) 3.54 (dd, 1H, J=12.6, 3.2 Hz), 4.85 (m, 1H), 6.5 (d, 1H, J=8.4 Hz), 6.69 (d, 1H, J=8.4 Hz).

EXAMPLE 180

[1,3-cis]5,6-Dihydroxy-3-phenyl-1-(2'-pyrrolidinyl)-1,2,3,4-tetrahydronaphthalene hydrobromide Step 1: 1-Cyano-5,6-dimethoxy-3-phenyl-3,4-dihydronaphthalene To a suspension of 10 g (35 mmol) of 5,6-dimethoxy-3-phenyl-1,2,3,4-tetrahydronaphthalen-1-one, the product of Example 1, was added 7.5 g (75.6 mmol) of trimethylsilyl cyanide (commercially available from Aldrich Chemical Company) and approximately 50 mg of anhydrous aluminum chloride (AlCl$_3$). The reaction mixture was heated at 60° C. for 3 h then cooled to ambient temperature and diluted with 150 mL of toluene. The volume of the reaction mixture was reduced in vacuo to approximately 50 mL. The resultant trimethylsilyl adduct was dehydrated by treatment with 15 mL of trifluoroacetic acid and 100 mg of p-toluenesulfonic acid in 200 mL of toluene at reflux temperature for 1 h. The reaction mixture was cooled to ambient temperature, the layers separated and the organic layer washed with water, aqueous sodium bicarbonate solution and brine, dried over anhydrous magnesium sulfate, filtered and concentrated under reduced pressure to a colorless oil. The oil was purified by column chromatography on silica gel eluted with 20% ethyl acetate in hexane to give 8.5 g (83% yield) of the title compound, m.p. 109°–110° C.

Step 2: 1-Cyano-5,6-dimethoxy-3-phenyl-1,2,3,4-tetrahydronaphthalene

Sodium borohydride (6.8 g) was added to a suspension of 6.8 g (23.3 mmol) of 1-cyano-5,6-dimethoxy-3-phenyl-3,4-dihydronaphthalene, from Step 1, in 100 mL of absolute ethanol and the reaction mixture was heated at reflux temperature for 1.5 h. The solvent was evaporated under reduced pressure and the residue was dissolved in ethyl acetate. The ethyl acetate solution was washed with 1N aqueous hydrochloric acid solution, aqueous sodium bicarbonate solution and brine, dried over anhydrous magnesium sulfate, filtered and concentrated to an oil. The oil was triturated with heptane to give 5.63 g (82% yield) of the title compound as a white crystalline solid, m.p. 118°–121° C.

Step 3: 5,6-Dimethoxy-3-phenyl-1,2,3,4-tetrahydronaphthalene-1-carboxylic acid

A mixture of 5.6 g (19.1 mmol) of 1-cyano-5,6-dimethoxy-3-phenyl-1,2,3,4-tetrahydronaphthalene, from Step 2, 40 mL of 5% aqueous potassium hydroxide solution and 90 mL of ethylene glycol was heated at reflux temperature for 8 h. The reaction mixture was then cooled to −20° C. and made acidic by the addition of cold concentrated aqueous hydrochloric acid solution. The acidic solution was extracted with methylene chloride and the organic extracts were washed with brine, dried over anhydrous magnesium sulfate, filtered and evaporated to give 5 g (84% yield) of the title compound which was used in the next step without purification.

Step 4: N-Methoxy-N-methyl-5,6-dimethoxy-3-phenyl-1,2,3,4-tetrahydro-naphthalene-1-carboxamide 5,6-Dimethoxy-3-phenyl-1,2,3,4-tetrahydronaphthalene-1-carboxylic acid (5 g, 16 mmol), from Step 3, was suspended in 100 mL of toluene and 5 mL of oxalyl chloride was added. The reaction mixture was heated at reflux temperature for 1.5 h under a nitrogen atmosphere. The solvent was evaporated and excess reagents removed from the residue as an azeotrope with toluene (2×40 mL). The acid chloride and 2g (20 mmol) of N,O-dimethylhydroxylamine hydrochloride was dissolved in 80 mL of ethanol-free chloroform. The solution was cooled to 0° C. and 3.3 mL of pyridine was added slowly. The reaction mixture was allowed to warm to ambient temperature and stirred at ambient temperature for approximately 4 h then evaporated to dryness. The residue was dissolved in a 1:1 mixture of diethyl ether and methylene chloride and washed with brine. The layers were separated and the organic layer dried over anhydrous magnesium sulfate, filtered and concentrated under reduced pressure to give the title compound as an oil in 98% yield. The product of Step 4 was used in the next step without purification.

Step 5: 5,6-Dimethoxy-3-phenyl-1-(2'-pyrrolidinyl)-1,2,3,4-tetrahydronaphthalene hydrochloride N-Methoxy-N-methyl-5,6-dimethoxy-3-phenyl-1,2,3,4-tetrahydronaph-thalene-1-carboxamide (3.3 g), from Step 4, was dissolved in 80 mL of dry THF and the solution was cooled to 0° C. An excess (3–4 equivalents) of 2,2,5,5-tetramethyl-1-aza-2,5-disilacyclopentane-1-propyl magnesium bromide was added and stirred overnight. The 2,2,5,5-tetramethyl-1-aza-2,5-disilacyclo-pentane-1-propyl magnesium bromide was prepared as described by Basha and DeBernardis in *Tetrahedron Letter*, 25, 5271–5274 (1984). The reaction mixture was cooled to 0° C., 10% hydrochloric acid solution in ethanol was added slowly, and it was allowed to warm to ambient temperature again. The reaction mixture was stirred at ambient temperature for 3 h and the solvent was evaporated. The residue was dissolved in 50 mL of methanol, cooled to 0° C. and treated with an excess of sodium cyanoborohydride. The reaction mixture was allowed to warm to ambient temperature and stirred at ambient temperature for 2 h. The solvent was removed in vacuo and the residue was redissolved in diethyl ether and washed with water. The layers were separated and the acidic aqueous layer was made basic and extracted with methylene chloride. The methylene chloride extract was dried over anhydrous magnesium sulfate, filtered and concentrated in vacuo. The residue was purified by column chromatography on silica gel eluted with ethyl acetate/formic acid/water (18:1:1) to give a total yield, after concentration in vacuo, of 2.42 g (42% yield) of the title compound as individual diastereomers as their formate salts. Each diastereomer was converted to its hydrochloride salt as follows: the formate salt was dissolved in water and the aqueous solution was made basic with sodium hydroxide. The free base was extracted with methylene chloride and the organic layer was washed with brine, dried over anhydrous magnesium sulfate, filtered and concentrated under reduced pressure. The residue was dissolved in diethyl ether and a saturated solution of hydrogen chloride gas in methanol was added to precipitate the hydrochloride salt. The first compound to elute from the column gave 274 mg (7% yield) of the [1R, 3S, 2'R] isomer, m.p. 105°106° C. The structure was confirmed by NMR and X-ray crystallographic analysis (after recrystallization from acetone by slow evaporation).

The final product to elute from the column gave 400 mg(11% yield) of the [1R, 3R, 2'R] isomer, m.p. 150°–152° C. The structure was confirmed by NMR and X-ray crystallographic analysis after recrystallization from acetone by slow evaporation.

Step 6: [1,3-cis]5,6-Dihydroxy-3-phenyl-1-(2'-pyrrolidinyl)-1,2,3,4-tetrahydronaphthalene hydrobromide 5,6-Dimethoxy-3-phenyl-1-(2'-pyrrolidinyl)-1,2,3,4-tetrahydronaphthalene hydrochloride (200 mg, m.p. 105°–106° C.), from Step 5, was dissolved in 10 mL of methylene chloride and the solution was cooled to −78° C. under a nitrogen atmosphere. Boron tribromide (0.25 mL of a 1M solution in methylene chloride) was added and the reaction mixture was stirred for 3 h at −78° C. The reaction mixture was then allowed to warm to −20° C. for 1 h, cooled to −78° C. and quenched with 10 mL of methanol. The solution was evaporated to dryness and distilled with methanol three times to azeotrope methyl borate from the residue. The solid residue was crystallized from methanol/ethyl acetate to give 130 mg (67% yield) of the title compound, m.p. 265° C. (with decomposition). Analysis calculated for $C_{20}H_{24}BrNO_2 \cdot \frac{1}{2}H_2$: C, 60.16; H, 6.31; N, 3.51. Found: C, 60.06; H, 6.17; N, 3.42.

EXAMPLE 181

[1,3-cis]5,6-Dihydroxy-3-phenyl-1-(2'-pyrrolidinyl)-1,2,3,4-tetrahydronaph-thalene hydrobromide According to the procedures described in Step 6 of Example 180, [1R, 3 R]5,6-dimethoxy-3-phenyl-1-(2'-pyrrolidinyl)-1,2,3,4- tetrahydronaphthalene hydrochloride (350 mg), from Step 5 of Example 180, in 10 mL of methylene chloride at −78° C., was treated with 472 μL of a 1M solution of boron tribromide in methylene chloride. The title compound was obtained (213 mg) in 61% yield after crystallization from methanol/ethyl acetate, m.p. 250° C. (with decomposition). Analysis calculated for $C_{20}H_{24}BrNO_2·½H_2O$: C, 60.16; H, 6.31; N, 3.51. Found: C, 60.23; H, 6.24; N, 3.38.

EXAMPLE 182

[1R*,8S*,9aR*]1-Amino-5,6-dihydroxy-8-phenyl-2,3,7,8,9,9a-hexahydro-phenalene hydrobromide Step 1: 1-(3'-(3'-Carbomethoxypropanoic acid)-5,6-dimethoxy-3-phenyl-3,4-dihydronaphthalene To a suspension of 4.0 g. (14.2 mmol) of 5,6-dimethoxy-3-phenyl-1,2,3,4-tetrahydronaphthalen-1-one, the product of Example 1, in 5 mL of t-butyl alcohol was added dropwise a mixture of 13 mL (99.4 mmol) of dimethyl succinate, 9.6 g (86 mmol) of potassium t-butoxide, and 65 mL of t-butyl alcohol. After 10 mL of the mixture was added, the reaction was heated to 55° C. and maintained at this temperature for the duration of the reaction. When the addition was complete, the reaction was heated for an addition 60 minutes and then cooled and poured into 50 mL of ice cold 2N aqueous hydrochloric acid solution. The aqueous phase was extracted with 5×100 mL of diethyl ether. The combined organic layers were extracted with 5×100 mL of aqueous saturated sodium bicarbonate solution. The combined aqueous layers were acidified to pH 3 with 6N aqueous hydrochloric acid solution and the product was extracted with 2×200 mL of 1:1 diethyl ether/ethyl acetate. The organic phase was dried over anhydrous magnesium sulfate, filtered, and concentrated in vacuo. The title compound (5.0 g, 86% yield) was obtained as an oil; MS DCI: 397 (M+H)$^+$; $^1$H NMR (CDCl$_3$) δ: 2.6–2.8 (m, 4H), 3.1–3.3 (m, 1H), 3.69 (s, 3H), 3.71 (s, 3H), 3.87 (s, 3H), 4.1–4.25 (m, 1H), 5.9–6.0 (m, 1H), 6.7–6.8 (m, 1H), 7.0–7.5 (m, 6H).

Step 2: 1-(3'-(3'-Carbomethoxypropanoic acid)-5,6-dimethoxy-3-phenyl-1,2,3,4-tetrahydronaphthalene To a solution of 15.8 g (39.9 mmol) of 1-(3'-(3'-carbomethoxypropanoic acid)-5,6-dimethoxy-3-phenyl-3,4-dihydronaphthalene, from step 1, in 200 mL of ethyl acetate was added 3.16 g. of 10% palladium supported on carbon. The reaction mixture was shaken under 4 atmospheres of hydrogen until hydrogen uptake ceased. The reaction mixture was filtered and concentrated under reduced pressure to give 12.2 g (74% yield) of the title compound as an oil. The product was carried on without further purification to the next step.

Step 3: 1-Carbomethoxy-5,6-dimethoxy-3-hydroxy-8-phenyl-7,8,9,9a-tetrahydrophenalene 1-(3'-(3'-Carbomethoxypropanoic acid)-5,6-dimethoxy-3-phenyl-1,2,3,4-tetrahydronaphthalene (3.5 g, 8.5 mmol), from Step 2, was added to 11 g of polyphosphoric acid at 0° C. The ice bath was removed and the mixture was stirred at ambient temperature for 3 hours. The aqueous solution was extracted with 3×50 mL of 1:1 ethyl acetate/diethyl ether. The combined organic layers were washed with 50 mL of saturated aqueous sodium bicarbonate solution, dried over anhydrous magnesium sulfate, filtered and concentrated under reduced pressure. The product was purified by chromatography on silica gel, eluted with 20% ethyl acetate in hexanes. Four diastereomeric products were obtained of which two were characterized.

The first diastereomer, [1R*,8S*,9aR*]-1-carbomethoxy-5,6-dimethoxy-3-hydroxy-8-phenyl-7,8,9,9a-tetrahydrophenalene (182-3A), was obtained in 18% yield (0.59 g) as a solid, m.p 170°–172° C.: DCI MS: 381 (M+H)$^+$, 398 (M+NH$_4$)$^+$; $^1$H NMR (CDCl$_3$) δ:1.6–1.7 (m, 1H), 2.1–2.2 (m, 1H), 2.6–2.7 (m, 1H), 2.9–3.1 (m, 4H), 3.2–3.4 (m, 2H), 3.71 (m, 3H), 3.87 (s, 3H), 3.91 (s, 3H), 7.2–7.4 (m, 5H), 7.53 (s, 1H).

The second diastereomer, [1S*,8S*,9aR*]-1-carbomethoxy-5,6-dimethoxy-3-hydroxy-8-phenyl-7,8,9,9a-tetrahydrophenalene (182-3B) was obtained in 18% yield (0.60 g) as a solid, m.p 160°–161° C.; DCI MS: 381 (M+H)$^+$, 398 (M+NH$_4$)$^+$; $^1$H NMR (CDCl$_3$) δ: 2.0–2.1 (m, 1H), 2.15–2.25 (m, 1H), 2.6–2.8 (m, 2H), 3.0–3.1 (m, 2H), 3.2–3.3 (m, 2H), 3.4–3.5 (m, 1H), 3.7 (s, 3H), 3.83 (s, 3H), 3.91 (s, 3H), 7.2–7.4 (m, 5H), 7.54 (s, 1H).

Step 4: [1R*,8S*,9aR*]1-Carbomethoxy-5,6-dimethoxy-8-phenyl-2,3,7,8,9,9a-hexahydrophenalene To a solution of 0.5 g (1.3 mmol) of [1R,8S,9aR]-1-carbomethoxy-5,6-dimethoxy-3-hydroxy-8-phenyl-7,8,9,9a-tetrahydrophenalene (182-3A) in 50 mL of methanol, 50 mL of ethyl acetate, and 0.1 mL of concentrated aqueous hydrochloric acid was solution was added 0.2 g of 5% palladium supported on carbon and the mixture was shaken under 4 atmospheres of hydrogen until the gas uptake had ceased. The palladium catalyst was removed by filtration through Celite® filter aid and the filtrate concentrated to give a white solid, which was carried on to the next step without purification.

Step 5: [1R*,8S*,9aR*]5,6-Dimethoxy-8-phenyl-2,3,7,8,9,9a-hexahydrophenalene-1-carboxylic acid Crude [1R*,8S*,9aR*]1-Carbomethoxy-5,6-dimethoxy-8-phenyl-2,3,7,8,9,9a-hexahydrophenalene (0.8 g., 2.1 mmol), from Step 4, was dissolved in 100 mL of methanol and 8 mL of 1N aqueous sodium hydroxide solution was added. After stirring for 3 days at ambient temperature, the methanol was removed under reduced pressure. The residue was partitioned between 50 mL of diethyl ether and 75 mL of water. The aqueous phase was acidified to pH 2 with 6M aqueous hydrochloric acid solution and extracted with 3×25 mL of 1:1 ethyl acetate/diethyl ether. The combined organic layers were washed with brine, dried over anhydrous magnesium sulfate, filtered and concentrated in vacuo to give 0.74 g (100% yield) of the title compound as an oil; DCI MS: 253 (M+H)$^+$. $^1$H NMR (CDCl$_3$) δ:2.0–2.3 (m, 2H), 2.65–2.85 (m, 2H), 2.9–3.1 (m, 6H), 3.2–3.3 (m, 1H), 3.73 (s, 3H), 3.83 (s, 3H), 6.56 (s, 1H), 7.2–7.4 (m, 5H).

Step 6: [1R*,8S*,9aR*]1-Carbobenzyloxyamino-5,6-dimethoxy-8-phenyl-2,3,7,8,9,9a-hexahydrophenalene

[1R*,8S*,9aR*]5,6-Dimethoxy-8-phenyl-2,3,7,8,9,9a-hexahydrophenalene-1-carboxylic acid (0.8 g, 2.3 mmol), from Step 5, and triethylamine (0.32 mL, 2.3 mmol) were dissolved in 16 mL of toluene and 0.55 mL (2.5 mmol) of diphenylphosphoryl azide was added. The reaction mixture was heated at 80° C. for 2.5 h then 0.5 mL (4.8 mmol) of benzyl alcohol was added and heating was continued at 80° C. for an additional 3 h and at 65° C. for 15 h. The reaction mixture was cooled and concentrated under reduced pressure. The residue was dissolved in 25 mL of diethyl ether and the ether solution was washed with 10 mL of 1N aqueous sodium hydroxide solution and brine, dried over anhydrous magnesium sulfate, filtered and concentrated in vacuo. The product was purified by chromatography on silica gel eluted with 20% ethyl acetate in hexanes to give 0.4 g (39% yield) of the title compound as a white solid; DCI MS: 475 (M+NH$_4$)$^+$, 458 (M+H)$^+$, 367 (M-benzyl+H)$^+$, 324 (M-benzyloxy-carbonyl+2H)$^+$. $^1$H NMR (CDCl$_3$) δ:1.6–1.7

(m, 3H), 2.2–2.35 (m, 2H), 2.6–2.75 (m, 2H), 2.9–3.0 (m, 3H), 3.2–3.3 (m, 1H), 3.73 (s, 3H), 3.82 (s, 3H), 4.65–4.7 (m, 1H), 5.08 (s, 2H), 6.54 (s, 1H), 7.2–7.4 (m, 10H).

Step 7: [1R*,8S*,9aR*]1-Amino-5,6-dimethoxy-8-phenyl-2,3,7,8,9,9a-hexahydrophenalene A suspension of 0.65 g (1.4 mmol) of [1R*,8S*,9aR*]1-carbobenzyloxy-amino-5,6-dimethoxy-8-phenyl-2,3,7,8,9,9a-hexahydrophenalene, from Step 6, in 50 mL of methanol and 0.1 g of 10% palladium supported on carbon was stirred under 1 atmosphere of hydrogen for 1 hour. The solid dissolved as the reaction proceeded. The catalyst was removed by filtration and the solution was concentrated under reduced pressure to give 0.4 g (87% yield) of crude title compound which was carried on to the next step without further purification.

Step 8: [1R*,8S*,9aR*]1-Amino-5,6-dihydroxy-8-phenyl-2,3,7,8,9,9a-hexahydrophenalene hydrobromide To a solution of 0.4 g (1.2 mmol) of [1R*,8S*,9aR*]1-amino-5,6-dimethoxy-8-phenyl-2,3,7,8,9,9a-hexahydrophenalene in 9 mL of methylene chloride at −78° C., was added dropwise 4.4 mL (4.4 mmol) of a 1M solution of boron tribromide in methylene chloride. The reaction mixture was warmed to ambient temperature for 1 hour and cooled to −78° C. and the reaction was quenched by the addition of 5 mL of methanol. The reaction was allowed to warm to ambient temperature and stirred for 1 hour. The solvent was removed in vacuo. Methanol (5 mL) was added and the solution was concentrated to remove methyl borate by azeotropic distillation. The title compound was obtained (0.32 g, 69% yield) after recrystallization from ethanol/diethyl ether as a white solid; DCI MS: 279 (M+H)$^+$, 296 (M-NH$_4$)$^+$. $^1$H NMR (d$_6$-DMSO) δ:1.4–1.6 (m, 1H), 1.7–1.9 (m, 1H), 2.1–2.2 (m, 1H), 2.2–2.3 (m, 1H), 2.4–2.5 (m, 2H), 2.7–3.2 (m, 5H), 6.41 (s, 1H), 7.2–7.4 (m, 5H), 8.0 (br s, 5H). Analysis calculated for C$_{19}$H$_{22}$BrNO$_2$+0.5 H$_2$O: C, 59.23; H, 5.99; N, 3.64. Found: C, 59.26; H, 5.86; N, 3.59.

EXAMPLE 183

[1S*,8S*,9aR*]1-Amino-5,6-dihydroxy-8-phenyl-2,3,7,8,9,9a-hexahydrophenalene hydrobromide

[1S*,8S*,9aR*]1-Amino-5,6-dimethoxy-8-phenyl-2,3,7,8,9,9a-hexahydrophenalene hydrobromide was prepared from the second isomeric product of Step 3 of Example 182 (3B) according to the procedures described in Steps 4 through 8 of Example 182; DCI MS 279 (M+H)$^+$, 296 (M-NH$_4$)$^+$. $^1$H NMR (d$_6$-DMSO) δ:1.6–1.75 (m, 1H), 1.8–2.05 (m, 2H), 2.25–2.7 (m, 5H), 2.85–3.05 (m, 3H), 6.37 (s, 1H), 7.1–7.4 (m, 5H), 7.7 (br s, 5H).

Analysis calculated for C$_{19}$H$_{22}$BrNO$_2$+1 H$_2$O: C, 57.88; H, 6.14; N, 3.55. Found: C, 57.82; H, 5.74; N, 3.56.

EXAMPLE 184

6,7-Dihydroxy-4-phenyl-2,3,4,5-tetrahydro-1H-benz[e]isoindole formic acid salt

Step 1: 5,6-Dimethoxy-3-phenyl-2-thiophenyl-1,2,3,4-tetrahydronaphthalen-1-one

To a solution of 28.9 g (0.102 mol) of 5,6-dimethoxy-3-phenyl-1,2,3,4-tetrahydronaphthalen-1-one, the product of Example 1, in 240 mL of THF was added 40.4 g (0.107 mol) of phenyltrimethylammonium tribromide. After stirring at ambient temperature for 1 h, 960 mL of water was added. The solution was extracted with 3×250 mL of ethyl acetate. The combined organic phase was washed with 3×250 mL of water, 250 mL of saturated aqueous sodium chloride, dried over anhydrous magnesium sulfate, filtered, and concentrated under reduced pressure to give an oil which was carried on without further purification or characterization.

A solution of sodium methoxide was prepared by the addition of 3.28 g (0.143 mol) of sodium metal to 97 mL of methanol with cooling to 0° C. Thiophenol (14.6 mL, 0.143 mol) was added dropwise over 10 minutes and then stirred an additional 10 minutes at 0° C. A solution of the above crude oil in 60 mL of THF was added dropwise over 30 minutes and the reaction was then allowed to warm to ambient temperature for 4 h. The solvents were removed in vacuo and the residue was dissolved in a mixture of 250 mL each of methylene chloride and water. The organic phase was collected and washed with saturated aqueous sodium chloride, dried over anhydrous sodium sulfate, filtered, and concentrated under reduced pressure. The product was recrystallized from ethyl acetate/hexanes to give 33.15 g (83% yield from the ketone) of 5,6-dimethoxy-3-phenyl-2-thiophenyl-1,2,3,4-tetrahydro-naphthalen-1-one as a white solid; MS DCI: 391 (M+H)$^+$; $^1$H NMR (CDCl$_3$) δ:3.35 (dd, 1H, J=6,18 Hz), 3.55 (dd, 1H, J=6,18 Hz), 3.71 (q, 1H, J=6 Hz), 3.82 (s, 3H), 3.93 (s, 3H), 4.19 (d, 1H, J=6 Hz), 6.91 (d, 1H, J=9 Hz), 7.1–7.3 (m, 8H), 7.4–7.5 (m, 2H), 7.37 (d, 1H, J=9 Hz).

Step 2: -5,6-Dimethoxy-3-phenyl-2-sulfoxophenyl-3,4-dihydronaphthalene

A solution of 20.96 g (53.7 mmol) of 5,6-dimethoxy-3-phenyl-2-thiophenyl-1,2,3,4-tetrahydronaphthalen-1-one in 320 mL of ethanol was treated with 20.03 g. (0.529 mol) of sodium borohydride. The reaction was heated to reflux temperature for 2 h, then cooled and 500 mL of water was added. The solvents were removed in vacuo and the residue was taken up in 500 mL of 1:1 diethyl ether/methylene chloride and 500 mL of water. The organic layer was removed and washed with 100 mL each of water and brine, dried over magnesium sulfate, filtered, and concentrated under reduced pressure. The crude resultant alcohol was dehydrated by the addition of 700 mL of toluene and 3.6 g (18.9 mmol) of p-toluenesulfonic acid monohydrate and heating to reflux with azeotropic removal of water for 30 minutes. After cooling, the solution was washed with 3×100 mL of saturated aqueous sodium bicarbonate, 100 mL of water, dried over anhydrous magnesium sulfate, filtered and concentrated in vacuo. The crude thio-enolether was carried on directly by first, dissolution in 360 mL of methylene chloride. This solution was cooled to −15° C. and a solution of 12.1 g of 3-chloroperoxybenzoic acid (mCPBA) in 160 mL of methylene chloride was added dropwise over 30 minutes. After the addition was complete, the reaction was quenched by the addition of 100 mL of aqueous saturated sodium thiosulfate. The organic layer was separated, and washed with 3×100 mL of saturated aqueous sodium bicarbonate, 100 mL of water, dried over anhydrous sodium sulfate, filtered and concentrated under reduced pressure. The product was chromatographed on silica gel eluted with 25% ethyl acetate in hexanes to give 18.65 (89% yield) of 5,6-dimethoxy-3-phenyl-2-sulfoxophenyl-3,4-dihydronaphthalene as a white solid as a mixture of diastereomers; MS DCI: 391 (M+H)$^+$; $^1$H NMR (CDCl$_3$) δ:2.9–3.1 (m, 1H), 3.1–3.3 (m, 1H), 3.46 and 3.51 (2×s, 3H total), 3.55 and 3.7 (2×m, 1H total), 3.83 and 3.86 (2×s,3H total), 6.75–7.15 (m, 7H), 7.3–7.6 (m, 6H).

Step 3: N-Trimethylsilylmethyl benzylamine

A mixture of 264 mL (2.42 mol) of benzylamine and 97.7 g. (0.796 mol) of chloromethyltrimethylsilane was heated to 200° C. for 2.5 h then cooled to 10° C. A 0.1M sodium hydroxide solution (400 mL) was added and the product was extracted with 3×200 mL of diethyl ether. The combined organic phase was washed with 100 mL of water, dried over anhydrous magnesium sulfate, filtered and concentrated under reduced pressure. The product was distilled at 115°–125° C. and 5 mm of Hg to give 125.4 g (81% yield) of N-trimethylsilylmethyl benzylamine as a clear liquid; $^1$H NMR (CDCl$_3$) δ:0.0 (s, 9H), 1.1 (br s, 1H), 2.01 (s, 2H), 3.76 (s, 2H), 7.1–7.3 (m, 5H).

Step 4: N-Methoxymethyl-N-trimethylsilylmethyl benzylamine

N-Trimethylsilylmethyl benzylamine (125.4 g, 0.649 mol), from Step 3, was added dropwise over a 10 minute period to a solution of 69.5 mL of 37% aqueous formaldehyde at 0° C. After an additional 10 minutes, 75.2 mL of methanol was added. The solution was then saturated with solid potassium carbonate and stirred at 0° C. for 1 h. The layers were separated and the organic phase was stirred over solid potassium carbonate at ambient temperature for 18 h. The solution was filtered and fractionally distilled at 20 mm of Hg to give a 145°–155° C. fraction as a viscous oil, identified as N-methoxymethyl-N-trimethylsilylmethyl benzylamine.

$^1$H NMR (CDCl$_3$) δ:0.0 (s, 9H), 2.13 (s, 2H), 3.18 (s, 3H), 3.71 (s, 2H), 3.96 (s, 2H), 7.1–7.3 (m, 5H).

Step 5: 2-Benzyl-6,7-dimethoxy-4-phenyl-2,3,4,5-tetrahydro-1H-benz[e]isoindole

To a solution of 1.22 g (3.13 mmol) of 5,6-dimethoxy-3-phenyl-2-sulfoxophenyl-3,4-dihydronaphthalene in 10 mL of methylene chloride was added 1 g (4.21 mmol) of N-methoxymethyl-N-trimethylsilylmethyl benzylamine, from Step 4, and 0.1 mL of trifluoroacetic acid. At 12 h intervals, the amine and acid additions were repeated 7 more times. The solvent was then removed under reduced pressure with heating to 100° C. and the product was chromatographed on silica gel, eluted with 25% ethyl acetate in hexanes to give 0.14 g (11% yield) of 2-benzyl-6,7-dimethoxy-4-phenyl-2,3,4,5-tetrahydrobenzo[e]isoindole; MS DCI: 398 (M+H)$^+$; $^1$H NMR (CDCl$_3$) δ:3.0–3.15 (m, 1H), 3.25–3.35 (m, 1H), 3.45–3.55 (m, 3H), 3.62 (s, 3H), 3.65–3.7 (m, 2H), 3.8–3.9 (m, 2H), 3.82 (s, 3H), 6.68 (m, 1H), 7.1–7.4 (m, 11H).

Step 6: 6,7-Dimethoxy-4-phenyl-2,3,4,5-tetrahydro-1H-benz[e]isoindole hydrochloride To a solution of 1.0 g (2.52 mmol) of 2-benzyl-6,7-dimethoxy-4-phenyl-2,3,4,5-tetrahydro-1H-benz[e]isoindole, from Step 5, in 22 mL of 1,2-dichloroethane was added 0.11 g (0.05 mmol) of 1,8-bis(dimethylamino)-naphthalene and 0.33 mL (3.15 mmol) of 1-chloroethyl chloroformate at 0° C. The solution was heated to reflux for 2 h and the solvent removed in vacuo. The residue was filtered through silica gel eluted with 25% ethyl acetate in hexanes. After concentration under reduced pressure, methanol (20 mL) was added and the solution was heated to reflux for 30 minutes, before the solvent was removed in vacuo. The product was crystallized from ethanol/ether to give 0.46 g. (75% yield) of 6,7-dimethoxy-4-phenyl-2,3,4,5-tetrahydro-1H-benz[e]isoindole hydrochloride as a white solid.; MS DCI: 308 (M+H)$^+$; $^1$H NMR (d$_6$-DMSO) δ:3.05–3.25 (m, 2H), 3.55 (s, 3H), 3.80 (s, 3H), 3.88 (m, 1H), 4.0–4.15 (m, 2H), 4.25–4.45 (m, 2H), 6.91 (m, 1H), 7.15–7.3 (m, 3H), 7.4–7.6 (m, 3H).

Step 7: 6,7-Dihydroxy-4-phenyl-2,3,4,5-tetrahydro-1H-benz[e]isoindole formic acid salt A suspension of 54.5 mg (0.159 mmol) of 6,7-dimethoxy-4-phenyl-2,3,4,5-tetrahydro-1H-benz[e]isoindole hydrochloride, from Step 6, in 2 mL of methylene chloride was cooled to −78° C. and 0.64 mL of a 1M solution of boron tribromide in methylene chloride was added. The reaction was warmed to ambient temperature for 1 h and cooled to −78° C. before 1 mL of methanol was added. After warming to ambient temperature for 1 h, the solvents were removed in vacuo. Additional methanol (5 mL) was added and removed in vacuo. The product was chromatographed on silica gel eluted with ethyl acetate/formic acid/water (18:1:1) to give 29.8 mg (58% yield) of the title compound as an off-white powder, m.p. 144° C.; MS DCI: 279 (M+H)$^+$; $^1$H NMR (d$_6$-DMSO) δ:2.95–3.15 (m, 2H), 3.6–3.9 (m, 3H), 4.1–4.3 (m, 2H), 6.43 (d, 1H, J=7.5 Hz), 6.62 (d, 1H, J=7.5 Hz), 7.1–7.3 (m, 5H), 8.3 (s, 1H).

EXAMPLE 185A

[1,3-cis]3-(1'-Adamantyl)-5,6-cyclohexylidenedioxy-3,4-dihydro-1-(N-formyl)aminomethyl-1H-2-benzopyran (Method A)

A mixture of 185 mg (0.5 mmol) of 1-(1'-adamantyl)-2-(spiro-[(1,3-benzo-dioxole)-2,1'-cyclohexane])-1-ethanol (from Example 179 Step 4 above), 110 mg (0.83 mmol) N-formyl-acetaldehyde dimethyl acetal and 46 mg (0.13 mmol) of zinc triflate in 3.0 mL of dry 1,2-dichloroethane was heated at reflux under a nitrogen atmosphere for 18 h. The reaction mixture was allowed to cool to ambient temperature and the reaction was quenched with~30 mL ethyl acetate and saturated aqueous sodium bicarbonate solution. The organic layer was washed with water and brine, dried over anhydrous magnesium sulfate, filtered and concentrated to an oil. The oil was triturated with methanol to give 191 mg (87% yield) of the title compound as a solid, m.p. 182°–184° C.

EXAMPLE 185B

[1,3-cis]3-(1'-Adamantyl)-5,6-cyclohexylidenedioxy-3,4-dihydro-1-(N-formyl)aminomethyl-1H-2-benzopyran (Method B)

To a mixture of 94 mg (0.26 mmol) of 1-(1'-adamantyl)-2-(spiro-[(1,3-benzodioxole)-2,1'-cyclohexane])-1-ethanol (from Example 59 Step 2 above), and 100 mg (0.75 mmol) of N-formylacetaldehyde dimethyl acetal in 2.0 mL of dry acetonitrile was added 3 μL (~0.1 equivalent) of methanesulfonic acid and the reaction mixture was heated at reflux for 12 h. The mixture was cooled to 0° C. The solid was removed by filtration, washed with cold acetonitrile and dried to give 79 mg (70% yield) of the title compound as a beige solid, m.p. 185°–187° C.

EXAMPLE 185C

[1,3-cis]3-(1'-Adamantyl)-5,6-cyclohexylidenedioxy-3,4-dihydro-1-(N-formyl)aminomethyl-1H-2-benzopyran (Method C)

To a mixture of 50 mg (0.14 mmol) of 1-(1'-adamantyl)-2-(spiro-[(1,3-benzodioxole)-2,1'-cyclohexane])-1-ethanol (from Example 59 Step 2 above), and 60 mg (0.45 mmol) of N-formylacetaldehyde dimethyl acetal was added a solution of 3 mg of polyphosphoric acid in ~0.5 mL of acetonitrile. The reaction mixture was heated at reflux for 48 h and then was cooled to 0° C. for 0.5 h and filtered. The solid was washed with cold acetonitrile and dried to give 10.9 mg (18% yield) of the title compound as an off-white solid, m.p. 185°–187° C.

EXAMPLE 185D

[1,3-cis]3-(1'-Adamantyl)-5,6-cyclohexylidenedioxy-3,4-dihydro-1-(N-formyl)aminomethyl-1H-2-benzopyran (Method D)

To a mixture of 181 mg (0.5 mmol) of 1-(1'-adamantyl)-2-(spiro-[(1,3-benzodioxole)-2,1'-cyclohexane])-1-ethanol (from Example 59 Step 2 above), and 107 mg (0.83 mmol) of N-formylacetaldehyde dimethyl acetal was added 25 µL of a 1.0M a solution of trimethylsilyl triflate in methylene chloride. The reaction mixture was heated at reflux for 4 h and then was cooled to 0° C. for 0.5 h and filtered through a sintered glass funnel. The solid was washed with cold acetonitrile and dried to give 198 mg (92% yield) of the title compound as a white solid, m.p. 187°–189° C.

EXAMPLE 186

[1,3-cis]1-Aminomethyl-3-phenyl-3,4-dihydro-5,6-dihydroxy-1H-2-benzothiopyran hydrochloride Step 1: 1-Phenyl-2-[3-(1,2-cyclohexylidenedioxy)pheny]ethanol Following the procedure of Example 47, Step 2, replacing the 3,3-dimethyl-1,2-epoxybutane with styrene oxide, the title compound was prepared and taken directly to the next step.

Step 2. S-Acetyl-1-phenyl-2-[3-(1,2-cyclohexylidenedioxy)pheny]ethanethiol

A solution of triphenylphosphine (1.86 g, 7.09 mmol) in 50 mL of dry THF was cooled to 0° C. Diisopropylazodicarboxylate (1.43 g, 7.09 mmol) was added dropwise via syringe and the reaction mixture was stirred at 0° C. for 30 min. A solution of 1.10 g (3.54 mmol) of 1-phenyl-2-[3-(1,2-cyclohexylidenedioxy)pheny]ethanol, from Step 1, and thiolacetic acid (0.67 g, 8.86 mmol) in 5 mL of THF was then added dropwise to the reaction mixture. The reaction mixture was stirred at 0° C. for 1 hour, warmed to ambient temperature and stirred for 1 hour at ambient temperature. The solvent was removed under reduced pressure, and the residue was purified by flash chromatography on silica gel eluted with 3% ethyl acetate in hexane to give 0.82 g (63% yield) of the title product as a colorless oil. MS (DCI/NH$_3$): 369 (M+H)$^+$, 386 (M+NH$_4$)$^+$.

Step 3. 1-Phenyl-2-[3-(1,2-cyclohexylidenedioxy)pheny]ethanethiol

The thiolacetate from step 2 was dissolved in 10 mL of anhydrous diethyl ether. The resultant solution was added dropwise to a solution of lithium aluminum hydride (2.2 mmol) in 15 mL of diethyl ether. After stirring for 15 min at ambient temperature the reaction was quenched by the careful addition of 20 mL of 1N aqueous hydrochloric acid solution. The diethyl ether layer was separated, dried over anhydrous magnesium sulfate, filtered and concentrated in vacuo to afford 680 mg of the title product as a colorless oil. MS (DCI/NH$_3$): 327 (M+H)$^+$, 344 (M+NH$_4$)$^+$.

Step 4. [1,3-cis]3-Phenyl-5,6-cyclohexylidenedioxy-3,4-dihydro-1-(N-formyl)aminomethyl-1H-2-benzothiopyran Trimethylsilyl trifluoromethanesulfonate (TMSOTf) (61 mg, 0.28 mmol) was added dropwise to a stirred solution of 0.600 g (1.84 mmol) of 1-phenyl-2-[3-(1,2-cyclohexylidenedioxy)pheny]ethanethiol, from step 3 above, and 0.388 g (2.94 mmol) of N-formylaminoacetaldehyde dimethyl acetal in 10 mL of anhydrous acetonitrile. The reaction was heated at reflux for 1 hour, then cooled and diluted with 50 mL of ethyl acetate. This solution was washed with 10% aqueous sodium carbonate solution, saturated NaCl solution, dried over anhydrous magnesium sulfate and concentrated in vacuo to a brown oil. The residue was purified by flash chromatography on silica gel eluted with 40% ethyl acetate/hexane to afford 357 mg of the title product as a white solid. MS (DCI/NH$_3$): 396 (M+H)$^+$, 413 (M+NH$_4$)$^+$.

Step 5. [1,3-cis]1-Aminomethyl-3-phenyl-3,4-dihydro-5,6-dihydroxy-1H-2-benzothiopyran hydrochloride To a solution of 174 mg of the formamide compound from step 4 in 2 mL of THF and 2 mL of methanol was added 1 mL of 15% NaOH solution. The mixture was heated to reflux and stirred for 4 hours. The reaction was cooled, diluted with 15 mL of ethyl acetate, and the layers separated. The aqueous layer was extracted with 10 mL of ethyl acetate. The organic layers were combined, washed with water and brine, dried over magnesium sulfate and concentrated in vacuo to yield 145 mg of the free amine product as a colorless oil. The oil was dissolved in 3 mL of absolute ethanol, and 3 mL of 18%HCl in ethanol was added. The mixture was heated at reflux for 5 hours and cooled at 5° C. for 64 hours. The precipitate was filtered, washed and dried in vacuo at 50° C. to afford 30 mg of the title product as a white solid. mp 230° C. (dec). MS (FAB): 288 (M+H)$^+$. $^1$H NMR (CD$_3$OD) δ:2.98 (dd, 1H), 3.31–3.35 (m, 2H), 3.65 (dd, 1H), 4.14 (dd, 1H), 4.24 (dr, 1H), 6.67 (d, 1H), 7.2–7.5 (m, 5H). Anal calc'd. for C$_{16}$H$_{18}$ClNO$_2$S: C, 59.34; H, 5.60; N, 4.33; found: C, 59.56; H, 5.73, N, 4.26.

EXAMPLE 187

[1,3-cis]1-(N-Methyl)aminomethyl-3-phenyl-3,4-dihydro-5,6-dihydroxy-1H-2-benzothiopyran hydrochloride To a solution of 139 mg (0.35 mmol) of 3-phenyl-5,6-cyclohexylidenedioxy-3,4-dihydro-1-(N-formyl)aminomethyl-1H-2-benzothiopyran, from Example 186 Step 4, in 4 mL of anhydrous THF was added 27 mg (0.70 mmol) of LAH (0.7 mL of 1N LAH in THF). The reaction was stirred and heated to reflux for 1.5 hours. The reaction was cooled to 0° C., diluted with 10 mL of ether and quenched by the careful addition of water (0.028 mL), 15% NaOH solution (0.028 mL), and water (0.084 mL). To this mixture was added a small amount of magnesium sulfate, and the mixture was filtered to give an ether solution of the product. The solvent was removed in vacuo to afford 125 mg of the free base as a colorless oil. The oil was dissolved in 2 mL of absolute ethanol, and 3 mL of 18% HCl in ethanol was added. The reaction was heated to reflux for 2 hours, cooled, concentrated to 2 mL, and diluted with ether. A white precipitate which formed upon standing was collected by filtration, washed with ether and dried in vacuo to afford 75 mg of the title product. mp 230° C. (dec). MS (FAB): 302 (M+H)$^+$. $^1$H NMR (CD$_3$OD) δ:2.65 (s, 3H) 2.9 (dd, 1H), 3.25 (dd, 1H), 3.38 (dd, 1H), 3.64 (dd, 1H), 4.12 (dd, 1H), 4.26 (dd, 1H), 6.65 (d, 1H), 6.7 (d, 1H), 7.2–7.5 (m, 5H). Anal calc'd. for C$_{17}$H$_{20}$ClNO$_2$S: C, 60.44; H, 5.97; N, 4.15; found: C, 60.17; H, 5.97, N, 4.10.

EXAMPLE 188

1'-Aminomethyl-5',6'-dimethoxyspiro[cycloheptane-1,3'-(3',4'-dihydro-2'H-2'H-naphthalene)]hydrobromide Step A. 2,3-Dimethoxybenzyl bromide.

To a stirred solution of 2,3-dimethoxybenzyl bromide (25 g, 148 mmol, Aldrich) in 500 mL anhydrous ether was added PBr$_3$ (7 mL, 74 mmol), via syringe. The resulting solution was stirred at room temperature for 2 hours. The reaction was quenched by the addition of cold water. The layers were separated and the ether layer was washed with water, Na₂CO₃ solution, water and brine. The ether layer was then dried over MgSO₄, filtered, and evaporated to give 34 g (100% yield) of the title product as a low melting white solid.

Step B. Ethyl 1-(2,3-dimethoxybenzyl)cycloheptane carboxylate

To a stirred solution of ethyl cycloheptane carboxylate (14 g, 82.4 mmol, prepared by esterification of the acid, which was obtained from Aldrich, by refluxing in ethanol in the presence of an acid catalyst), in 600 mL anhydrous THF cooled to −78° C. was added 60 mL of 1.5M LDA (monotetrahydrofuran in hexane, Aldrich) via syringe. The resulting light yellow reaction solution was stirred at 31 78° C. for 45 min and the benzyl bromide (from step A above) was added (19 g dissolved in 75 mL of THF, 82.4 mmol). The reaction was stirred at −78° C. for 4 hours, then it was quenched by addition of sat'd. NH₄Cl, water and ether. The layers were separated, and the organic layer was washed with 1M HCl, water, and brine. The organic layer was dried over MgSO₄, filtered, and evaporated to yield a light amber oil (28 g) which was used without further purification.

Step C. [1-(2,3-dimethoxybenzyl)cycloheptyl]methanol

The crude ester (26 g, 82 mmol, from Step B above), was dissolved in 400 mL anhydrous THF to which was added solid LiAlH₄ (4.6 g, 123 mmol) in small portions at room temperature. The reaction was stirred at room temperature until TLC indicated completion. The reaction was then quenched with 1M HCl and diluted with ether. The layers were separated, and the organic layer was washed with 1M HCl, water, and brine. The organic layer was dried over MgSO₄, filtered and evaporated. The resulting oil was purified by silica gel chromatography to give 20 g of the title product as a colorless oil.

Step D. 1-(2,3-dimethoxybenzy)cycloheptane carbaldehyde

The alcohol from Step C above (25 g, 89 mmol) was dissolved in 500 mL of anhydrous DMSO. To this solution was added Et₃N (50 mL, 358 mmol). Then SO₃.Pyridine (57 g, 358 mmol), was dissolved in 400 mL of DMSO, and this solution was added to the reaction vessel. The solution was then stirred at room temperature for two hours. The reaction solution was then poured over ice and the resulting mixture was warmed to room temperature and extracted with CH₂Cl₂. The organic layer was washed with 1M HCl, water, and brine, then the organic layer was dried over MgSO₄, filtered and evaporated. The crude product was chromatographed on silica gel, eluting with 10:1 hexane:EtOAc to give the title product as a colorless oil (20 g, 81% yield).

Step E. 2-[1-(2,3-dimethoxybenzyl)cycloheptymethylene-[13]-dithiane

To a solution of TMS-dithiane (18 mL, 94 mmol, Aldrich) in 500 mL of anhydrous THF cooled to −78° C. was added nBuLi (37.5 mL of a 2.5M soln in hexane, 94 mmol), slowly via syringe. The resulting solution was stirred at −78° C. for 30 min. and the aldehyde from Step D above (20 g, 72 mmol) was added as a solution in 50 mL of anhydrous THF. The reaction solution was then stirred for 1 h at −78° C. The reaction was quenched with sat'd. NH₄Cl at room temperature and diluted with ether. The resulting layers were separated, and the organic layer was washed with 1M HCl, water and brine. The organic layer was then dried over MgSO₄, filtered and evaporated to give 27 g (100% yield) of the title product, which was used without further purification.

Step F. 5',6'-Dimethoxyspiro[cycloheptane-1,3'-(3',4'-dihydro-2'H-naphthalene)]-1'-one The crude product from Step E above (27 g, 72 mmol) was dissolved in 500 mL of 5% aq. MeCN. To this solution was added HgCl₂ (39 g, 144 mmol) in one portion. The resulting suspension was refluxed for 1 hour, cooled to room temperature, filtered and the filtrate evaporated to a solid. The solid was dissolved in 500 mL CH₂Cl₂, which was washed with 1M HCl, water, dried over MgSO₄, filtered, evaporated and chromatographed (silica gel, 6:1 hexane/EtOAc) to give the spirotetralone title product (15 g).

Step G-1'-Aminomethyl-5',6'-dimethoxyspiro[cycloheptane-1,3'-(3',4'-dihydro-2'H-naphthalene)]hydrochloride Following the procedure of Example 2, Steps 1 and 2, the compound from Step F above was reacted and the title product was isolated.

Step H. 1'-Aminomethyl-5',6'-dihydroxyspiro[cycloheptane-1,3'-(3',4'-dihydro-2'H-naphthalene)]hydrobromide Following the procedure described in Example 2, Step 3, the title compound was prepared. mp 157°–8° C. MS (DCI) M/Z: 274. anal. calc. for C₁₇H₂₄BrNO₂: C, 57.63; H, 6.82; N, 3.95; found: C, 57.70; H, 6.80; N, 3.97.

TABLE 9

Examples 189–198

| Ex. No. | Compound* | Ester | mp °C. | MS** | Elemental Analysis C H N |
|---|---|---|---|---|---|
| 189 | 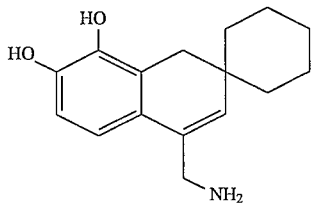 | 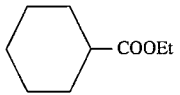 | 140-2 | 260 | c: 57.62 7.04 3.65<br>f: 57.52 7.15 3.47 |

TABLE 9-continued

Examples 189–198

| Ex. No. | Compound* | Ester | mp °C. | MS** | Elemental Analysis C  H  N |
|---|---|---|---|---|---|
| 190 | | COOEt | 263–4 | 248 | c: 54.89 6.76 4.27<br>f: 55.02 6.83 4.38 |
| 191 | | COOEt | 285–6 | 288 | c: 59.82 7.23 3.48<br>f: 59.85 7.27 3.54 |
| 192 | | COOEt | 174–5 | 276 | c: 57.02 7.37 3.91<br>+0.1 H$_2$O<br>f: 56.64 7.38 2.87 |
| 193 | | COOEt | 240–1 | 276 | c: 57.02 7.37 3.91<br>+0.1 H$_2$O<br>f: 56.86 7.07 3.87 |
| 194 | | COOEt | 176–8 | 262 | c: 55.27 7.13 4.03<br>f: 55.18 6.87 3.99 |
| 195 | | COOEt | 242–3 | 250 | c: 54.55 7.32 4.24<br>f: 54.75 7.43 4.25 |
| 196 | | COOEt | 210–1 | 248 | c: 52.86 6.92 4.11<br>f: 52.72 6.77 3.95 |

TABLE 9-continued

Examples 189–198

| Ex. No. | Compound* | Ester | mp °C. | MS** | Elemental Analysis C H N |
|---|---|---|---|---|---|
| 197 | HO, HO — tricyclic with NH₂ and cyclooctane spiro | cyclooctane-COOEt | 182–3 | 290 | c: 58.38 7.62 3.78  f: 57.92 7.70 4.02 |
| 198 | HO, HO — tricyclic with NH₂ and dipropyl spiro | dipropyl-COOEt | 242–4 | 278 | c: 55.05 7.62 3.73  +0.2 CH₂Cl₂  f: 55.18 7.46 3.64 |

*As the HBr salt unless indicated otherwise (FB = free base); all compounds 1–3 cis unless indicated otherwise
***DCl MS (M + H)+

EXAMPLES 189–198

Following the synthesis outlined in Example 188, using the appropriate ester as indicated, Examples 189 to 192 were made, as their HBr salts, as shown above in Table 9 The structure of each was confirmed by melting point, mass spectrum and elemental analysis as designated.

Examples 193 to 198 were prepared, using the appropriate ester, as described in Example 188, hydrogenated and deprotected as described in Example 35 as their HBr salts, as shown above in Table 9. The structure of each was confirmed by melting point, mass spectrum and elemental analysis as designated.

EXAMPLE 199

Spiro[cycloheptane-1,5'-(1',2',3',4',5',6'-hexahydro-benzo[h]isoquinoline)]-7',8'-diolhydrobromide Step A. 5',6'-Dimethoxyspiro[cycloheptane-1,3'-(3',4'-dihydro-2'H-naphthalene)]acetic acid ethyl ester A stirred solution of 5',6'-dimethoxyspiro[cycloheptane-1,3'-(3',4'-dihydro-2'H-naphthalen)]-1'-one, from Step F of Example 188 above, (15.75 g, 54.5 mmol) in 500 mL of anhydrous THF was cooled to −78° C. To this solution was added 1M LDA in THF via cannula (60 mL, 60 mmol). The reaction was stirred at −78° C. for 45 min and ethylbromoacetate (6.34 mL, 57.2 mmol) was added via syringe. The resulting reaction solution was slowly warmed to room temperature and stirred for an additional 24 hours. The reaction was quenched by the addition of sat'd. NH₄Cl, then water, and diluted with ether. The organic layer was separated and washed with 1M HCl, water and brine, dried over MgSO₄, filtered, evaporated and chromatographed on silica gel eluting with 7:1 hexane:EtOAc to furnish the title product as a light amber oil (7.6 g).

Step B. 9b'-Cyano-5',6'-dimethoxyspiro[cycloheptane-1,4'-(3'a, 4, 5, 9b-tetrahydro-3H-naphtho[1',2'-b]furan)]-2'-one To a stirred solution of the ester from Step A above (16 g, 42.8 mmol) in 500 mL of anhydrous toluene was added 1M Et₂AlCN in toluene (86 mL, 86 mmol) quickly via syringe. The resulting reaction solution was stirred for 2 hours. The reaction was poured into 400 mL of ice cold 2M HCl, diluted with ether, and the organic layer separated and washed with 1M HCl, water and brine. The organic layer was then dried over MgSO₄, filtered and evaporated to yield the tricyclic lactone title product as a light yellow solid (15 g, 100% yield).

Step C. 1'-Aminomethyl-5',6'-dimethoxy-1'-hydroxyspiro [cycloheptane-1,3'-(1',2',3',4'-tetrahydronaphthalene)]-2-ethanol To a stirred solution of the tricyclic lactone (15 g, 42.3 mmol, from Step B above) in 500 mL of anhydrous THF was added LiAlH4 (6.4 g, 169 mmol) in portions, causing the THF to reflux. The THF was refluxed for 2 hours then cooled to room temperature, transferred to a 2L Erlenmeyer flask, diluted with 200 mL of THF and quenched with solid Na₂SO₄.10H₂O. After the quench was completed, celite filter aid was added to the slurry, and the slurry was filtered over celite, the filter cake was washed with warm THF, and the filtrate was evaporated under reduced pressure to yield 12 g of crude product as an off-white solid. The crude product was triturated with a minimal amount of CH₂Cl₂ and filtered to yield 6.3 g of the title product as a fluffy white solid. The filtrate was concentrated and purified by column chromatography eluting with 89:9:1 CH₂Cl₂:MeOH:NH₄OH diluted to 150% of its volume with CH₂Cl₂) to yield another 3.6 g. (Total yield: 65%).

Step D. 7',8'-Dimethoxyspiro[cycloheptane-1,5'-(1',2',3',4', 5',6'-hexahydrobenzo[h]isoquinoline)]

To a stirred solution of the product from Step C above (6.3 g, 17.36 mmol) in 170 mL of anhydrous CH₂Cl₂ cooled to −78° C. was added PBr₃ (4.9 mL, 52.1 mmol) slowly via syringe. The cooling bath was removed and the reaction was stirred at room temperature for 48 hours, and the CH₂Cl₂ was then evaporated. The resulting oil was partitioned between 200 mL of ethyl acetate and 200 mL of 50% ammonium hydroxide/water. The layers were separated, and the aqueous layer was washed with EtOAc. The organic layers were combined and washed with water, dried over MgSO₄, filtered and evaporated to furnish 3 g of crude title product. The product was purified by column chromatography on silica gel, eluting with 89:9:1 CH$_2$Cl$_2$:MeOH:NH$_4$OH diluted with CH$_2$Cl$_2$ 60:40), to yield pure title product (2.4 g, 42% yield).

Step E. Spiro[cycloheptane-1,5'-(1',2',3',4',5',6'-hexahydrobenzo[h]isoquinoline)]-7',8'-diol hydrobromide To a stirred solution of the compound from Step D (1.5 g, 4.59 mmol) in anhydrous CH$_2$Cl$_2$ cooled to −78° C. was added 1M BBr$_3$ in CH$_2$Cl$_2$ (9.2 mL, 9.2 mmol) slowly via syringe. The cooling bath was removed and the reaction solution was warmed to room temperature. The reaction solution was again cooled to −78° C. and quenched with 100 mL of absolute methanol. The reaction solution was evaporated to a residue which was re-dissolved with 100 mL of absolute methanol and heated to reflux on a steam bath. The solution was then cooled to room temperature by bubbling nitrogen into the solution. The solvent was removed under reduced pressure to provide a residue which was triturated with CH$_2$Cl$_2$ to precipitate the product. The product was filtered and dried in a vacuum oven at 55° over night to furnish the title product as a white solid (1.3 g, 76% yield). mp 288–290. MS (DCI) M/Z: 300. anal. calc. for C$_{19}$H$_{25}$NO$_2$.HBr.0.5 H$_2$: C, 58.35; H, 7.00; N, 3.58; found: C, 58.55; H, 7.07; N, 3.46.

TABLE 10

Examples 200–209

| Ex. No. | Compound* | Ester | mp °C. | MS** | Elemental Analysis C H N |
|---|---|---|---|---|---|
| 200 | (structure) | (benzyl COOEt) | 268–70 | 294 | c: 60.97 5.39 3.74<br>f: 60.84 5.39 3.77 |
| 201 | (structure) | (benzyl COOEt) | 229–231 | 294 | c: 60.97 5.39 3.74<br>f: 60.81 5.35 3.74 |
| 202 | (structure) | (cyclohexylmethyl COOEt) | 236–7 | 300 | c: 60.00 6.89 3.68<br>f: 60.08 6.95 3.72 |
| 203 | (structure) | (neopentyl COOEt) | na | 274 | c:<br>f: na |
| 204 | (structure) | (cyclopentyl COOEt) | 279–281 | 272 | c: 56.52 6.72 3.88<br>f: 56.48 6.18 3.73 |

TABLE 10-continued

Examples 200–209

| Ex. No. | Compound* | Ester | mp °C. | MS** | Elemental Analysis C H N |
|---|---|---|---|---|---|
| 205 | (structure: 5-phenyl hexahydrobenzo[h]isoquinoline-7,8-diol) | cyclohexyl-COOEt | 274–5 | 286 | c: 56.26 6.82 3.65<br>f: 56.27 6.86 3.43 |
| 206 | (structure: spiro-cycloheptyl hexahydrobenzo[h]isoquinoline-7,8-diol) HCl | cycloheptyl-COOEt | 279–280 | 300 | c: 60.00 6.89 3.68<br>f: 59.87 6.72 3.50 |
| 207 | (structure: spiro-cyclooctyl hexahydrobenzo[h]isoquinoline-7,8-diol) | cyclooctyl-COOEt | 184–6 | 314 | c: 58.70 7.11 3.80<br>f: 59.03 7.23 3.61 |
| 208 | (structure: 5,5-dipropyl hexahydrobenzo[h]isoquinoline-7,8-diol) | dipropyl-COOEt | 248–9 | 302 | c: 57.26 7.13 3.51<br>+0.2 HBr<br>f: 57.42 7.00 3.41 |
| 209 | (structure: 5-(cyclopentylmethyl) hexahydrobenzo[h]isoquinoline-7,8-diol) | spirocyclopentyl-CH2-COOEt | 229–230 | 300 | c: 60.00 6.89 3.68<br>f: 60.09 6.93 3.56 |

*As the HBr salt unless indicated otherwise (FB = free base)
***DCl MS (M + H)+

EXAMPLES 200–209

Following the synthesis outlined in Example 199, using the appropriate tetralone, Examples 200–209 were made as their HBr salts, as shown above in Table 10. The structure of each was confirmed by melting point, mass spectrum and elemental analysis as designated.

EXAMPLE 210

2-Methyl-5-phenyl-1, 2, 3, 4, 5, 6-hexahydrobenzo[h]isoquinoline-7,8-diol hydrobromide Step A. 7,8-Dimethoxy-2-formyl-5-phenyl-1, 2, 3, 4, 5, 6-hexahydro-benzo[h]isoquinoline To a solution of the free base 7,8-dimethoxy-5-phenyl-1, 2, 3, 4, 5, 6-hexahydrobenzo[h]isoquinoline, (390 mg, 1.2 mmol, from Example 200) in THF (25 mL) was added ethyl formate (40 mL). The resulting solution was heated at reflux for 17 hours, concentrated, and the concentrate was chased with THF. The crude product was used directly in the next step.

Step B. 7,8-Dimethoxy-2-methyl-5-phenyl-1, 2, 3, 4, 5, 6-hexahydrobenzo[h]isoquinoline To a solution of the compound from Step A (1.2 mmol) in THF (25 mL) was added LAH (60 mg, 1.6 mmol). The reaction was refluxed for 3 hours, diluted to 300 mL with THF, quenched with excess sodium sulfate decahydrate, and filtered over celite. The filtrate was concentrated then subjected to flash chromatography on silica gel with NH$_4$OH/MeOH/EtOAc/CH$_2$Cl$_2$ (1:4:50:50) as the eluting solvent to give the title product (270 mg, 67% yield).

Step C. 2-Methyl-5-phenyl-1, 2, 3, 4, 5, 6-hexahydrobenzo[h]isoquinoline-7,8-diol hydrobromide To a solution of the free base from Step B above (270 mg, 81 mmol) in acetic acid (30 mL) was added 48% HBr (28 mL). The resulting solution was heated at reflux for 6 hours, cooled and concentrated in vacuo to 5 mL. This concentrate was chased with ethanol, methanol and heptane until dry. The product was dried under vacuum overnight and then crystallized from MeOH/Et$_2$O to afford 230 mg (73% yield) of the title product as a tan powder. Analysis calculated for C$_{20}$H$_{22}$BrNO$_2$ (0.2 H$_2$O): C, 61.30; H, 5.76; N, 3.57. Found: C, 61.30; H, 5.67; N, 3.44. MS DCI/NH3 M/Z: 308 (M+H)$^+$. Melting point: 259°–261°.

EXAMPLES 211–212

Following the synthesis outlined in Example 210, using the appropriate spiro aldehyde, Examples 211 and 212 were made as their HBr salts, as shown below in Table 11. The structure of each was confirmed by melting point, mass spectrum and elemental analysis.

TABLE 11

Examples 211–212

| Ex. No. | Compound* | mp °C. | MS** | Elemental Analysis C H N |
|---|---|---|---|---|
| 211 | (structure) | 163–5 | 286 | c: 59.02 6.60 3.82<br>f: 59.11 6.58 3.79 |
| 212 | (structure) | 289–290 | 300 | c: 58.08 7.03 3.57<br>f: 57.81 6.73 3.43 |

*As the HBr salt unless indicated otherwise (FB = free base)
**DCI MS (M + H)+

EXAMPLE 213

1-Acetylaminomethyl-3-phenyl-5,6-dihydroxy-3,4-dihydronaphthalene

Approximately 1 mmol of 1-aminomethyl-3-phenyl-5,6-dihydroxy-3,4-dihydronaphthalene, from Example 2, was reacted with 1.2 mmol of acetic anhydride in the presence of 1.2 mmol of triethylamine in an excess of methylene chloride. The mixture was washed with 0.1N HCl, and dried. The product was precipitated by addition of ether, collected, and dried. mp 238° C. MS M/Z: 310. Anal. calc. for C$_{19}$H$_{19}$NO$_3$.HBr C: 65.03; H, 5.72; N, 3.61; found: C, 73.46; H, 6.13; N, 4.49.

EXAMPLE 214

1-Aminomethyl-3-(2,2-dimethylpropyl)-3,4-dihydro-5,6-dihydroxy-1H-2-benzopyran hydrochloride Step 1. Diphenylmethylenedioxybenzene Catechol (14.7 g, 0.134 mol, Aldrich Chemical Co.) was placed in a 3-neck flask flushed with Argon. The flask was immersed in a 180° C. oil bath, the catechol allowed to melt, and neat dichlorophenylmethane (24.6 mL, 0.134 mol) was carefully added in small portions, with resulting vigorous gas evolution. Heating was continued for an additional 10 min, the flask was cooled, and the crude product was dissolved in 300 mL of ether. The organic layer was separated and washed with 1N NaOH and brine, dried over MgSO$_4$ and concentrated in vacuo to give a yellow solid. The crude product was triturated with 5% ethyl acetate in hexane, which was filtered to yield 13.1 of an off-white solid. A second crop was obtained, and the total yield was 24.8 g (68% yield) of the title compound. MS (DCI/NH$_3$) M/Z: 275 (M+H)$^+$.

$^1$H NMR (CDCl$_3$, 300 MHz) δ:6.8–6.9 (m, 4H), 7.3–7.45 (m, 6H), 7.5–7.65 (m, 4H).

Step 2. (2S)-3-chloro-1-(2,3-diphenylmethylenedioxyphenyl)-2-propanol n-Butyl lithium (2.3 mL of a 9.5M solution in hexane, 22 mmol) was added dropwise to a solution of 5.47 g of diphenylmethylenedioxybenzene (from step 1) in 75 mL of THF at 0° C. After 5 hr the solution was cooled to −78° C., and a solution of 1.85 g (20 mmol) of (S) (+)-epichlorohydrin (Aldrich Chemical Co.) in 10 mL of THF was added. Boron trifluoride etherate (2.4 mL, 20 mmol) was then added dropwise, and the reaction was stirred for 1.5 hr. The reaction was quenched by addition of 50 mL of saturated NaHCO$_3$, and the mixture was warmed to ambient temperature and partitioned between 100 mL of ether and 100 mL of water. The aqueous phase was extracted with ether (2×40 mL), and the ether extracts were combined and washed with brine, dried over MgSO$_4$ and concentrated in vacuo to give a brown oil, which was purified by flash chromatography over silica gel, eluting with 15% ethyl acetate in hexane, to afford after removal of the solvent 4.23 g of the title compound as a light yellow oil (58% yield). MS (DCI/NH$_3$) M/Z: 367 (M+H)$^+$, 384 (M+NH$_4$)$^+$. $^1$H NMR (CDCl$_3$, 300 MHz) δ: 2.3 (d, 1H), 2.9–3.0 (m, 2H), 3.5 (dd, 1H), 3.6 (dd, 1H), 4.1–4.23 (m, 1H), 6.65–6.85 (m, 3H), 7.37 (m, 6H), 7.55 (m, 4H).

Step 3. (2S)-3-(2,3-diphenylmethylenedioxyphenyl)-1,2-epoxypropane

A 15% aqueous NaOH solution (60 mL) was added to a solution of 9.51 g (25.9 mmol) of (2S)-3-chloro-1-(2,3-diphenylmethylenedioxyphenyl)-2-propanol (from step 2 above) in 180 mL of 2:1 ether:methanol. The mixture was stirred vigorously and heated to reflux for 3 hr. The reaction was poured into 100 mL of water, and the aqueous phase was extracted with ether (2×75 mL). The combined organic extracts were washed with brine, dried over MgSO$_4$ and concentrated in vacuo to give 8.35 g of the title compound as a light brown oil. This material was taken directly to the next step. MS (DCI/NH$_3$) M/Z: 331 (M+H)$^+$, 348 (M+NH$_4$)$^+$.

Step 4. (2R)-4,4-Dimethyl-1-(2,3-diphenylmethylenedioxyphenyl)-2-pentanol t-Butyl lithium (21.4 mL of a 1.7M solution in pentane, 36.4 mmol) was added dropwise to a suspension of CuCN (1.63 g, 18.2 mmol) in 120 mL of THF at −78° C. The mixture was stirred for 30 min and allowed to warm to −10° C. A solution of 8.01 g (2S)-3-(2,3-diphenylmethylenedioxyphenyl)-1,2-epoxypropane (24.2 mmol) of (from step 3 above) in 20 mL of THF was added dropwise. The reactions was stirred for 18 hr, then quenched by addition of 100 mL of 9:1 saturated NH$_4$Cl: conc. NH$_4$OH. The mixture was stirred vigorously for 30 min and partitioned between 50 mL of water and 150 mL of ether. The aqueous phase was extracted twice with 50 mL of ether, and the combined layers were washed with water and saturated NH$_4$Cl and dried over MgSO$_4$. The solvents were removed under vacuum to give an amber oil. The oil was purified by flash chromatography over silica gel, eluting with 20% ethyl acetate:hexane to afford 5.95 g (63% yield) of the title compound as a yellow oil. MS (DCI/NH$_3$) M/Z: 389 (M+H)$^+$, 406 (M+NH$_4$)$^+$. $^1$H NMR (CDCl$_3$, 300 MHz) δ:0.95 (s, 9H), 1.45 (m, 2H), 2.73 (dd, 1H), 2.85 (dd, 1H), 4.08 (m, 1H), 6.65–6.8 (m, 3H), 7.37 (m, 6H), 7.57 (m, 4H).

Step 5. 1-aminomethyl-3-(2,2-dimethylpropyl)-5,6-diphenylmethylenedioxy-3,4-dihydro-1H-2-benzopyran hydrochloride Following the procedures of steps 5 and 6 of Example 179, the (2R)-4,4-Dimethyl-1-(2,3-diphenylmethylenedioxyphenyl)-2-pentanol compound from step 4 above was converted into the title product.

Step 6. 1-aminomethyl-3-(2,2-dimethylpropyl)-3,4-dihydro-5,6-dihydroxy-1H-2-benzopyran hydrochloride To as solution of 1-aminomethyl-3-(2,2-dimethylpropyl)-5,6-diphenylmethylenedioxy-3,4-dihydro-1H-2-benzopyran hydrochloride, from step 5 above, in 50 ml of methanol, was added 210 mg of 10%Pd/C. The mixture was purged and hydrogenated at 1 atm for 18 hr. The catalyst was removed by filtration, and the filtrate was concentrated in vacuo, dissolved in 10 mL of 1N HCl, washed with ether, and taken to dryness. The residue was crystallized from ethanol/ether to afford 300 mg of the title compound. mp 220° C. MS (DCI/NH$_3$) M/Z: 266 (M+H)$^+$, 283 (M+NH$_4$)$^+$. $^1$H NMR (DMSO-d$_6$, 300 MHz) δ:0.97 (s, 9H), 1.45 (dd, 1H), 1.65 (dd, 1H), 2.32 (dd, 1H), 2.65 (dd, 1H), 2.87 (dd, 1H), 3.38 (dd, 1H), 3.65 (m, 1H), 4.85 (m, 1H), 6.52 (d, 1H), 6.67 (d, 1H), 7.8 (bs, 3H), 8.45 (bs, 1H), 9.28 (bs, 1H).

EXAMPLES 215–220

Following the synthesis outlined in Example 214, using the appropriate organocuprate reagent, Examples 215 and 216 were prepared. Following the procedures described in Examples 214 and 111, Examples 217–219. Example 220 was prepared by the procedures described in Examples 214 and 111, repeating the procedure of Example 111 in order to place the second methyl group on the amino function. The structures of Examples 215–220 were confirmed by melting point, mass spectra and elemental analysis as designated. The data for examples 215–220 are shown below in Table 12.

EXAMPLES 221–230

Following the synthesis outlined in Examples 47 and 48, using the appropriate epoxide and the appropriate aldehyde diacetal, Examples 221–223 were made as shown below in Table 13. The structure of each was confirmed by melting point (m.p), elemental analysis and mass spectra as designated.

Following the synthesis outlined in Examples 47, 48 and 111 using the appropriate epoxide and the appropriate aldehyde diacetal, Examples 224–226 were made as disclosed in Table 13. The structure of each was confirmed by melting point (m.p), elemental analysis and mass spectra as designated.

Following the synthesis outlined in Examples 47, 48 and 111, and repeating the procedure of Example 111, using the appropriate epoxide and the appropriate aldehyde diacetal, Examples 227–230 were made as disclosed in Table 13. The structure of each was confirmed by melting point (m.p), elemental analysis and mass spectra as designated.

EXAMPLES 231–237

Following the synthesis outlined in Example 188, using the appropriate ester as indicated, Examples 231 to 234 were made, as their HBr salts, as shown below in Table 14 The structure of each was confirmed by melting point, mass spectrum and elemental analysis as designated.

Examples 235 to 237 were prepared, using the appropriate ester, as described in Example 188, hydrogenated and deprotected as described in Example 35, as their HBr salts, as shown below in Table 14. The structure of each was confirmed by melting point, mass spectrum and elemental analysis as designated.

TABLE 12

Examples 215–220

| Ex. No. | Compound* | mp °C. | MS** | Elemental Analysis C H N |
|---|---|---|---|---|
| 215 | (structure) | na | 278 | na |
| 216 | (structure) | 189 | 252 | c: 56.65 7.81 4.72<br>f: 56.87 7.42 4.65<br>+0.5H$_2$O |
| 217 | (structure) | 230 dec | 280 | c: 59.16 8.34 4.31<br>f: 59.15 8.01 4.19<br>+0.5H$_2$O |
| 218 | (structure) | 187 | 292 | c: 61.27 8.05 4.20<br>f: 61.00 7.66 4.06<br>+0.3H$_2$O |
| 219 | (structure) | 170 | 266 | c: 56.94 7.77 4.34<br>f: 57.13 7.70 4.64<br>+0.4HCl |
| 220 | (structure) | 215 | 294 | c: 60.90 8.60 4.18<br>f: 60.79 8.34 4.19<br>+0.3H$_2$O |

*As the HBr salt unless indicated otherwise (FB = free base)
**DCl MS (M + H)+

TABLE 13
Examples 221–230
| Ex. No. | Compound* | Epoxide** | mp °C. | MS*** | Elemental Analysis C H N |
|---|---|---|---|---|---|
| 221 | 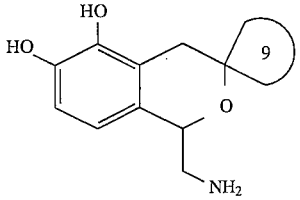 | 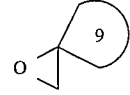 | >240 | 306 | c: 62.26 8.30 4.03<br>f: 61.88 8.17 4.31<br>+0.3H₂O |
| 222 | 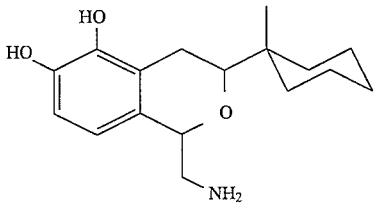 | 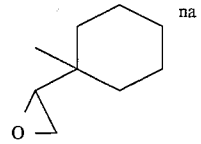 | na | 292 | c: 62.28 7.99 4.27<br>f: 62.29 8.05 4.09 |
| 223 | 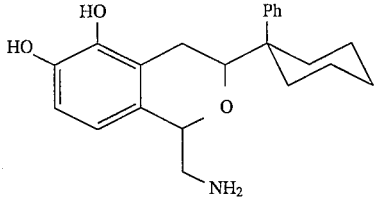 | 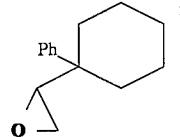 | na | 354 | c: 65.35 7.38 3.46<br>f: 65.43 7.33 3.11<br>+0.8H₂O |
| 224 | 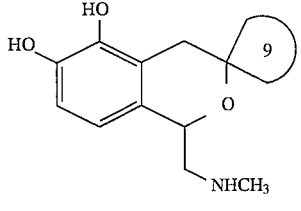 | 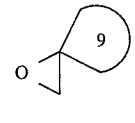 | >215 dec | 320 | c: 63.16 8.54 3.88<br>f: 63.00 8.53 3.92<br>+0.3H₂O |
| 225 | 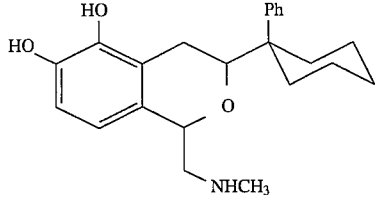 | 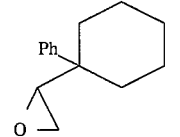 | na | 368 | c: 66.90 7.57 3.39<br>f: 66.80 7.88 3.02<br>+0.5H₂O |
| 226 | 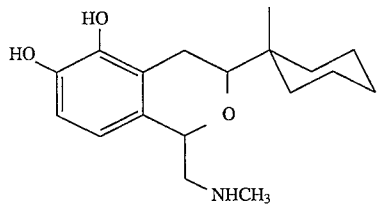 | 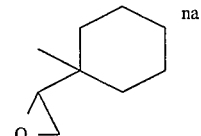 | na | 305 | c: 63.24 8.25 4.10<br>f: 62.92 8.27 3.91 |
| 227 | 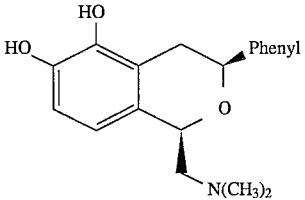 | 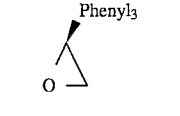 | 222(dec) | 300 | c: na<br>f: na |

TABLE 13-continued

Examples 221–230

| Ex. No. | Compound* | Epoxide** | mp °C. | MS*** | Elemental Analysis C H N |
|---|---|---|---|---|---|
| 228 | [structure: dihydroxyphenyl with cyclohexyl-CH and N(CH₃)₂ groups] | [cyclohexyl-epoxide] | 239(d) | 306 | c: 61.62 8.33 3.99<br>f: 61.59 8.22 4.33<br>+0.5H₂O |
| 229 | [structure: dihydroxyphenyl with phenyl-cyclohexyl and N(CH₃)₂ groups] | [Ph-cyclohexyl epoxide] | na | 382 | c: 66.95 7.82 3.25<br>f: 66.75 7.57 3.27<br>+0.7H₂O |
| 230 | [structure: dihydroxyphenyl with methyl-cyclohexyl and N(CH₃)₂ groups] | [methyl-cyclohexyl epoxide] | na | 320 | c: 63.80 8.51 3.92<br>f: 63.70 8.32 3.85<br>+0.1H₂O |

*As the HBr salt unless indicated otherwise (FB = free base); all comounds 1–3 cis unless indicated otherwise
**1 = commercially available, 2 = synthesized by method A of Example 47, 3 = synthesized by Method B of Example 47; 4 = synthesized by Method C of Example 47.
***DCl MS (M + H)+
****Prepared by the procedure described in Examples 47, 48 and old 130 using (−)B-chlorodiidopinocamphorylborane

TABLE 14

Examples 231–237

| Ex. No. | Compound* | Ester | mp °C. | MS** | Elemental Analysis C H N |
|---|---|---|---|---|---|
| 231 | [structure: dihydroxy-tetrahydronaphthalene with Adam and NH₂] | Adam-CH₂—COOEt | 240(dec) | 326 | c: 61.53 6.98 3.42<br>f: 61.22 7.29 3.09<br>+0.2H₂O |
| 232 | [structure: dihydroxy-tetrahydronaphthalene with cyclo-9 and NH₂] | [cyclo-9]—COOEt | 210–1 | 302 | c: 58.69 7.28 3.60<br>f: 58.72 7.19 3.71<br>+0.08HBr |

TABLE 14-continued

Examples 231–237

| Ex. No. | Compound* | Ester | mp °C. | MS** | Elemental Analysis C H N |
|---|---|---|---|---|---|
| 233 | HO, HO-naphthalene-t-butyl, CH₂NH₂ | t-bu-(CH₂)₂—COOEt | 140-3 | 262 | c: 54.97 7.00 3.95<br>f: 55.34 6.78 3.57<br>+0.1MeOH + 0.1CH₂Cl₂ |
| 234 | HO, HO-naphthalene-spiro(10), CH₂NH₂ | (10)—COOEt | 204-5 | 316 | c: 59.39 7.50 3.46<br>f: 59.41 7.46 3.39<br>+0.1 H$_{Br}$ |
| 235 | HO, HO-tetralin-Adam, CH₂NH₂ | Adam-CH₂—COOEt | 254 | 328 | c: 44.87 5.72 2.49<br>f: 44.73 5.81 3.58<br>+1.8 HBr |
| 236 | HO, HO-tetralin-spiro(9), CH₂NH₂ | (9)—COOEt | 184-6 | 304 | c: 56.97 7.60 3.50<br>f: 57.01 7.51 3.69<br>+0.2 HBr |
| 237 | HO, HO-tetralin-spiro(10), CH₂NH₂ | (10)—COOEt | 146-8 | 318 | c: 52.72 7.80 3.37<br>f: 57.77 7.73 3.39<br>+0.22 HBr |

*As the HBr salt unless indicated otherwise (FB = free base); all compounds 1–3 cis unless indicated otherwise
**DCl MS (M + H)+

EXAMPLES 238–243

Following the synthesis outlined in Example 199, using the appropriate tetralone, Examples 238–243 were made as their HBr salts, as shown in Table 15. The structure of each was confirmed by melting point, mass spectrum and elemental analysis as designated.

TABLE 15

Examples 238–243

| Ex. No. | Compound* | Ester | mp °C. | MS** | Elemental Analysis C H N |
|---|---|---|---|---|---|
| 238 | (structure with Adam substituent) | Adam—COOEt | 226 | 352 | c: 61.96 6.94 3.14<br>f: 61.83 6.83 3.09<br>+0.2 HBr |
| 239 | (structure with phenyl substituent) | Ph-CH-COOEt | na | 294 | c: 59.94 5.52 3.65<br>f: 59.48 5.30 3.75<br>+0.5H$_2$O |
| 240 | (structure with cyclodecyl "10") | (10)—COOEt | 281–4 | 342 | c: 59.32 7.63 3.01<br>f: 59.09 7.40 3.01<br>+0.25HBr + 0.25EtOH |
| 241 | (structure with cyclononyl "9") | (9)—COOEt | 294–6 | 328 | c: 60.00 7.78 3.18<br>f: 59.97 7.49 3.16<br>+0.5H2O + 0.5EtOH |
| 242 | (structure with t-bu substituent) | t-bu—CH$_2$—COOEt | 229–31 | 288 | c: na<br>f: na |
| 243 | (structure with n-bu substituent) | n-bu-CH$_2$—COOEt | 125–30 | 274 | c: na<br>f: na |

*As the HBr salt unless indicated otherwise (FB = free base)
**DCl MS (M + H)+

TABLE 16

Examples 244–252

| Ex. No. | Compound* | Ester | mp °C. | MS** | Elemental Analysis C H N |
|---|---|---|---|---|---|
| 244 | HO, HO– / t-butyl / N-Me | t-butyl—COOEt | 276 | 288 | c: 58.41 7.14 3.78<br>f: 58.09 7.03 3.77<br>+0.1 H₂O |
| 245 | HO, HO– / cyclopentylmethyl / N-Me | cyclopentyl-CH₂-COOEt | 150–3 | 314 | c: 44.19 5.60 2.58<br>f: 44.22 5.30 2.63<br>+0.08HBr + 0.5H₂O |
| 246 | HO, HO– / phenyl / N-Me | Ph-CH—COOEt | na | 308 | c: 59.52 5.72 3.47<br>f: 59.60 5.57 3.45<br>+0.2HBr |
| 247 | HO, HO– / cyclohexadienyl / N-Me | cyclohexadienyl-COOEt | na | 308 | c: na<br>f: na |
| 248 | HO, HO– / (9) / N-Me | (9)—COOEt | 170–180d | 342 | c: 58.10 7.18 3.08<br>f: 58.24 7.21 2.94<br>+0.4HBr |
| 249 | HO, HO– / (7) / N-Me | (7)—COOEt | 155–7 | 314 | c: 59.29 7.26 3.46<br>f: 59.09 6.96 3.31<br>+0.6 H₂O |

TABLE 16-continued

Examples 244–252

| Ex. No. | Compound* | Ester | mp °C. | MS** | Elemental Analysis C H N |
|---|---|---|---|---|---|
| 250 | HO, HO-[benzo ring]-CH2-[spiro cyclooctane(8)]-CH=C-CH2-N(Me)-CH2 | (8)—COOEt | 167–70d | 328 | c: na<br>f: na |
| 251 | HO, HO-[benzo ring]-CH2-[spiro cycloheptane(7)]-CH=C-CH2-N(Et)-CH2 | (7)—COOEt | 119–21 | 328 | c: 54.26 6.61 2.89<br>f: 54.48 6.51 3.28<br>+0.9CH₂Cl₂ |
| 252 | HO, HO-[benzo ring]-CH2-[spiro cycloheptane(7)]-CH-CH-CH2-N-CH2 | (7)—COOEt | 165–7 | 302 | c: 51.41 6.47 3.00<br>f: 51.63 6.49 3.01<br>+1.0CH₂Cl₂ |

*As the HBr salt unless indicated otherwise (FB = free base)
**DCl MS (M + H)+

EXAMPLES 244–250

Following the synthesis outlined in Examples 199 and 210, using the appropriate tetralone, Examples 244–250 were made as their HBr salts, as shown above in Table 16. The structure of each was confirmed by melting point, mass spectrum and elemental analysis as designated.

EXAMPLE 251

Following the synthesis outlined in Examples 199 and 210, using the appropriate tetralone, and substituting acetic anhydride for the ethyl formate of Example 210 followed by reduction with LAH, Example 251 was made as the HBr salt, as shown above in Table 16. The structure was confirmed by melting point, mass spectrum and elemental analysis as designated.

EXAMPLE 252

Following the procedure of Example 35, the compound of Example 206 was hydrogenated, and the compound of Example 252 was isolated as the HBr salt, as shown above in Table 16. The structure was confirmed by melting point, mass spectrum and elemental analysis as designated.

EXAMPLE 253

Determination of Competitive Binding in D-1 and D-2 Receptor Binding Assays

Homogenized rat caudate was incubated in the presence of [$^{125}$I]SCH-23982 (a selective antagonist of the dopamine D-1 receptor) and the compounds of this invention, according to procedures described by A. Sidhu et al. in *European J Pharmacology* 113:437 (1985) and in *European J Pharmacology* 128:213 (1986). The compounds compete with the radiolabeled ligand for occupancy of the receptors and the molar potency of each compound was quantified. The affinity of the compound for the receptor (Ki) was calculated as described by Y. C. Cheng and W. H. Prusoff in *Biochemical Pharmacology* 22:3099 (1973) from the relationship $Ki=IC_{50}(1+[L]/K_D)$ where $IC_{50}$ is the concentration of test compound which produces a 50% inhibition in the specific binding of the radioligand, L; [L] is the concentration of radioligand; and $K_D$ is the affinity of the radioligand for the receptor.

The procedure for the dopamine D-2 receptor binding assay was similar to that used for the D-1 receptor assay. Homogenized rat caudate was the source of the D-2 receptors. The tissue homogenate was incubated in the presence of [$^{125}$I]p-aminophenylethyl spiropefidol (a selective antagonist of the dopamine D-2 receptor) and the compounds being evaluated, according to the protocol described by T. Agui, N. Amlaiky, M. G. Caron and J. W. Kebabian in *Molecular Pharmacology*, 33:163 (1988). The molar affinity of the compound for the receptor binding site was calculated by the same method used for the D-1 receptor assay, assuming a competitive interaction between the compound and the radiolabeled ligand.

The competitive binding data (Ki values) from the D-1 and D-2 receptor binding assays are shown above in Table 17. The Ki values are inversely proportional to the affinity of the compound for the receptor.

TABLE 17

Competitive Binding to D-1 and D-2 Receptors

| Example # | D-1 Ki (µM) | D-2 Ki (µM) |
|---|---|---|
| dopamine | 8.0 | 6.3 |
| 2A | 0.15 | >10 |
| 17 | 0.8 | >10 |
| 18 | 1.3 | >10 |
| 19 | 0.6 | >10 |
| 20 | 1.9 | >10 |
| 23 | 0.5 | >10 |
| 24 | 0.9 | >10 |
| 27 | >10 | 6.6 |
| 29 | 6.0 | >10 |
| 30 | >10 | 32 |
| 35 | 0.03 | 0.76 |
| 36 | 0.20 | >10 |
| 37 | 0.057 | 10 |
| 38 | 0.12 | 30 |
| 39 | 1.4 | >10 |
| 40 | 5.0 | 27 |
| 41 | 0.7 | 2.5 |
| 42 | 0.061 | 3.9 |
| 43 | 2.4 | 12 |
| 45 | 4.6 | >10 |
| 46 | 1.7 | >10 |
| 48 | 0.036 | 13. |
| 49 | 0.002 | 1.0 |
| 50 | 0.007 | 1.2 |
| 51 | 0.235 | 3.9 |
| 52 | 0.90 | 6.2 |
| 53 | 0.25 | 0.65 |
| 54 | 0.004 | 0.91 |
| 55 | 0.38 | 1.5 |
| 56 | 2.2 | 1.3 |
| 57 | 1.1 | 0.73 |
| 58 | 0.26 | 1.2 |
| 59 | 0.037 | 1.4 |
| 60 | 0.53 | 2.2 |
| 61 | 0.29 | 1.3 |
| 62 | 0.21 | 3.7 |
| 63 | 71 | >10 |
| 64 | 0.64 | 0.54 |
| 65 | 14 | 16 |
| 66 | 0.48 | 0.64 |
| 67 | 1.9 | |
| 68 | 0.10 | 5.5 |
| 69 | 0.087 | 2.7 |
| 70 | 0.005 | 0.65 |
| 71 | 15 | 2.8 |
| 72 | 0.015 | 8.2 |
| 73 | 0.064 | 34 |
| 74 | 0.10 | 2.0 |
| 75 | 0.48 | 4.6 |
| 76 | 0.098 | 0.44 |
| 77 | 2.3 | 0.50 |
| 78 | 0.049 | 0.81 |
| 79 | 0.73 | 0.92 |
| 80 | 0.014 | 1.1 |
| 81 | 0.21 | 4.6 |
| 82 | 0.011 | 0.82 |
| 83 | 2.8 | 4.5 |
| 84 | 1.3 | 1.3 |
| 85 | 8.1 | 10 |
| 86 | 1.5 | 3.5 |
| 87 | 11 | 0.7 |
| 88 | 0.13 | 1.5 |
| 89 | 0.021 | 1.4 |
| 90 | 0.076 | 0.9 |
| 91 | 0.29 | >10 |
| 92 | 1.5 | 5.4 |
| 93 | 0.47 | >10 |
| 94 | 0.084 | >10 |

TABLE 17-continued

Competitive Binding to D-1 and D-2 Receptors

| Example # | D-1 Ki (µM) | D-2 Ki (µM) |
|---|---|---|
| 95 | 0.52 | >10 |
| 96 | 0.027 | 0.87 |
| 97 | 0.071 | 6.0 |
| 98 | 0.22 | 1.9 |
| 99 | 0.022 | 8.9 |
| 100 | 0.019 | 54 |
| 101 | 0.012 | 0.91 |
| 102 | 0.24 | >10 |
| 103 | 0.036 | 2.0 |
| 104 | 0.037 | >10 |
| 105 | 0.017 | 1.0 |
| 106 | 0.35 | >10 |
| 107 | 2.5 | >10 |
| 108 | 4.1 | >10 |
| 110 | 0.55 | 1.1 |
| 111 | 0.014 | 0.72 |
| 112 | 0.038 | 1.5 |
| 113 | 0.22 | 1.4 |
| 114 | 0.42 | 0.90 |
| 115 | 12 | 3.0 |
| 117 | 1.2 | 1.0 |
| 118 | 2.5 | 6.7 |
| 119 | 3 | >10 |
| 120 | 3.5 | 3.0 |
| 123 | 8.2 | >10 |
| 124 | 1.9 | 0.47 |
| 125 | 2.7 | >10 |
| 126 | 0.16 | 6.6 |
| 127 | 1.3 | >10 |
| 128 | 0.57 | 23 |
| 129 | 2.1 | 3.1 |
| 130 | 0.051 | 0.19 |
| 131 | 0.52 | 2.7 |
| 132 | 0.086 | 0.64 |
| 134 | 0.035 | 1.0 |
| 135 | 0.18 | 1.6 |
| 136 | 0.10 | 2.5 |
| 137 | 2.9 | 0.55 |
| 138 | 0.003 | 2.2 |
| 139 | 0.45 | 3.2 |
| 140 | 0.06 | 1.5 |
| 141 | 0.12 | 2.6 |
| 142 | 0.19 | >10 |
| 143 | 1.2 | >10 |
| 144 | 0.10 | 0.091 |
| 145 | 0.067 | 12 |
| 146 | 0.049 | 1.4 |
| 147 | 0.40 | >10 |
| 148 | 0.064 | 4.6 |
| 148A | 0.71 | 2.6 |
| 149 | 0.46 | 19 |
| 150 | 0.025 | 12 |
| 151 | 5.8 | 2.5 |
| 152 | 59 | 12 |
| 153 | 0.85 | >10 |
| 154 | 1.4 | 17 |
| 155 | 2.6 | 8.2 |
| 156 | 6.3 | 16 |
| 157 | 1.3 | 16 |
| 158 | 2.3 | 6.0 |
| 159 | 3.1 | 3.7 |
| 160 | 1.3 | 1.7 |
| 161 | 1.3 | 0.17 |
| 162 | 0.67 | 0.71 |
| 163 | 0.79 | 0.83 |
| 164 | 3.6 | 0.25 |
| 165 | 1.8 | 17 |
| 166 | 4.8 | 2.4 |
| 167 | 0.31 | 0.0021 |
| 168 | 17 | >10 |
| 169 | 8.0 | >10 |
| 170 | 0.57 | 0.14 |
| 171 | 0.53 | 0.81 |
| 172 | 1.1 | >10 |

TABLE 17-continued

Competitive Binding to D-1 and D-2 Receptors

| Example # | D-1 Ki (µM) | D-2 Ki (µM) |
|---|---|---|
| 173 | 3.6 | 14 |
| 174 | 1.2 | 3.5 |
| 176 | 0.65 | 2.6 |
| 177 | 0.13 | 6.6 |
| 178 | 7.3 | >10 |
| 179 | 0.063 | 1.3 |
| 180 | 1.1 | 4.7 |
| 181 | 0.39 | 4.6 |
| 182 | 0.28 | 2.2 |
| 183 | 6.5 | >10 |
| 184 | 0.07 | >10 |
| 186 | 1.9 | 34 |
| 187 | 2.5 | 6.4 |
| 188 | 2.0 | 7.0 |
| 189 | 3.3 | >10 |
| 190 | 0.33 | 6.3 |
| 191 | 1.1 | >10 |
| 192 | 3.2 | >10 |
| 193 | 0.65 | 3.2 |
| 194 | 4 | >10 |
| 195 | 0.25 | 3.3 |
| 196 | 6.0 | >10 |
| 197 | 0.88 | >5 |
| 198 | 3.7 | >10 |
| 199 | 0.054 | 1.4 |
| 200 | 0.038 | 3.3 |
| 201 | 0.045 | 1.5 |
| 202 | 0.20 | 1.6 |
| 203 | 1.0 | 4.3 |
| 204 | 0.16 | 1.5 |
| 205 | 0.21 | 1.5 |
| 206 | 0.026 | 1.6 |
| 207 | 0.07 | 1.2 |
| 208 | 0.53 | 3.1 |
| 209 | 0.49 | 2.8 |
| 210 | 0.047 | 1.3 |
| 211 | 0.58 | >10 |
| 212 | 0.63 | 0.70 |
| 214 | 0.02 | 5.2 |
| 215 | 0.02 | 0.80 |
| 216 | 0.003 | 3.7 |
| 217 | 0.03 | 1.0 |
| 218 | 0.02 | 0.41 |
| 219 | 4.0 | 1.6 |
| 220 | 0.41 | 3.1 |
| 221 | 0.09 | >10 |
| 222 | 0.01 | 3.2 |
| 223 | 0.04 | 2.7 |
| 224 | 0.23 | 2.3 |
| 225 | 0.09 | 1.7 |
| 226 | 0.02 | 1.5 |
| 227 | 0.02 | >10 |
| 228 | 0.03 | >10 |
| 229 | 0.26 | 3.6 |
| 230 | 0.026 | >10 |
| 231 | 0.30 | >10 |
| 232 | 3.8 | >10 |
| 233 | 3.2 | >10 |
| 234 | 3.9 | >10 |
| 235 | 0.55 | >10 |
| 236 | 4.4 | >10 |
| 237 | 6.5 | >10 |
| 238 | 5.1 | >10 |
| 239 | 0.04 | 2.0 |
| 240 | 0.75 | 5.2 |
| 241 | 0.40 | 2.9 |
| 242 | 1.50 | 2.0 |
| 243 | 0.07 | 3.0 |
| 244 | 0.24 | 1.2 |
| 245 | 0.35 | 0.18 |
| 246 | 0.19 | 3.2 |
| 247 | 0.02 | 1.8 |
| 248 | 0.58 | 0.88 |
| 249 | 0.05 | 0.60 |
| 250 | 0.15 | 1.6 |
| 251 | 0.53 | 1.2 |
| 252 | 1.0 | >10 |

EXAMPLE 254

In Vitro Assay of Intrinsic Activity

The interaction of dopamine or a dopamine D-1 receptor agonist with the D-1 receptor causes a dose-dependent increase in the adenylate cyclase-catalyzed conversion of adenosine triphosphate (ATP) to cyclic adenosine monophosphate (cAMP). The functional activity of the compounds of the invention was determined by assaying, in vitro, their ability to either stimulate the enzyme adenylate cyclase to produce more cAMP (agonist activity) or to antagonize a dopamine-induced increase in cAMP levels. The protocol for the adenylate cyclase assays was described by K. J. Watling and J. E. Dowling in *J Neurochemistry* 36:559 (1981) and by J. W. Kebabian et al. in *Proc Natl Acad Sci*, USA 69:2145 (1972). In order to determine agonist activity, cell-free tissue homogenates are incubated in an ionic buffer solution containing ATP and the compound being evaluated. The tissue was obtained from either goldfish retina or rat striatum.

Table 18 shows the intrinsic activity in an adenylate cyclase assay indicating that the compounds of the present invention are dopamine agonists.

TABLE 18

Agonist Activity in Adenylate Cyclase Assay

| Example # | EC50 (µM) | Intrinsic Activity |
|---|---|---|
| dopamine | 2.5 | 100 |
| 2A | 0.043 | 56 |
| 17 | 2.8 | 42 |
| 18 | 1.5 | 46 |
| 20 | 0.5 | 80 |
| 23 | 1.1 | 65 |
| 24 | 0.5 | 71 |
| 27 | 0.2 | |
| 29 | 1.0 | 54 |
| 35 | 0.010 | 66 |
| 36 | 0.079 | 57 |
| 37 | 0.031 | 56 |
| 38 | 0.033 | 91 |
| 39 | 0.05 | 84 |
| 40 | 1.1 | 86 |
| 41 | 1.8 | 81 |
| 42 | 0.006 | 98 |
| 43 | 0.15 | 70 |
| 45 | 0.06 | 62 |
| 46 | 0.22 | 69 |
| 48 | 0.019 | 112 |
| 49 | 0.0024 | 66 |
| 50 | 0.005 | 71 |
| 51 | 0.18 | 88 |
| 52 | 0.071 | 65 |
| 53 | 0.023 | 67 |
| 54 | 0.002 | 71 |
| 55 | 0.024 | 51 |
| 56 | 0.43 | 46 |
| 57 | 0.030 | 56 |
| 58 | 0.019 | 63 |
| 59 | 0.006 | 92 |
| 60 | 0.037 | 93 |
| 61 | 0.006 | 76 |

TABLE 18-continued

Agonist Activity in Adenylate Cyclase Assay

| Example # | EC50 (µM) | Intrinsic Activity |
|---|---|---|
| 62 | 0.17 | 111 |
| 63 | 0.71 | 43 |
| 64 | 0.39 | 80 |
| 65 | 0.32 | 91 |
| 66 | 0.013 | 84 |
| 67 | 0.23 | 92 |
| 68 | 0.014 | 90 |
| 69 | 0.072 | 108 |
| 70 | 0.004 | 110 |
| 71 | 0.71 | 66 |
| 72 | 0.17 | 80 |
| 73 | 0.16 | 138 |
| 74 | 0.84 | 105 |
| 75 | 0.29 | 60 |
| 76 | 0.0058 | 122 |
| 77 | 0.093 | 107 |
| 78 | 0.015 | 147 |
| 79 | 0.007 | 151 |
| 67 | 0.008 | 161 |
| 81 | 0.067 | 61 |
| 82 | 0.007 | 107 |
| 83 | 0.30 | 64 |
| 84 | 0.11 | 72 |
| 85 | 0.65 | 68 |
| 86 | 0.081 | 87 |
| 87 | 0.05 | 54 |
| 88 | 0.012 | 133 |
| 89 | 0.007 | 130 |
| 90 | 0.022 | 128 |
| 91 | 0.67 | 135 |
| 92 | 0.60 | 69 |
| 145 | 0.038 | 49 |
| 146 | 0.12 | 82 |
| 147 | 0.066 | 89 |
| 148 | 0.022 | 79 |
| 149 | 0.036 | 78 |
| 150 | 0.006 | 102 |
| 151 | 7.0 | 58 |
| 153 | 3.1 | 53 |
| 154 | 0.10 | 95 |
| 155 | 0.15 | 95 |
| 156 | 9.5 | 127 |
| 157 | 0.52 | ill |
| 158 | 0.33 | 100 |
| 159 | 0.15 | 129 |
| 160 | 0.14 | 136 |
| 161 | 0.45 | 58 |
| 162 | 0.69 | 107 |
| 163 | 1.45 | 140 |
| 164 | 0.20 | 96 |
| 165 | 0.031 | 105 |
| 166 | 0.18 | 97 |
| 167 | 0.12 | 125 |
| 168 | 0.27 | 103 |
| 169 | 0.20 | 150 |
| 170 | 0.13 | 151 |
| 171 | 0.18 | 124 |
| 172 | 0.22 | 116 |
| 173 | 0.39 | 63 |
| 174 | 0.065 | 90 |
| 176 | 0.32 | 90 |
| 177 | 0.17 | 62 |
| 178 | 8.6 | 99 |
| 179 | 0.01 | 107 |
| 180 | 0.08 | 71 |
| 181 | 0.017 | 65 |
| 182 | 0.021 | 65 |
| 183 | 0.60 | 56 |
| 184 | 0.022 | 47 |
| 186 | 1.3 | 95 |
| 187 | 1.2 | 70 |
| 189 | 1.5 | 65 |
| 190 | 0.11 | 92 |
| 191 | 1.5 | 58 |
| 193 | 0.68 | 63 |
| 194 | 0.058 | 82 |
| 195 | 0.40 | 73 |
| 196 | 1.1 | 80 |
| 197 | 0.18 | 56 |
| 199 | 0.033 | 83 |
| 200 | 0.033 | 120 |
| 201 | 0.0036 | 110 |
| 202 | 0.078 | 84 |
| 203 | >10 | 0 |
| 204 | 0.048 | 110 |
| 205 | 0.068 | 100 |
| 206 | 0.068 | 79 |
| 207 | 0.027 | 64 |
| 209 |  | 25 |
| 210 | 0.052 | 98 |
| 211 | 0.063 | 38 |
| 212 | 0.48 | 43 |
| 213 |  | 70 |
| 214 | 0.02 | 106 |
| 215 | 0.02 | 114 |
| 216 | 0.005 | 114 |
| 217 | 0.02 | 108 |
| 218 | 0.01 | 115 |
| 220 | 0.40 | 72 |
| 221 | 0.08 | 84 |
| 222 | 0.04 | 87 |
| 223 | 0.07 | 52 |
| 224 | 0.24 | 64 |
| 225 | 0.13 | 76 |
| 226 | 0.04 | 89 |
| 227 | 0.37 | 94 |
| 228 | 0.28 | 71 |
| 229 | 0.33 | 34 |
| 230 | 0.12 | 59 |
| 231 | 0.09 | 85 |
| 232 | 1.7 | 49 |
| 234 | 2.7 | 53 |
| 235 | 0.30 | 83 |
| 236 | 0.70 | 36 |
| 237 | 1.9 | 34 |
| 239 | 0.04 | 103 |
| 240 | 0.13 | 70 |
| 241 | 0.40 | 48 |
| 243 | 0.95 | 83 |
| 246 | 0.22 | 78 |
| 247 | 0.03 | 75 |
| 249 | 0.20 | 32 |
| 251 | 0.47 | 41 |
| 252 | 1.7 | 49 |

EXAMPLE 255

Rotation Behavior Assay of In Vivo Activity

The behavioral assay used was based on the rat rotational model. Striatal dopamine was depleted by the intracranial injection of 6-hydroxydopamine, a neurotoxin which specifically destroys catecholaminergic neurons. The intracranial injection was conducted on anesthetized animals using standard stereotaxic techniques (U. Ungerstedt and G. W. Arbuthnott, Brain Research 24: 485, 1970, and U. Ungerstedt, Acta Physiol. Scand. Suppl. 367, 69: 1973). This unilateral lesioning of dopamine-containing neurons causes the post synaptic dopamine receptors to become supersensitive to dopaminergic stimulation in behavioral assays. When these striatal dopamine receptors are stimulated by the test compounds, the rats rotate or physically turn, in a direction that is away from the side of their body that receives the greater dopaminergic activation due to the receptor supersensitivity. Agonist activity was measured by the ability of the test compound to induce rotation.

The results of this testing, shown in Tables 19 and 20, demonstrate the rotation behavior of selected compounds of the present invention.

TABLE 19

Rotation Behavior

| Example No. | ED50 (mmol/kg) s.c.* | ED50 (mmol/kg) oral |
|---|---|---|
| 2A | 1.2 | 27 |
| 3 | 0.91 | — |
| 35 | — | 21.4 |
| 36 | 0.5 | 170 |
| 48 | 0.12 | — |
| 49 | 0.39 | 19.5 |
| 50 | 0.35 | 10.9 |
| 55 | 13.6 | — |
| 59 | 1.02 | 29.5 |
| 51 | 7 | — |
| 64 | 58 | — |
| 86 | 0.45 | >37 |
| 88 | 0.61 | 32 |
| 89 | 0.12 | 7 |
| 90 | 0.6 | 8 |
| 93 | 0.9 | — |
| 100 | 0.12 | — |
| 103 | 0.05 | 8 |
| 104 | 0.13 | 5 |
| 105 | 0.17 | — |
| 111 | 0.25 | 6.25 |
| 112 | 0.10 | 1.0 |
| 126 | 0.16 | 28 |
| 130 | 0.13 | 8 |
| 138 | 0.15 | — |
| 139 | 0.4 | 23 |
| 145 | 0.31 | — |
| 146 | 0.12 | 7 |
| 147 | 0.05 | — |
| 148 | 0.12 | 11 |
| 199 | 1.5 | 31 |
| 200 | 0.7 | 19 |
| 201 | 0.34 | — |
| 204 | 1.1 | 18 |
| 205 | 3.4 | — |
| 210 | 0.005 | 1.6 |
| 214 | 0.085 | |
| 215 | 0.55 | |
| 216 | 0.07 | |
| 217 | 0.12 | |
| 218 | 0.93 | |
| 219 | 0.09 | |
| 220 | 0.52 | |
| 221 | >3 | |
| 222 | 0.3 | |
| 223 | >3 | |
| 225 | >3 | |
| 226 | >1 | |
| 227 | 0.045 | |
| 228 | 0.1 | |
| 231 | >3 | |
| 239 | >3 | |
| 240 | >3 | |
| 241 | >3 | |
| 244 | >3 | |
| 246 | 0.54 | |
| 247 | 0.014 | |
| 249 | 0.12 | |
| 250 | 0.51 | |

*injected subcutaneously

TABLE 20

Rotation Behavior

| Example Number | mean rotations over 360 minutes* |
|---|---|
| 4 | 3329 |
| 6 | 2564 |
| 10 | 1516 |
| 14 | 3653 |
| 15 | 1760 |
| 16 | 4844 |

*dose = 143 micromoles/kg p.o.
**mean rotations over 20 hours

EXAMPLE 256

Cardiovascular Pharmacology—Hemodynamic Studies in Anesthetized Dogs

Male Beagle dogs were anesthetized with pentobarbital (30 mg/kg. i.v.) and maintained with i.v. infusion (Abbott/Shaw Life Care Pump, Model II/D) to maintain stable cardiovascular function. The dogs were incubated with a cuffed endotracheal tube and ventilated with room air by means of a positive pressure respiratory pump. Expired respiratory $CO_2$ was monitored with a Beckman LB-2 gas analyzer and maintained at 5% by appropriate pump adjustments. The dogs were maintained at a body temperature of 37.5°±1.0° C. with a thermostatically controlled animal table. Polyethylene catheters were placed in the abdominal aorta via the femoral and carotid arteries for blood pressure and left ventricular pressure recordings. A Swan-Ganz thermodilution catheter with a 15 cm proximal port was placed in the jugular vein for central venous and pulmonary arterial recordings and for determination of cardiac output (American Edwards Cardiac Output Computer, Model COM-1). Heart rate and electrocardiogram (ECG) recordings were made from a Lead II ECG connection. With the dog on its right side the abdominal cavity was surgically entered laterally, immediate inferior to the rib cage, to expose the left renal artery. A calibrated electromagnetic flow probe (Carolina Medical Electronics) was positioned around the renal artery. The abdominal cavity is closed with wound clips. Recordings were made on a Grass polygraph.

An additional small polyethylene catheter was inserted into a branch of the left femoral artery and the tip positioned in the aorta above the renal arteries. Compounds were continuously infused intrarterially (Harvard Infusion Pump, Model 975) for approximately 5 minutes per dose. A thirty-fold dose-response-curve was administered by varying flow rate from 0.01 to 0.30 mL/minute.

Table 21 below shows the effects of selected compounds of the present invention on cardiovascular phammcology.

TABLE 21

Effects Of Selected Dopaminergic Agonists On The Renal Blood Flow (RBF) And Mean Arterial Blood Pressure (MAP) In Anesthetized Dogs

| Example # | Dose range g/kg/min | Max Increase RBF (%) | Max Decrease MAP (%) |
|---|---|---|---|
| 2A | 3–10 | 27 | 32 |
| 3 | 1–10 | 83 | 8 |
| 35 | 1–3 | 35 | 26 |
| 36 | 1–10 | 94 | 13 |
| 37 | 1–30 | 48 | 39 |

*Cumulative intraaortic (above renal) infusion

EXAMPLE 257

Diuretic Effects in Spontaneously Hypertensive Rats

Male, spontaneously hypertensive rats (SHR), weighing 285–350 grams were used to evaluate the diuretic effects of one of the compounds of the invention. Following an overnight fasting period with free access to drinking water, the rats received an intragastric fluid load of 0.9 saline at 5% of their body weight. Simultaneously with the load, the rats were dosed with a test compound or vehicle and placed individually in stainless steel metabolic cages where they had access to drinking water throughout the duration of the experiment. For intravenous administration, the rats were instrumented with indwelling cannulas placed into the jugular vein at least one week prior to the experiment.

Urine was collected at 2 and 4 hours following drug administration. The volume of excreted urine at each collection interval was measured accurately and the samples were analyzed for sodium, potassium and chloride ions. Sodium and potassium were measured using a Digital Readout Flame Photometer (Instrumentation Labs). Chloride was measured by the method of Shales and Shales, *J Biol Chem* 140:879 (1941). The statistical analysis of the data was computed by an off-line computer program. In this program, a comparison test is made between the vehicle (control) group and each treatment group for all variables at each time interval of the experiment. The test of statistical significance is based on the Student's t-test, where the calculated t is a measure of the probability density function.

The compound of Example 2A was administered to six rats intravenously at a dose of 0.3, 1.0 and 3.0 mg/kg. A control group of six rats received 0.1 mg/kg of saline solution acidified by ascorbic acid (0.3 mL). This solution was also the vehicle for the test compound.

Table 22 shows the diuretic and saliuretic effects of the compound of Example 2A.

TABLE 22

Diuretic Effects of 3.0 Mg/Kg in Hydrated Spontaneously Hypertensive Rats

| Sample | Urine Analysis At 2 Hour Interval After Administration | | | | |
|---|---|---|---|---|---|
| | Volume (mL/kg) | Sodium (meq/kg) | Potassium (meq/kg) | Chloride (meq/kg) | Na/K Ratio |
| Control Group | 13.02 | 1.60 | 0.29 | 1.87 | 9.99 |
| Example 2A Group | 22.57 | 2.35 | 0.55 | 2.71 | 5.06 |
| Control Group SD | 4.29 | 0.59 | 0.17 | 0.83 | 10.27 |
| Example 2A Group SD | 8.30 | 0.84 | 0.22 | 0.75 | 2.85 |
| p <= 0.05 | 0.0313* | 0.1043 | 0.0423* | 0.0950 | 0.28134 |

*statistically significant, n = 6

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula

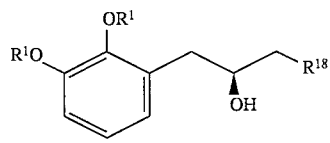

wherein $R^1$ is a catechol-protecting group, and $R^{18}$ is substituted $C_3$–$C_9$-alkyl.

* * * * *